United States Patent
Di Padova et al.

(10) Patent No.: US 9,193,788 B2
(45) Date of Patent: Nov. 24, 2015

(54) ANTI-IL-17A ANTIBODIES AND THEIR USES

(71) Applicants: Franco E. Di Padova, Basel (CH);
Thomas Huber, Basel (CH);
Jean-Michel Rene Rondeau, Basel (CH)

(72) Inventors: Franco E. Di Padova, Basel (CH);
Thomas Huber, Basel (CH);
Jean-Michel Rene Rondeau, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/174,942

(22) Filed: Feb. 7, 2014

(65) Prior Publication Data
US 2015/0175692 A1  Jun. 25, 2015

Related U.S. Application Data

(60) Provisional application No. 61/762,406, filed on Feb. 8, 2013.

(51) Int. Cl.
*A61K 39/395* (2006.01)
*C07K 16/24* (2006.01)
*A61K 39/00* (2006.01)

(52) U.S. Cl.
CPC ............ *C07K 16/244* (2013.01); *A61K 39/3955* (2013.01); *A61K 2039/505* (2013.01); *C07K 2299/00* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2007/0218065 A1   9/2007  Jaspers et al.

FOREIGN PATENT DOCUMENTS

| WO | WO2006013107 A1 | 2/2006 |
| WO | WO2007106769 A2 | 9/2007 |
| WO | WO2007149032 A1 | 12/2007 |
| WO | WO2008021156 A2 | 2/2008 |
| WO | WO2008133684 A1 | 11/2008 |
| WO | WO2010128407 A2 | 11/2010 |
| WO | WO2011053763 A2 | 5/2011 |
| WO | WO2011053763 A2 | 5/2011 |
| WO | WO2012093254 A1 | 7/2012 |

OTHER PUBLICATIONS

Ambadi-Obi, et al, "TH17 cells contribute to uveitis and scleritis and are expanded by IL-2 and inhibited by IL-27/STAT1", Nature Med., vol. 13, No. 6, pp. 711-718, 2007.
Weaver, et al, "IL-17 Family Cytokines and the Expanding Diversity of Effector T Cell Lineages", Annu Rev Immunol., vol. 25, pp. 821-852, 2007.
Witowski et al., "Interleukin-17: a mediator of inflammatory responses", Cell Mol Life Sci., vol. 61, pp. 567-579, 2004.
Miossec et al., "Interleukin-17 and Type 17 Helper T Cells", NEJM, vol. 361, pp. 888-898, 2009.
Rouvier E et al, "CTLA-8, Cloned from an Activated T Cell, Bearing AU-Rich Messenger RNA Instability Sequences, and Homologous to a Herpesvirus Saimiri Gene", J. Immunol., vol. 150, No. 12, pp. 5445-5456, Jun. 15, 1993.
Pappu R, et al., "Regulation of epitheiial immunity by IL-17 family cytokines", 343-9, Trends Immunol, vol. 33, No. 7, 99. 343-349, Jul. 2012.
Kolls JK and Linden A., "Interieuking-17 Family Members and inflammation", Immunity vol. 21, pp. 467-476, 2004.
Kawaguchi M, et al., "Molecular mechanisms in allergy and clinical immunology/IL-17 Cytokine family", J. Allergy Clin. Immunol., vol. 114, No. 6, pp. 1265-1273, Dec. 2004.
Moseley TA, et al., "Interleukin-17 family and IL-17 receptors", Cytokine Growth Factor Rev., vol. 14 pp. 155-174, 2003.
Yao Z, et al., "Human IL-17: a novel cytokine derived from T cells", J. Immunol., vol. 155, pp. 5483-5486, 1995.
Hymowitz et al., "IL-17s adopt a cystine knot fold: structure and activity of a novel cytokine, IL-17F, and implications for receptor binding", EMBO J. vol. 20, No. 19, pp. 5332-5341, 2001.
Ely et al., "Structural basis of receptor sharing by interleukin 17 cytokines", Nature Immunology, vol. 10, No. 12, pp. 1245-1251, Dec. 2009.
Gerhardt at al., "Structure of IL-17A in Complex with a potent, Fully Human Neutralizing Antibody", Journal of Molecular Biology, vol. 394, pp. 905-921, 2009.
Aggarwal S and Gurney AL , "IL-17: Protype member of an emerging cytokine family", J. Leukoc. Biol. vol. 71, pp. 1-8, Jan. 2002.

(Continued)

*Primary Examiner* — Bridget E Bunner
*Assistant Examiner* — Fozia Hamud
(74) *Attorney, Agent, or Firm* — Leslie Fischer

(57) ABSTRACT

The present disclosure relates to antibodies and proteins comprising an antigen-binding portion thereof that specifically bind to the pro-inflammatory cytokine IL-17A. The disclosure more specifically relates to specific antibodies and proteins that are IL-17A antagonists (inhibit the activities of IL-17A and IL-17AF) and are capable of inhibiting IL-17A induced cytokine production in in vitro assays, and having an inhibitory effect in an antigen-induced arthritis model in vivo. The disclosure further relates to compositions and methods of use for the antibodies and proteins to treat pathological disorders that can be treated by inhibiting IL-17A or IL17AF mediated activity, such as rheumatoid arthritis, psoriasis, systemic lupus erythematosus (SLE), lupus nephritis, chronic obstructive pulmonary disease, asthma or cystic fibrosis or other autoimmune and inflammatory disorders.

20 Claims, 26 Drawing Sheets

(56) References Cited

OTHER PUBLICATIONS

Zhang X et al., "Structure and function of interleukin-17 family Cytokines", Protein Cell, vol. 2, No. 1 pp. 26-40 (2011).

Dumont et at., "IL-17 cytokine/receptor families:emerging targets for the modulation of inflammatory responses", Expert opinion on therapeutic patents, vol. 13, No. 3, p. 287-303, 2003.

Rudikoff et al., "Single amino acid substitution altering antigen-binding specipity", Proceedings of the National Academy of Sciences. VI. 79, p. 1979-1983, 1982.

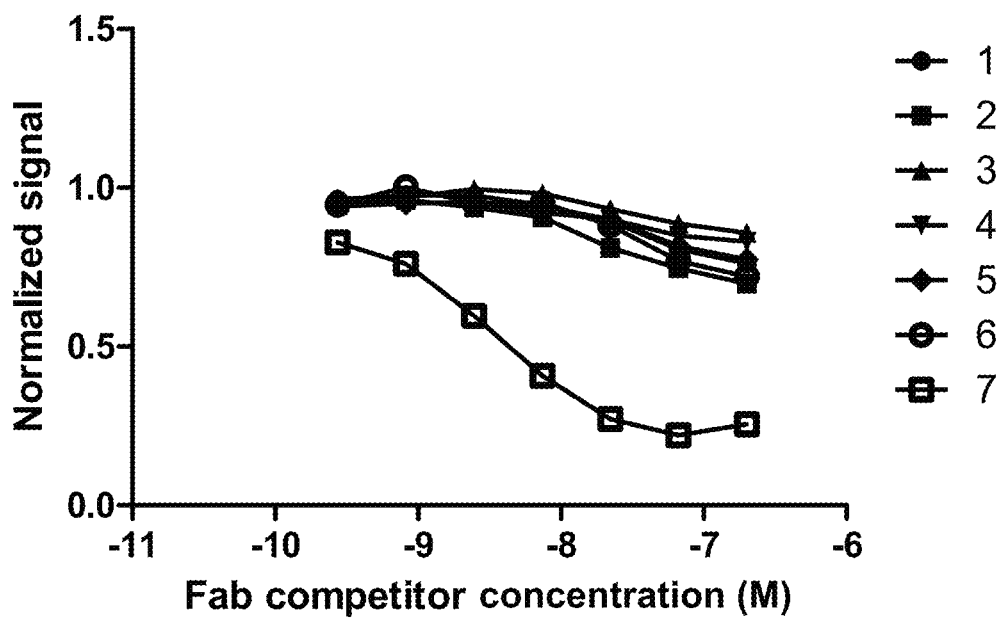

SEQUENCE LISTING

<160> NUMBER OF SEQ ID NOS: 86

<210> SEQ ID NO 1
<211> LENGTH: 7
<212> TYPE: PRT
<213> ORGANISM: Homo sapiens

<400> SEQUENCE: 1

Gly Phe Thr Phe Ser Ser Tyr
1               5

<210> SEQ ID NO 2
<211> LENGTH: 6
<212> TYPE: PRT
<213> ORGANISM: Homo sapiens

<400> SEQUENCE: 2

Lys Gln Asp Gly Ser Glu
1               5

<210> SEQ ID NO 3
<211> LENGTH: 7
<212> TYPE: PRT
<213> ORGANISM: Homo sapiens

<400> SEQUENCE: 3

Asp Arg Gly Ser Leu Tyr Tyr
1               5

```
<210> SEQ ID NO 4
<211> LENGTH: 7
<212> TYPE: PRT
<213> ORGANISM: Homo sapiens

<400> SEQUENCE: 4

Ser Gln Gly Ile Ile Ser Ala
1               5

<210> SEQ ID NO 5
<211> LENGTH: 3
<212> TYPE: PRT
<213> ORGANISM: Homo sapiens

<400> SEQUENCE: 5

Asp Ala Ser
1

<210> SEQ ID NO 6
<211> LENGTH: 6
<212> TYPE: PRT
<213> ORGANISM: Homo sapiens

<400> SEQUENCE: 6

Phe Asn Ser Tyr Pro Leu
1               5

<210> SEQ ID NO 7
<211> LENGTH: 5
<212> TYPE: PRT
<213> ORGANISM: Homo sapiens

<400> SEQUENCE: 7

Ser Tyr Trp Met Ser
1               5

<210> SEQ ID NO 8
<211> LENGTH: 17
<212> TYPE: PRT
<213> ORGANISM: Homo sapiens

<400> SEQUENCE: 8

Asn Ile Lys Gln Asp Gly Ser Glu Lys Tyr Tyr Val Asp Ser Val Lys
1               5                   10                  15

Gly

<210> SEQ ID NO 9
<211> LENGTH: 11
<212> TYPE: PRT
<213> ORGANISM: Homo sapiens

<400> SEQUENCE: 9

Arg Pro Ser Gln Gly Ile Ile Ser Ala Leu Ala
1               5                   10

<210> SEQ ID NO 10
<211> LENGTH: 7
<212> TYPE: PRT
<213> ORGANISM: Homo sapiens

<400> SEQUENCE: 10

Asp Ala Ser Ser Leu Glu Asn
1               5
```

```
<210> SEQ ID NO 11
<211> LENGTH: 9
<212> TYPE: PRT
<213> ORGANISM: Homo sapiens

<400> SEQUENCE: 11

Gln Gln Phe Asn Ser Tyr Pro Leu Thr
1               5

<210> SEQ ID NO 12
<211> LENGTH: 116
<212> TYPE: PRT
<213> ORGANISM: Homo sapiens

<400> SEQUENCE: 12

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ser Leu Tyr Tyr Trp Gly Gln Gly Thr Leu Val
            100                 105                 110

Thr Val Ser Ser
        115

<210> SEQ ID NO 13
<211> LENGTH: 107
<212> TYPE: PRT
<213> ORGANISM: Homo sapiens

<400> SEQUENCE: 13

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 14
<211> LENGTH: 446
<212> TYPE: PRT
<213> ORGANISM: Homo sapiens
```

```
<400> SEQUENCE: 14

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Ser Leu Tyr Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415
```

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 15
<211> LENGTH: 214
<212> TYPE: PRT
<213> ORGANISM: Homo sapiens

<400> SEQUENCE: 15

Ala Ile Gln Leu Thr Gln Ser Pro Ser Ser Leu Ser Ala Ser Val Gly
 1               5                   10                  15

Asp Arg Val Thr Ile Thr Cys Arg Pro Ser Gln Gly Ile Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Asn Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 348
<212> TYPE: DNA
<213> ORGANISM: Homo sapiens

<400> SEQUENCE: 16
gaggtgcagc tggtcgagtc tggcggcgac ctggtgcagc ctggcggcag cctgagactg      60
agctgcgccg ccagcggctt caccttcagc agctactgga tgtcctgggt ccgccaggcc     120
cctggcaaag gcctcgaatg ggtggccaac atcaagcagg acggcagcga agtactac       180 gtggacagcg tgaagggccg gttcaccatc agcgggaca acgccaagaa cagcctgtac      240
ctgcagatga acagcctgcg ggccgaggac accgccgtgt actactgcgc cagggaccgg     300
ggcagcctgt actattgggg ccagggcacc ctggtcaccg tgtccagc                  348

<210> SEQ ID NO 17

```
<211> LENGTH: 321
<212> TYPE: DNA
<213> ORGANISM: Homo sapiens

<400> SEQUENCE: 17
gccatccagt tgacccagtc tccatcctcc ctgtctgcat ctgtgggaga cagagtcacc    60
atcacttgcc ggccaagtca gggcattatc agtgctttag cctggtatca gcagaaacca   120
gggaaagctc ctaagctcct gatctatgat gcctccagtt tggaaaatgg ggtcccatca   180
aggttcagcg gcagtggatc tgggacagat ttcactctca ccatcagcag cctgcagcct   240
gaagattttg caacttatta ctgtcaacag tttaatagtt accctctcac tttcggcgga   300
gggaccaagg tggagatcaa a                                              321

<210> SEQ ID NO 18
<211> LENGTH: 1338
<212> TYPE: DNA
<213> ORGANISM: Homo sapiens

<400> SEQUENCE: 18
gaggtgcagc tggtcgagtc tggcggcgac ctggtgcagc ctggcggcag cctgagactg    60
agctgcgccg ccagcggctt caccttcagc agctactgga tgtcctgggt ccgccaggcc   120
cctggcaaag gcctcgaatg ggtggccaac atcaagcagg acggcagcga aagtactac    180 gtggacagcg tgaagggccg gttcaccatc agccgggaca cgccaagaa cagcctgtac   240 ctgcagatga acagcctgcg ggccgaggac accgccgtgt actactgcgc cagggaccgg   300
ggcagcctgt actattgggg ccagggcacc ctggtcaccg tgtccagcgc tagcaccaag   360
ggccccagcg tgttccccct ggccccccagc agcaagagca ccagcggcgg cacagccgcc   420
ctgggctgcc tggtgaagga ctacttcccc gagcccgtga ccgtgtcctg aacagcgga    480 gccctgacct ccggcgtgca caccttcccc gccgtgctgc agagcagcgg cctgtacagc   540
ctgtccagcg tggtgacagt gcccagcagc agcctgggca cccagaccta catctgcaac   600
gtgaaccaca agcccagcaa caccaaggtg gacaagagag tggagcccaa agctgcgac    660 aagacccaca cctgcccccc ctgcccagcc ccagagctgc tgggcggacc ctccgtgttc   720
ctgttccccc ccaagcccaa ggacaccctg atgatcagca ggaccccgca ggtgacctgc   780
gtggtggtgg acgtgagcca cgaggaccca gaggtgaagt tcaactggta cgtggacggc   840
gtggaggtgc acaacgccaa gaccaagccc agagaggagc agtacaacag cacctacagg   900
gtggtgtccg tgctgaccgt gctgcaccag gactggctga acggcaagga atacaagtgc   960
aaggtctcca acaaggccct gccagccccc atcgaaaaga ccatcagcaa ggccaagggc  1020
cagccacggg agcccagat gtacaccctg ccccctccc gggaggagat gaccaagaac  1080
caggtgtccc tgacctgtct ggtgaagggc ttctacccca gcgacatcgc cgtggagtgg  1140
gagagcaacg gccagcccga gaacaactac aagaccaccc ccccagtgct ggacagcgac  1200
ggcagcttct tcctgtacag caagctgacc gtggacaagt ccaggtggca gcagggcaac  1260
gtgttcagct gcagcgtgat gcacgaggcc ctgcacaacc actacaccca gaagagcctg  1320
agcctgtccc ccggcaag                                                 1338

<210> SEQ ID NO 19
<211> LENGTH: 642
<212> TYPE: DNA
<213> ORGANISM: Homo sapiens

<400> SEQUENCE: 19
```

```
gccatccagt tgacccagtc tccatcctcc ctgtctgcat ctgtgggaga cagagtcacc      60
atcacttgcc ggccaagtca gggcattatc agtgctttag cctggtatca gcagaaacca     120
gggaaagctc ctaagctcct gatctatgat gcctccagtt tggaaaatgg ggtcccatca     180
aggttcagcg gcagtggatc tgggacagat ttcactctca ccatcagcag cctgcagcct     240
gaagattttg caacttatta ctgtcaacag tttaatagtt accctctcac tttcggcgga     300
gggaccaagg tggagatcaa acgtacggtg gccgctccca gcgtgttcat cttcccccc      360 agcgacgagc agctgaagag cggcaccgcc agcgtggtgt gcctgctgaa caacttctac     420 ccccggagg ccaaggtgca gtggaaggtg gacaacgccc tgcagagcgg caacagccag      480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                        642
```

<210> SEQ ID NO 20
<211> LENGTH: 7
<212> TYPE: PRT
<213> ORGANISM: Homo sapiens

<400> SEQUENCE: 20

Ser Gln Val Ile Ile Ser Ala
1               5

<210> SEQ ID NO 21
<211> LENGTH: 6
<212> TYPE: PRT
<213> ORGANISM: Homo sapiens

<400> SEQUENCE: 21

Phe Asp Ser Tyr Pro Leu
1               5

<210> SEQ ID NO 22
<211> LENGTH: 11
<212> TYPE: PRT
<213> ORGANISM: Homo sapiens

<400> SEQUENCE: 22

Arg Pro Ser Gln Val Ile Ile Ser Ala Leu Ala
1               5                   10

<210> SEQ ID NO 23
<211> LENGTH: 7
<212> TYPE: PRT
<213> ORGANISM: Homo sapiens

<400> SEQUENCE: 23

Asp Ala Ser Ser Leu Glu Gln
1               5

<210> SEQ ID NO 24
<211> LENGTH: 9
<212> TYPE: PRT
<213> ORGANISM: Homo sapiens

<400> SEQUENCE: 24

Gln Gln Phe Asp Ser Tyr Pro Leu Thr
1               5

```
<210> SEQ ID NO 25
<211> LENGTH: 107
<212> TYPE: PRT
<213> ORGANISM: Homo sapiens

<400> SEQUENCE: 25

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Val Ile Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Tyr Pro Leu
                85                  90                  95

Thr Phe Gly Gly Gly Thr Lys Val Glu Ile Lys
            100                 105

<210> SEQ ID NO 26
<211> LENGTH: 214
<212> TYPE: PRT
<213> ORGANISM: Homo sapiens

<400> SEQUENCE: 26

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Val Ile Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 321
<212> TYPE: DNA
<213> ORGANISM: Homo sapiens

<400> SEQUENCE: 27

| | |
|---|---|
| gccatccagc tgacccagag ccccagcagc ctgagcgcca gcgtgggcga cagagtgacc | 60 |
| atcacctgtc ggcccagcca ggtcatcatc agcgccctgg cctggtatca gcagaagcct | 120 |
| ggcaaggccc ccaagctgct gatctacgac gccagctccc tggaacaggg cgtgcccagc | 180 |
| cggttcagcg gcagcgtgtc cggcaccgac ttcaccctga ccatcagctc cctgcagccc | 240 |
| gaggacttcg ccacctacta ctgccagcag ttcgacagct accccctgac cttcggcgga | 300 |
| ggcaccaagg tggaaatcaa g | 321 |

<210> SEQ ID NO 28
<211> LENGTH: 642
<212> TYPE: DNA
<213> ORGANISM: Homo sapiens

<400> SEQUENCE: 28

| | |
|---|---|
| gccatccagc tgacccagag ccccagcagc ctgagcgcca gcgtgggcga cagagtgacc | 60 |
| atcacctgtc ggcccagcca ggtcatcatc agcgccctgg cctggtatca gcagaagcct | 120 |
| ggcaaggccc ccaagctgct gatctacgac gccagctccc tggaacaggg cgtgcccagc | 180 |
| cggttcagcg gcagcgtgtc cggcaccgac ttcaccctga ccatcagctc cctgcagccc | 240 |
| gaggacttcg ccacctacta ctgccagcag ttcgacagct accccctgac cttcggcgga | 300 |
| ggcaccaagg tggaaatcaa gcgtacggtg gccgctccca gcgtgttcat cttcccccc | 360 |
| agcgacgagc agctgaagag cggcaccgcc agcgtggtgt gcctgctgaa caacttctac | 420 |
| ccccgggagg ccaaggtgca gtggaaggtg acaacgccc tgcagagcgg caacagccag | 480 |
| gagagcgtca ccgagcagga cagcaaggac tccacctaca gcctgagcag caccctgacc | 540 |
| ctgagcaagg ccgactacga aagcataag gtgtacgcct gcgaggtgac ccaccagggc | 600 |
| ctgtccagcc ccgtgaccaa gagcttcaac aggggcgagt gc | 642 |

<210> SEQ ID NO 29
<211> LENGTH: 348
<212> TYPE: DNA
<213> ORGANISM: Homo sapiens

<400> SEQUENCE: 29

| | |
|---|---|
| gaggtgcagc tggtggaatc aggaggcgac ctggtgcagc ctggcggctc actgagactg | 60 |
| agctgcgccg ctagtggctt caccttagt agctactgga tgagctgggt gcgacaggcc | 120 |
| cctggcaagg gactggagtg ggtggccaat attaagcagg acggctcaga gaagtactac | 180 |
| gtggactcag tgaagggccg gttcactatt agccgggata acgctaagaa tagcctgtac | 240 |
| ctgcagatga atagcctgag agccgaggac accgccgtgt actactgcgc tagagataga | 300 |
| ggctcactgt actactgggg ccagggcacc ctggtgacag tgtcttct | 348 |

<210> SEQ ID NO 30
<211> LENGTH: 321
<212> TYPE: DNA
<213> ORGANISM: Homo sapiens

<400> SEQUENCE: 30

| | |
|---|---|
| gctattcagc tgactcagtc acctagtagc ctgagcgcta gtgtgggcga tagagtgact | 60 |

| | |
|---|---|
| atcacctgta gacctagtca ggtgatcatt agcgccctgg cctggtatca gcagaagccc | 120 |
| ggcaaggccc ctaagctgct gatctacgac gctagtagtc tggaacaggg cgtgccctct | 180 |
| aggtttagcg gctcagtgtc aggcaccgac ttcaccctga ctattagtag cctgcagccc | 240 |
| gaggacttcg ctacctacta ctgtcagcag ttcgatagct accccctgac cttcggcgga | 300 |
| ggcactaagg tggaaatcaa g | 321 |

<210> SEQ ID NO 31
<211> LENGTH: 1338
<212> TYPE: DNA
<213> ORGANISM: Homo sapiens

<400> SEQUENCE: 31

| | |
|---|---|
| gaggtgcagc tggtggaatc aggaggcgac ctggtgcagc ctggcggctc actgagactg | 60 |
| agctgcgccg ctagtggctt caccttagt agctactgga tgagctgggt gcgacaggcc | 120 |
| cctggcaagg gactggagtg ggtggccaat attaagcagg acggctcaga gaagtactac | 180 |
| gtggactcag tgaagggccg gttcactatt agccgggata cgctaagaa tagcctgtac | 240 |
| ctgcagatga atagcctgag agccgaggac accgccgtgt actactgcgc tagagataga | 300 |
| ggctcactgt actactgggg ccagggcacc ctggtgacag tgtcttctgc tagcaccaag | 360 |
| ggcccaagtg tctttcccct ggcccccagc agcaagtcca agtggcgagg cactgcagct | 420 |
| ctgggttgtc tggtgaagga ctacttcccc gagcccgtga cagtgtcctg aacagcgga | 480 |
| gccctgacct ccggcgtgca caccttcccc gccgtgctgc agagcagcgg cctgtacagc | 540 |
| ctgagcagcg tcgtgactgt gcctagttcc agctgggca cccagaccta tatctgcaac | 600 |
| gtgaaccaca agcccagcaa caccaaggtg gacaagagag tggagcccaa agctgcgac | 660 |
| aagacccaca cctgccccc ctgcccagct ccagaactgc tgggaggacc cagcgtgttc | 720 |
| ctgttccccc ccaagcccaa ggacaccctg atgatcagca ggacccccga ggtgacctgc | 780 |
| gtggtggtgg acgtgtccca cgaggaccca gaggtgaagt tcaactggta cgtggacggg | 840 |
| gtggaggtgc acaacgccaa gaccaagccc agagaggagc agtacaacag cacctacagg | 900 |
| gtggtgtccg tcctgacagt gctgcaccag gattggctga acggcaaaga atacaagtgc | 960 |
| aaagtctcca acaaggccct gccagcccca atcgaaaaga caatcagcaa ggccaagggc | 1020 |
| cagccacggg agccccaggt gtacaccctg ccccccagcc gggaggagat gaccaagaac | 1080 |
| caggtgtccc tgacctgtct ggtgaagggc ttctacccca gcgatatcgc cgtggagtgg | 1140 |
| gagagcaacg gccagcccga gaacaactac aagaccaccc cccagtgct ggacagcgac | 1200 |
| ggcagcttct tcctgtacag caagctgacc gtggacaagt ccaggtggca gcagggcaac | 1260 |
| gtgttcagct gcagcgtgat gcacgaggcc ctgcacaacc actacaccca gaagtccctg | 1320 |
| agcctgagcc ccggcaag | 1338 |

<210> SEQ ID NO 32
<211> LENGTH: 642
<212> TYPE: DNA
<213> ORGANISM: Homo sapiens

<400> SEQUENCE: 32

| | |
|---|---|
| gctattcagc tgactcagtc acctagtagc ctgagcgcta gtgtgggcga tagagtgact | 60 |
| atcacctgta gacctagtca ggtgatcatt agcgccctgg cctggtatca gcagaagccc | 120 |
| ggcaaggccc ctaagctgct gatctacgac gctagtagtc tggaacaggg cgtgccctct | 180 |
| aggtttagcg gctcagtgtc aggcaccgac ttcaccctga ctattagtag cctgcagccc | 240 |

```
gaggacttcg ctacctacta ctgtcagcag ttcgatagct acccctgac cttcggcgga      300 ggcactaagg tggaaatcaa gcgtacggtg gccgctccca gcgtgttcat cttccccccc      360
agcgacgagc agctgaagag cggcaccgcc agcgtggtgt gcctgctgaa caacttctac      420
ccccggggag ccaaggtgca gtggaaggtg gacaacgccc tgcagagcgg caacagccag      480
gagagcgtca ccgagcagga cagcaaggac tccacctaca gcctgagcag caccctgacc      540
ctgagcaagg ccgactacga gaagcataag gtgtacgcct gcgaggtgac ccaccagggc      600
ctgtccagcc ccgtgaccaa gagcttcaac aggggcgagt gc                        642
```

<210> SEQ ID NO 33
<211> LENGTH: 7
<212> TYPE: PRT
<213> ORGANISM: Homo sapiens

<400> SEQUENCE: 33

Ser Gln Gly Ile Tyr Trp Glu
1               5

<210> SEQ ID NO 34
<211> LENGTH: 11
<212> TYPE: PRT
<213> ORGANISM: Homo sapiens

<400> SEQUENCE: 34

Arg Pro Ser Gln Gly Ile Tyr Trp Glu Leu Ala
1               5                   10

<210> SEQ ID NO 35
<211> LENGTH: 107
<212> TYPE: PRT
<213> ORGANISM: Homo sapiens

<400> SEQUENCE: 35

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Tyr Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105

<210> SEQ ID NO 36
<211> LENGTH: 214
<212> TYPE: PRT
<213> ORGANISM: Homo sapiens

<400> SEQUENCE: 36

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Tyr Trp Glu
            20                  25                  30

```
Leu Ala Trp Tyr Gln Gln Lys Pro Gly Lys Ala Pro Lys Leu Leu Ile
         35                  40                  45
Tyr Asp Ala Ser Ser Leu Glu Gln Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Phe Asn Ser Tyr Pro Leu
                 85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
        210

<210> SEQ ID NO 37
<211> LENGTH: 321
<212> TYPE: DNA
<213> ORGANISM: Homo sapiens

<400> SEQUENCE: 37
gccatccagc tgacccagag ccccagcagc ctgagcgcca gcgtgggcga cagagtgacc      60
atcacctgtc ggcccagcca gggcatctac tgggagctgg cctggtatca gcagaagcct     120
ggcaaggccc ccaagctgct gatctacgac gccagctccc tggaacaggg cgtgcccagc     180
cggttcagcg gcagcggatc cggcaccgac ttcaccctga ccatcagctc cctgcagccc     240
gaggacttcg ccacctacta ctgccagcag ttcaacagct accccctgac cttcggcgga     300
ggcaccaagg tggaaatcaa g                                               321

<210> SEQ ID NO 38
<211> LENGTH: 642
<212> TYPE: DNA
<213> ORGANISM: Homo sapiens

<400> SEQUENCE: 38
gccatccagc tgacccagag ccccagcagc ctgagcgcca gcgtgggcga cagagtgacc      60
atcacctgtc ggcccagcca gggcatctac tgggagctgg cctggtatca gcagaagcct     120
ggcaaggccc ccaagctgct gatctacgac gccagctccc tggaacaggg cgtgcccagc     180
cggttcagcg gcagcggatc cggcaccgac ttcaccctga ccatcagctc cctgcagccc     240
gaggacttcg ccacctacta ctgccagcag ttcaacagct accccctgac cttcggcgga     300
ggcaccaagg tggaaatcaa gcgtacggtg gccgctccca gcgtgttcat cttccccccc     360
agcgacgagc agctgaagag cggcaccgcc agcgtggtgt gcctgctgaa caacttctac     420
```

```
cccgggagg  ccaaggtgca  gtggaaggtg  acaacgccc   tgcagagcgg  caacagccag   480
gagagcgtca  ccgagcagga  cagcaaggac  tccacctaca  gcctgagcag  cacccctgacc  540 ctgagcaagg  ccgactacga  gaagcataag  gtgtacgcct  gcgaggtgac  ccaccagggc   600
ctgtccagcc  ccgtgaccaa  gagcttcaac  aggggcgagt  gc                       642
```

```
<210> SEQ ID NO 39
<211> LENGTH: 321
<212> TYPE: DNA
<213> ORGANISM: Homo sapiens

<400> SEQUENCE: 39
gctattcagc  tgactcagtc  acctagtagc  ctgagcgcta  gtgtgggcga  tagagtgact   60
atcacctgta  gacctagcca  gggaatctac  tgggagctgg  cctggtatca  gcagaagccc  120
ggcaaggccc  ctaagctgct  gatctacgac  gctagtagtc  tggaacaggg  cgtgccctct  180
aggtttagcg  gctcaggctc  aggcaccgac  ttcaccctga  ctattagtag  cctgcagccc  240
gaggacttcg  ctacctacta  ctgtcagcag  tttaactcct  accccctgac  cttcggcgga  300
ggcactaagg  tggaaatcaa  g                                                321
```

```
<210> SEQ ID NO 40
<211> LENGTH: 642
<212> TYPE: DNA
<213> ORGANISM: Homo sapiens

<400> SEQUENCE: 40
gctattcagc  tgactcagtc  acctagtagc  ctgagcgcta  gtgtgggcga  tagagtgact   60
atcacctgta  gacctagcca  gggaatctac  tgggagctgg  cctggtatca  gcagaagccc  120
ggcaaggccc  ctaagctgct  gatctacgac  gctagtagtc  tggaacaggg  cgtgccctct  180
aggtttagcg  gctcaggctc  aggcaccgac  ttcaccctga  ctattagtag  cctgcagccc  240
gaggacttcg  ctacctacta  ctgtcagcag  tttaactcct  accccctgac  cttcggcgga  300
ggcactaagg  tggaaatcaa  gcgtacggtg  gccgctccca  gcgtgttcat  cttcccccc   360 agcgacgagc  agctgaagag  cggcaccgcc  agcgtggtgt  gcctgctgaa  caacttctac  420
ccccgggagg  ccaaggtgca  gtggaaggtg  gacaacgccc  tgcagagcgg  caacagccag  480
gagagcgtca  ccgagcagga  cagcaaggac  tccacctaca  gcctgagcag  cacccctgacc 540 ctgagcaagg  ccgactacga  gaagcataag  gtgtacgcct  gcgaggtgac  ccaccagggc  600
ctgtccagcc  ccgtgaccaa  gagcttcaac  aggggcgagt  gc                      642
```

```
<210> SEQ ID NO 41
<211> LENGTH: 7
<212> TYPE: PRT
<213> ORGANISM: Homo sapiens

<400> SEQUENCE: 41

Ser Gln Gly Ile Asn Trp Glu
1               5
```

```
<210> SEQ ID NO 42
<211> LENGTH: 11
<212> TYPE: PRT
<213> ORGANISM: Homo sapiens

<400> SEQUENCE: 42

Arg Pro Ser Gln Gly Ile Asn Trp Glu Leu Ala
1               5                   10
```

<210> SEQ ID NO 43
<211> LENGTH: 107
<212> TYPE: PRT
<213> ORGANISM: Homo sapiens

<400> SEQUENCE: 43

```
Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

<210> SEQ ID NO 44
<211> LENGTH: 214
<212> TYPE: PRT
<213> ORGANISM: Homo sapiens

<400> SEQUENCE: 44

```
Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 45
<211> LENGTH: 321
<212> TYPE: DNA
<213> ORGANISM: Homo sapiens

<400> SEQUENCE: 45

```
gccatccagc tgacccagag ccccagcagc ctgagcgcca gcgtgggcga cagagtgacc      60
atcacctgtc ggcccagcca gggcatcaac tgggagctgg cctggtatca gcagaagcct     120
ggcaaggccc ccaagctgct gatctacgac gccagctccc tggaacaggg cgtgcccagc     180
cggttcagcg gcagcggatc cggcaccgac ttcaccctga ccatcagctc cctgcagccc     240
gaggacttcg ccacctacta ctgccagcag ttcaacagct accccctgac cttcggcgga     300
ggcaccaagg tggaaatcaa g                                               321
```

<210> SEQ ID NO 46
<211> LENGTH: 642
<212> TYPE: DNA
<213> ORGANISM: Homo sapiens

<400> SEQUENCE: 46

```
gccatccagc tgacccagag ccccagcagc ctgagcgcca gcgtgggcga cagagtgacc      60
atcacctgtc ggcccagcca gggcatcaac tgggagctgg cctggtatca gcagaagcct     120
ggcaaggccc ccaagctgct gatctacgac gccagctccc tggaacaggg cgtgcccagc     180
cggttcagcg gcagcggatc cggcaccgac ttcaccctga ccatcagctc cctgcagccc     240
gaggacttcg ccacctacta ctgccagcag ttcaacagct accccctgac cttcggcgga     300
ggcaccaagg tggaaatcaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc     600
ctgtccagcc ccgtgaccaa gagcttcaac aggggcgagt gc                        642
```

<210> SEQ ID NO 47
<211> LENGTH: 321
<212> TYPE: DNA
<213> ORGANISM: Homo sapiens

<400> SEQUENCE: 47

```
gctattcagc tgactcagtc acctagtagc ctgagcgcta gtgtgggcga tagagtgact      60
atcacctgta gacctagtca ggggattaac tgggagctgg cctggtatca gcagaagccc     120
ggcaaggccc ctaagctgct gatctacgac gctagtagtc tggaacaggg cgtgccctct     180
aggtttagcg gctcaggctc aggcaccgac ttcaccctga ctattagtag cctgcagccc     240
gaggacttcg ctacctacta ctgtcagcag tttaactcct accccctgac cttcggcgga     300
ggcactaagg tggaaatcaa g                                               321
```

<210> SEQ ID NO 48
<211> LENGTH: 642
<212> TYPE: DNA
<213> ORGANISM: Homo sapiens

<400> SEQUENCE: 48

```
gctattcagc tgactcagtc acctagtagc ctgagcgcta gtgtgggcga tagagtgact    60
atcacctgta gacctagtca ggggattaac tgggagctgg cctggtatca gcagaagccc   120
ggcaaggccc ctaagctgct gatctacgac gctagtagtc tggaacaggg cgtgccctct   180
aggtttagcg gctcaggctc aggcaccgac ttcaccctga ctattagtag cctgcagccc   240
gaggacttcg ctacctacta ctgtcagcag tttaactcct accccctgac cttcggcgga   300
ggcactaagg tggaaatcaa gcgtacggtg gccgctccca gcgtgttcat cttcccccc    360 agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag caccctgacc   540
ctgagcaagg ccgactacga aagcataag gtgtacgcct gcgaggtgac ccaccagggc   600
ctgtccagcc ccgtgaccaa gagcttcaac aggggcgagt gc                      642
```

<210> SEQ ID NO 49
<211> LENGTH: 348
<212> TYPE: DNA
<213> ORGANISM: Homo sapiens

<400> SEQUENCE: 49

```
gaggtgcagc tggtggaatc tggcggcgac ctggtgcagc ctggcggctc tctgagactg    60
tcttgcgccg cctccggctt caccttctcc agctactgga tgtcctgggt gcgacaggcc   120
cctggcaagg gactggaatg ggtggccaac atcaagcagg acggctccga gaagtactac   180
gtggactccg tgaagggccg gttcaccatc tcccgggaca cgccaagaa ctccctgtac    240 ctgcagatga actccctgcg ggccgaggac accgccgtgt actactgcgc cagggaccgg   300
ggctccctgt actattgggg ccagggcacc ctggtgacag tgtcctcc                348
```

<210> SEQ ID NO 50
<211> LENGTH: 321
<212> TYPE: DNA
<213> ORGANISM: Homo sapiens

<400> SEQUENCE: 50

```
gccatccagc tgacccagtc cccctccagc ctgtctgcct ccgtgggcga cagagtgacc    60
atcacctgtc ggccctccca gggcatcaac tgggaactgg cctggtatca gcagaagccc   120
ggcaaggccc ccaagctgct gatctacgac gccagctccc tggaacaggg cgtgccctcc   180
agattctccg gctctggctc cggcaccgac ttcaccctga ccatctccag cctgcagccc   240
gaggacttcg ccacctacta ctgccagcag ttcaactcct accccctgac cttcggcgga   300
ggcaccaagg tggaaatcaa g                                              321
```

<210> SEQ ID NO 51
<211> LENGTH: 1338
<212> TYPE: DNA
<213> ORGANISM: Homo sapiens

<400> SEQUENCE: 51

```
gaggtgcagc tggtggaatc tggcggcgac ctggtgcagc ctggcggctc tctgagactg    60
tcttgcgccg cctccggctt caccttctcc agctactgga tgtcctgggt gcgacaggcc   120
cctggcaagg gactggaatg ggtggccaac atcaagcagg acggctccga gaagtactac   180
gtggactccg tgaagggccg gttcaccatc tcccgggaca cgccaagaa ctccctgtac    240 ctgcagatga actccctgcg ggccgaggac accgccgtgt actactgcgc cagggaccgg   300
```

```
ggctccctgt actattgggg ccagggcacc ctggtgacag tgtcctccgc ctccaccaag      360 gcccaagcg  tgttccccct ggcccccagc agcaagagca ccagcggcgg cacagccgcc      420
ctgggctgcc tggtgaagga ctacttcccc gagcccgtga ccgtgtcctg aacagcgga       480 gccctgacct ccggcgtgca caccttcccc gccgtgctgc agagcagcgg cctgtacagc      540
ctgagcagcg tggtgaccgt gcccagcagc agcctgggca cccagaccta catctgtaac     600
gtgaaccaca agcccagcaa caccaaggtg gacaagagag tggagcccaa gagctgtgac     660
aagacccaca cctgccccccc ctgcccagcc ccgagctgc tgggcggacc cagcgtgttc     720
ctgttccccc ccaagcccaa ggacaccctg atgatcagca gaacccccga ggtgacctgt     780
gtggtggtgg acgtgtccca cgaggaccca gaggtgaagt tcaactggta cgtggacggc     840
gtggaggtgc acaacgccaa gaccaagccc agagaggagc agtacaacag cacctacagg     900
gtggtgtccg tgctgaccgt gctgcaccag gactggctga acggcaagga gtacaagtgt     960
aaggtgtcca acaaggccct gccagcccca atcgaaaaga ccatcagcaa ggccaagggc     1020
cagccaagag agccccaggt gtacaccctg ccacccagca gggaggagat gaccaagaac     1080
caggtgtccc tgacctgtct ggtgaagggc ttctacccaa gcgacatcgc cgtggagtgg     1140
gagagcaacg gccagcccga gaacaactac aagaccaccc cccagtgct ggacagcgac     1200 ggcagcttct tcctgtacag caagctgacc gtggacaaga gcagatggca gcagggcaac     1260
gtgttcagct gctccgtgat gcacgaggcc ctgcacaacc actacaccca aagagcctg     1320 agcctgtccc caggcaag                                                    1338

<210> SEQ ID NO 52
<211> LENGTH: 642
<212> TYPE: DNA
<213> ORGANISM: Homo sapiens

<400> SEQUENCE: 52
gccatccagc tgacccagtc cccctccagc ctgtctgcct ccgtgggcga cagagtgacc       60
atcacctgtc ggccctccca gggcatcaac tgggaactgg cctggtatca gcagaagccc      120
ggcaaggccc ccaagctgct gatctacgac gccagctccc tggaacaggg cgtgccctcc      180
agattctccg gctctggctc cggcaccgac ttcaccctga ccatctccag cctgcagccc      240
gaggacttcg ccacctacta ctgccagcag ttcaactcct acccctgac cttcggcgga      300 ggcaccaagg tggaaatcaa gcgtacggtg gccgctccca gcgtgttcat cttcccccca     360
agcgacgagc agctgaagag cggcaccgcc agcgtggtgt gtctgctgaa caacttctac      420
cccagggagg ccaaggtgca gtggaaggtg gacaacgccc tgcagagcgg caacagccag     480
gagagcgtca ccgagcagga cagcaaggac tccacctaca gcctgagcag cacccctgacc    540 ctgagcaagg ccgactacga gaagcacaag gtgtacgcct gtgaggtgac ccaccagggc     600
ctgtccagcc ccgtgaccaa gagcttcaac aggggcgagt gc                          642

<210> SEQ ID NO 53
<211> LENGTH: 107
<212> TYPE: PRT
<213> ORGANISM: Homo sapiens

<400> SEQUENCE: 53

Ala Ile Gln Leu Thr Gln Ser Pro Ser Ser Leu Ser Ala Ser Val Gly
1               5                   10                  15

Asp Arg Val Thr Ile Thr Cys Arg Pro Ser Gln Gly Ile Asn Trp Glu
```

```
            20                  25                  30
Leu Ala Trp Tyr Gln Gln Lys Pro Gly Lys Ala Pro Lys Leu Leu Ile
        35                  40                  45

Tyr Asp Ala Ser Ser Leu Glu Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
                100                 105
```

<210> SEQ ID NO 54
<211> LENGTH: 214
<212> TYPE: PRT
<213> ORGANISM: Homo sapiens

<400> SEQUENCE: 54

```
Ala Ile Gln Leu Thr Gln Ser Pro Ser Ser Leu Ser Ala Ser Val Gly
 1               5                  10                  15

Asp Arg Val Thr Ile Thr Cys Arg Pro Ser Gln Gly Ile Asn Trp Glu
                20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Asn Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 321
<212> TYPE: DNA
<213> ORGANISM: Homo sapiens

<400> SEQUENCE: 55

```
gccatccagc tgacccagag ccccagcagc ctgagcgcca gcgtgggcga cagagtgacc      60
atcacctgtc ggcccagcca gggcatcaac tgggagctgg cctggtatca gcagaagcct     120
```

```
ggcaaggccc ccaagctgct gatctacgac gccagctccc tggaaaacgg cgtgcccagc      180
cggttcagcg gcagcggatc cggcaccgac ttcaccctga ccatcagctc cctgcagccc      240
gaggacttcg ccacctacta ctgccagcag ttcaacagct accccctgac cttcggcgga      300
ggcaccaagg tggaaatcaa g                                                 321
```

<210> SEQ ID NO 56
<211> LENGTH: 642
<212> TYPE: DNA
<213> ORGANISM: Homo sapiens

<400> SEQUENCE: 56

```
gccatccagc tgacccagag ccccagcagc ctgagcgcca gcgtgggcga cagagtgacc      60
atcacctgtc ggcccagcca gggcatcaac tgggagctgg cctggtatca gcagaagcct      120
ggcaaggccc ccaagctgct gatctacgac gccagctccc tggaaaacgg cgtgcccagc      180
cggttcagcg gcagcggatc cggcaccgac ttcaccctga ccatcagctc cctgcagccc      240
gaggacttcg ccacctacta ctgccagcag ttcaacagct accccctgac cttcggcgga      300
ggcaccaagg tggaaatcaa gcgtacggtg gccgctccca gcgtgttcat cttccccccc      360
agcgacgagc agctgaagag cggcaccgcc agcgtggtgt gcctgctgaa caacttctac      420
ccccgggagg ccaaggtgca gtggaaggtg gacaacgccc tgcagagcgg caacagccag      480
gagagcgtca ccgagcagga cagcaaggac tccacctaca gcctgagcag caccctgacc      540
ctgagcaagg ccgactacga aagcataag gtgtacgcct gcgaggtgac ccaccagggc      600
ctgtccagcc ccgtgaccaa gagcttcaac aggggcgagt gc                         642
```

<210> SEQ ID NO 57
<211> LENGTH: 321
<212> TYPE: DNA
<213> ORGANISM: Homo sapiens

<400> SEQUENCE: 57

```
gctattcagc tgactcagtc acctagtagc ctgagcgcta gtgtgggcga tagagtgact      60
atcacctgta gacctagtca ggggattaac tgggagctgg cctggtatca gcagaagccc      120
ggcaaggccc ctaagctgct gatctacgac gctagtagtc tggaaaacgg cgtgccctct      180
aggtttagcg gctcaggctc aggcaccgac ttcaccctga ctattagtag cctgcagccc      240
gaggacttcg ctacctacta ctgtcagcag tttaactcct accccctgac cttcggcgga      300
ggcactaagg tggaaatcaa g                                                 321
```

<210> SEQ ID NO 58
<211> LENGTH: 642
<212> TYPE: DNA
<213> ORGANISM: Homo sapiens

<400> SEQUENCE: 58

```
gctattcagc tgactcagtc acctagtagc ctgagcgcta gtgtgggcga tagagtgact      60
atcacctgta gacctagtca ggggattaac tgggagctgg cctggtatca gcagaagccc      120
ggcaaggccc ctaagctgct gatctacgac gctagtagtc tggaaaacgg cgtgccctct      180
aggtttagcg gctcaggctc aggcaccgac ttcaccctga ctattagtag cctgcagccc      240
gaggacttcg ctacctacta ctgtcagcag tttaactcct accccctgac cttcggcgga      300
ggcactaagg tggaaatcaa gcgtacggtg gccgctccca gcgtgttcat cttccccccc      360
agcgacgagc agctgaagag cggcaccgcc agcgtggtgt gcctgctgaa caacttctac      420
```

```
ccccgggagg ccaaggtgca gtggaaggtg acaacgccc tgcagagcgg caacagccag      480
gagagcgtca ccgagcagga cagcaaggac tccacctaca gcctgagcag cacccctgacc    540 ctgagcaagg ccgactacga aagcataag gtgtacgcct gcgaggtgac ccaccagggc      600
ctgtccagcc ccgtgaccaa gagcttcaac aggggcgagt gc                        642
```

```
<210> SEQ ID NO 59
<211> LENGTH: 19
<212> TYPE: PRT
<213> ORGANISM: Artificial Sequence
<220> FEATURE:
<223> OTHER INFORMATION: Heavy chain leader sequence

<400> SEQUENCE: 59

Met Glu Phe Gly Leu Ser Trp Val Phe Leu Val Ala Ile Leu Glu Gly
1               5                   10                  15

Val His Cys
```

```
<210> SEQ ID NO 60
<211> LENGTH: 22
<212> TYPE: PRT
<213> ORGANISM: Artificial sequence
<220> FEATURE:
<223> OTHER INFORMATION: Light chain leader sequence

<400> SEQUENCE: 60

Met Asp Met Arg Val Pro Ala Gln Leu Leu Gly Leu Leu Leu Leu Trp
1               5                   10                  15

Leu Pro Gly Ala Arg Cys
                20
```

```
<210> SEQ ID NO 61
<211> LENGTH: 57
<212> TYPE: DNA
<213> ORGANISM: Artificial sequence
<220> FEATURE:
<223> OTHER INFORMATION: Coding sequence for heavy chain leader sequence

<400> SEQUENCE: 61
atggaattcg gcctgagctg ggtgttcctg gtcgcgattc tggaaggcgt gcactgc         57
```

```
<210> SEQ ID NO 62
<211> LENGTH: 66
<212> TYPE: DNA
<213> ORGANISM: Artificial sequence
<220> FEATURE:
<223> OTHER INFORMATION: Coding sequence for light chain leader sequence

<400> SEQUENCE: 62
atggacatga gggtccccgc tcagctcctg gggcttctgc tgctctggct cccaggcgcc      60
agatgt                                                                66
```

```
<210> SEQ ID NO 63
<211> LENGTH: 19
<212> TYPE: PRT
<213> ORGANISM: Artificial sequence
<220> FEATURE:
<223> OTHER INFORMATION: Alternative heavy chain leader sequence

<400> SEQUENCE: 63

Met Ala Trp Val Trp Thr Leu Pro Phe Leu Met Ala Ala Ala Gln Ser
1               5                   10                  15
```

-continued

Val Gln Ala

<210> SEQ ID NO 64
<211> LENGTH: 20
<212> TYPE: PRT
<213> ORGANISM: Artificial sequence
<220> FEATURE:
<223> OTHER INFORMATION: Alternative light chain leader sequence

<400> SEQUENCE: 64

Met Ser Val Leu Thr Gln Val Leu Ala Leu Leu Leu Leu Trp Leu Thr
1               5                   10                  15

Gly Thr Arg Cys
            20

<210> SEQ ID NO 65
<211> LENGTH: 57
<212> TYPE: DNA
<213> ORGANISM: Artificial sequence
<220> FEATURE:
<223> OTHER INFORMATION: Coding sequence for alternative heavy chain
      leader sequence

<400> SEQUENCE: 65
atggcctggg tgtggaccct gcccttcctg atggccgctg ctcagtcagt gcaggcc        57

<210> SEQ ID NO 66
<211> LENGTH: 60
<212> TYPE: DNA
<213> ORGANISM: Artificial sequence
<220> FEATURE:
<223> OTHER INFORMATION: Coding sequence for alternative light chain
      leader sequence

<400> SEQUENCE: 66
atgagcgtgc tgactcaggt gctggccctg ctgctgctgt ggctgaccgg cacccgctgc     60

<210> SEQ ID NO 67
<211> LENGTH: 19
<212> TYPE: PRT
<213> ORGANISM: Artificial sequence
<220> FEATURE:
<223> OTHER INFORMATION: Second alternative heavy chain leader sequence

<400> SEQUENCE: 67

Met Glu Trp Ser Trp Val Phe Leu Phe Phe Leu Ser Val Thr Thr Gly
1               5                   10                  15

Val His Ser

<210> SEQ ID NO 68
<211> LENGTH: 20
<212> TYPE: PRT
<213> ORGANISM: Artificial sequence
<220> FEATURE:
<223> OTHER INFORMATION: Second alternative light chain leader sequence

<400> SEQUENCE: 68

Met Ser Val Pro Thr Gln Val Leu Gly Leu Leu Leu Leu Trp Leu Thr
1               5                   10                  15

Asp Ala Arg Cys
            20

<210> SEQ ID NO 69
<211> LENGTH: 57
<212> TYPE: DNA

-continued

```
<213> ORGANISM: Artificial sequence
<220> FEATURE:
<223> OTHER INFORMATION: Coding sequence for second alternative heavy
      chain leader sequence

<400> SEQUENCE: 69
atggaatggt cctgggtgtt cctgttcttc ctgtccgtga ccacaggcgt gcactcc        57

<210> SEQ ID NO 70
<211> LENGTH: 60
<212> TYPE: DNA
<213> ORGANISM: Artificial sequence
<220> FEATURE:
<223> OTHER INFORMATION: Coding sequence for second alternative light
      chain leader sequence

<400> SEQUENCE: 70
atgtccgtgc ccacacaggt gctgggcctg ctgctgctgt ggctgaccga cgccagatgc    60

<210> SEQ ID NO 71
<211> LENGTH: 7
<212> TYPE: PRT
<213> ORGANISM: Homo sapiens
<220> FEATURE:
<221> NAME/KEY: Xaa
<222> LOCATION: (3)..(3)
<223> OTHER INFORMATION: Variable
<220> FEATURE:
<221> NAME/KEY: Xaa
<222> LOCATION: (5)..(7)
<223> OTHER INFORMATION: Variable

<400> SEQUENCE: 71

Ser Gln Xaa Ile Xaa Xaa Xaa
1               5

<210> SEQ ID NO 72
<211> LENGTH: 6
<212> TYPE: PRT
<213> ORGANISM: Homo sapiens
<220> FEATURE:
<221> NAME/KEY: Xaa
<222> LOCATION: (2)..(2)
<223> OTHER INFORMATION: Variable

<400> SEQUENCE: 72

Phe Xaa Ser Tyr Pro Leu
1               5

<210> SEQ ID NO 73
<211> LENGTH: 11
<212> TYPE: PRT
<213> ORGANISM: Homo sapiens
<220> FEATURE:
<221> NAME/KEY: Xaa
<222> LOCATION: (5)..(5)
<223> OTHER INFORMATION: Variable
<220> FEATURE:
<221> NAME/KEY: Xaa
<222> LOCATION: (7)..(9)
<223> OTHER INFORMATION: Variable

<400> SEQUENCE: 73

Arg Pro Ser Gln Xaa Ile Xaa Xaa Xaa Leu Ala
1               5                   10

<210> SEQ ID NO 74
<211> LENGTH: 7
<212> TYPE: PRT
```

<213> ORGANISM: Homo sapiens
<220> FEATURE:
<221> NAME/KEY: Xaa
<222> LOCATION: (7)..(7)
<223> OTHER INFORMATION: Variable

<400> SEQUENCE: 74

Asp Ala Ser Ser Leu Glu Xaa
1               5

<210> SEQ ID NO 75
<211> LENGTH: 9
<212> TYPE: PRT
<213> ORGANISM: Homo sapiens
<220> FEATURE:
<221> NAME/KEY: Xaa
<222> LOCATION: (4)..(4)
<223> OTHER INFORMATION: Variable

<400> SEQUENCE: 75

Gln Gln Phe Xaa Ser Tyr Pro Leu Thr
1               5

<210> SEQ ID NO 76
<211> LENGTH: 136
<212> TYPE: PRT
<213> ORGANISM: Homo sapiens

<400> SEQUENCE: 76

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala Glu Phe Arg His
    130                 135

<210> SEQ ID NO 77
<211> LENGTH: 134
<212> TYPE: PRT
<213> ORGANISM: Homo sapiens

<400> SEQUENCE: 77

Met Arg Lys Ile Pro Lys Val Gly His Thr Phe Phe Gln Lys Pro Glu
1               5                   10                  15

Ser Cys Pro Pro Val Pro Gly Gly Ser Met Lys Leu Asp Ile Gly Ile
            20                  25                  30

Ile Asn Glu Asn Gln Arg Val Ser Met Ser Arg Asn Ile Glu Ser Arg
        35                  40                  45

Ser Thr Ser Pro Trp Asn Tyr Thr Val Thr Trp Asp Pro Asn Arg Tyr

Pro Ser Glu Val Val Gln Ala Gln Cys Arg Asn Leu Gly Cys Ile Asn
65                  70                  75                  80

Ala Gln Gly Lys Glu Asp Ile Ser Met Asn Ser Val Pro Ile Gln Gln
                85                  90                  95

Glu Thr Leu Val Val Arg Arg Lys His Gln Gly Cys Ser Val Ser Phe
            100                 105                 110

Gln Leu Glu Lys Val Leu Val Thr Val Gly Cys Thr Cys Val Thr Pro
        115                 120                 125

Val Ile His His Val Gln
    130

<210> SEQ ID NO 78
<211> LENGTH: 138
<212> TYPE: PRT
<213> ORGANISM: Homo sapiens

<400> SEQUENCE: 78

Gly Pro Ile Val Lys Ala Gly Ile Thr Ile Pro Arg Asn Pro Gly Cys
1               5                   10                  15

Pro Asn Ser Glu Asp Lys Asn Phe Pro Arg Thr Val Met Val Asn Leu
            20                  25                  30

Asn Ile His Asn Arg Asn Thr Asn Thr Asn Pro Lys Arg Ser Ser Asp
        35                  40                  45

Tyr Tyr Asn Arg Ser Thr Ser Pro Trp Asn Leu His Arg Asn Glu Asp
    50                  55                  60

Pro Glu Arg Tyr Pro Ser Val Ile Trp Glu Ala Lys Cys Arg His Leu
65                  70                  75                  80

Gly Cys Ile Asn Ala Asp Gly Asn Val Asp Tyr His Met Asn Ser Val
                85                  90                  95

Pro Ile Gln Gln Glu Ile Leu Val Leu Arg Arg Glu Pro Pro His Cys
            100                 105                 110

Pro Asn Ser Phe Arg Leu Glu Lys Ile Leu Val Ser Val Gly Cys Thr
        115                 120                 125

Cys Val Thr Pro Ile Val His His Val Ala
    130                 135

<210> SEQ ID NO 79
<211> LENGTH: 132
<212> TYPE: PRT
<213> ORGANISM: Macaca fascicularis

<400> SEQUENCE: 79

Gly Ile Ala Ile Pro Arg Asn Ser Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Ser Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Val Lys Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Arg His Cys Pro Asn Ser Phe Arg Leu

```
                         100                 105                 110
Glu Lys Ile Leu Val Ser Val Gly Cys Thr Cys Val Thr Pro Ile Val
            115                 120                 125

His His Val Ala
        130

<210> SEQ ID NO 80
<211> LENGTH: 134
<212> TYPE: PRT
<213> ORGANISM: Macaca fascicularis

<400> SEQUENCE: 80

Met Arg Lys Ile Pro Lys Val Gly His Thr Phe Phe Gln Lys Pro Glu
1               5                   10                  15

Ser Cys Pro Pro Val Pro Glu Gly Ser Met Lys Leu Asp Thr Gly Ile
            20                  25                  30

Ile Asn Glu Asn Gln Arg Val Ser Met Ser Arg Asn Ile Glu Ser Arg
        35                  40                  45

Ser Thr Ser Pro Trp Asn Tyr Thr Val Thr Trp Asp Pro Asn Arg Tyr
    50                  55                  60

Pro Ser Glu Val Val Gln Ala Gln Cys Lys His Leu Gly Cys Ile Asn
65                  70                  75                  80

Ala Gln Gly Lys Glu Asp Ile Ser Met Asn Ser Val Pro Ile Gln Gln
                85                  90                  95

Glu Thr Leu Val Leu Arg Arg Lys His Gln Gly Cys Ser Val Ser Phe
            100                 105                 110

Gln Leu Glu Lys Val Leu Val Thr Val Gly Cys Thr Cys Val Thr Pro
        115                 120                 125

Val Val His His Val Gln
    130

<210> SEQ ID NO 81
<211> LENGTH: 132
<212> TYPE: PRT
<213> ORGANISM: Macaca mulatta

<400> SEQUENCE: 81

Gly Ile Ala Ile Pro Arg Asn Ser Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Ser Thr Ser Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Val Lys Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Arg His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130
```

-continued

```
<210> SEQ ID NO 82
<211> LENGTH: 127
<212> TYPE: PRT
<213> ORGANISM: Callithrix jacchus

<400> SEQUENCE: 82

Ser Pro Gln Asn Pro Gly Cys Pro Asn Ala Glu Asp Lys Asn Phe Pro
1               5                   10                  15

Arg Thr Val Met Val Asn Leu Asn Ile Arg Asn Arg Asn Thr Asn Ser
            20                  25                  30

Lys Arg Ala Ser Asp Tyr Tyr Asn Arg Ser Ser Pro Trp Asn Leu
        35                  40                  45

His Arg Asn Glu Asp Pro Glu Arg Tyr Pro Ser Val Ile Trp Glu Ala
    50                  55                  60

Lys Cys Arg His Leu Gly Cys Val Asp Ala Asp Gly Asn Val Asp Tyr
65                  70                  75                  80

His Met Asn Ser Val Pro Ile Gln Gln Glu Ile Leu Val Leu Arg Arg
                85                  90                  95

Glu Pro Arg His Cys Thr Asn Ser Phe Arg Leu Glu Lys Met Leu Val
            100                 105                 110

Ser Val Gly Cys Thr Cys Val Thr Pro Ile Val His Val Ala
        115                 120                 125

<210> SEQ ID NO 83
<211> LENGTH: 134
<212> TYPE: PRT
<213> ORGANISM: Mus musculus

<400> SEQUENCE: 83

Met Ala Ala Ile Ile Pro Gln Ser Ser Ala Cys Pro Asn Thr Glu Ala
1               5                   10                  15

Lys Asp Phe Leu Gln Asn Val Lys Val Asn Leu Lys Val Phe Asn Ser
            20                  25                  30

Leu Gly Ala Lys Val Ser Ser Arg Arg Pro Ser Asp Tyr Leu Asn Arg
        35                  40                  45

Ser Thr Ser Pro Trp Thr Leu His Arg Asn Glu Asp Pro Asp Arg Tyr
    50                  55                  60

Pro Ser Val Ile Trp Glu Ala Gln Cys Arg His Gln Arg Cys Val Asn
65                  70                  75                  80

Ala Glu Gly Lys Leu Asp His His Met Asn Ser Val Leu Ile Gln Gln
                85                  90                  95

Glu Ile Leu Val Leu Lys Arg Glu Pro Glu Ser Cys Pro Phe Thr Phe
            100                 105                 110

Arg Val Glu Lys Met Leu Val Gly Val Gly Cys Thr Cys Val Ala Ser
        115                 120                 125

Ile Val Arg Gln Ala Ala
    130

<210> SEQ ID NO 84
<211> LENGTH: 141
<212> TYPE: PRT
<213> ORGANISM: Mus musculus

<400> SEQUENCE: 84

Ala Pro Glu Pro Glu Phe Arg His Arg Lys Asn Pro Lys Ala Gly Val
1               5                   10                  15

Pro Ala Leu Gln Lys Ala Gly Asn Cys Pro Pro Leu Glu Asp Asn Thr
            20                  25                  30
```

Val Arg Val Asp Ile Arg Ile Phe Asn Gln Asn Gln Gly Ile Ser Val
    35                  40                  45

Pro Arg Glu Phe Gln Asn Arg Ser Ser Ser Pro Trp Asp Tyr Asn Ile
 50                  55                  60

Thr Arg Asp Pro His Arg Phe Pro Ser Glu Ile Ala Glu Ala Gln Cys
 65                  70                  75                  80

Arg His Ser Gly Cys Ile Asn Ala Gln Gly Gln Glu Asp Ser Thr Met
                 85                  90                  95

Asn Ser Val Ala Ile Gln Gln Glu Ile Leu Val Leu Arg Arg Glu Pro
            100                 105                 110

Gln Gly Cys Ser Asn Ser Phe Arg Leu Glu Lys Met Leu Leu Lys Val
            115                 120                 125

Gly Cys Thr Cys Val Lys Pro Ile Val His Gln Ala Ala
        130                 135                 140

<210> SEQ ID NO 85
<211> LENGTH: 134
<212> TYPE: PRT
<213> ORGANISM: Rattus norvegicus

<400> SEQUENCE: 85

Met Ala Val Leu Ile Pro Gln Ser Ser Val Cys Pro Asn Ala Glu Ala
1               5                   10                  15

Asn Asn Phe Leu Gln Asn Val Lys Val Asn Leu Lys Val Ile Asn Ser
            20                  25                  30

Leu Ser Ser Lys Ala Ser Ser Arg Arg Pro Ser Asp Tyr Leu Asn Arg
        35                  40                  45

Ser Thr Ser Pro Trp Thr Leu Ser Arg Asn Glu Asp Pro Asp Arg Tyr
 50                  55                  60

Pro Ser Val Ile Trp Glu Ala Gln Cys Arg His Gln Arg Cys Val Asn
 65                  70                  75                  80

Ala Glu Gly Lys Leu Asp His His Met Asn Ser Val Leu Ile Gln Gln
                 85                  90                  95

Glu Ile Leu Val Leu Lys Arg Glu Pro Glu Lys Cys Pro Phe Thr Phe
            100                 105                 110

Arg Val Glu Lys Met Leu Val Gly Val Gly Cys Thr Cys Val Ser Ser
            115                 120                 125

Ile Val Arg His Ala Ser
        130

<210> SEQ ID NO 86
<211> LENGTH: 295
<212> TYPE: PRT
<213> ORGANISM: Homo sapiens

<400> SEQUENCE: 86

Asn Cys Thr Val Lys Asn Ser Thr Cys Leu Asp Asp Ser Trp Ile His
1               5                   10                  15

Pro Arg Asn Leu Thr Pro Ser Ser Pro Lys Asp Leu Gln Ile Gln Leu
            20                  25                  30

His Phe Ala His Thr Gln Gln Gly Asp Leu Phe Pro Val Ala His Ile
        35                  40                  45

Glu Trp Thr Leu Gln Thr Asp Ala Ser Ile Leu Tyr Leu Glu Gly Ala
 50                  55                  60

Glu Leu Ser Val Leu Gln Leu Asn Thr Asn Glu Arg Leu Cys Val Arg
 65                  70                  75                  80

-continued

```
Phe Glu Phe Leu Ser Lys Leu Arg His His His Arg Arg Trp Arg Phe
                85              90                  95
Thr Phe Ser His Phe Val Val Asp Pro Asp Gln Glu Tyr Glu Val Thr
            100             105                 110
Val His His Leu Pro Lys Pro Ile Pro Asp Gly Asp Pro Asn His Gln
        115             120                 125
Ser Lys Asn Phe Leu Val Pro Asp Cys Glu His Ala Arg Met Lys Val
    130             135                 140
Thr Thr Pro Cys Met Ser Ser Gly Ser Leu Trp Asp Pro Asn Ile Thr
145             150             155                 160
Val Glu Thr Leu Glu Ala His Gln Leu Arg Val Ser Phe Thr Leu Trp
            165             170                 175
Asn Glu Ser Thr His Tyr Gln Ile Leu Leu Thr Ser Phe Pro His Met
            180             185                 190
Glu Asn His Ser Cys Phe Glu His Met His His Ile Pro Ala Pro Arg
            195             200                 205
Pro Glu Glu Phe His Gln Arg Ser Asn Val Thr Leu Thr Leu Arg Asn
    210             215                 220
Leu Lys Gly Cys Cys Arg His Gln Val Gln Ile Gln Pro Phe Phe Ser
225             230             235                 240
Ser Cys Leu Asn Asp Cys Leu Arg His Ser Ala Thr Val Ser Cys Pro
            245             250                 255
Glu Met Pro Asp Thr Pro Glu Pro Ile Pro Asp Tyr Met Pro Leu Trp
            260             265                 270
Glu Phe Arg His Asp Ser Gly Gly Leu Asn Asp Ile Phe Glu Ala
            275             280                 285
Gln Lys Ile Glu Trp His Glu
    290             295
```

ANTI-IL-17A ANTIBODIES AND THEIR USES

RELATED APPLICATIONS

The present disclosure claims priority to U.S. 61/762,406, filed 8 Feb. 2013, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Apr. 25, 2014, is named Sequence listing_ST25.txt and is 63 KB in size.

FIELD OF THE INVENTION

The present disclosure relates to antibodies and proteins comprising an antigen-binding portion thereof that specifically bind to IL-17A. The disclosure more specifically relates to specific antibodies and proteins that inhibit the effects of IL-17A and are capable of inhibiting IL-17A-induced activity, as well as compositions and methods of use for said antibodies and proteins, e.g. to treat pathological disorders that can be treated by inhibition of IL-17A signaling, for example autoimmune and inflammatory disorders such as rheumatoid arthritis, psoriasis, systemic lupus erythematosus (SLE), lupus nephritis, multiple sclerosis, or chronic obstructive pulmonary disease, asthma or cystic fibrosis.

BACKGROUND OF THE INVENTION

Interleukin-17A (IL-17A also sometimes called IL-17) is the central lymphokine produced by a newly defined subset of inflammatory T cells, the Th17 cells. In several animal models, these cells are pivotal for various autoimmune and inflammatory processes. Increased levels of IL-17A have been associated with uveitis (Ambadi-Obi, et al 2007, Nature Med; 13:711-718), rheumatoid arthritis (RA), psoriasis, airway inflammation, chronic obstructive pulmonary disease (COPD), inflammatory bowel disease (Crohn's disease and ulcerative colitis), allograft rejection, cancer, intra-peritoneal abscesses and adhesions, and multiple sclerosis (Weaver, et al 2007, Annu Rev Immunol; 25:821-852; Witowski et al 2004, Cell Mol Life Sci; 61:567-579). Th17 cells can rapidly initiate an inflammatory response that is dominated by neutrophils (Miossec, et al 2009, NEJM; 361:888-98). IL-17A was originally identified as a transcript from a rodent T-cell hybridoma. It is the founding member of a group of cytokines called the IL-17 family. Known as CTLA8 in rodents, IL-17A shows high homology to viral IL-17A encoded by an open reading frame of the T-lymphotropic rhadinovirus herpesvirus saimiri (Rouvier E, et al 1993, J. Immunol. 150: 5445-56).

IL-17A is a cytokine that acts as a potent mediator in delayed-type reactions by increasing chemokine production in various tissues to recruit monocytes and neutrophils to the site of inflammation, similar to interferon gamma. The IL-17 family functions in the role of proinflammatory cytokines that respond to the invasion of the immune system by extracellular pathogens and induces destruction of the pathogen's cellular matrix. IL-17A acts synergistically with tumor necrosis factor and interleukin-1 (Miossec P, et al 2009, N. Engl. J. Med. 361:888-98).

To elicit its functions, IL-17A binds to a type I cell surface receptor called IL-17R of which there are at least two variants, IL-17RA and IL-17RC (Pappu R, et al 2012, Trends Immunol.; 33:343-9). IL-17RA binds IL-17A, IL-17AF and IL-17F and is expressed in multiple tissues: vascular endothelial cells, peripheral T cells, B cell lineages, fibroblast, lung, myelomonocytic cells, and marrow stromal cells (Kolls J K, Lindén A 2004, Immunity 21:467-76; Kawaguchi M, et al 2004, J. Allergy Clin. Immunol. 114:1265-73; Moseley T A, et al 2003, Cytokine Growth Factor Rev. 14:155-74).

In addition to IL-17A, members of the IL-17 family include IL-17B, IL-17C, IL-17D, IL-17E (also called IL-25), and IL-17F. All members of the IL-17 family have a similar protein structure, with four highly conserved cysteine residues critical to their 3-dimensional shape. Phylogenetic analysis reveals that among IL-17 family members, the IL-17F isoforms 1 and 2 (ML-1) have the highest homology to IL-17A (sharing 55 and 40% amino acid identity to IL-17A respectively), followed by IL-17B (29%), IL-17D (25%), IL-17C (23%), and IL-17E being most distantly related to IL-17A (17%). These cytokines are all well conserved in mammals, with as much as 62-88% of amino acids conserved between the human and mouse homologs (Kolls J K, Lindén A 2004, Immunity 21:467-76).

IL-17A is a 155-amino acid protein that is a disulfide-linked, homodimeric, secreted glycoprotein with a molecular mass of 35 kDa (Kolls J K, Lindén A 2004, Immunity 21:467-76). The structure of IL-17A consists of a signal peptide followed by the amino acid region characteristic of the IL-17 family. An N-linked glycosylation site on the protein was first identified after purification of the protein revealed two bands in standard SDS-PAGE analysis, one at 15 kDa and another at 20 kDa. Comparison of different members of the IL-17 family revealed four conserved cysteines that form two disulfide bonds (Yao Z, et al 1995, J. Immunol. 155:5483-6). IL-17 is unique in that it bears no resemblance to other known interleukins. Furthermore, IL-17 bears no resemblance to any other known proteins or structural domains (Kolls J K, Lindén A 2004, Immunity 21:467-76). Generally, other members of the IL-17 family such as IL-17F form homodimers (like IL-17A).

IL-17A is also known to form a heterodimer with IL-17F under certain circumstances. Heterodimeric IL-17AF is also produced by Th17 cells following stimulation by IL-23.

IL-17AF is thought to signal through the IL-17RA and IL-17RC receptors like IL-17A and IL-17F. The biological functions of IL-17AF are similar to those of IL-17A and IL-17F. Stimulation of target cells by IL-17AF induces the production of a variety of chemokines, in addition to airway neutrophilia in appropriate circumstances. IL-17AF is considered to be less potent in these activities than homodimeric IL-17A, but more potent than homodimeric IL-17F. For example, if the potency of IL-17A is 1, then the relative potency of IL-17AF is about $1/10$ of that of IL-17A and the relative potency of IL-17F is about $1/100$ of that of IL-17A. Human and mouse IL-17AF both show activity on mouse cells. IL-17AF consists of a total of 271 amino acids and has a molecular weight of approximately 30.7 kDa (data from product description of Human IL-17AF Heterodimer from Shenandoah Biotechnology).

A number of relevant crystal structures have been published. These include the crystal structure for homodimeric IL-17F (Hymowitz et al 2001, EMBO J, 19:5332-5341). The crystal structure of IL-17F in complex with the receptor IL-17RA has also been published (Ely et al., 2009 Nature Immunology 10:1245-1251). In addition at least one crystal structure of IL-17A in complex with the Fab fragment of an antibody has been published (Gerhardt et al., 2009 Journal of Molecular Biology, 5:905-921).

Several inflammatory and autoimmune diseases including psoriasis are linked to exacerbated Th1 and/or Th17 responses. Many of them are currently treated either with general immunosuppressants or very selectively acting biologicals such as anti-TNF-α antibodies that are not effective in all patients. These were found to increase the risk for infections and to become ineffective after repeated treatment. Therefore, there is an unmet medical need for treatments with increased safety profiles and simultaneous capacity to induce long-term remission or cure of the disease.

Numerous immune regulatory functions have been reported for the IL-17 family of cytokines, it is presumed due to their induction of many immune signaling molecules. The most notable role of IL-17A is its involvement in inducing and mediating proinflammatory responses. IL-17A is also associated with allergic responses. IL-17 induces the production of many other cytokines (such as IL-6, G-CSF, GM-CSF, IL-16, TGF-β, TNF-α), chemokines (including IL-8, GRO-α, and MCP-1), and prostaglandins (e.g., PGE2) from many cell types (fibroblasts, endothelial cells, epithelial cells, keratinocytes, and macrophages). The release of cytokines causes many functions, such as airway remodeling, a characteristic of IL-17A responses. The increased expression of chemokines attracts other cells including neutrophils but not eosinophils. IL-17 function is also essential to a subset of CD4+ T-cells called T helper 17 (Th17) cells. As a result of these roles, the IL-17 family has been linked to many immune/autoimmune related diseases including rheumatoid arthritis, asthma, lupus, allograft rejection and anti-tumor immunity (Aggarwal S, Gurney A L 2002, J. Leukoc. Biol. 71:1-8). Additionally, links have been drawn to further conditions such as osteoarthritis, septicemia, septic or endotoxic shock, allergic reactions, bone loss, psoriasis, ischemia, systemic sclerosis, fibrosis, and stroke.

Thus, there is a need for specific antibodies that antagonize the effects of IL-17A and are capable of inhibiting IL-17A induced activity, and especially compositions and methods of use for said antibodies to treat pathological disorders that can be treated by inhibition of IL-17A signaling.

SUMMARY OF THE INVENTION

Therefore, in one aspect, the disclosure provides an isolated antibody or protein comprising an antigen-binding portion of an antibody, comprising CDR amino acid sequences having at least 95% identity to those encoded by SEQ ID NO: 7, SEQ ID NO: 8 and SEQ ID NO: 3, and CDR amino acid sequence having at least 64% identity to those encoded by SEQ ID NO: 42, SEQ ID NO: 23 and SEQ ID NO: 11, and wherein said antibody or molecule specifically binds to homodimeric IL-17A and heterodimeric IL-17AF, but does not specifically bind to homodimeric IL-17F.

In one embodiment, the IL-17A, IL-17AF or IL-17F are selected from one or more, such as two or three or more, of cynomolgus monkey, rhesus macaque monkey, marmoset monkey, rat, mouse or human. In one specific embodiment, the IL-17A, IL-17AF or IL-17F is from human. In one specific embodiment, the IL-17A, IL-17AF or IL-17F is from human and mouse. In one specific embodiment, the IL-17A, IL-17AF or IL-17F is from cynomolgus monkey, rhesus macaque monkey, marmoset monkey, rat, mouse and human.

In one specific embodiment, the isolated antibody or protein comprising an antigen-binding portion thereof of the disclosure, comprises an amino acid sequence having at least 95% identity to SEQ ID NO: 12, and an amino acid sequence having at least 90% identity to SEQ ID NO: 43. In one embodiment, the isolated antibody or comprises an amino acid sequence having at least 95% identity to SEQ ID NO: 14, and an amino acid sequence having at least 95% identity to SEQ ID NO: 44.

In one embodiment, the isolated antibody or protein comprising an antigen-binding portion thereof comprises a light chain variable region comprising a CDR1, a CDR2, and a CDR3 domain selected from the group consisting of a) a light chain CDR1 domain of SEQ ID NO: 73, wherein the first variable amino acid is selected from the group consisting of Gly (G) and Val (V); the second variable amino acid is selected from the group consisting of Tyr (Y), Asn (N) and Ile (I); the third variable amino acid is selected from the group consisting of Trp (W) and Ser (S); and the fourth variable amino acid is selected from the group consisting of Glu (E) and Ala (A); b) a light chain CDR2 domain of SEQ ID NO: 74, wherein the variable amino acid is selected from the group consisting of Asn (N) and Gln (Q); and c) a light chain CDR3 domain of SEQ ID NO: 75, wherein the variable amino acid is selected from the group consisting of Asn (N) and Asp (D).

In one embodiment, the isolated antibody or protein comprising an antigen-binding portion thereof comprises heavy chain CDRs comprising, in sequence, a) SEQ ID NO: 7, SEQ ID NO: 8 and SEQ ID NO: 3, and light chain CDRs comprising, in sequence, b) SEQ ID NO: 42, SEQ ID NO: 23 and SEQ ID NO: 11, c) SEQ ID NO: 42, SEQ ID NO: 10 and SEQ ID NO: 11, d) SEQ ID NO: 34, SEQ ID NO: 23 and SEQ ID NO: 11, e) SEQ ID NO: 22, SEQ ID NO: 23 and SEQ ID NO: 24, or f) SEQ ID NO: 9, SEQ ID NO: 10 and SEQ ID NO: 11.

In one specific embodiment, the isolated antibody or protein comprising an antigen-binding portion thereof comprises heavy chain CDRs, in sequence, SEQ ID NO: 7, SEQ ID NO: 8 and SEQ ID NO: 3 and light chain CDRs, in sequence, SEQ ID NO: 42, SEQ ID NO: 23 and SEQ ID NO: 11.

In another specific embodiment, the isolated antibody or protein comprising an antigen-binding portion thereof comprises heavy chain CDRs, in sequence, SEQ ID NO: 7, SEQ ID NO: 8 and SEQ ID NO: 3 and light chain CDRs, in sequence SEQ ID NO: 42, SEQ ID NO: 10 and SEQ ID NO: 11.

In another specific embodiment, the isolated antibody or protein comprising an antigen-binding portion thereof comprises heavy chain CDRs, in sequence, SEQ ID NO: 7, SEQ ID NO: 8 and SEQ ID NO: 3 and light chain CDRs, in sequence, SEQ ID NO: 34, SEQ ID NO: 23 and SEQ ID NO: 11.

In another specific embodiment, the isolated antibody or protein comprising an antigen-binding portion thereof comprises heavy chain CDRs, in sequence, SEQ ID NO: 7, SEQ ID NO: 8 and SEQ ID NO: 3 and light chain CDRs, in sequence, SEQ ID NO: 22, SEQ ID NO: 23 and SEQ ID NO: 24.

In another specific embodiment, the isolated antibody or protein comprising an antigen-binding portion thereof comprises heavy chain CDRs, in sequence, SEQ ID NO: 7, SEQ ID NO: 8 and SEQ ID NO: 3 and light chain CDRs, in sequence, SEQ ID NO: 9, SEQ ID NO: 10 and SEQ ID NO: 11.

In one embodiment, the isolated antibody or protein comprising an antigen-binding portion thereof comprises an immunoglobulin heavy chain comprising a) SEQ ID NO: 12, and an immunoglobulin light chain comprising b) SEQ ID NO: 43, c) SEQ ID NO: 53, d) SEQ ID NO: 35, e) SEQ ID NO: 25, or f) SEQ ID NO: 13.

In one specific embodiment, the isolated antibody or protein comprising an antigen-binding portion thereof comprises an immunoglobulin heavy chain according to SEQ ID NO: 12 and an immunoglobulin light chain according to SEQ ID NO: 43.

In one specific embodiment, the isolated antibody or protein comprising an antigen-binding portion thereof comprises an immunoglobulin heavy chain according to SEQ ID NO: 12 and an immunoglobulin light chain according to SEQ ID NO: 53.

In one specific embodiment, the isolated antibody or protein comprising an antigen-binding portion thereof comprises an immunoglobulin heavy chain according to SEQ ID NO: 12 and an immunoglobulin light chain according to SEQ ID NO: 35.

In one specific embodiment, the isolated antibody or protein comprising an antigen-binding portion thereof comprises an immunoglobulin heavy chain according to SEQ ID NO: 12 and an immunoglobulin light chain according to SEQ ID NO: 25.

In one specific embodiment, the isolated antibody or protein comprising an antigen-binding portion thereof comprises an immunoglobulin heavy chain according to SEQ ID NO: 12 and an immunoglobulin light chain according to SEQ ID NO: 13.

In one embodiment, the isolated antibody or protein comprising an antigen-binding portion thereof comprises an immunoglobulin heavy chain comprising a) SEQ ID NO: 14, and an immunoglobulin light chain comprising b) SEQ ID NO: 44, c) SEQ ID NO: 54, d) SEQ ID NO: 36, e) SEQ ID NO: 26, or f) SEQ ID NO: 15.

In one specific embodiment, the isolated antibody or protein comprising an antigen-binding portion thereof comprises an immunoglobulin heavy chain according to SEQ ID NO: 14, and an immunoglobulin light chain according to SEQ ID NO: 44.

In one specific embodiment, the isolated antibody or protein comprising an antigen-binding portion thereof comprises an immunoglobulin heavy chain according to SEQ ID NO: 14, and an immunoglobulin light chain according to SEQ ID NO: 54.

In one specific embodiment, the isolated antibody or protein comprising an antigen-binding portion thereof comprises an immunoglobulin heavy chain according to SEQ ID NO: 14, and an immunoglobulin light chain according to SEQ ID NO: 36.

In one specific embodiment, the isolated antibody or protein comprising an antigen-binding portion thereof comprises an immunoglobulin heavy chain according to SEQ ID NO: 14, and an immunoglobulin light chain according to SEQ ID NO: 26.

In one specific embodiment, the isolated antibody or protein comprising an antigen-binding portion thereof comprises an immunoglobulin heavy chain according to SEQ ID NO: 14, and an immunoglobulin light chain according to SEQ ID NO: 15.

In one aspect of the disclosure, an isolated antibody or protein comprising an antigen-binding portion thereof is provided, which binds to the same epitope as an isolated antibody or molecule according to specific embodiments of the disclosure.

In one embodiment, the isolated antibody or protein comprising an antigen-binding portion thereof binds to an IL-17A epitope, such as a human IL-17A epitope, which comprises Arg78, Glu80, and Trp90.

The IL-17A epitope may further comprise Tyr85 or Arg124.

In one embodiment, the IL-17A epitope, such as a human IL-17A epitope, further comprises one or more of Pro82, Ser87 or Val88.

In one aspect of the disclosure, an isolated antibody or protein comprising an antigen-binding portion thereof is provided, which comprises an antigen recognition surface having epitope recognition characteristics equivalent to an antibody or molecule according to specific embodiments.

In one aspect of the disclosure, an isolated antibody or protein comprising an antigen-binding portion thereof is provided which is cross-blocked from binding to IL-17A, such as human IL-17A, or IL-17AF, such as human IL-17AF, by at least one antibody or protein comprising an antigen-binding portion thereof according to specific embodiments.

In one embodiment, the antibody or protein comprising an antigen-binding portion thereof does not specifically bind to a) any one or more of human IL-17F homodimer, IL-17B homodimer, IL-17C homodimer, IL-17D homodimer, IL-17E homodimer, and/or b) any one or more of cynomolgus monkey IL-17F homodimer, mouse IL-17F homodimer, and/or c) any one or more of other human cytokines selected from the group consisting of IL-1, IL-3, IL-4, IL-6, IL-8, gIFN, TNF alpha, EGF, GMCSF, TGF beta 2, and/or d) any one or more of other mouse cytokines, selected from the group consisting of IL-1 b, IL-2, IL-4, IL-6, IL-12, IL18, IL23, IFN or TNF.

In one embodiment, the antibody or protein comprising an antigen-binding portion thereof binds to IL-17A, such as human IL-17A, so that the antibody or protein comprising an antigen-binding portion thereof inhibits or blocks binding between IL-17A and its receptor, and reduces or neutralizes IL-17A activity.

In one embodiment, the binding affinity of the antibody or protein comprising an antigen-binding portion thereof for human IL-17A is 100 nM or less, 10 nM or less, 1 nM or less, 100 pM or less, or 10 pM or less as measured by Biacore™. In a specific embodiment, the binding affinity of the antibody or protein comprising an antigen-binding portion thereof for human IL-17A is below 200 pM, or below 100 pM, as measured by Biacore™.

In one embodiment, the antibody or protein comprising an antigen-binding portion thereof is capable of inhibiting IL-6 secretion, or GRO-alpha secretion when assessed in vitro, preferably using cultured chondrocytes or fibroblasts.

In one embodiment, the antibody or protein comprising an antigen-binding portion thereof is capable of inhibiting knee swelling in an antigen induced arthritis experimental model in vivo, such as a rat AIA-model.

In one embodiment, the antibody or protein comprising an antigen-binding portion thereof is conjugated to a further active moiety.

The antibody or protein comprising an antigen-binding portion thereof may be monoclonal antibody or an antigen-binding portion thereof, preferably a chimeric, humanized, or human antibody or portion thereof.

In an aspect of the disclosure, a pharmaceutical composition is provided, comprising an antibody or protein comprising an antigen-binding portion thereof according to embodiments of the disclosure, in combination with one or more pharmaceutically acceptable excipient, diluent or carrier.

In an embodiment, the pharmaceutical composition comprises one or more additional active ingredients.

In one specific embodiment, said pharmaceutical composition is a lyophilisate. In another specific embodiment, the pharmaceutical composition is a liquid formulation comprising a therapeutically acceptable amount of an antibody or molecule of the disclosure, preferably prepared as a pre-filled syringe.

The disclosure further relates to the use of said antibody or protein comprising an antigen-binding portion thereof of the disclosure, in particular XAB1, XAB2, XAB3, XAB4 or XAB5 antibodies, for use as a medicament, more preferably, for the treatment of a pathological disorder that is mediated by IL-17A or that can be treated by inhibition of IL-17A signaling, or IL-6 or GRO-alpha secretion.

In one specific embodiment, the antibodies or proteins comprising an antigen-binding portion thereof of the disclosure may be used for the treatment of autoimmune and inflammatory disorders, such as arthritis, rheumatoid arthritis, psoriasis, chronic obstructive pulmonary disease, systemic lupus erythematosus (SLE), lupus nephritis, asthma, multiple sclerosis, or cystic fibrosis.

In one aspect of the disclosure, a use of said antibody or protein comprising an antigen-binding portion thereof of the disclosure, in particular XAB1, XAB2, XAB3, XAB4 or XAB5 antibodies, in the manufacture of a medicament for use in the treatment of a pathological disorder mediated by IL-17A or that can be treated by inhibiting IL-6 or GRO-alpha secretion is provided.

In one specific embodiment, the a pathological disorder mediated by IL-17A or that can be treated by inhibiting IL-6 or GRO-alpha secretion is an inflammatory disorder or condition, such as arthritis, rheumatoid arthritis, psoriasis, chronic obstructive pulmonary disease, systemic lupus erythematosus (SLE), lupus nephritis, asthma, multiple sclerosis or cystic fibrosis.

In one aspect of the disclosure, a method of treating a pathological disorder mediated by IL-17A, or that can be treated by inhibiting IL-6 or GRO-alpha secretion is provided, said method comprising administering an effective amount of an isolated antibody or molecule according to the disclosure, in particular XAB1, XAB2, XAB3, XAB4 or XAB5 antibodies, such that the condition is alleviated.

In an embodiment, the condition is an inflammatory disorder or condition, such as arthritis, rheumatoid arthritis, psoriasis, chronic obstructive pulmonary disease, systemic lupus erythematosus (SLE), lupus nephritis, asthma, multiple sclerosis or cystic fibrosis.

The disclosure also relates to the means for producing the antibodies or protein comprising an antigen-binding portion thereof of the disclosure. Such means include isolated nucleic acid molecules encoding at least the heavy and/or light variable region(s) of the antibody or protein of the disclosure or cloning expression vectors comprising such nucleic acids, in particular, for the recombinant production of an antibody or protein according to the disclosure, for example XAB1, XAB2, XAB3, XAB4 or XAB5, in a host cell. In a specific embodiment, such cloning or expression vector comprises at least one nucleic acid sequence selected from the group consisting of SEQ ID NO: 18, 31, 51, 19, 28, 32, 38, 40, 46, 48, 52, 56, and 58. In another embodiment, it comprises at least one of the following coding sequences of variable heavy and light chain sequences selected from the group consisting of SEQ ID NO: 16, 29, 49, 17, 27, 30, 37, 39, 45, 47, 50, 55, and 57, operatively linked to suitable promoter sequences, which are well known to a person skilled in the art.

In an embodiment, the nucleic acid molecule is a messenger RNA (mRNA),

The disclosure further relates to a host cell comprising one or more cloning or expression vectors as described above and to the process for the production of an antibody or protein comprising an antigen-binding portion thereof of the disclosure, in particular XAB1, XAB2, XAB3, XAB4 or XAB5, said process comprising culturing the host cell, purifying and recovering said antibody or protein.

Definitions

In order that the present disclosure may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34

(LCDR1), 50-56 (LCDR2), and 89-97 (LCDR3). Under Chothia the CDR amino acids in the VH are numbered 26-32 (HCDR1'), 52-56 (HCDR2'), and 95-102 (HCDR3'); and the amino acid residues in VL are numbered 26-32 (LCDR1'), 50-52 (LCDR2'), and 91-96 (LCDR3'). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

The term "antigen-binding portion" of an antibody (or simply "antigen portion"), as used herein, refers to full length or one or more fragments of an antibody, such as a protein, that retain the ability to specifically bind to an antigen (e.g., a portion of IL-17A). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al. 1989, Nature 341:544-546), which consists of a $V_H$ domain; and an isolated complementarity determining region (CDR), or any fusion proteins comprising such antigen-binding portion.

Accordingly, the term "antigen-binding portion" may also refer to the portions corresponding to the antibody of the disclosure that may be comprised within alternative frameworks or scaffolds such as camelid antibodies or 'non-antibody' molecules as described below.

Furthermore, although the two domains of the Fv fragment, $V_L$ and $V_H$, are coded for by separate genes, they can be joined, using recombinant methods, by a synthetic linker that enables them to be made as a single chain protein in which the $V_L$ and $V_H$ regions pair to form monovalent molecules (known as single chain Fv (scFv); see e.g., Bird et al. 1988, Science 242:423-426; and Huston et al. 1988, Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds to IL-17A, such as human IL-17A, is substantially free of antibodies that specifically bind to other antigens than IL-17A). An isolated antibody that specifically binds to IL-17A may, however, have cross-reactivity to other antigens, such as IL-17A molecules from other species, or IL-17A heterodimers, such as IL-17AF. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term IL-17A refers to human IL-17A as defined in SEQ ID NO: 76 or SEQ ID NO: 78 unless otherwise described. The term IL-17F refers to human IL-17F as defined in SEQ ID NO: 77 unless otherwise described. IL-17AF is a heterodimer of an IL-17A subunit and an IL-17F subunit, as will be appreciated by a person skilled in the art. Recombinant proteins, designated with the prefix "r", from different species were used in the assays described below. For example, recombinant human IL-17A is designated rhuIL-17. A person skilled in the art knows how to express such proteins using starting materials and standard protocols as known in the art. However, in order to aid the skilled artisan, unless otherwise stated, the following amino acid sequences may be used: cynomolgus monkey (cyno) IL-17A, SEQ ID NO: 79; cynoIL-17F, SEQ ID NO: 80; rhesus monkey (rhesus) IL-17A, SEQ ID NO: 81; marmoset monkey (marmoset) IL-17A, SEQ ID NO: 82; mouse (m) IL-17A, SEQ ID NO: 83; mIL-17F, SEQ ID NO: 84; rat IL-17A, SEQ ID NO: 85; human IL-17 receptor A (huIL-17RA), SEQ ID NO: 86. As is known to a person skilled in the art, the abovementioned sequences may vary slightly, i.e. due to originating from different population groups. In the examples, tool antibodies are also used e.g. for screening purposes. Such antibodies are standard antibodies and can be readily obtained by a person skilled in the art.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutant versions of human germline sequences or antibody containing consensus framework sequences derived from human framework sequences analysis, for example, as described in Knappik, et al. 2000, J Mol Biol 296:57-86).

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al. 1984, Proc. Natl. Acad. Sci. USA, 81:6851-6855; Morrison and Oi, 1988, Adv. Immunol., 44:65-92; Verhoeyen et al. 1988, Science, 239:1534-1536; Padlan 1991, Molec. Immun., 28:489-498; and Padlan 1994, Molec. Immun., 31:169-217. Other examples of human engineering technology include, but are not limited to Xoma technology disclosed in U.S. Pat. No. 5,766,886.

The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene sequence to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG, such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody or a protein that "specifically binds to IL-17A polypeptide" is intended to refer to an antibody or protein that binds to human IL-17A polypeptide with a $K_D$ of 100 nM or less, 10 nM or less, 1 nM or less, 100 pM or less, or 10 pM or less. An antibody that "cross-reacts with an antigen other than IL-17A" is intended to refer to an antibody that binds that antigen with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 μM or grater, or a $K_D$ of 10 μM or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore™ system, well known to a person skilled in the art and operated e.g. as described in the Examples.

The inhibition of the binding of IL-17 to its receptor may be conveniently tested in various assays including such assays are described hereinafter in the text. By the term "to the same extent" is meant that the reference and the equivalent molecules exhibit, on a statistical basis, essentially identical IL-17 inhibitory activity in one of the assays referred to herein (see Examples). For example, IL-17 binding molecules of the disclosure typically have a half maximal inhibitory concentration ($IC_{50}$), for the inhibition of human IL-17 on IL-6 production induced by human IL-17 in human dermal fibroblasts, which is within +/−$10^5$, i.e. below 10 nM, more preferably 9, 8, 7, 6, 5, 4, 3 or 2 nM of that of, preferably substantially the same as, the $IC_{50}$ of the respective reference molecule when assayed e.g. as described in the Examples. Alternatively, the assay used may be an assay of competitive inhibition of binding of IL-17 by soluble IL-17 receptors and the IL-17 binding molecules of the disclosure.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a $K_D$ of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can 10 vary for other antibody isotypes. For example, high affinity binding for an IgM isotype refers to an antibody having a $K_D$ of $10^{-7}$ M or less, or $10^{-8}$ M or less.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used herein, an antibody or protein that inhibits IL-17A binding to IL-17R is intended to refer to an antibody or protein that inhibits IL-17A binding to IL-17R with an $IC_{50}$ of 10 nM or less, preferably with an $IC_{50}$ of 1 nM or less, more preferably with an $IC_{50}$ of 100 pM, or less, as measured in an in vitro competitive binding assay. Such assay is described in more details in the examples below.

As used herein, the term "IL-17A antagonist" or "IL-17A blocking molecule" is intended to refer to an antibody or protein that inhibits IL-17A induced signaling activity through the IL-17R and thereby reduces or neutralizes IL-17A activity. This can be shown in a human cell assay such as the IL-17A dependent IL-6 or GRO-alpha production assay in human cells. Such assay is described in more detail in the Examples below. In some embodiments, the antibodies or proteins of the disclosure inhibit IL-17A dependent IL-6 or GRO-alpha production as measured in an in vitro human cell assay at an $IC_{50}$ of 10 nM or less, 1 nM or less, or 100 pM or less. Such an assay is described in more details in the Examples below. In some embodiments the antibodies or proteins of the disclosure inhibit antigen induced arthritis in in vivo assays in mice and rats. Such assays are described in the Examples in more detail below.

As used herein, the term "ADCC" or "antibody dependent cell cytotoxicity" activity refers to cell depleting activity. ADCC activity can be measured by standard ADCC assay, well known to a person skilled in the art.

As used herein, the term "selectivity" for an antibody or protein of the disclosure refers to an antibody or protein that binds to a certain target polypeptide, but not to closely related polypeptides. The phrases "an antibody recognizing an antigen" and "an antibody specific for an antigen" are used interchangeably herein with the term "an antibody which binds specifically to an antigen".

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. (See, U.S. Pat. No. 8,278,036 to Kariko et al., which discloses mRNA molecules with uridine replaced by pseudouridine, methods of synthesizing the same, and methods for the delivery of therapeutic proteins in vivo.) Methods for packaging mRNA can be used, for example, those disclosed in U.S. Pat. No. 8,278,036 to Kariko et al; and patent application WO2013/090186A1, to Moderna. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc. As used herein, the terms "cyno" or "cynomolgus" refer to the cynomolgus monkey (*Macaca fascicularis*). As used herein, the terms "rhesus" or "rhesus macaque" refer to the rhesus macaque monkey (*Macaca mulatta*). As used herein, the term "marmoset" refers to a marmoset monkey.

As used herein, the term "treating" or "treatment" of any disease or disorder (i.e., rheumatoid arthritis) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described herein.

As used herein, "selecting" and "selected" in reference to a patient is used to mean that a particular patient is specifically chosen from a larger group of patients due to the particular patient having a predetermined criterion. Similarly, "selectively treating a patient" refers to providing treatment to a patient that is specifically chosen from a larger group of patients due to the particular patient having a predetermined criteria. Similarly, "selectively administering" refers to administering a drug to a patient that is specifically chosen from a larger group of patients due to the particular patient having a predetermined criterion.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells, however optimized expression of these sequences in other eukaryotic cells is also envisioned herein. The amino acid sequences encoded by optimized nucleotide sequences are also referred to as optimized.

As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller 1988, Comput. Appl. Biosci., 4:11-17, which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch 1970, J. Mol, Biol. 48:444-453 algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

The terms "cross-block", "cross-blocked", "cross-blocking" are used interchangeably herein to mean the ability of an antibody or other binding agent to interfere with the binding of other antibodies or binding agents to IL-17A in a standard competitive binding assay.

The ability or extent to which an antibody or other binding agent, such as a protein comprising an antigen-binding portion of an antibody, is able to interfere with the binding of another antibody or binding molecule to IL-17A, and therefore whether it can be said to cross-block according to the disclosure, can be determined using standard competition binding assays. One suitable assay involves the use of the Biacore™ technology (e.g. by using the Biacore™ 3000 instrument (Biacore™, Uppsala, Sweden)), which can measure the extent of interactions using surface plasmon resonance technology. Another assay for measuring cross-blocking uses an ELISA-based approach. Further details on these methods are given in the Examples.

For example, the antibodies exemplified herein (i.e. XAB1, XAB2, XAB3, XAB4 and XAB5) and proteins comprising an antigen-binding portion thereof will all "cross-block" one another. All of these antibodies target the same epitope on IL-17A. Other cross-blocking antibodies would be anticipated to bind to the same, or a related, epitope.

According to the disclosure, a cross-blocking antibody or other binding agent, such as a protein comprising an antigen-binding portion of an antibody, according to the disclosure binds to IL-17A in the described Biacore™ cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination An antibody is defined as cross-blocking in the ELISA assay as described in the Examples, if the solution phase anti-IL-17A antibody is able to cause a reduction of between 60% and 100%, specifically between 70% and 100%, and more specifically between 80% and 100%, of the IL-17A detection signal (i.e. the amount IL-17A bound by the coated antibody) as compared to the IL-17A detection signal obtained in the absence of the solution phase anti-IL-17A antibody (i.e. the positive control wells).

DETAILED DESCRIPTION OF THE INVENTION

The present disclosure is based, in part, on the discovery of antibody molecules that specifically bind to homodimeric IL-17A and heterodimeric IL-17AF, but do not specifically bind to homodimeric IL-17F. The disclosure relates to both full IgG format antibodies as well as proteins comprising an antigen-binding portion thereof, which will be further described below.

Accordingly, the present disclosure provides antibodies as well as proteins comprising an antigen-binding portion thereof with binding capabilities that are surprisingly similar for several species, such as selected from one or more of cynomolgus, rhesus macaque, marmoset, rat, mouse or human, as well as pharmaceutical compositions, production methods, and methods of use of such antibodies and compositions.

Recombinant Antibodies

Antibodies of the disclosure include the human recombinant antibody XAB1 and antibody derivates XAB2, XAB3, XAB4 and XAB5, which were derived, isolated and structurally characterized by their full length heavy and light chain amino acid sequences as described in Table 1 below.

TABLE 1

Full length heavy and light chain amino acid sequences of XAB1, XAB2, XAB3, XAB4 and XAB5.

| Antibody | Full Length Heavy Chain Amino acid sequence | Full Length Light Chain Amino acid sequence |
|---|---|---|
| XAB1 | SEQ ID NO: 14 | SEQ ID NO: 15 |
| XAB2 | SEQ ID NO: 14 | SEQ ID NO: 26 |
| XAB3 | SEQ ID NO: 14 | SEQ ID NO: 36 |
| XAB4 | SEQ ID NO: 14 | SEQ ID NO: 44 |
| XAB5 | SEQ ID NO: 14 | SEQ ID NO: 54 |
| SEQUENCE IDENTITY | 100% | 97% |

The corresponding variable regions, $V_H$ and $V_L$ amino acid sequences of such isolated antibodies XAB1, XAB2, XAB3, XAB4 and XAB5 of the disclosure are shown in Table 2 below.

TABLE 2

Variable heavy and light chain amino acid sequences of XAB1, XAB2, XAB3, XAB4 and XAB5.

| Antibody | Variable Heavy Chain Amino acid sequence | Variable Light Chain Amino acid sequence |
|---|---|---|
| XAB1 | SEQ ID NO: 12 | SEQ ID NO: 13 |
| XAB2 | SEQ ID NO: 12 | SEQ ID NO: 25 |

TABLE 2-continued

Variable heavy and light chain amino acid sequences of XAB1, XAB2, XAB3, XAB4 and XAB5.

| Antibody | Variable Heavy Chain Amino acid sequence | Variable Light Chain Amino acid sequence |
|---|---|---|
| XAB3 | SEQ ID NO: 12 | SEQ ID NO: 35 |
| XAB4 | SEQ ID NO: 12 | SEQ ID NO: 43 |
| XAB5 | SEQ ID NO: 12 | SEQ ID NO: 53 |
| SEQUENCE IDENTITY | 100% | 94% |

Other antibodies of the disclosure include those having amino acids that have been mutated by amino acid deletion, insertion or substitution, yet have at least 70%, 75%, 80%, 85%, 90%, 91%, 92%, 93%, 94%, 95%, 96%, 98%, 99% or 100% identity to the antibodies described above, in particular in the CDR regions depicted in the sequences described above. In some embodiments, the antibody of the disclosure is a mutant variant of any one of XAB1, XAB2, XAB3, XAB4 and XAB5, wherein said mutant variant antibody include mutant amino acid sequences wherein no more than 1, 2, 3, 4 or 5 amino acids have been mutated by amino acid deletion, insertion or substitution in the CDR regions when compared with the CDR regions depicted in the sequences described above.

Full length light and heavy chains nucleotide coding sequences of XAB1, XAB2, XAB3, XAB4 and XAB5 are shown in Table 3 below.

TABLE 3

Full length heavy and light chain DNA coding sequences.

| Antibody | Full Length Heavy Chain DNA coding sequence | Full Length Light Chain DNA coding sequence |
|---|---|---|
| XAB1 | SEQ ID NO: 18, SEQ ID NO: 31, SEQ ID NO: 51 | SEQ ID NO: 19 |
| XAB2 | SEQ ID NO: 18, SEQ ID NO: 31, SEQ ID NO: 51 | SEQ ID NO: 28, SEQ ID NO: 32 |
| XAB3 | SEQ ID NO: 18, SEQ ID NO: 31, SEQ ID NO: 51 | SEQ ID NO: 38, SEQ ID NO: 40 |
| XAB4 | SEQ ID NO: 18, SEQ ID NO: 31, SEQ ID NO: 51 | SEQ ID NO: 46, SEQ ID NO: 48, SEQ ID NO: 52 |
| XAB5 | SEQ ID NO: 18, SEQ ID NO: 31, SEQ ID NO: 51 | SEQ ID NO: 56, SEQ ID NO: 58 |

Variable light and heavy chains nucleotide coding sequences of XAB1, XAB2, XAB3, XAB4 and XAB5 are shown in Table 4 below.

TABLE 4

Variable heavy and light chain amino acid sequences DNA coding sequences.

| Antibody | Variable Heavy Chain DNA coding sequence | Variable Light Chain DNA coding sequence |
|---|---|---|
| XAB1 | SEQ ID NO: 16, SEQ ID NO: 29, SEQ ID NO: 49 | SEQ ID NO: 17 |
| XAB2 | SEQ ID NO: 16, SEQ ID NO: 29, SEQ ID NO: 49 | SEQ ID NO: 27, SEQ ID NO: 30 |

TABLE 4-continued

Variable heavy and light chain amino acid sequences DNA coding sequences.

| Antibody | Variable Heavy Chain DNA coding sequence | Variable Light Chain DNA coding sequence |
|---|---|---|
| XAB3 | SEQ ID NO: 16, SEQ ID NO: 29, SEQ ID NO: 49 | SEQ ID NO: 37, SEQ ID NO: 39 |
| XAB4 | SEQ ID NO: 16, SEQ ID NO: 29, SEQ ID NO: 49 | SEQ ID NO: 45, SEQ ID NO: 47, SEQ ID NO: 50 |
| XAB5 | SEQ ID NO: 16, SEQ ID NO: 29, SEQ ID NO: 49 | SEQ ID NO: 55, SEQ ID NO: 57 |

Other nucleic acids encoding antibodies of the disclosure include nucleic acids that have been mutated by nucleotide deletion, insertion or substitution, yet have at least 60, 70, 80, 90, 95 or 100 percent identity to the CDR corresponding coding regions depicted in the sequences described above or in Table 5 and Table 6 below.

In some embodiments, it include variant nucleic acids wherein no more than 1, 2, 3, 4 or 5 nucleotides have been changed by nucleotide deletion, insertion or substitution in the CDR coding regions with the CDR coding regions depicted in the sequences described above or in Table 5 and Table 6 below.

For antibodies that bind to the same epitope, the $V_H$, $V_L$, full length light chain, and full length heavy chain sequences (nucleotide sequences and amino acid sequences) can be "mixed and matched" to create other anti-IL-17A binding molecules of the disclosure. IL-17A binding of such "mixed and matched" antibodies can be tested using the binding assays described above or other conventional binding assays (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the disclosure provides an isolated recombinant antibody or protein comprising an antigen-binding portion thereof having: a heavy chain variable region comprising an amino acid sequence selected from the group consisting of SEQ ID NO: 12 and a light chain variable region comprising an amino acid sequence selected from the group consisting of SEQ ID NO: 13, 25, 35, 43 and 53; wherein said heavy and light chain regions are selected such that the antibody specifically binds to IL-17A.

Examples of the amino acid sequences of the $V_H$ CDR1s (also called HCDR1 or HCDR1' depending of the CDR definition that is used), $V_H$ CDR2s (also called HCDR2 or HCDR2' depending of the CDR definition that is used), $V_H$ CDR3s (also called HCDR1 or HCDR1' depending of the CDR definition that is used), $V_L$ CDR1s (also called LCDR1 or LCDR1' depending of the CDR definition that is used), $V_L$ CDR2s (also called LCDR2 or LCDR2' depending of the CDR definition that is used), $V_L$ CDR3s (also called HCDR3 or HCDR3' depending of the CDR definition that is used) of some antibodies and proteins comprising an antigen-binding portion thereof according to the disclosure are shown in Table 5 and Table 6.

In Table 5, the CDR regions of some antibodies of the disclosure are delineated using the Kabat system (Kabat, E. A., et al. 1991, Sequences of Proteins of Immunological Interest, Fifth Edition, U.S. Department of Health and Human Services, NIH Publication No. 91-3242, see also Zhao & Lu 2009, Molecular Immunology 47:694-700)

For the ease of reading, when CDR regions are delineated according to Kabat definition, they are called hereafter HCDR1, HCDR2, HCDR3, LCDR1, LCDR2, LCDR3 respectively.

TABLE 5

CDR regions of XAB1, XAB2, XAB3, XAB4 and XAB5 according to Kabat definition.

| Original antibody | HCDR1 | HCDR2 | HCDR3 | LCDR1 | LCDR2 | LCDR3 |
|---|---|---|---|---|---|---|
| XAB1 | SEQ ID NO: 7 | SEQ ID NO: 8 | SEQ ID NO: 3 | SEQ ID NO: 9 | SEQ ID NO: 10 | SEQ ID NO: 11 |
| XAB2 | SEQ ID NO: 7 | SEQ ID NO: 8 | SEQ ID NO: 3 | SEQ ID NO: 22 | SEQ ID NO: 23 | SEQ ID NO: 24 |
| XAB3 | SEQ ID NO: 7 | SEQ ID NO: 8 | SEQ ID NO: 3 | SEQ ID NO: 34 | SEQ ID NO: 23 | SEQ ID NO: 11 |
| XAB4 | SEQ ID NO: 7 | SEQ ID NO: 8 | SEQ ID NO: 3 | SEQ ID NO: 42 | SEQ ID NO: 23 | SEQ ID NO: 11 |
| XAB5 | SEQ ID NO: 7 | SEQ ID NO: 8 | SEQ ID NO: 3 | SEQ ID NO: 42 | SEQ ID NO: 10 | SEQ ID NO: 11 |
| CONSENSUS | SEQ ID NO: 7 | SEQ ID NO: 8 | SEQ ID NO: 3 | SEQ ID NO: 73 | SEQ ID NO: 74 | SEQ ID NO: 75 |
| SEQUENCE IDENTITY | 100% | 100% | 100% | 64% | 86% | 89% |

The consensus sequences SEQ ID NO: 73, SEQ ID NO: 74 and SEQ ID NO: 75 comprise a number of variable amino acids, designated X. Based on sequence alignment of the sequences for XAB2 to XAB5, the four variable amino acids in SEQ ID NO: 73 can advantageously be selected according to the following: The first variable amino acid (X1) can be selected from the group consisting of Gly (G) and Val (V); the second variable amino acid (X2) can be selected from the group consisting of Tyr (Y), Asn (N) and Ile (I); the third variable amino acid (X3) can be selected from the group consisting of Trp (W) and Ser (S); and the fourth variable amino acid (X4) can be selected from the group consisting of Glu (E) and Ala (A). SEQ ID NO: 9 has a sequence identity of 91% compared to SEQ ID NO: 22 and a sequence identity of 73% compared to SEQ ID NO: 34 and SEQ ID NO: 42. SEQ ID NO: 22 has a sequence identity of 64% compared to SEQ ID NO: 34 and SEQ ID NO: 42. SEQ ID NO: 34 has a sequence identity of 91% compared to SEQ ID NO: 42.

Similarly, the one variable amino acid in SEQ ID NO: 74 can advantageously be selected according to the following: X1 can be selected from the group consisting of Asn (N) and Gln (Q). SEQ ID NO: 10 has a sequence identity of 86% compared to SEQ ID NO: 23.

The one variable amino acid in SEQ ID NO: 75 can advantageously be selected according to the following: X1 can be selected from the group consisting of Asn (N) and Asp (D). SEQ ID NO: 11 has a sequence identity of 89% compared to SEQ ID NO: 24.

In Table 6, the CDR regions of some antibodies of the disclosure are delineated using the Chothia system, Al-Lazikani et al. 1997, J. Mol. Biol. 273:927-948. For ease of reading, when the CDR regions are delineated according to Chothia definition, they are called hereafter HCDR1', HCDR2', HCDR3', LCDR1', LCDR2', LCDR3' respectively.

TABLE 6

CDR regions from XAB1, XAB2, XAB3, XAB4 and XAB5 according to Chothia definition.

| Original antibody | HCDR1' | HCDR2' | HCDR3' | LCDR1' | LCDR2' | LCDR3' |
|---|---|---|---|---|---|---|
| XAB1 | SEQ ID NO: 1 | SEQ ID NO: 2 | SEQ ID NO: 3 | SEQ ID NO: 4 | SEQ ID NO: 5 | SEQ ID NO: 6 |
| XAB2 | SEQ ID NO: 1 | SEQ ID NO: 2 | SEQ ID NO: 3 | SEQ ID NO: 20 | SEQ ID NO: 5 | SEQ ID NO: 21 |
| XAB3 | SEQ ID NO: 1 | SEQ ID NO: 2 | SEQ ID NO: 3 | SEQ ID NO: 33 | SEQ ID NO: 5 | SEQ ID NO: 6 |
| XAB4 | SEQ ID NO: 1 | SEQ ID NO: 2 | SEQ ID NO: 3 | SEQ ID NO: 41 | SEQ ID NO: 5 | SEQ ID NO: 6 |
| XAB5 | SEQ ID NO: 1 | SEQ ID NO: 2 | SEQ ID NO: 3 | SEQ ID NO: 41 | SEQ ID NO: 5 | SEQ ID NO: 6 |
| CONSENSUS | SEQ ID NO: 1 | SEQ ID NO: 2 | SEQ ID NO: 3 | SEQ ID NO: 71 | SEQ ID NO: 5 | SEQ ID NO: 72 |
| SEQUENCE IDENTITY | 100% | 100% | 100% | 43% | 100% | 83% |

The consensus sequences SEQ ID NO: 71 and SEQ ID NO: 72 comprise a number of variable amino acids, designated X. Based on sequence alignment of the sequences for XAB2 to XAB5, the four variable amino acids in SEQ ID NO: 71 can advantageously be selected according to the following: the first variable amino acid (X1) can be selected from the group consisting of Gly (G) and Val (V), the second variable amino acid (X2) can be selected from the group consisting of Tyr (Y), Asn (N) and Ile (I); the third variable amino acid (X3) can be selected from the group consisting of Trp (W) and Ser (S); and the fourth variable amino acid (X4) can be selected from the group consisting of Glu (E) and Ala (A). SEQ ID NO: 4 has a sequence identity of 86% compared to SEQ ID NO: 20 and a sequence identity of 57% compared to SEQ ID NO: 33 and SEQ ID NO: 41. SEQ ID NO: 20 has a sequence identity of 43% compared to SEQ ID NO: 33 and SEQ ID NO: 41. SEQ ID NO: 33 has a sequence identity of 86% compared to SEQ ID NO: 41.

Similarly, the one variable amino acid in SEQ ID NO: 72 can advantageously be selected according to the following: X1 can be selected from the group consisting of Asn (N) and Asp (D). SEQ ID NO: 6 has a sequence identity of 86% compared to SEQ ID NO: 21.

Given that each of these antibodies can bind to IL-17A and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and matched, each antibody containing a $V_H$ CDR1, 2 and 3 and a $V_L$ CDR1, 2 and 3 create other anti-IL-17A binding molecules of the disclosure). IL-17A binding of such "mixed and matched" antibodies can be tested using the binding assays described above and in the Examples or other conventional assays (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region(s) sequence(s) with structurally similar sequences from the CDR sequences shown herein for monoclonal antibodies of the present disclosure.

In one embodiment, an isolated recombinant antibody, or a protein comprising an antigen-binding portion thereof, has: a heavy chain variable region CDR1 according to SEQ ID NO: 7; a heavy chain variable region CDR2 according to SEQ ID NO: 8; a heavy chain variable region CDR3 according to SEQ ID NO: 3; a light chain variable region CDR1 comprising an amino acid sequence selected from the group consisting of SEQ ID NO: 9, 22, 34, 42, and 73, and preferably selected from the group consisting of selected from the group consisting of SEQ ID NO: 9, 22, 34, 42; a light chain variable region CDR2 comprising an amino acid sequence selected from the group consisting of SEQ ID NO: 10, 23, and 74, and preferably selected from the group consisting of selected from the group consisting of SEQ ID NO: 10 and 23; and a light chain variable region CDR3 comprising an amino acid sequence selected from the group consisting of SEQ ID NO: 11, 24, and 75 and preferably selected from the group consisting of selected from the group consisting of SEQ ID NO: 11 and 24; wherein said CDR regions are selected so that the antibody or protein of the disclosure specifically binds to IL-17A In another embodiment, an isolated recombinant antibody, or a protein comprising an antigen-binding portion thereof has: a heavy chain variable region HCDR1' according to SEQ ID NO: 1; a heavy chain variable region HCDR2' according to SEQ ID NO: 2; a heavy chain variable region HCDR3' according to SEQ ID NO: 3; a light chain variable region LCDR1' comprising an amino acid sequence selected from the group consisting of SEQ ID NO: 4, 20, 33, 41, and 71, and preferably selected from the group consisting of selected from the group consisting of SEQ ID NO: 4, 20, 33, 41; a light chain variable region LCDR2' according to SEQ ID NO: 5; and a light chain variable region LCDR3' comprising an amino acid sequence selected from the group consisting of SEQ ID NO: 6, 21, and 72, and preferably selected from the group consisting of selected from the group consisting of SEQ ID NO: 6 and 21; wherein said CDR regions are selected so that the antibody or protein of the disclosure specifically binds to IL-17A.

In certain embodiments, the antibody or protein comprising an antigen-binding portion thereof comprises either SEQ ID NO: 7, SEQ ID NO: 8 and SEQ ID NO: 3; SEQ ID NO: 12; or c) SEQ ID NO: 14.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

In the present disclosure, an epitope on IL-17A has been identified that is particularly preferred as a target for the binding of potentially therapeutic antibodies. This epitope is bound by XAB1, and the variant antibodies XAB2, XAB3, XAB4 and XAB5 which have been developed by modification of the sequence of XAB1. This epitope is found on the IL-17A sequence, between residues Arg 78 and Trp 90.

The epitope may be considered to comprise the following most preferred amino acid residues from within the IL-17A: Arg 78, Glu 80, Trp 90. In addition, the following amino acid residues are also preferred: Tyr 85, Arg 124. Other important amino acid residues are Pro 82, Ser 87, Val 88. Further contributing amino acid residues are Val 45*, Leu 49, Asp 81, Glu 83, Pro 86, Pro 130, Phe 133, Lys 137*, where amino acids marked with (*) designate residue contributed by the second IL-17A subunit of the homodimer IL-17A.

Antibodies that target this epitope on IL-17A have been shown to block the binding of IL-17A to its receptor to inhibit IL-17A mediated effects in vitro, and to reduce the severity of an experimental in vivo model of antigen induced arthritis. In addition, antibodies that bind to this epitope have unexpectedly been shown to inhibit the in vitro effects mediated by the IL-17AF heterodimer, and also to retain an unexpectedly high affinity for IL-17A and IL-17AF derived from mouse and other species variations of the target molecule.

Thus, this epitope is especially preferred since it is also unexpectedly preserved in an accessible format within the structure of the IL-17AF heterodimer. Accordingly, preferred antibodies of the disclosure will also bind to IL-17AF heterodimers. Without wishing to be bound by theory, it is anticipated that the structure of the IL-17AF heterodimer is sufficiently similar, to IL-17A, or that interaction with the antibodies of the disclosure renders it sufficiently similar to IL-17A, that binding may still occur.

This is unexpected because structural analyses based on the available structures for IL-17A, IL-17F and interactions between these molecules and antibodies or receptors that have been obtained by X-ray crystallography (published in the art and conducted by the inventors) in combination with in silico predictions, suggested that binding to, or cross-reactivity of the antibodies of the disclosure with IL-17AF would not necessarily occur. More specifically, the N-terminal region of the IL-17F monomeric subunit of the heterodimer was predicted to sterically hamper the binding of antibodies of the disclosure to the IL-17AF heterodimer. The expectation was thus that there would not be significant cross-reactivity for the antibodies with IL-17AF.

However, despite these predictions, we have determined that cross-binding to IL-17AF by the disclosed antibodies does occur. This may in fact be advantageous for a number of reasons. As discussed above, IL-17AF is also implicated as a pro-inflammatory cytokine and may be involved in many of the same pathological conditions or undesirable biological events as described or suspected for IL-17A. The antibodies of the disclosure may therefore be especially valuable therapeutically because they can target or interfere with both IL-17A and IL-17AF.

Moreover, the present inventors have demonstrated that this binding between the antibodies of the disclosure and IL-17AF also correlates to an inhibition of the biological activity of IL-17AF as observed in in vitro assays. Accordingly, the antibodies of the disclosure not only efficiently target and antagonize/neutralize the activity of IL-17A, but also IL-17AF activity as well.

A further unexpected consequence of the work conducted by the present inventors is as follows. The affinity maturation of the original 'parent' antibody XAB1 has also resulted in a set of antibodies retaining a high affinity, or an improved affinity for IL-17A variants derived from other species such as cynomolgus, rhesus macaque, marmoset, rat, or mouse.

This is unexpected because in striving to improve the affinity of the antibodies of the disclosure for human IL-17A it would not be expected to also improve the affinity of the resulting antibodies for species variants of IL-17A. In fact, the opposite might normally be expected. Efforts to improve antibody affinity for a specific species variant (i.e. human) of a target antigen would usually be expected to reduce affinity for other species variants of that antigen. The concept of the species variant (or homolog/paralog) recognizes a common ancestry for a given species, but accepts that divergence has taken place over the course of evolutionary history. Accordingly, even where there is a good degree of sequence conservation between variants of a particular molecule that have been identified in different species, it cannot be assumed that an improved affinity for one species variant will have an improvement on the affinity for another species variant. In fact, the divergence between the sequences for different species generally leads to the expectation that improvement in affinity for one variant will be more likely to lead to a reduction (or even abolishment) of the binding affinity for another species variant. The sequence identity between mouse and human IL-17A is only 62% (Moseley et al. 2003, Cytokine & Growth Factor Reviews 14:155-174).

However, in the present case this was not observed and the antibody variants generated by the inventors retained high affinity for IL-17A variants from other species.

This is useful because during the work necessary to develop a candidate antibody molecule as a useful therapeutic molecule a variety of tests and assays may be required to be carried out in other species or on cells, molecules or systems comprising components of, or derived from other species (such as cynomolgus, rhesus macaque, marmoset, rat, or mouse). This makes the antibodies of the disclosure are especially suitable for further development.

Accordingly, antibodies and proteins comprising an antigen-binding portion thereof as disclosed herein may share a range of desirable properties including, high affinity for IL-17A, cross-reactivity with IL-17A from other species such as mouse, rat, cynomolgus and marmoset, lack of cross-reactivity for other IL-17 isotypes such as IL-17F, lack of cross-reactivity for other cytokines (such as human or mouse cytokines), cross-reactivity with heterodimeric IL-17AF, the ability to block binding of IL-17A to its receptor such as IL-17RA, the ability to inhibit or neutralize IL-17A induced biological effects such as the stimulation of IL-6 or GRO-alpha secretion, and/or the ability to inhibit in vivo effects mediated by IL-17A (and/or IL-17AF) such as the swelling that is observed in antigen induced arthritis models.

The antibodies and proteins comprising an antigen-binding portion thereof as disclosed herein have also been shown to provide a slow elimination of the antibody-IL17A complex, a slow turnover of the ligand and a long duration of IL17A capture. Further advantageous features of these antibodies and proteins are provided in the detailed embodiments.

Homologous Antibodies

In yet another embodiment, an antibody or protein comprising an antigen-binding portion thereof as disclosed herein has full length heavy and light chain amino acid sequences; full length heavy and light chain nucleotide sequences, variable region heavy and light chain nucleotide sequences, or variable region heavy and light chain amino acid sequences, or all 6 CDR regions amino acid sequences or nucleotide coding sequences that are homologous to the amino acid or nucleotide sequences of the antibodies XAB1, XAB2, XAB3, XAB4 and XAB5 described above, in particular in Table 1, and wherein the antibodies or proteins of the disclosure retain the desired functional properties of the original XAB1, XAB2, XAB3, XAB4 and XAB5 antibodies.

Desired functional properties of the original XAB1, XAB2, XAB3, XAB4 and XAB5 antibodies may be selected from the group consisting of:

(i) binding affinity to IL-17A (specific binding to IL-17A), for example, a $K_D$ being 1 nM or less, 100 pM or less, or 10 pM or less, as measured in the Biacore™ assay, e.g. as described the Examples;

(ii) competitive inhibition of IL-17R binding to IL-17A, for example, an $IC_{50}$ being 10 nM or less, or 1 nM or less, or 100 pM or less, as measured in an in vitro competitive binding assay, e.g. as described in the Examples;

(iii) inhibition of IL-17A dependent activity, for example production of IL-6 or GRO-alpha, for example, an $IC_{50}$ being 10 nM or less, or 1 nM or less, or 100 pM or less, as measured in a cellular assay as described in the Examples;

(iv) inhibition of the effects observed, for example knee swelling, as measured in an in vivo antigen induced arthritis assay as described in the Examples;

(v) cross-reactivity with cynomolgus, rhesus macaque, rat, or mouse IL-17A polypeptide;

(vi) cross-reactivity with human or mouse IL-17AF polypeptide;

(vii) binding affinity to IL-17AF (specific binding to IL-17AF), for example, a $K_D$ being 1 nM or less, 100 pM or less, or 10 pM or less, as measured in the Biacore™ assay, e.g. as described in the Examples;

(viii) inhibition of IL-17AF, for example, an $IC_{50}$ being 200 nM or less, 150 nM or less, or 100 nM or less, as measured in an in vitro competitive binding assay as described in the Examples;

(ix) suitable properties for drug development, in particular, it is stable and does not aggregate at in a formulation at high concentration, i.e., above 50 mg/ml.

For example, the disclosure relates to homologous antibodies of XAB1, XAB2, XAB3, XAB4 and XAB5 (or a protein comprising an antigen-binding portion thereof), comprising a variable heavy chain ($V_H$) and a variable light chain ($V_L$) sequences where the CDR sequences, i.e. the 6 CDR regions; HCDR1, HCDR2, HCDR3, LCDR1, LCDR2, LCDR3 or HCDR1', HCDR2', HCDR3', LCDR1', LCDR2', LCDR3', share at least 60, 70, 90, 95 or 100 percent sequence identity to the corresponding CDR sequences of at least one antibody of XAB1, XAB2, XAB3, XAB4 and XAB5, wherein said homologous antibody or antigen-binding fragment thereof, such as a protein comprising an antigen-binding portion thereof, specifically binds to IL-17A, and the antibody or protein exhibits at least one of the following functional properties: it inhibits binding of IL-17A to its receptors, it inhibits IL-17A dependent IL-6 or GRO-alpha production in cellular assays, or inhibition of the effects observed in an in vivo antigen induced arthritis assay. In a related specific embodiment, the homologous antibody or protein binds to IL-17A with a $K_D$ of 1 nM or less and inhibits binding of IL-17A to its receptors as measured in an in vitro competitive binding assay with an $IC_{50}$ of 1 nM or less. The CDRs of XAB1, XAB2, XAB3, XAB4 and XAB5 are defined in the above Table 5 and Table 6.

The disclosure further relates to homologous antibodies of XAB1, XAB2, XAB3, XAB4 and XAB5 (or antigen-binding fragments thereof, such as a protein comprising an antigen-binding portion thereof) comprising a heavy chain variable region and a light chain variable region that are at least 80%, 90%, or at least 95% or 100% identical to the corresponding heavy and light chain variable regions of any one of the antibodies XAB1, XAB2, XAB3, XAB4 or XAB5; the homologous antibody or protein specifically binds to IL-17A, and it exhibits at least one of the following functional properties: it inhibits binding of IL-17A to its receptor(s), it inhibits IL-17A dependent IL-6 or GRO-alpha production in cellular assays, or inhibition of the effects observed in an in vivo antigen induced arthritis assay. In a related specific embodiment, the homologous antibody or antigen binding fragment thereof, such as a protein comprising an antigen-binding portion thereof binds to IL-17A with a $K_D$ of 1 nM or less and inhibits binding of IL-17A to its receptor(s), as measured in an in vitro competitive binding assay with an $IC_{50}$ of 1 nM or less. The $V_H$ and $V_L$ amino acid sequences of XAB1, XAB2, XAB3, XAB4 and XAB5 are defined in the above Table 2.

In another example, the disclosure relates to homologous antibodies of XAB1, XAB2, XAB3, XAB4 and XAB5 (or antigen-binding fragments thereof, such as a protein comprising an antigen-binding portion thereof) comprising a full length heavy chain and a full length light chain, wherein: the variable heavy chain is encoded by a nucleotide sequence that is at least 80%, at least 90%, at least 95%, or 100% identical to the corresponding coding nucleotide sequence of the variable heavy and light chains of XAB1, XAB2, XAB3, XAB4 and XAB5, the homologous antibody or antigen-binding fragments thereof, such as a protein comprising an antigen-binding portion thereof, specifically binds to IL-17A, and it exhibits at least one of the following functional properties: it inhibits binding of IL-17A to its receptor(s), it inhibits IL-17A dependent production of IL-6 or GRO-alpha in cellular assays, or inhibition of the effects observed in an in vivo antigen induced arthritis assay. In a related specific embodiment, the homologous antibody or antigen-binding fragments thereof, such as a protein comprising an antigen-binding portion thereof binds to IL-17A with a $K_D$ of 1 nM or less and inhibits binding to IL-17A as measured in an in vitro competitive binding assay with an $IC_{50}$ of 1 nM or less. The coding nucleotide sequences of the variable regions of XAB1, XAB2, XAB3, XAB4 and XAB5 can be derived from the Table 3 showing the full length coding nucleotide sequences of XAB1, XAB2, XAB3, XAB4 and XAB5 and Table 2 showing the amino acid sequences of the variable regions of XAB1, XAB2, XAB3, XAB4 and XAB5.

In various embodiments, the antibody or antigen-binding fragment thereof, such as a protein comprising an antigen-binding portion of an antibody, may exhibit one or more, two or more, three or more, or four or more of the desired functional properties discussed above. The antibody or protein of the disclosure can be, for example, a human antibody, a humanized antibody or a chimeric antibody. In one embodiment, the antibody or protein is a fully human silent antibody, such as a fully human silent IgG1 antibody.

Silenced effector functions can be obtained by mutation in the Fc constant part of the antibodies and have been described in the Art: Strohl 2009 (LALA & N297A); Baudino 2008, D265A (Baudino et al. 2008, J. Immunol. 181:6664-69, Stroh), CO 2009, Biotechnology 20:685-91). Examples of silent IgG1 antibodies comprise the so-called LALA mutant comprising L234A and L235A mutation in the IgG1 Fc amino acid sequence. Another example of a silent IgG1 antibody comprises the D265A mutation. The D265A mutation can also preferably be combined with the P329A mutation (DAPA). Another silent IgG1 antibody comprises the N297A mutation, which results in aglycosylated or non-glycosylated antibodies.

Antibodies with mutant amino acid sequences can be obtained by mutagenesis (e.g., site-directed or PCR-mediated mutagenesis) of the coding nucleic acid molecules, followed by testing of the encoded altered antibody for retained function (i.e., the functions set forth above) using the functional assays described herein.

Antibodies with Conservative Modifications

In certain embodiments, an antibody (or a protein comprising antigen-binding portion thereof) of the disclosure has a heavy chain variable region comprising HCDR1, HCDR2, and HCDR3 sequences (or HCDR1', HCDR2' and HCDR3') and a light chain variable region comprising LCDR1, LCDR2, and LCDR3 sequences (or LCDR1', LCDR2', and LCDR3'), wherein one or more of these CDR sequences have specified amino acid sequences based on the antibodies XAB1, XAB2, XAB3, XAB4 or XAB5 described herein or conservative modifications thereof, and wherein the antibody or protein retains the desired functional properties of the anti-IL-17A antibodies of the disclosure.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Modifications can be introduced into an antibody as disclosed herein by standard techniques known in the art, such as site-directed mutagenesis and PCR-mediated mutagenesis.

Engineered and Modified Antibodies

Other antibodies and antigen-binding fragments, such as proteins comprising an antigen-binding portion thereof can be prepared using an antibody having one or more of the $V_H$ and/or $V_L$ sequences of XAB1, XAB2, XAB3, XAB4 or XAB5 shown above as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chains complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. 1998, Nature 332:323-327; Jones, P. et al. 1986, Nature 321:522-525; Queen, C. et al. 1989, Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the disclosure pertains to an isolated recombinant CDR-grafted anti-IL-17A antibody, comprising the 6 CDR regions of any one of XAB1, XAB2, XAB3, XAB4 or XAB5 as defined in Table 5 or Table 6, yet containing different framework sequences from the original antibodies.

Such framework sequences can be obtained from public DNA databases or published references that include germline antibody gene sequences. For example, germline DNA sequences for human heavy and light chains variable region genes can be found in the "VBase" human germline sequence database (available on the Internet at www.mrc-cpe.cam.ac.uk/vbase), as well as in Kabat, E. A., et al. 1991, Sequences of Proteins of Immunological Interest, Fifth Edition, U.S. Department of Health and Human Services, NIH Publication No. 91-3242; Tomlinson, I. M., et al. 1992, J. Mol. Biol. 227:776-798; and Cox, J. P. L. et al. 1994, Eur. J Immunol. 24:827-836.

Examples of framework sequences are those that are structurally similar to the framework sequences used in any one of XAB1, XAB2, XAB3, XAB4 or XAB5. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Therefore, in one embodiment, the disclosure relates to affinity matured antibodies derived from one of XAB1, XAB2, XAB3, XAB4 or XAB5 antibodies. Conservative modifications (as discussed above) can be introduced. The mutations may be amino acid substitutions, additions or deletions. Moreover, typically no more than one, two, three, four or five residues within a CDR region are altered. For example, an antibody of the disclosure is an affinity-matured antibody comprising the 6 CDRs of one of XAB1, XAB2, XAB3, XAB4 or XAB5 and wherein no more than one, two, three, four or five residues within a CDR region are altered.

Accordingly, in another embodiment, the disclosure provides isolated engineered anti-IL-17A antibodies comprising a heavy chain variable region and a light chain variable region which are identical to the corresponding heavy and light chain variable regions of at least one of XAB1, XAB2, XAB3, XAB4 or XAB5 antibodies except that the heavy and/or light chain amino acid sequences of said engineered antibodies contain one, two, three, four or five amino acid substitutions, deletions or additions as compared to the original sequences.
Grafting Antigen-Binding Domains into Alternative Frameworks or Scaffolds A wide variety of antibody/immunoglobulin frameworks or scaffolds can be employed so long as the resulting polypeptide includes at least one binding region of XAB1, XAB2, XAB3, XAB4 or XAB5, which specifically binds to IL-17A. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies or proteins comprising an antigen-binding portion thereof using non-immunoglobulin scaffolds onto which CDRs of the disclosure can be grafted. Known or future non-immunoglobulin frameworks and scaffolds may be employed, as long as they comprise a binding region specific for the target protein of SEQ ID NO: 76. Such compounds are referred herein as "polypeptides comprising a target-specific binding region". Examples of non-immunoglobulin framework are further described in the sections below (camelid antibodies and non-antibody scaffold).
Camelid Antibodies Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT Publication No. WO 94/04678.

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al. 2004, J Biol Chem 279: 1256-1261; Dumoulin, M. et al. 2003, Nature 424: 783-788; Pleschberger, M. et al. 2003, Bioconjugate Chem 14: 440-448; Cortez-Retamozo, V. et al. 2002, Int J Cancer 89: 456-62; and Lauwereys, M. et al. 1998, EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detecting antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. Patent Publication No. 20040161738 published Aug. 19, 2004. These features combined with the low antigenicity to humans indicate great therapeutic potential. Further, these molecules can be fully expressed in prokaryotic cells such as *E. coli* and are expressed as fusion proteins in bacteriophage and are functional.

Engineered nanobodies can further be customized by genetic engineering to have a half-life in a recipient subject of from 45 minutes to two weeks. In a specific embodiment, the camelid antibody or nanobody is obtained by grafting the CDRs sequences of the heavy or light chain of one of the human antibodies of the disclosure, XAB1, XAB2, XAB3, XAB4 or XAB5, into nanobody or single domain antibody framework sequences, as described for example in PCT Publication No. WO 94/04678.
Non-Antibody Scaffold Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(a) Fibronectin Scaffold

The fibronectin scaffolds are based preferably on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of one of XAB1, XAB2, XAB3, XAB4 or XAB5 using standard cloning techniques.

(b) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(c) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US Patent Publication Nos 20040175756; 20050053973; 20050048512; and 20060008844.

(d) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies; they have a molecular weight of 6 kDa, compared to the molecular weight of antibodies, which is 150 kDa. In spite of its small size, the binding site of Affibody® molecules is similar to that of an antibody.

(e) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of Pieris Brassicae has been used to develop anticalins by mutagenizing the set of four loops. One example of a patent application describing "anticalins" is PCT Publication WO 199916873.

(f) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

(g) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Framework or Fc Engineering

Engineered antibodies and proteins comprising an antigen-binding portion thereof of the disclosure include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the disclosure.

Another type of framework modification involves mutating one or more residues within the framework region, or even within one or more CDR regions, to remove T cell—epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation, again to alter one or more functional properties of the antibody. Each of these embodiments is described in further detail below.

As used herein, the term "Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the disclosure may comprise antibody populations with all K447 residues removed, antibody populations with no K447 residues removed, and antibody populations having a mixture of antibodies with and without the K447 residue.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody or protein comprising an antigen-binding portion thereof is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody or protein comprising an antigen-binding portion thereof. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody or protein comprising an antigen-binding portion thereof to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. 2001, J. Biol. Chem 276:6591-6604). In certain embodiments, the Fc domain of the IgG1 isotype is used. In some specific embodiments, a mutant variant of the IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant is IgG1 wherein Leucine is replaced by Alanine at amino acid positions 234 and 235 as described by Hezareh et al. 2001, J. Virol 75:12161-8 Another example of an IgG1 isotype silent mutant is IgG1 with D265A mutation (aspartate being substituted by alanine at position 265). In certain embodiments, the Fc domain is a silent Fc mutant preventing glycosylation at position 297 of the Fc domain. For example, the Fc domain contains an amino acid substitution of asparagine at position 297. An example of such amino acid substitution is the replacement of N297 by a glycine or an alanine.

In still another embodiment, the glycosylation of an antibody or protein comprising an antigen-binding portion thereof is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody or protein comprising an antigen-binding portion thereof can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1 176 195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the disclosure are produced by recombinant expression in a cell line which exhibits a hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. 2002, J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al. 1999, Nat. Biotech. 17:176-180). Alternatively, the antibodies and proteins comprising an antigen-binding portion thereof of the disclosure can be produced in a yeast or a filamentous fungus engineered for mammalian-like glycosylation pattern, and capable of producing antibodies lacking fucose as glycosylation pattern (see for example EP 1 297 172).

Another modification of the antibodies and proteins comprising an antigen-binding portion thereof as disclosed herein that is contemplated by the disclosure is pegylation. These molecules can be pegylated to, for example, increase their biological (e.g., serum) half-life. For example, to pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See for example, EP 0 154 316 by Nishimura et al. and EP 0 401 384 by Ishikawa et al.

Another modification of the antibodies and proteins comprising an antigen-binding portion thereof that is contemplated by the disclosure is a conjugate or a protein fusion of at least the antigen-binding region of the antibody of the disclosure to serum protein, such as human serum albumin or a fragment thereof to increase half-life of the resulting molecule. Such approach is for example described in Ballance et al. EP 0 322 094.

Another possibility is a fusion of at least the antigen-binding region of the antibody of the disclosure to proteins capable of binding to serum proteins, such human serum albumin to increase half-life of the resulting molecule. Such approach is for example described in Nygren et al., EP 0 486 525.

Methods of Engineering Altered Antibodies

As discussed above, the anti-IL-17A antibodies having $V_H$ and $V_L$ sequences or full length heavy and light chain sequences shown herein can be used to create new anti-IL-17A antibodies by modifying full length heavy chain and/or light chain sequences, $V_H$ and/or $V_L$ sequences, or the constant region(s) attached thereto. Thus, in another aspect of the disclosure, the structural features of an anti-IL-17A antibody of the disclosure are used to create structurally related anti-IL-17A antibodies or protein comprising an antigen-binding portion thereof that retain at least one functional property of the antibodies disclosed herein, such as binding to human IL-17A and also inhibiting one or more functional properties of IL-17A (e.g., inhibiting binding of IL-17A or IL-17AF to its receptor(s), inhibiting IL-17A or IL-17AF induced production of IL-6, GRO-alpha, etc.) inhibitory activity in in vivo assays.

Other antibodies retaining substantially the same binding properties to IL-17A include chimeric antibodies or CDR grafted antibodies of any one of XAB1, XAB2, XAB3, XAB4 or XAB5 which retain the same VH and VL regions, or the CDR regions, of any one of XAB1, XAB2, XAB3, XAB4 or XAB5 and different constant regions or framework regions (for example a different Fc region selected from a different isotype, for example IgG4 or IgG2).

For example, one or more CDR regions of any one of XAB1, XAB2, XAB3, XAB4 or XAB5, or mutations thereof, can be combined recombinantly with known framework regions and/or other CDRs to create additional, recombinantly-engineered, anti-IL-17A antibodies of the disclosure, as discussed above. Other types of modifications include those described in the previous section. The starting material for the engineering method is one or more of the $V_H$ and/or $V_L$ sequences of XAB1, XAB2, XAB3, XAB4 or XAB5 provided in the tables above, or one or more CDR region thereof. To create the engineered antibody, it is not necessary to actually prepare (i.e., express as a protein) an antibody having one or more of the $V_H$ and/or $V_L$ sequences of XAB1, XAB2, XAB3, XAB4 or XAB5, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

The second generation sequences are derived for example by altering the DNA coding sequence of at least one amino acid residue within the heavy chain variable region antibody sequence and/or the light chain variable region antibody sequence of any one of XAB1, XAB2, XAB3, XAB4 or XAB5, to create at least one altered antibody sequence; and expressing the altered antibody sequence as a protein.

Accordingly, in another embodiment, the disclosure provides a method for preparing an anti-IL-17A antibody optimized for expression in a mammalian cell consisting of: a full length heavy chain antibody sequence a full length light chain antibody sequence of any one of XAB1, XAB2, XAB3, XAB4 or XAB5; altering at least one codon in the nucleotide coding sequence, said codon encoding an amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having unique heavy and light CDR3 sequences of any one of XAB1, XAB2, XAB3, XAB4 or XAB5 respectively, or minimal essential binding determinants as described in US Patent Publication No. 20050255552, and alternative sequences for CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the desired functional properties of the anti-IL-17A antibodies described herein, which functional properties include, but are not limited to, specifically binding to human IL-17A; and/or it inhibits binding of IL-17A to its receptor(s); and/or it inhibits IL-17A induced production of, for example, IL-6 or GRO-alpha etc.

The altered antibody may exhibit one or more, two or more, or three or more of the functional properties discussed above.

In certain embodiments of the methods of engineering antibodies of the disclosure, mutations can be introduced randomly or selectively along all or part of an anti-IL-17A antibody coding sequence and the resulting modified anti-IL-17A antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Disclosure

Another aspect of the disclosure pertains to nucleic acid molecules that encode the antibodies or proteins of the disclosure. Examples of variable light chain nucleotide sequences are those encoding the variable light chain amino acid sequences of any one of XAB1, XAB2, XAB3, XAB4 and XAB5, the latter sequences being derived from the Table 3 (showing the entire nucleotide coding sequences of heavy and light chains of XAB1, XAB2, XAB3, XAB4 or XAB5) and Table 2 (showing the amino acid sequences of the variable regions of XAB1, XAB2, XAB3, XAB4 or XAB5).

The disclosure also pertains to nucleic acid molecules that derive from the latter sequences having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987, Current Protocols in Molecular Biology, Greene Publishing and Wiley Interscience, New York. A nucleic acid of the disclosure can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the disclosure can be obtained using standard molecular biology techniques. Once DNA fragments encoding, for example, $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E.A., et al. 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al. 1988, Science 242:423-426; Huston et al. 1988, Proc. Natl. Acad. Sci. USA 85:5879-5883; McCafferty et al. 1990, Nature 348:552-554).

Isolation of Recombinant Antibodies of the Disclosure

A variety of methods of screening antibodies and proteins comprising an antigen-binding portion thereof have been described in the Art. Such methods may be divided into in vivo systems, such as transgenic mice capable of producing fully human antibodies upon antigen immunization and in vitro systems, consisting of generating antibody DNA coding libraries, expressing the DNA library in an appropriate system for antibody production, selecting the clone that express antibody candidate that binds to the target with the affinity selection criteria and recovering the corresponding coding sequence of the selected clone. These in vitro technologies are known as display technologies, and include without limitation, phage display, RNA or DNA display, ribosome display, yeast or mammalian cell display. They have been well described in the Art (for a review see for example: Nelson et al. 2010, Nature Reviews Drug discovery, "Development trends for human monoclonal antibody therapeutics" (Advance Online Publication) and Hoogenboom et al. 2001, Method in Molecular Biology 178:1-37, O'Brien et al., ed., Human Press, Totowa, N.J.). In one specific embodiment, human recombinant antibodies of the disclosure are isolated using phage display methods for screening libraries of human recombinant antibody libraries, such as HuCAL® libraries.

Repertoires of $V_H$ and $V_L$ genes or related CDR regions can be separately cloned by polymerase chain reaction (PCR) or synthesized by DNA synthesizer and recombined randomly in phage libraries, which can then be screened for antigen-binding clones. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

In a certain embodiment, human antibodies directed against IL-17A can be identified using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (µ and γ) and κ ight chain immunoglobulin sequences, together with targeted mutations that inactivate the endogenous µ and κ chain loci (see e.g., Lonberg, et al. 1994, Nature 368:856-859). Accordingly, the mice exhibit reduced expression of mouse IgM or κ, and in response to immunization, the introduced human heavy and light chain transgenes undergo class switching and somatic mutation to generate high affinity human IgGK monoclonal (Lonberg, N. et al. 1994, supra; reviewed in Lonberg, N., 1994 Handbook of Experimental Pharmacology 113:49-101; Lonberg, N. and Huszar, D. 1995, Intern. Rev. Immunol. 13:65-93, and Harding, F. and Lonberg, N. 1995, Ann. N. Y. Acad. Sci. 764:536-546). The preparation and use of HuMAb mice, and the genomic modifications carried by such mice, is further described in Taylor, L. et al. 1992, Nucleic Acids Research 20:6287-6295; Chen, J. et al. 1993, International Immunology 5:647-656; Tuaillon et al. 1993, Proc. Natl. Acad. Sci. USA 94:3720-3724; Choi et al. 1993, Nature Genetics 4:117-123; Chen, J. et al. 1993, EMBO J. 12: 821-830; Tuaillon et al. 1994, J. Immunol. 152:2912-2920; Taylor, L. et al. 1994, International Immunology 579-591; and Fishwild, D. et al. 1996, Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the disclosure can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IL-17A antibodies of the disclosure. For example, an alternative transgenic system referred to as the Xenomouse from Abgenix, Inc. can be used. Such mice are described in, e.g., U.S. Pat. Nos. 5,939,598; 6,075,181; 6,114,598; 6, 150,584 and 6,162,963 to Kucherlapati et al. As will be appreciated by a person skilled in the art, several other mouse models may be used, such as the Trianni™ mouse from Trianni, Inc., the VelocImmune™ mouse from Regeneron Pharmaceuticals, Inc., or the Kymouse™ mouse from Kymab Limited.

Moreover, alternative transchromosomic animal systems expressing human immunoglobulin genes are available in the art and can be used to raise anti-IL-17A antibodies of the disclosure. For example, mice carrying both a human heavy chain transchromosome and a human light chain transchromosome, referred to as "TC mice" can be used; such mice are described in Tomizuka et al. 2000, Proc. Natl. Acad. Sci. USA 97:722-727.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Monoclonal Antibodies of the Disclosure from the Murine System

Monoclonal antibodies (mAbs) can be produced by a variety of techniques, including conventional monoclonal antibody methodology e.g., the standard somatic cell hybridization technique of Kohler and Milstein 1975, Nature 256:495. Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

Generation of Hybridomas Producing Human Monoclonal Antibodies

To generate hybridomas producing human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific or epitope-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1X HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned once or twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the disclosure can be produced in a host cell transfectoma using, for example, a combination of recombinant DNA techniques and gene transfection methods as is well known in the art (e.g., Morrison, S. 1985, Science 229: 1202).

For example, to express the antibodies, or antibody fragments thereof, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide, also called leader sequence, which facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein). Examples of such signal peptides are found in Table 7, and examples of polynucleotide sequences coding for the signal peptides are found in Table 8.

TABLE 7

Signal peptides for heavy and light peptide chains.

| Signal peptide | Sequence ID no. | Used for heavy or light peptide chain |
| --- | --- | --- |
| 1 | SEQ ID NO: 59 | Heavy |
| 2 | SEQ ID NO: 60 | Light |
| 3 | SEQ ID NO: 63 | Heavy |
| 4 | SEQ ID NO: 64 | Light |
| 5 | SEQ ID NO: 67 | Heavy |
| 6 | SEQ ID NO: 68 | Light |

TABLE 8

Polynucleotide sequences coding for the signal peptides.

| Coding for signal peptide no. | Sequence ID no. | Coding signal peptide sequence for heavy or light chain |
| --- | --- | --- |
| 1 | SEQ ID NO: 61 | Heavy |
| 2 | SEQ ID NO: 62 | Light |
| 3 | SEQ ID NO: 65 | Heavy |
| 4 | SEQ ID NO: 66 | Light |
| 5 | SEQ ID NO: 69 | Heavy |
| 6 | SEQ ID NO: 70 | Light |

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel 1990, Gene Expression Technology. Methods in Enzymology 185, Academic Press, San Diego, Calif.). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. 1988, Mol. Cell. Biol. 8:466-472).

In addition to the antibody chain genes and regulatory sequences, the recombinant expression vectors of the disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr− host cells with methotrexate selection/amplification) and the neo gene (for G418 selection).

For expression of the light and heavy chains, standard techniques were applied to transfect a host cell with the expression vector(s) encoding the heavy and light chains. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the disclosure in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the disclosure comprises either at least one of coding sequences from Table 3, operatively linked to suitable promoter sequences. In another specific embodiment, a cloning or expression vector according to the disclosure comprises either at least one of coding sequences from Table 4, operatively linked to suitable promoter sequences.

Mammalian host cells for expressing the recombinant antibodies of the disclosure include Chinese Hamster Ovary (CHO cells) (including dhfr− CHO cells, described Urlaub and Chasin 1980, Proc. Natl. Acad. Sci. USA 77:4216-4220 used with a DH FR selectable marker, e.g., as described in R. J. Kaufman and P. A. Sharp 1982, Mol. Biol. 159:601-621), CHOK1 dhfr+ cell lines, NSO myeloma cells, COS cells and SP2 cells. In particular, for use with NSO myeloma cells, another expression system is the GS gene expression system shown in PCT Publications WO 87/04462, WO 89/01036 and EP 0 338 841. In one embodiment, mammalian host cells for expressing the recombinant antibodies of the disclosure include mammalian cell lines deficient for FUT8 gene expression, for example as described in U.S. Pat. No. 6,946,292.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods (See for example Abhinav et al. 2007, Journal of Chromatography 848:28-37).

In one specific embodiment, the host cell of the disclosure is a host cell transfected with an expression vector having the coding sequences selected from the group consisting of SEQ ID NO: 18, 31, 51, 19, 28, 32, 38, 40, 46, 48, 52, 56, and 58, suitable for the expression of XAB1, XAB2, XAB3, XAB4 or XAB5 respectively, operatively linked to suitable promoter sequences.

The latter host cells may then be further cultured under suitable conditions for the expression and production of an antibody of the disclosure selected from the group consisting of XAB1, XAB2, XAB3, XAB4 or XAB5 respectively.
Immunoconjugates In another aspect, the present disclosure features an anti-IL-17A antibody of the disclosure, or a fragment thereof, conjugated to an active or therapeutic moiety, such as a cytotoxin, a drug (e.g., an immunosuppressant) or a radiotoxin. Such conjugates are referred to herein as "immunoconjugates". This may be particularly preferred if IL-17A is expressed on the surface of Th17 cells (Brucklacher-Waldert et al. 2009, J Immunol. 183:5494-501).

Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, teroposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the disclosure include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. 2003, Adv. Drug Deliv. Rev. 55:199-215; Trail, P. A. et al. 2003, Cancer Immunol. Immunother. 52:328-337; Payne, G. 2003, Cancer Cell 3:207-212; Allen, T. M. 2002, Nat. Rev. Cancer 2:750-763; Pastan, I. and Kreitman, R. J. 2002, Curr. Opin. Investig. Drugs 3:1089-1091; Senter, P. D. and Springer, C. J. 2001, Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the disclosure.

The antibody conjugates of the disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL1"), interleukin-2 ("IL2"), interleukin-6 ("IL6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al. 1985, "Monoclonal Antibodies For Immunotargeting Of Drugs In Cancer Therapy", in Monoclonal Antibodies And Cancer Therapy, Reisfeld et al. (eds.), pp. 243-56; Hellstrom et al. 1987, "Antibodies For Drug Delivery", in Controlled Drug Delivery (2nd Ed.), Robinson et al. (eds.), pp. 623-53; Thorpe 1985, "Antibody Carriers Of Cytotoxic Agents In Cancer Therapy: A Review", in Monoclonal Antibodies '84: Biological And Clinical Applications, Pinchera et al. (eds.), pp. 475-506; Thorpe et al. 1982, Immunol. Rev., 62:119-58.

Bispecific Molecules

In another aspect, the present disclosure features bispecific or multispecific molecules comprising an anti-IL-17A/AF antibody or protein comprising an antigen-binding portion thereof of the disclosure. An antibody or protein of the disclosure can be derivatized or linked to another functional molecule, e.g., another peptide or protein (e.g., another antibody or ligand for a receptor) to generate a bispecific molecule that binds to at least two different binding sites or target molecules. The antibody or protein of the disclosure may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the disclosure, an antibody or protein of the disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for IL-17A, for example, one antigen-binding portion of any one of XAB1, XAB2, XAB3, XAB4 or XAB5 and a second binding specificity for a second target epitope. For example, the second target epitope is another epitope of IL-17A different from the first target epitope. Another example is a bispecific molecule comprising at least one first binding specificity for IL-17A, for example, one antigen-binding portion of any one of XAB1, XAB2, XAB3, XAB4 or XAB5 and a second binding specificity for an epitope elsewhere within IL-17A or within another target antigen.

Additionally, for the disclosure in which the bispecific molecule is multi-specific, the molecule can further include a third binding specificity, in addition to the first and second target epitope.

In one embodiment, the bispecific molecules of the disclosure comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules of the disclosure are murine, chimeric and humanized monoclonal antibodies.

The bispecific molecules of the present disclosure can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al. 1984, J. Exp. Med. 160: 1686; Liu, M A et al. 1985, Proc. Natl. Acad. Sci. USA 82:8648). Other methods include those described in Paulus 1985, Behring Ins. Mitt. No. 78,118-132; Brennan et al. 1985, Science 229:81-83), and Glennie et al. 1987, J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present disclosure provides multivalent antibodies comprising at least two identical or different antigen-binding portions of the antibodies of the disclosure binding to IL-17A, for example, selected from antigen-binding portions of any one of XAB1, XAB2, XAB3, XAB4 or XAB5. In one embodiment, the multivalent antibodies provide at least two, three or four antigen-binding portions of the antibodies. The antigen-binding portions can be linked together via protein fusion or covalent or non-covalent linkage. Alternatively, methods of linkage have been described for the bispecific molecules. Tetravalent compounds can be obtained for example by cross-linking antibodies of the disclosure with an antibody that binds to the constant regions of the antibodies of the disclosure, for example the Fc or hinge region.

Pharmaceutical Compositions

In another aspect, the present disclosure provides a composition, e.g., a pharmaceutical composition, containing one or a combination of antibodies or proteins comprising an antigen-binding portion thereof of the present disclosure, for example, one antibody selected from the group consisting of XAB1, XAB2, XAB3, XAB4 and XAB5, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies or proteins that bind to different epitopes on the target antigen or that have complementary activities.

Pharmaceutical compositions of the disclosure also can be administered in combination therapy, i.e., combined with other agents. For example, the combination therapy can include an anti-IL-17A antibody or protein of the present disclosure, for example one antibody selected from the group consisting of XAB1, XAB2, XAB3, XAB4 and XAB5, combined with at least one other anti-inflammatory or another chemotherapeutic agent, for example, an immunosuppressant agent. Examples of therapeutic agents that can be used in combination therapy are described in greater detail below in the section on uses of the antibodies or proteins of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody, immunoconjugate, or bispecific molecule, may be coated in a material to protect the compound from the action of acids and other natural conditions that may inactivate the compound.

The pharmaceutical compositions of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. 1977, J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Reviews on the development of stable protein (e.g. antibody) formulations may be found in Cleland et al. 1993, Crit. Reviews. Ther. Drug Carrier Systems 10(4):307-377 and Wei Wang 1999, Int. J. Pharmaceutcs 185:129-88. Additional formulation discussions for antibodies may be found, e.g., in Daugherty and Mrsny 2006, Advanced Drug Delivery Reviews 58: 686-706; U.S. Pat. Nos. 6,171,586, 4,618,486, US Publication No. 20060286103, PCT Publication WO 06/044908, WO 07/095337, WO 04/016286, Colandene et al. 2007, J. Pharm. Sci 96: 1598-1608; Schulman 2001, Am. J. Respir. Crit. Care Med. 164:S6-S11 and other known references.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. Such preparations may be enclosed in ampoules, disposables syringes or multiple dose vials made of glass or plastic.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the antibodies or proteins of the disclosure into a sterile vehicle that contains a basic dispersion medium and the required other ingredients from those enumerated above.

In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

In one specific embodiment, the antibodies XAB1, XAB2, XAB3, XAB4 or XAB5 were administered as a liquid formulation in a vial. The amount of drug per vial was 150 mg. The liquid contained 150 mg/mL antibody, 4.8 mM L-Histidine, 15.2 mM L-Histidine-HCl 220 mM Sucrose and 0.04% Polysorbate 20, at pH 6.0±0.5. A 20% overfill was added to permit complete removal of the intended dose.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 per cent to about ninety-nine percent of active ingredient, from about 0.1 per cent to about 70 per cent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of sensitivity in individuals.

For administration of the antibody or protein, the dosage ranges from about 0.0001 to 150 mg/kg, such as 5, 15, and 50 mg/kg subcutaneous administration, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once per month, once every 3 months or once every three to 6 months. Dosage regimens for an anti-IL-17A antibody or protein of the disclosure include 1 mg/kg body weight, 3 mg/kg body weight, 5 mg/kg, 10 mg/kg, 20 mg/kg or 30 mg/kg by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more antibodies with different binding specificities are administered simultaneously, in which case the dosage of each antibody administered falls within the ranges indicated. Antibodies or proteins of the disclosure are usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody or protein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IL-17A antibody or protein of the disclosure can result in a decrease in severity of disease symptoms, an increase in frequency and duration of disease symptom-free periods, or a prevention of impairment or disability due to the disease affliction.

A composition of the present disclosure can be administered by one or more routes of administration using one or more of a variety of methods known in the art. As will be appreciated by the skilled artisan, the route and/or mode of administration will vary depending upon the desired results. Routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Alternatively, an antibody or protein of the disclosure can be administered by a non-parenteral route, such as a topical, epidermal or mucosal route of administration, for example, intranasally, orally, vaginally, rectally, sublingually or topically.

The antibodies or proteins of the disclosure can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the disclosure can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well-known implants and modules useful in the present disclosure include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art.

In certain embodiments, the antibodies or proteins of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade 1989, J. Cline Pharmacol. 29:685). Exemplary targeting moieties include folate or biotin (see, e.g., U.S. Pat. No. 5,416,016 to Low et al.); mannosides (Umezawa et al. 1988, Biochem. Biophys. Res. Commun. 153:1038); antibodies (P. G. Bloeman et al. 1995, FEBS Lett. 357:140; M. Owais et al. 1995, Antimicrob. Agents Chernother. 39:180); surfactant protein A receptor (Briscoe et al. 1995, Am. J. Physiol. 1233:134); p120 (Schreier et al. 1994, J. Biol. Chem. 269:9090); see also Keinanen and Laukkanen 1994, FEBS Lett. 346:123; Killion and Fidler 1994, Immunomethods 4:273.

Uses and Methods of the Disclosure

The antibodies or proteins of the present disclosure have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The methods are particularly suitable for treating, preventing or diagnosing IL-17A-related disorders and/or autoimmune and inflammatory disorders, e.g., rheumatoid arthritis, or psoriasis.

Specifically, the disclosure provides a method of treating IL-17A-related disorders and/or autoimmune and inflammatory disorders. In certain embodiments the method comprises the step of administering isolated antibody or protein comprising an antigen-binding portion thereof, according to the disclosure, to a subject in need thereof.

The disclosure also provides methods for decreasing or suppressing IL-17A or IL-17AF induced signaling response in target cells or tissues by contacting a cell with a composition comprising a therapeutically effective dose of the antibodies of the disclosure.

The disclosure also provides methods for decreasing levels of IL6, CXCL1, IL-8, GM-CSF and/or CCL2 in a cell comprising the step of contacting a cell with antibody or antigen binding fragment, such as a protein comprising an antigen-binding portion thereof, according to the disclosure.

In the present description the phrase "IL-17A/AF mediated disease" or "IL-17A/AF-related disorder" encompasses all diseases and medical conditions in which IL-17A or IL-17AF plays a role, whether directly or indirectly, in the disease or medical condition, including the causation, development, progress, persistence or pathology of the disease or condition. Accordingly these terms include conditions associated with or characterized by aberrant IL-17A/AF levels and/or diseases or conditions that can be treated by reducing or suppressing IL-17A/AF induced activity in target cells or tissues e.g. the production of IL-6 or GRO-alpha. These include inflammatory conditions and autoimmune diseases, such as arthritis, rheumatoid arthritis, or psoriasis. These further include allergies and allergic conditions, hypersensitivity reactions, chronic obstructive pulmonary disease, cystic fibrosis and organ or tissue transplant rejection.

For example, the antibodies or proteins of the disclosure may be used for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

The antibodies or proteins of the disclosure, whilst not being limited to, are useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarthropathies including ankylosing spondylitis, Reiter syndrome, reactive arthritis, psoriatic arthritis, juvenile idiopathic arthritis and enterophathis arthritis, enthesitis, hypersensitivity (including both airways hypersensitivity and dermal hypersensitivity) and allergies. Specific auto-immune diseases for which antibodies of the disclosure may be employed include autoimmune haematological disorders (including e.g. hemolytic anaemia, aplastic anaemia, pure red cell anaemia and idiopathic thrombocytopenia), systemic lupus erythematosus (SLE), lupus nephritis, inflammatory muscle diseases (dermatomyosytis), periodontitis, polychondritis, scleroderma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and irritable bowel syndrome), endocrine ophthalmopathy, Graves' disease, sarcoidosis, multiple sclerosis, systemic sclerosis, fibrotic diseases, primary biliary cirrhosis, juvenile diabetes (diabetes mellitus type I), uveitis, keratoconjunctivitis sicca and vernal keratoconjunctivitis, interstitial lung fibrosis, periprosthetic osteolysis, glomerulonephritis (with and without nephrotic syndrome, e.g. including idiopathic nephrotic syndrome or minimal change nephropathy), multiple myeloma other types of tumors, inflammatory disease of skin and cornea, myositis, loosening of bone implants, metabolic disorders, (such as obesity, atherosclerosis and other cardiovascular diseases including dilated cardiomyopathy, myocarditis, diabetes mellitus type II, and dyslipidemia), and autoimmune thyroid diseases (including Hashimoto thyroiditis), small and medium vessel primary vasculitis, large vessel vasculitides including giant cell arteritis, hidradenitis suppurativa, neuromyelitis optica, Sjogren's syndrome, Behçet's disease, atopic and contact dermatitis, bronchiolitis, inflammatory muscle diseases, autoimmune peripheral neurophaties, immunological renal, hepatic and thyroid diseases, inflammation and atherothrombosis, autoinflammatory fever syndromes, immunohematological disorders, and bullous diseases of the skin and mucous membranes. Anatomically, uveitis can be anterior, intermediate, posterior, or pan-uveitis. It can be chronic or acute. The etiology of uveitis can be autoimmune or non-infectious, infectious, associated with systemic disease, or a white-dot syndrome.

The antibodies or proteins of the disclosure may also be useful for the treatment, prevention, or amelioration of asthma, bronchitis, bronchiolitis, idiopathic interstitial pneumonias, pneumoconiosis, pulmonary emphysema, and other obstructive or inflammatory diseases of the airways.

The antibodies or proteins of the disclosure may also be useful for treating diseases of bone metabolism including osteoarthritis, osteoporosis and other inflammatory arthritis, and bone loss in general, including age-related bone loss, and in particular periodontal disease.

In addition, the antibodies or proteins of the disclosure may also be useful for treating chronic candidiasis and other chronic fungal diseases, as well as complications of infections with parasites, and complications of smoking are considered to be promising avenues of treatment, as well as viral infection and complications of viral infection.

Inhibition of IL-17 and its receptor is among the most promising new modes of actions (MOA) for the treatment of chronic inflammatory diseases, with psoriasis being the most advanced indication among several diseases currently being studied for IL-17 modulator drug development (Miossec P and Kolls J K. 2012, Nat Rev Drug Discov. 10:763-76). Several studies have unambiguously demonstrated that blocking IL-17A in patients with moderate to severe plaque psoriasis is safe in the short term and induces very remarkable improvements (e.g. Hueber W, Patel DD, Dryja T, et al 2010, Sci Transl Med.; 2:52ra72). These findings exceeded expectations and confirmed the hypothesis that IL-17A is a key signaling molecule in the pathogenesis of psoriasis (Garber K. 2012, Nat Biotechnology 30:475-477).

Furthermore, in several animal models including the most common multiple sclerosis (MS) model experimental autoimmune encephalomyelitis, IL-17 is pivotal in the inflammatory processes (Bettelli E, et al 2008, Nature; 453: 1051-57, Wang H H, et al 2011, J Clin Neurosci; 18(10): 1313-7, Matsushita T, et al 2013, PLoS One; 8(4):e64835). IL-17 effects are mainly proinflammatory, and synergize with other cytokines. IL-17 effects such as induction of chemokine production by epithelial cells, upregulation of interleukin (IL)-1b, tumor necrosis factor alpha (TNFa) and matrix metalloproteinase (MMP)-9 in macrophages, and induction of the secretion of IL 6, IL-8 and prostaglandin E2, fit well with many aspects of the MS pathology. There is also data arguing against a pivotal role of IL-17 in neuroinflammation, including transgenic overexpression models in mice (Haak S et al 2009, JCI; 119:61-69).

Asthma is a heterogeneous inflammatory disease of the airways that is manifested clinically by symptoms of airflow obstruction that varies in severity either spontaneously or in response to treatment. While asthma has been considered to be driven by T helper cell type 2 (Th2) cells and their products, recent data suggest that a Th2-high gene signature is present in the airways of only ~50% of subjects with asthma (Woodruff P G et al 2009, Am J Respir Crit Care Med 180: 388-95). Neutrophilic inflammation is dominant in acute severe asthma; some individuals with asthma present with prominent sputum neutrophilia and a poor clinical response to inhaled steroids; and sputum neutrophilia is prominent in asthmatic individuals taking large doses of inhaled and/or oral steroids (Wenzel 2012, Nature Med 18:716-25).

Increased levels of IL-17A that correlate with the severity of asthma have been reported in the circulation and airways of individuals with asthma compared to healthy controls. Preclinical studies in mouse models of allergic pulmonary inflammation have implicated a requirement for IL-17A and its receptor (IL-17RA) in neutrophilic airway inflammation and steroid-resistant airway hyper responsiveness. Thus, the properties of IL-17A in vitro, its presence in increased amounts in asthma, and the pre-clinical models of the disease support a role for IL-17A in neutrophilic and/or Th2-low forms of the disease that are poorly responsive to steroids (Cosmi L et al 2009, Am J Respir Crit Care Med 180:388-95).

Thus, the following list of conditions comprises particularly preferred targets for treatment with antibodies or proteins comprising an antigen-binding portion thereof according to the disclosure: Multiple sclerosis, psoriasis, asthma, systemic lupus erythematosus (SLE), and lupus nephritis.

The antibodies or proteins of the disclosure may be administered as the sole active ingredient or in conjunction with, e.g. as an adjuvant to or in combination to, other drugs e.g. immunosuppressive or immunomodulating agents or other anti-inflammatory agents or other cytotoxic or anti-cancer agents, e.g. for the treatment or prevention of diseases mentioned above. For example, the antibodies of the disclosure may be used in combination with DMARD, e.g. Gold salts, sulphasalazine, antimalarias, methotrexate, D-penicillamine, azathioprine, mycophenolic acid, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CC1779, ABT578, AP23573 or TAFA-93; an ascomycin having immuno-suppressive properties, e.g. ABT-281, ASM981, etc.; corticosteroids; cyclophosphamide; azathioprine; leflunomide; mizoribine; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL1 blockers, e.g. Anakinra or IL1 trap, canakinumab, IL13 blockers, IL4 blockers, IL6 blockers, other IL17 blockers (such as secukinumab, broadalumab, ixekizumab); chemokines blockers, e.g inhibitors or activators of proteases, e.g. metalloproteases, anti-IL15 antibodies, anti-IL6 antibodies, anti-IL4 antibodies, anti-IL13 antibodies, anti-CD20 antibodies, NSAIDs, such as aspirin or an anti-infectious agent (list not limited to the agent mentioned).

In accordance with the foregoing the present disclosure provides in a yet further aspect: A method as defined above comprising co-administration, e.g. concomitantly or in sequence, of a therapeutically effective amount of an anti-IL-17A antibody or protein comprising an antigen-binding portion thereof as disclosed herein, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an antibody or protein or protein comprising an antigen-binding portion thereof as disclosed herein, and b) at least one second substance selected from an immuno-suppressive/immunomodulatory, anti-inflammatory chemotherapeutic or anti-infectious drug, e.g. as indicated above. The kit may comprise instructions for its administration.

Where the antibodies or proteins comprising an antigen-binding portion thereof as disclosed herein are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL1 blocker or others, on the specific drug employed, on the condition being treated and so forth.

In one embodiment, the antibodies or proteins comprising an antigen-binding portion thereof can be used to detect levels of IL-17A, or levels of cells that contain IL-17A. This can be achieved, for example, by contacting a sample (such as an in vitro sample) and a control sample with the anti-IL-17A antibody (or protein) under conditions that allow for the formation of a complex between the antibody and IL-17A. Any complexes formed between the antibody (or protein) and IL-17A are detected and compared in the sample and the control. For example, standard detection methods, well known in the art, such as ELISA and flow cytometric assays, can be performed using the compositions of the disclosure.

Accordingly, in one aspect, the disclosure further provides methods for detecting the presence of IL-17A (e.g., human IL-17A antigen) in a sample, or measuring the amount of IL-17A, comprising contacting the sample, and a control sample, with an antibody or protein of the disclosure, or an antigen-binding portion thereof, which specifically binds to IL-17A, under conditions that allow for formation of a complex between the antibody or portion thereof and IL-17A. The formation of a complex is then detected, wherein a difference in complex formation between the sample and the control sample is indicative of the presence of IL-17A in the sample.

Also within the scope of the disclosure are kits consisting of the compositions (e.g., antibodies, proteins, human antibodies and bispecific molecules) of the disclosure and instructions for use. The kit can further contain a least one additional reagent, or one or more additional antibodies or proteins of the disclosure (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an anti-IL-17A antibody treatment, as defined above.

The disclosure having been fully described is now further illustrated by the following examples and claims, which are illustrative and are not meant to be further limiting.

BRIEF DESCRIPTION OF THE DRAWINGS

FIG. 3C is a graph showing the normalized signal versus the Fab competitor concentration (M). These graphs are ELISA results according to an example. The graph numbering corresponds to the candidate designation as follows: 1 is MB440; 2 is MB464; 3 is MB468; 4 is MB444; 5 is MB435; 6 is MB463; 7 is XAB1.

EXAMPLES

Figure 1A:
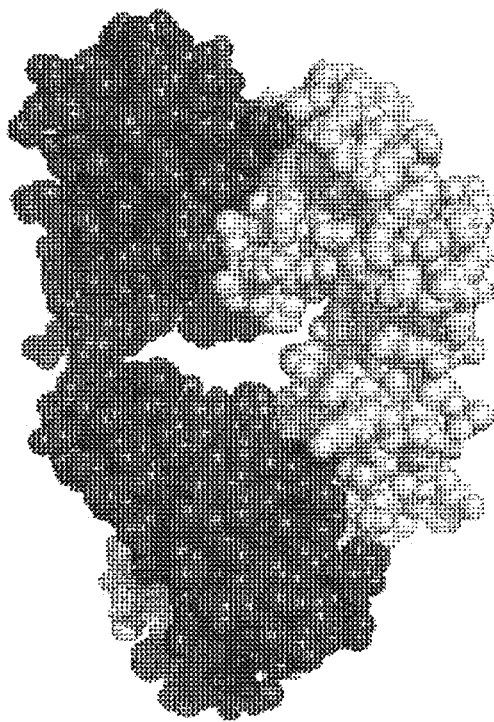
FIG. 1A is a space-filling representation of the XAB1 Fab.

XAB1 is a human IgG1/κ monoclonal antibody. It was generated using standard molecular biological techniques. In brief, the Medarex system was used. Mice were immunized with recombinant human IL-17A. Mice were euthanized by $CO_2$ inhalation and spleen cells were harvested and fused with a myeloma cell line using PEG 4000. Fused cells were plated into wells with a feeder layer of peritoneal cells. Supernatants were taken from cultured cells and assayed for IL-17A reactive mAbs by ELISA. Clones positive for the production of IL-17A mAbs were selected and plated out.

The hybridoma responsible for the secretion of XAB1 was identified for further characterization on the basis of initial promising antibody/antigen binding characteristics such as binding affinity for IL-17A, ability to block IL-17A binding to its receptor, and ability to block IL-17A mediated biological effects in in vitro assays.

The amino acid sequence of XAB1 is SEQ ID NO: 14 (heavy chain) and SEQ ID NO: 15 (light chain). XAB1 was chosen for subsequent affinity maturation.

As a first step toward structure-guided affinity maturation, the crystal structure of the XAB1 Fab in the free state as well as the corresponding Fv complex with human IL-17A were determined as described below. The analysis of the three-dimensional structure of the XAB1 Fv complex with human IL-17A allowed for a rational affinity maturation process to be carried out alongside, and as an alternative to, a more randomised process. Further details are provided below.

In addition, X-ray crystallography was used to characterise some of the affinity matured variant antibodies that were generated. Analysis of crystal data from the affinity matured variants allowed for a deeper understanding of the binding behaviour of the variant antibodies and some unexpected properties were discovered as will be described further below.

Example 1

Crystal Structure of the XAB1 Fab in the Free State (i) Material and Methods

Standard molecular biological protocols were used to obtain the XAB1 Fab antibody fragment. In brief, the Fab was cloned and expressed in *E. coli* W3110 with a C-terminal hexahistidine tag on the heavy-chain. The recombinant protein was purified by Ni-chelate chromatography followed by size-exclusion chromatography on a SPX-75 column in 10 mM TRIS pH 7.4, 25 mM NaCl. The XAB1 Fab was then concentrated by ultra-filtration to 10.4 mg/ml and crystallized.

Standard crystallization protocols were followed. In brief, crystals were grown at 19° C. in SD2 96 well-plates, using the method of vapour diffusion in sitting drops. The protein stock was mixed 1:1 with a crystallization buffer containing 40% PEG 300, 0.1 M sodium phosphate-citrate pH 4.2. Total drop size was 0.4 μl. Prior to X-ray data collection, one crystal was mounted in a nylon cryo-loop and directly flash cooled into liquid nitrogen.

X-ray data collection and processing was carried out using standard protocols. Briefly, X-ray data to 2.1 Å resolution were collected at the Swiss Light Source, beamline X10SA, with a MAR225 CCD detector, using 1.0000 Å X-ray radiation. In total, 180 images of 1.0° oscillation each were recorded at a crystal-to-detector distance of 190 mm and processed with the HKL2000 software package. The crystal belonged to space group C2 with cell parameters a=51.63 Å, b=132.09 Å, c=77.25 Å, α=90.00°, β=98.88°, γ=90.00° and one XAB1 Fab molecule in the asymmetric unit. R-sym to 2.1 Å resolution was 10.4% and data completeness 99.0%.

The structure was determined by molecular replacement with the program PHASER. Search models for the $V_H/V_L$ and $C_{H1}/C_L$ domains were generated from PDB entry 1 HEZ. Iterative model building and refinement were performed with the programs Coot (Crystallographic Object-Oriented Toolkit) and CNX (Crystallography & NMR eXplorer) version 2002, until no further significant improvements could be made to the model. Final R- and R-free for all data were 0.188 and 0.231, respectively. The final refined model showed a root-mean-square deviation (RMSD) from ideal bond lengths and bond angles of 0.004 Å and 0.9°, respectively.

(ii) Results

The results of the X-ray refinement of the XAB1 Fab are provided in

Table 9 and the three-dimensional structure is shown in FIG. 1.

TABLE 9

X-ray refinement of the XAB1 Fab with the program CNX.

| | | |
|---|---|---|
| REMARK 3 | | |
| REMARK 3 | REFINEMENT. | |
| REMARK 3 | PROGRAM | : CNX 2002 |
| REMARK 3 | AUTHORS | : Brunger, Adams, Clore, Delano, |

TABLE 9-continued

X-ray refinement of the XAB1 Fab with the program CNX.

REMARK 3   Gros, Grosse-Kunstleve, Jiang,
REMARK 3   Kuszewski, Nilges, Pannu, Read,
REMARK 3   Rice, Simonson, Warren
REMARK 3     and
REMARK 3   Accelrys Inc.,
REMARK 3     Yip, Dzakula).
REMARK 3
REMARK 3  DATA USED IN REFINEMENT.
REMARK 3   RESOLUTION RANGE HIGH (ANGSTROMS) : 2.10
REMARK 3   RESOLUTION RANGE LOW  (ANGSTROMS) : 33.33
REMARK 3   DATA CUTOFF    (SIGMA(F)) : 0.0
REMARK 3   DATA CUTOFF HIGH   (ABS(F)) : 19645630.62
REMARK 3   DATA CUTOFF LOW    (ABS(F)) :  0.000000
REMARK 3   COMPLETENESS (WORKING+TEST) (%) : 98.2
REMARK 3   NUMBER OF REFLECTIONS     : 29298
REMARK 3
REMARK 3  FIT TO DATA USED IN REFINEMENT.
REMARK 3   CROSS-VALIDATION METHOD   : THROUGHOUT
REMARK 3   FREE R VALUE TEST SET SELECTION : RANDOM
REMARK 3   R VALUE     (WORKING SET) : 0.188
REMARK 3   FREE R VALUE           : 0.231
REMARK 3   FREE R VALUE TEST SET SIZE (%) : 4.9
REMARK 3   FREE R VALUE TEST SET COUNT  : 1436
REMARK 3   ESTIMATED ERROR OF FREE R VALUE : 0.006
REMARK 3
REMARK 3  FIT IN THE HIGHEST RESOLUTION BIN.
REMARK 3   TOTAL NUMBER OF BINS USED    : 6
REMARK 3   BIN RESOLUTION RANGE HIGH   (A) : 2.10
REMARK 3   BIN RESOLUTION RANGE LOW    (A) : 2.23
REMARK 3   BIN COMPLETENESS (WORKING+TEST) (%) : 94.7
REMARK 3   REFLECTIONS IN BIN  (WORKING SET) : 4478
REMARK 3   BIN R VALUE     (WORKING SET) : 0.201
REMARK 3   BIN FREE R VALUE         : 0.241
REMARK 3   BIN FREE R VALUE TEST SET SIZE (%) : 4.5
REMARK 3   BIN FREE R VALUE TEST SET COUNT  : 213
REMARK 3   ESTIMATED ERROR OF BIN FREE R VALUE : 0.016
REMARK 3
REMARK 3  NUMBER OF NON-HYDROGEN ATOMS USED IN REFINEMENT.
REMARK 3   PROTEIN ATOMS   : 3311
REMARK 3   NUCLEIC ACID ATOMS  :  0
REMARK 3   HETEROGEN ATOMS   :  5
REMARK 3   SOLVENT ATOMS   : 313
REMARK 3
REMARK 3  B VALUES.
REMARK 3   FROM WILSON PLOT     (A**2) : 21.1
REMARK 3   MEAN B VALUE    (OVERALL, A**2) : 27.4
REMARK 3   OVERALL ANISOTROPIC B VALUE.
REMARK 3    B11 (A**2) : −6.02
REMARK 3    B22 (A**2) : 3.30
REMARK 3    B33 (A**2) : 2.73
REMARK 3    B12 (A**2) : 0.00
REMARK 3    B13 (A**2) : 3.82
REMARK 3    B23 (A**2) : 0.00
REMARK 3
REMARK 3  BULK SOLVENT MODELING.
REMARK 3   METHOD USED : FLAT MODEL
REMARK 3   KSOL    : 0.399279
REMARK 3   BSOL    : 54.4727 (A**2)
REMARK 3
REMARK 3  ESTIMATED COORDINATE ERROR.
REMARK 3   ESD FROM LUZZATI PLOT   (A) : 0.21
REMARK 3   ESD FROM SIGMAA     (A) : 0.12
REMARK 3   LOW RESOLUTION CUTOFF   (A) : 5.00
REMARK 3
REMARK 3  CROSS-VALIDATED ESTIMATED COORDINATE ERROR.
REMARK 3   ESD FROM C-V LUZZATI PLOT  (A) : 0.29
REMARK 3   ESD FROM C-V SIGMAA     (A) : 0.14
REMARK 3
REMARK 3  RMS DEVIATIONS FROM IDEAL VALUES.
REMARK 3   BOND LENGTHS       (A) : 0.004
REMARK 3   BOND ANGLES    (DEGREES) : 0.9
REMARK 3   DIHEDRAL ANGLES  (DEGREES) : 21.4
REMARK 3   IMPROPER ANGLES   (DEGREES) : 0.58
REMARK 3
REMARK 3  ISOTROPIC THERMAL MODEL : RESTRAINED
REMARK 3
REMARK 3  ISOTROPIC THERMAL FACTOR RESTRAINTS. RMS SIGMA
REMARK 3   MAIN-CHAIN BOND  (A**2) : 1.41 ; 1.50

TABLE 9-continued

X-ray refinement of the XAB1 Fab with the program CNX.

| | | | |
|---|---|---|---|
| REMARK 3 | MAIN-CHAIN ANGLE | (A**2) : 2.21 ; 2.00 | |
| REMARK 3 | SIDE-CHAIN BOND | (A**2) : 2.31 ; 2.00 | |
| REMARK 3 | SIDE-CHAIN ANGLE | (A**2) : 3.44 ; 2.50 | |
| REMARK 3 | | | |
| REMARK 3 | NCS MODEL : NONE | | |
| REMARK 3 | | | |
| REMARK 3 | NCS RESTRAINTS. | | RMS SIGMA/WEIGHT |
| REMARK 3 | GROUP 1 POSITIONAL | (A) : NULL ; NULL | |
| REMARK 3 | GROUP 1 B-FACTOR | (A**2) : NULL ; NULL | |
| REMARK 3 | | | |
| REMARK 3 | PARAMETER FILE 1 : protein_rep.param | | |
| REMARK 3 | PARAMETER FILE 2 : water_rep.param | | |
| REMARK 3 | TOPOLOGY FILE 1 : protein_no_cter.top | | |
| REMARK 3 | TOPOLOGY FILE 2 : water.top | | |
| REMARK 3 | | | |
| REMARK 3 | OTHER REFINEMENT REMARKS: NULL | | |
| SSBOND 1 | CYS L 23   CYS L 88 | | |
| SSBOND 2 | CYS L 134   CYS L 194 | | |
| SSBOND 3 | CYS H 22   CYS H 96 | | |
| SSBOND 4 | CYS H 143   CYS H 199 | | |
| CRYST1 | 51.627 132.089   77.247 90.00 98.88 90.00 C 1 2 1     8 | | |
| ORIGX1 | 1.000000 0.000000 0.000000     0.00000 | | |
| ORIGX2 | 0.000000 1.000000 0.000000     0.00000 | | |
| ORIGX3 | 0.000000 0.000000 1.000000     0.00000 | | |
| SCALE1 | 0.019370 0.000000 0.003027     0.00000 | | |
| SCALE2 | 0.000000 0.007571 0.000000     0.00000 | | |
| SCALE3 | 0.000000 0.000000 0.013103     0.00000 | | |

Figure 1B:
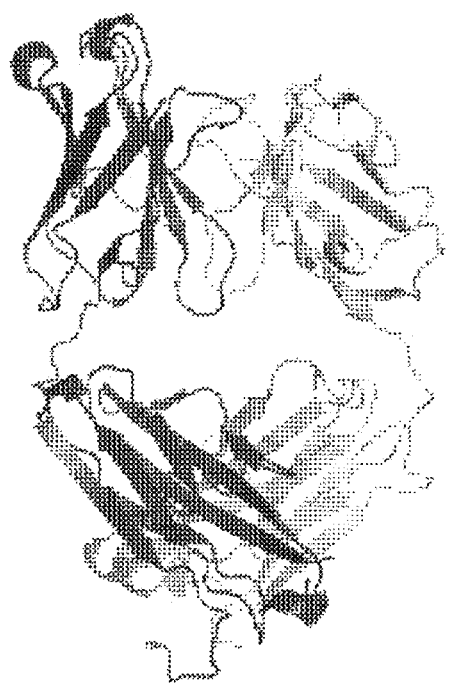
FIG. 1B is a cartoon representation of the XAB1 Fab.

FIG. 1 provides the three-dimensional structure of the XAB1 Fab as obtained in Example 1. FIG. 1A is a space-filling representation. FIG. 1B is a cartoon representation. The heavy- and lightchain of the XAB1 Fab appears in dark and light grey, respectively.

Example 2

Crystal Structure of the XAB1 Fv Complex with Human IL-17A: Analysis of the Paratope for Structure-Guided Affinity Maturation (i) Material and Methods Standard molecular biological protocols were used to obtain the XAB1 Fv antibody fragment. In brief, the Fv was cloned and expressed in E. coli W3110 with a C-terminal hexahistidine tag on the heavy-chain and a C-terminal Strep-tag on the light-chain. The recombinant protein was purified by Ni-chelate chromatography.

The XAB1 Fv fragment complex with human IL-17A was then prepared using standard methodology. In brief, human IL-17A (1.1 mg) was mixed with an excess of Fv (2.7 mg) and the complex was run on a S100 size-exclusion chromatography, in 10 mM TRIS pH 7.4, 25 mM NaCl. The protein complex was then concentrated by ultra-filtration to 21.2 mg/ml and crystallized.

Standard crystallization protocols were followed. In brief, crystals were grown at 19° C. in SD2 96 well-plates, using the method of vapour diffusion in sitting drops. The protein stock was mixed 1:1 with a crystallization buffer containing 10% PEG 20,000, 0.1M Bicine pH 9.0, 2.0% (v/v) dioxane. Total drop size was 0.4 µl. Prior to X-ray data collection, one crystal was briefly transferred into a 1:1 mix of the crystallization buffer with 20% PEG 20,000, 30% glycerol, and then flash cooled into liquid nitrogen.

X-ray data collection and processing was carried out using standard protocols. Briefly, X-ray data to 3.0 Å resolution were collected at the Swiss Light Source, Beamline X10SA, with a MAR225 CCD detector, using 1.0000 Å X-ray radiation. In total, 110 images of 1.0° oscillation each were recorded at a crystal-to-detector distance of 300 mm and processed with the HKL2000 software package. The crystal belonged to space group $P2_12_12$ with cell parameters a=184.31 Å, b=55.81 Å, c=70.99 Å, α=β=γ=90°. R-sym to 3.0 Å resolution was 11.2% and data completeness 99.9%.

The structure was determined by molecular replacement with the program PHASER. A search model for the XAB1 Fv was generated from the crystal structure of the XAB1 Fab previously determined (see Example 1). A search model for IL-17A was generated from the published human IL-17F crystal structure (PDB entry 1jpy). Iterative model building and refinement were performed with Coot (Crystallographic Object-Oriented Toolkit) and CNX (Crystallography & NMR eXplorer) version 2002, until no further significant improvements could be made to the model. Final R- and R-free for all data were 0.215 and 0.269, respectively. The final refined model showed a root-mean-square deviation (RMSD) from ideal bond lengths and bond angles of 0.007 Å and 1.0°, respectively.

(ii) Results

The molecular replacement calculations revealed a dimeric complex comprising one IL-17A homodimer with two XAB1 Fv fragments bound. The results of the X-ray refinement of the XAB1 Fv complex with human IL-17A are provided in Table 10 and the three-dimensional structure of this complex is shown in FIG. 2. Each XAB1 Fv makes contacts to both IL-17A subunits, but the vast majority of the intermolecular contacts (about 96% of the buried surface) are contributed by one IL-17A subunit only.

TABLE 10

X-ray refinement of the XAB1 Fv complex
with IL-17A obtained by the program CNX.

```
REMARK 3
REMARK 3   REFINEMENT.
REMARK 3       PROGRAM    : CNX 2002
REMARK 3       AUTHORS    : Brunger, Adams, Clore, Delano,
REMARK 3           Gros, Grosse-Kunstleve, Jiang,
REMARK 3           Kuszewski, Nilges, Pannu, Read,
REMARK 3           Rice, Simonson, Warren
REMARK 3             and
REMARK 3           Accelrys Inc.,
REMARK 3           (Badger, Berard, Kumar, Szalma,
REMARK 3             Yip, Dzakula).
REMARK 3
REMARK 3   DATA USED IN REFINEMENT.
REMARK 3       RESOLUTION RANGE HIGH (ANGSTROMS) : 3.01
REMARK 3       RESOLUTION RANGE LOW  (ANGSTROMS) : 47.74
REMARK 3       DATA CUTOFF    (SIGMA(F)) : 0.0
REMARK 3       DATA CUTOFF HIGH    (ABS(F)) : 15276175.80
REMARK 3       DATA CUTOFF LOW     (ABS(F)) :  0.000000
REMARK 3       COMPLETENESS (WORKING+TEST) (%) : 99.5
REMARK 3       NUMBER OF REFLECTIONS    : 15190
REMARK 3
REMARK 3   FIT TO DATA USED IN REFINEMENT.
REMARK 3       CROSS-VALIDATION METHOD   : THROUGHOUT
REMARK 3       FREE R VALUE TEST SET SELECTION : RANDOM
REMARK 3       R VALUE       (WORKING SET) : 0.215
REMARK 3       FREE R VALUE            : 0.269
REMARK 3       FREE R VALUE TEST SET SIZE (%) : 4.9
REMARK 3       FREE R VALUE TEST SET COUNT    : 748
REMARK 3       ESTIMATED ERROR OF FREE R VALUE : 0.010
REMARK 3
REMARK 3   FIT IN THE HIGHEST RESOLUTION BIN.
REMARK 3       TOTAL NUMBER OF BINS USED     : 6
REMARK 3       BIN RESOLUTION RANGE HIGH    (A) : 3.00
REMARK 3       BIN RESOLUTION RANGE LOW     (A) : 3.19
REMARK 3       BIN COMPLETENESS (WORKING+TEST) (%) : 94.6
REMARK 3       REFLECTIONS IN BIN (WORKING SET) : 2234
REMARK 3       BIN R VALUE   (WORKING SET) : 0.301
REMARK 3       BIN FREE R VALUE         : 0.350
REMARK 3       BIN FREE R VALUE TEST SET SIZE (%) : 5.3
REMARK 3       BIN FREE R VALUE TEST SET COUNT   : 124
REMARK 3       ESTIMATED ERROR OF BIN FREE R VALUE : 0.031
REMARK 3
REMARK 3   NUMBER OF NON-HYDROGEN ATOMS USED IN REFINEMENT.
REMARK 3       PROTEIN ATOMS   : 5007
REMARK 3       NUCLEIC ACID ATOMS   :   0
REMARK 3       HETEROGEN ATOMS      :   0
REMARK 3       SOLVENT ATOMS   : 33
REMARK 3
REMARK 3   B VALUES.
REMARK 3       FROM WILSON PLOT       (A**2) : 54.9
REMARK 3       MEAN B VALUE     (OVERALL, A**2) : 44.8
REMARK 3       OVERALL ANISOTROPIC B VALUE.
REMARK 3       B11 (A**2) : 5.66
REMARK 3       B22 (A**2) : 0.97
REMARK 3       B33 (A**2) : −6.63
REMARK 3       B12 (A**2) : 0.00
REMARK 3       B13 (A**2) : 0.00
REMARK 3       B23 (A**2) : 0.00
REMARK 3
REMARK 3   BULK SOLVENT MODELING.
REMARK 3       METHOD USED : FLAT MODEL
REMARK 3       KSOL   : 0.313124
REMARK 3       BSOL   : 20.608 (A**2)
REMARK 3
REMARK 3   ESTIMATED COORDINATE ERROR.
REMARK 3       ESD FROM LUZZATI PLOT   (A) : 0.33
REMARK 3       ESD FROM SIGMAA      (A) : 0.39
REMARK 3       LOW RESOLUTION CUTOFF   (A) : 5.00
REMARK 3
REMARK 3   CROSS-VALIDATED ESTIMATED COORDINATE ERROR.
REMARK 3       ESD FROM C-V LUZZATI PLOT   (A) : 0.44
REMARK 3       ESD FROM C-V SIGMAA      (A) : 0.51
REMARK 3
REMARK 3   RMS DEVIATIONS FROM IDEAL VALUES.
REMARK 3       BOND LENGTHS        (A) : 0.007
REMARK 3       BOND ANGLES     (DEGREES) : 1.0
REMARK 3       DIHEDRAL ANGLES  (DEGREES) : 22.1
```

TABLE 10-continued

X-ray refinement of the XAB1 Fv complex
with IL-17A obtained by the program CNX.

| | | |
|---|---|---|
| REMARK 3 | IMPROPER ANGLES (DEGREES) : 0.78 | |
| REMARK 3 | | |
| REMARK 3 | ISOTROPIC THERMAL MODEL : RESTRAINED | |
| REMARK 3 | | |
| REMARK 3 | ISOTROPIC THERMAL FACTOR RESTRAINTS. RMS SIGMA | |
| REMARK 3 | MAIN-CHAIN BOND (A**2) : 1.46 ; 1.50 | |
| REMARK 3 | MAIN-CHAIN ANGLE (A**2) : 2.62 ; 2.00 | |
| REMARK 3 | SIDE-CHAIN BOND (A**2) : 1.63 ; 2.00 | |
| REMARK 3 | SIDE-CHAIN ANGLE (A**2) : 2.62 ; 2.50 | |
| REMARK 3 | | |
| REMARK 3 | NCS MODEL : NONE | |
| REMARK 3 | | |
| REMARK 3 | NCS RESTRAINTS. | RMS SIGMA/WEIGHT |
| REMARK 3 | GROUP 1 POSITIONAL (A) : NULL ; NULL | |
| REMARK 3 | GROUP 1 B-FACTOR (A**2) : NULL ; NULL | |
| REMARK 3 | | |
| REMARK 3 | PARAMETER FILE 1 : protein_rep.param | |
| REMARK 3 | PARAMETER FILE 2 : water_rep.param | |
| REMARK 3 | TOPOLOGY FILE 1 : protein_no_cter.top | |
| REMARK 3 | TOPOLOGY FILE 2 : water.top | |
| REMARK 3 | | |
| REMARK 3 | OTHER REFINEMENT REMARKS: NULL | |
| SSBOND 1 | CYS L 23 CYS L 88 | |
| SSBOND 2 | CYS H 22 CYS H 96 | |
| SSBOND 3 | CYS A 23 CYS A 88 | |
| SSBOND 4 | CYS B 22 CYS B 96 | |
| SSBOND 5 | CYS C 94 CYS C 144 | |
| SSBOND 6 | CYS C 99 CYS C 146 | |
| SSBOND 7 | CYS D 94 CYS D 144 | |
| SSBOND 8 | CYS D 99 CYS D 146 | |
| CRYST1 | 184.306 55.813 70.991 90.00 90.00 90.00 P 21 21 2   24 | |
| ORIGX1 | 1.000000 0.000000 0.000000   0.00000 | |
| ORIGX2 | 0.000000 1.000000 0.000000   0.00000 | |
| ORIGX3 | 0.000000 0.000000 1.000000   0.00000 | |
| SCALE1 | 0.005426 0.000000 0.000000   0.00000 | |
| SCALE2 | 0.000000 0.017917 0.000000   0.00000 | |
| SCALE3 | 0.000000 0.000000 0.014086   0.00000 | |

Figure 2A:
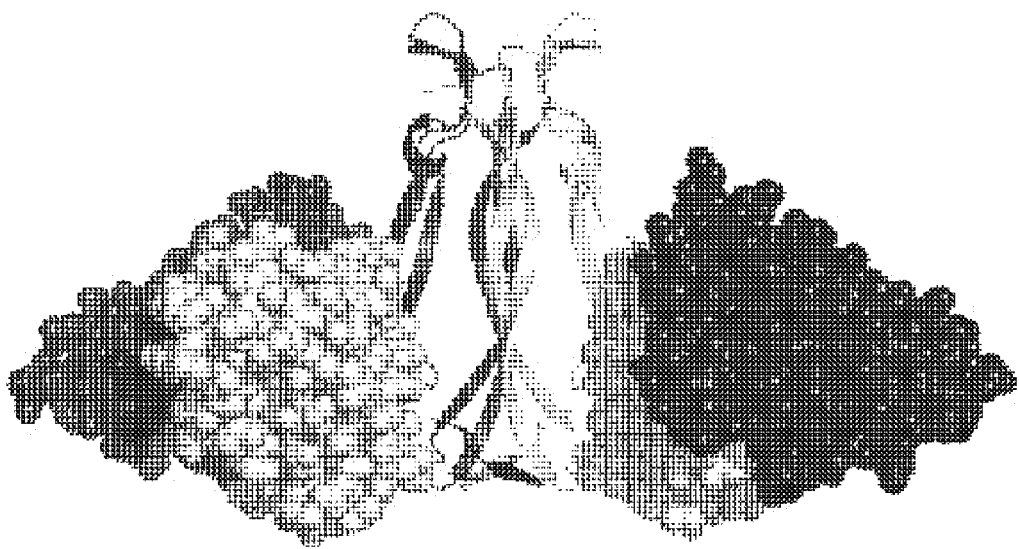
FIG. 2A shows the two XAB1 Fv fragments in space-filling representation of the XAB1 Fv complex with human IL-17A and FIG. 2B shows the two XAB1 Fv fragments in cartoon representation of the XAB1 Fv complex with human IL-17A.
Figure 2B:
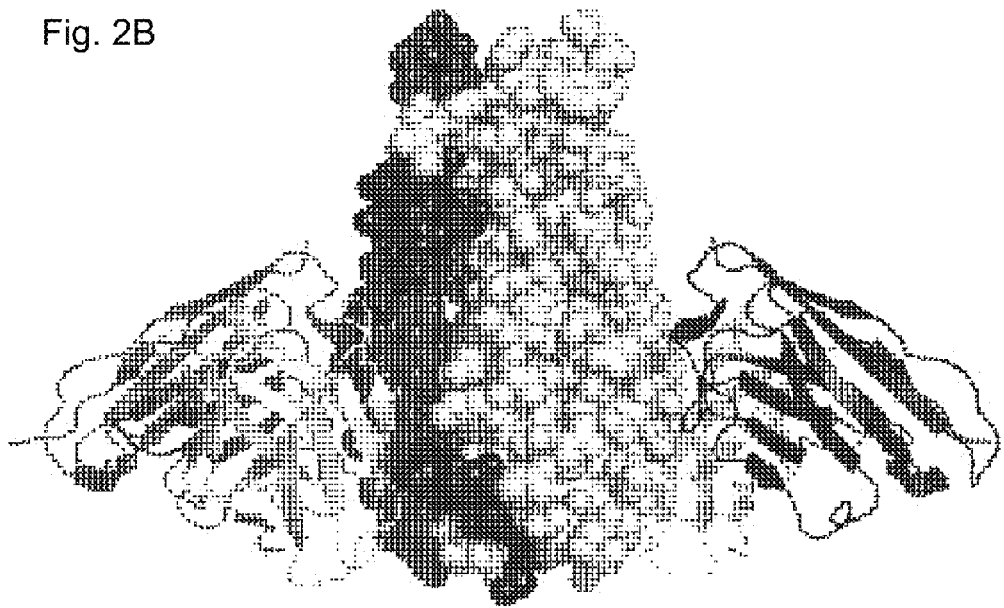

FIG. 2 provides the three-dimensional structure of the XAB1 Fv complex with human IL-17A, as obtained in Example 2. FIG. 2A shows the two XAB1 Fv fragments in space-filling representation; the IL-17A homodimer is shown in cartoon representation. FIG. 2B shows the two XAB1 Fv fragments in cartoon representation; the IL-17A homodimer is shown in space-filling representation. The heavy- and light-chain of the XAB1 Fv are represented as dark and light grey, respectively. One chain of the IL-17A homodimer is represented as light grey, the other is represented as dark grey.

A detailed analysis of the complex was performed. A careful visual inspection of the crystal structure with the programs Coot and Pymol was carried out, and the amount of protein surface buried at the antibody-antigen interface was calculated with the program AREAIMOL of the CCP4 program suite. Intermolecular contacts were defined using a cut-off distance of 3.9 Å between antibody and antigen atoms. An overview of binding can be summarized as follows. Binding of XAB1 is symmetrical; each Fv fragment binds to an equivalent epitope on the IL17A homodimer.

The binding of each Fv fragment buried on average 1732$A^2$ of combined surface, and involved 30 antibody and 25 IL-17A amino acid residues. The contribution to the buried surface of the XAB1 light-chain (around 560$A^2$) was greater than that of the heavy chain (around 275$A^2$). In addition, CDRH2 did not make any direct contacts to IL-17A and appeared to be too far from the protein antigen to provide opportunities for affinity maturation. The CDRH1 contribution appeared to be limited to one amino-acid side-chain only (Tyr32); this CDR was also too far from IL-17A to offer opportunities for affinity maturation through amino acid substitutions. The XAB1 CDRH3 made multiple tight contacts with IL-17A. However, careful inspection of the structure in this region failed to reveal any opportunity for further enhancing these contacts by point mutations; therefore, CDRH3 was deemed unsuitable as a target region for affinity enhancement. In contrast, inspection of the light-chain CDRs showed multiple opportunities for affinity maturation. Among the three light-chain CDRs, CDRL1 was considered most promising, and based on this observation, the inventors proposed to randomize positions 30 to 32 of the light-chain in an attempt to strengthen contacts to IL-17A residues Arg124, Phe133 and Tyr85.

Affinity Maturation by Rational Design

Based on the results above, it was seen that the XAB1 interface with homodimeric IL-17A was comparatively small and was characterized by a dominant contribution from the light chain, no involvement from CDRH2, and mainly indirect contribution by CDRH1 (i.e. via stabilization of CDRH3). Accordingly, the heavy chain of XAB1 did not appear to offer promising opportunities for affinity maturation.

In contrast, the XAB1 light chain did offer some opportunities in amino acid residues 30 to 32, with an optional insertion of up to 4 amino acid residues (CDRL1), amino acids 51 to 53 and 56 (CDRL2) and amino acid residues 92 and 93, with an optional insertion of up to 4 amino acid residues.

The availability of the published crystal structure for homodimeric human IL-17F, and the structure of homodimeric IL-17F in complex with the human receptor IL-17RA allowed for predictions to be made based on the observed structures of crystallized IL-17A and IL-17A in complex with XAB1 (and variants thereof).

The structural similarities predicted between IL-17F and IL-17A (on the basis of sequence identity and homology) were investigated. IL-17F and IL-17A bore a structural resemblance. The inventors hypothesized that IL-17A would bind to the N-terminal domain of its receptor in the same manner as has been shown for the published IL-17F/IL-17RA complex (Ely L K et al 2009, Nat Immunol. 10:1245-51).

On the basis of the observed structure and comparison of the known sequences for human IL-17A and IL-17F, along with the sequence of IL-17A derived from other species, a number of additional predictions were made by the inventors:

It was expected that XAB1 (and antibodies variants derived there from having an improved affinity for the epitope targeted by XAB1) would be highly specific for human IL-17A. It was hypothesized that such antibodies would retain some cross-reactivity with IL-17A from other species (on the basis of the high degree of conserved sequence identity or homology between species). However, on the basis of the available sequence data and structural predictions it was not clear to what extent cross-reactivity with species variants of IL-17A could be expected. Given the lack of structural similarity with other Interleukins, cross-reactivity with such molecules (from humans or other species) was expected to be very unlikely.

In addition, differences between the sequences of IL-17A and IL-17F (in particular N-terminal region) gave rise to predictions that the anti-IL-17A antibodies of the disclosure would not bind to IL-17F. For example, overlays of the two crystal structures indicated that steric hindrance would prevent binding between these antibodies and IL-17F. Furthermore, an extrapolation to the structure of IL-17AF heterodimers also suggested that such interference, in particular in the N-terminal region, would hamper binding of the antibodies to IL-17AF heterodimers and thereby result in a lack of binding to IL-17AF, i.e. a lack of cross-reactivity by these antibodies for IL-17AF heterodimers.

Example 3

Generation of Affinity Matured Antibody Variants

Actual affinity maturation of the initial antibody XAB1 focused on the light chain, for reasons discussed above. The work was carried out in three steps: (i) library generation, (ii) library screening, and (iii) candidate characterisation.

The protein engineering work (i.e. affinity maturation) was carried out in the Fab fragment format for ease of handling. Candidates were formatted back to full IgG after engineering.

(i) Library Generation

The DNA sequence encoding the variable domain of the light chain was mutated to create a library of gene variants. Two different approaches (A and B) were used for library generation, providing two separate libraries.

1) Method A—Random Mutation by Error Prone PCR:

The DNA region encoding the variable domain of the light chain of XAB1 was randomly mutated using error prone PCR. In more detail, this region was amplified using the polymerase Mutazyme II, which introduced mutations at a high frequency (for more detail, see the guidance supplied with the GeneMorph II random mutagenesis kit, supplied by Stratagene #200550). However, any suitable random mutation technique or strategy could be used.

The pool of PCR fragment variants was then cloned by cutting and pasting into the expression vector of XAB1. Essentially, the parent, unmutated sequence was cut out of the expression vector and replaced by a randomly mutagenized sequence which was pasted in its place. Standard molecular biology techniques were used to accomplish this.

This resulted in a library of expression vector variants comprising a variety of randomly mutagenized variable domain sequences.

2) Method B—Mutation by Rational Design:

Under this approach, the generation of the library was guided by the structural analysis carried out as a precursor to affinity maturation. Specific amino acid residues (in particular in CDR1 of the light chain of XAB1) were targeted based on the epitope and paratope information derived from the crystal structure described above.

Three amino acid residues, selected on the basis of the crystal structure information, were fully randomised. Standard molecular biology approaches were used for the construction.

Firstly, a fragment of the variable region encoding the appropriate CDR and a first part of the light chain framework was amplified by PCR, using degenerate oligonucleotides. That is, the oligonucleotides, encoding the CDR were synthesised in such a way as to provide a variety of bases at a defined position or positions. Design of the oligonucleotide enabled randomization of specifically targeted amino acid positions in the CDR by NNK degenerated codons (in which N stands for all 4 bases, A, T, C and G and K for G and T) and allowed all 20 natural amino acids at those positions.

Following this first step, a second fragment overlapping the first one and encoding the remaining part of the light chain, was also amplified by PCR. Both fragments were then assembled by an "assembly" PCR to generate the complete variable light chain and cloned back into the expression vector in a 'cut and paste' manner. Thereby the parental sequence was replaced with a range of rationally mutated sequences, whereby at specific amino acid positions all 20 natural amino acids were represented.

(ii) Library Screening

Once libraries comprising sequences encoding XAB1 variants had been generated it was necessary to screen them in order to select those which had superior characteristics to the parental XAB1 sequence, for example higher affinity for IL-17A.

Two screening techniques were used. Firstly, a high throughput screening was done by "colony filtration screening" (CFS). This assay permitted a convenient screening of large number of clones. It allowed reduction to positive hits prior to ELISA screening, which was useful in particular for the random approach "method A" as the library size was much larger ($>10^5$) compared to the library size in "method B" (only 8000). ELISA screening is convenient for $10^4$ clones or less and gives more quantitative results.

1) Colony Filtration Screening (CFS):

The protocol for CFS was based on Skerra et al. 1991, Anal Biochem 196:151-155. Some adaptations were made.

E. coli colonies expressing the Fab variant libraries were grown on a filter on top of a Petri dish containing LB agar and glucose. In parallel, a PVDF membrane was coated with the target protein (IL-17A). The coated membrane was placed on the agar plate. The filter with colonies of Fab fragment expressing E. coli was placed on top of the membrane. The Fab fragments expressed by the cells diffused from the colonies and bound the target IL-17A. The Fab fragment thus captured on the PVDF membrane was then detected using a secondary antibody conjugated with alkaline phosphatase for Western staining. The conditions for selecting only variants with improved binding properties were previously established using XAB1 as reference.

More specifically, after transformation of *E. coli* cells with the library, the cells were spread on a Durapore™ membrane filter (0.22 μm GV, Millipore®, cat #GVWP09050) placed on a Petri dish containing LB agar+1% glucose+antibiotic of interest. The plates were incubated overnight at 30° C.

The PVDF membrane (Immobilon-P, Millipore®, cat #IPVH08100) was pre-wet in methanol, washed in PBS and coated with a huIL-17A solution at 1 μg/ml in PBS. The membrane was incubated overnight at room temperature. After coating, the membrane was washed 2 times in Tris buffered saline (TBS)+0.05% Tween (TBST) and blocked two hours at room temperature in 5% milk TBST. Then, the membrane was washed four times in TBST and soaked in 2xYT medium with 1 mM IPTG. This membrane, called the capture membrane was placed onto a LB agar plate with 1 mM IPTG+antibiotic of interest, and was covered with the Durapore membrane with the colonies on top. The resulting sandwich was incubated four hours at 30° C.

After this incubation, the capture membrane was washed 4 times with TBST and blocked in 5% milk TBST for 1 hour at room temperature. Then, the membrane was washed once with TBST and incubated with a secondary antibody (anti-hu_kappa light chain antibody, alkaline-phosphatase (AP) conjugated, Sigma # A3813, diluted 1:5000 in 2% milk TBST), 1 hour at room temperature. Afterward, the membrane was washed 4 times in TBST, once in TBS and incubated in the substrate solution (SigmaFast BCIP/NBT tablet, 1 tablet in 10 ml $H_2O$). When the signal reached the expected intensity the membrane was washed with water and allowed to dry.

After development of the signal on the capture membrane, the colonies giving stronger signal than the parental XAB1 were picked and allowed to proceed to a secondary ELISA screening described below.

2) ELISA Screening:

Following the CFS, ELISA was used to screen the candidates selected by CFS. In brief, for the relative low number of variants identified by error-prone PCR mutagenesis (i.e. library A) the ELISA was performed manually in a 96 well format. In contrast, for the libraries constructed by rational design (method B), a larger number of improved clones needed to be screened at ELISA level to be able to discriminate between their different binding affinity to IL-17A and identify the clones with the highest affinity. An ELISA robot was used for that purpose in a 384 well plate format. However, the ELISA protocol was the same in each case, the only difference being the volumes of reagents.

a) Cell Cultures:

Clones were first grown overnight at 30° C., 900 rpm, in 2xYT medium+1% glucose+antibiotic of interest. The plates containing these cultures were called master plates.

The next day, aliquots of cultures from the master plates were transferred into expression plates containing 2xYT medium+0.1% glucose+antibiotic of interest. These plates were incubated at 30° C., 900 rpm about 3 hours. Then isopropyl 8-D-1-thiogalactopyranoside (IPTG) solution was added to a final concentration of 0.5 mM. The plates were incubated overnight at 30° C., 990 rpm.

The next day, lysis buffer (2×) Borate buffered saline (BBS) solution (Teknova #B0205)+2.5 mg/ml lysosyme+10 u/ml Benzonase) was added to the cultures. Plates were incubated 1 hour at room temperature, then 12.5% milk TBST was added for blocking. After 30 min incubation, cells lysates were diluted 1:10 in 2% milk TBST and were transferred into the ELISA plates.

b) ELISA:

ELISA plates (Nunc Maxisorp) were coated with a huIL-17A solution at 1 μg/ml during 1 hour. The plates were washed once with TBST and blocked 1 hour with 5% milk TBST. After blocking, plates were washed 3 times with TBST and then, diluted cell lysates were loaded on the plates and incubated 1 hour. Afterward, plates were washed 3 times with TBST and were incubated 1 hour with a secondary antibody AP conjugated.

The plates were finally washed 3 times with TBST and then incubated with the substrate solution (AttoPhos substrate Set, Roche #11 681 982 001). The whole process was performed at room temperature.

In addition to the "classic" ELISA described above, modified ELISA were also undertaken for a better discrimination between clones with very high affinity (in the pico-molar range) for the target protein. An "off-rate" ELISA and a "competition" ELISA were developed for this purpose, as detailed below.

c) "Off-Rate" ELISA:

For this assay, the modification compared to the "classic" ELISA protocol regarded the washing step after the binding step (incubation of cell lysate in ELISA plates). In the "classic" protocol, the plate was washed 3 times with TBST. The washing solution was dispensed and immediately aspirated, without any incubation time. For the "off-rate" ELISA, the plate was washed 6 times during at least 3 hours. This long wash increased the stringency of the assay, and allowed identifying clones with a slow off-rate.

d) "Competition" ELISA:

This modified ELISA protocol included an extra step after the binding step. After incubation of cell lysate, the plates were washed 3 times with TBST and then, a solution of the parental XAB1 (200 nM in 2% milk TBST) was incubated overnight at room temperature. This long incubation with an excess of the parental Fab allowed, as in the case of "off-rate" ELISA, to identify clones with slow off-rate, which lead to better discrimination between clones with an affinity in the picomolar range. The rest of the protocol was similar to the "classic" ELISA protocol. The secondary antibody used in this case was an AP conjugated anti-Flag tag antibody, since the Fabs variants from the library had a Flag tag at the C-terminus of the heavy chain but not the parental XAB1 Fab used for the competition.

(iii) Candidate Characterisation

The hits identified during the screening were produced on a larger scale for further physicochemical characterisation and to confirm high affinity binding to IL-17A, and/or other advantageous properties in additional assays. These are described below in more detail.

(iv) Results: Screening and Initial Characterization of Candidates Following Affinity Maturation of XAB1

1) Random Mutagenesis Approach (Method A):

The mutation rate after the error-prone PCR library generation was found to peak at 2 to 3 mutations per gene. Around $3 \times 10^4$ clones were screened by colony filter screening and a number of 94 clones were identified as improved and allowed to proceed to binding, off-rate and competition ELISA. ELISA data in combination with sequencing results led to the identification of 6 candidates highlighting 3 potential hot spots for improvement, Gly at position 28 to Val (G28V) in LCDR1; Gly at position 66 to Val (G66V) or Ser (G66S) in framework 3; Asn92 to Asp (N92D) in LCDR3 (data not shown, but positioning is identical to that of XAB2, VL, i.e. SEQ ID NO: 25).

A stop codon was observed in one of the clones, but was not relevant as the *E. coli* strain used was an amber suppressor strain allowing read-through. Based on the data obtained, a G28V and G66V mutation appeared to cause the best improvement. A variant of XAB1 was generated by standard molecular biology techniques carrying the two point mutations mentioned. A further variant was cloned having the N92D substitution in addition, in order to test whether the removal of the potential post-translational deamidation site (N92, S93) would be beneficial. More detailed profiling was done on those two variants, in particular of the triple mutant variant referred to as XAB_A2 which finally led to XAB2. In XAB2, amino acids number 1 to 23 according to the Kabat definition constitute framework 1, amino acids number 24 to 34 (Kabat) constitute LCDR1, amino acids number 35 to 49 (Kabat) constitute framework 2, amino acids 50 to 56 (Kabat) constitute LCDR2, amino acids 57 to 88 (Kabat) constitute framework 3, amino acids 89 to 97 (Kabat) constitute LCDR3 and amino acids 98 to 107 (Kabat) constitute framework 4. The same subdivision of other VL sequences according to embodiments of the disclosure also applies.

Thus, the G66V substitution mentioned above is in a framework region, which is called the outer loop. This framework region is able to contribute to binding in some cases. Based on the available structural information it was retrospectively suggested that this mutation indeed might be able to interact with a region of IL-17A which cannot be resolved from the crystal structure but may be in proximity to the outer loop.

2) Rational Mutagenesis Approach (Method B):

A snapshot of the amino acid distribution at the randomized positions was generated by sequencing of 32 randomly picked members. There was no significant bias, though statistics with this low number of sequences cannot be done. Around 4×10$^4$ clones were screened which oversampled the theoretical library size of 8000. A high number of hits were identified and 2630 clones were allowed to proceed to ELISA screening. Performing binding, off-rate and competition ELISA, 60 clones with the highest improvements were sequenced. In those 60 clones 22 unique sequences were found, and the result is summarized in Table 11.

TABLE 11

ELISA of all selected 22 unique candidates. Values are normalized to parental Fab XAB1. The representation indicates how often a certain sequence was found within the 60 hits. The difference in amino acid sequence is given in the three last columns. XAB1 has the amino acids I S A at those positions. ELISA signals determined from crude extract of Fab expression culture from E. coli.

| Candidate name | Classic ELISA | Off-rate ELISA | Competiton ELISA | Representation % | 30 | 31 | 32 |
| --- | --- | --- | --- | --- | --- | --- | --- |
| MB491 | 2.1 | 43.0 | 44.2 | 5 | F | F | W |
| MB483 | 3.1 | 47.1 | 45.2 | 2 | F | W | T |
| MB447 | 3.0 | 45.5 | 57.0 | 5 | F | W | W |
| MB457 | 2.7 | 34.7 | 41.0 | 5 | I | W | S |
| MB464 | 2.7 | 34.9 | 36.9 | 7 | I | Y | Q |
| MB432 | 2.3 | 44.2 | 37.3 | 12 | L | F | A |
| MB454 | 2.9 | 34.2 | 36.6 | 2 | L | W | A |
| MB444 | 3.2 | 48.9 | 52.4 | 2 | L | W | E |
| MB456 | 2.4 | 45.1 | 46.7 | 2 | L | W | H |
| MB440 | 2.8 | 52.5 | 54.0 | 5 | L | W | Q |
| MB450 | 2.9 | 41.5 | 53.3 | 5 | M | W | W |
| MB435 | 2.7 | 44.7 | 44.6 | 2 | N | W | E |
| MB438 | 2.7 | 41.5 | 41.1 | 7 | P | Y | A |
| MB453 | 2.7 | 43.3 | 46.4 | 9 | V | F | W |
| MB448 | 2.9 | 40.4 | 51.5 | 5 | V | W | M |
| MB486 | 1.9 | 58.5 | 64.9 | 2 | W | W | M |
| MB434 | 2.4 | 44.4 | 39.5 | 7 | W | W | Y |
| MB458 | 2.7 | 33.0 | 42.1 | 5 | W | Y | Q |
| MB463 | 2.7 | 34.2 | 31.6 | 2 | Y | F | E |
| MB468 | 2.8 | 43.9 | 60.0 | 5 | Y | W | E |
| MB433 | 2.3 | 39.7 | 29.3 | 2 | Y | W | G |
| MB461 | 2.9 | 49.8 | 62.8 | 2 | Y | W | T |

Of the 22 unique clones, 6 were selected for 0.5 L scale standard E. coli expression and two step purification by IMAC (Ni-NTA) and SEC. Purified Fabs were then used to confirm the improvement in binding by ELISA.

ELISA results of selected and purified Fab candidates in comparison to XAB1 are shown in FIG. 3, where the graph numbering corresponds to the candidate designation as follows: 1 is MB440; 2 is MB464; 3 is MB468; 4 is MB444; 5 is MB435; 6 is MB463; 7 is XAB1.

Figure 3A:
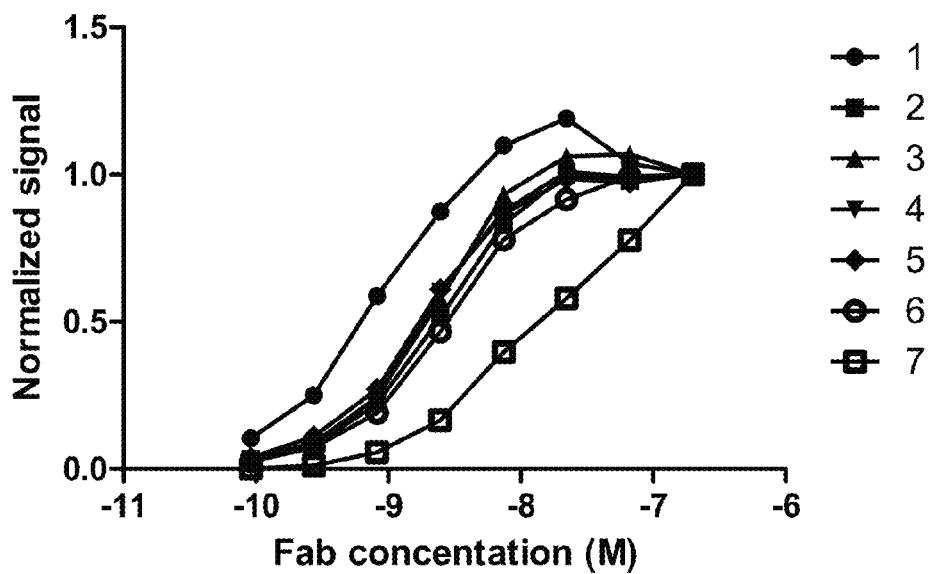
FIG. 3A is a graph showing the normalized signal versus the Fab Concentration (M).
Figure 3B:
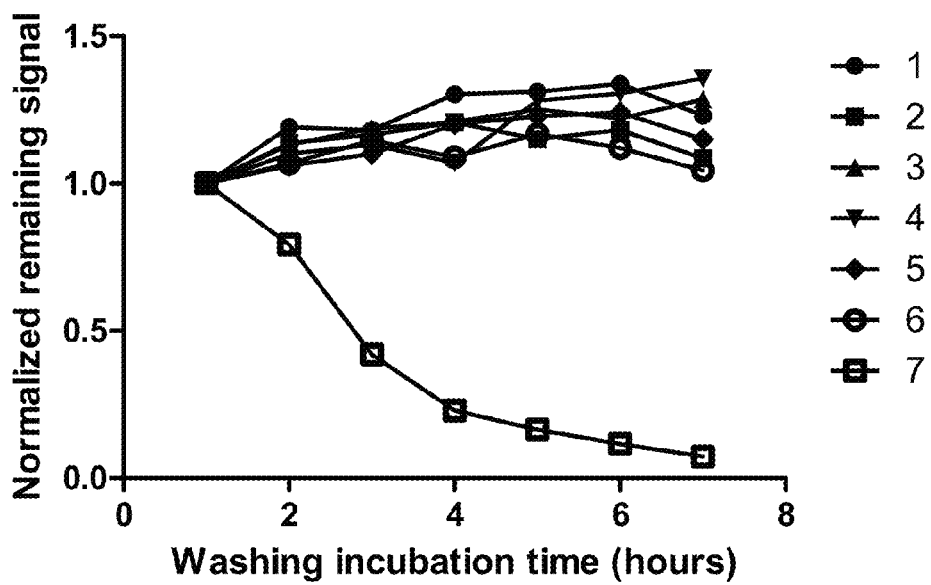
FIG. 3B is a graph showing the normalized remaining signal versus the washing incubation time (hours).

FIG. 3A is a graph showing the normalized signal versus the Fab concentration (M). It can be seen that all the selected clones resulted in a higher signal than XAB1. FIG. 3B is a graph showing the normalized remaining signal versus the washing incubation time (hours). All the selected clones result in a higher signal than XAB1. FIG. 3C is a graph showing the normalized signal versus the Fab competitor concentration (M). Again, it can be seen that all the selected clones result in a higher signal than XAB1.

Example 4

Targeting a Potential Post-Translational Deamidation Site

The inventors hypothesized that the amino acid motif asparagine followed by glycine (NG) or, to lower extend also when followed by serine (NS), may be susceptible to post-translational deamidation. Such motifs are present in L-CDR2 (position 56/57) and L-CDR3 (92/93) of the antibody XAB1. Four IgG variants were generated in order to test whether the NG site could be removed without affecting binding and activity properties. These four point mutation variants were cloned by standard molecular biology procedures and produced by standard transient transfection of HEK cells in 100 ml scale and purified via a protein A column.

Purified IgG variants were analyzed in an in vitro neutralization assay (e.g. as described in examples 12 and 13) to compare their activity to the parental XAB1 IgG. Results showed that out of these four variants, three had a reduced activity. But the candidate XAB_B12 (mutation N56Q) retained activity compared to the parental XAB1.

TABLE 12

Overview of sequence modifications to XAB1, and corresponding effect on in vitro neutralization.

| Kabat CDR | | L-CDR2 | | | | | | | | | IC50(nM) Hu | IC50(nM) Hu |
|---|---|---|---|---|---|---|---|---|---|---|---|---|
| Residue# | | 49 | 50 | 51 | 52 | 53 | 54 | 55 | 56 | 57 | IL-6 | IL-8 |
| Kabat# | | 49 | 50 | 51 | 52 | 53 | 54 | 55 | 56 | 57 | sec | sec |
| IgG variants | Generic name | | | | | | | | | | | |
| XAB1 | XAB1 | Y | D | A | S | S | L | E | N | G | 4 | 3 |
| XAB_G57T | XAB_A6 | Y | D | A | S | S | L | E | N | T | 22 | 23 |
| XAB_N56Q | XAB_B12 | Y | D | A | S | S | L | E | Q | G | 2 | 3 |
| XAB_N56T | XAB_B13 | Y | D | A | S | S | L | E | T | G | 11 | 15 |
| XAB_N56S | XAB_B14 | Y | D | A | S | S | L | E | S | G | 13 | 17 |

Having thus identified the most suitable substitution, it was introduced to the most promising hits identified during the affinity maturation process, resulting in XAB2 (XAB_A2 N56Q), XAB3 (MB468 N56Q), XAB4 (MB435 N56Q). They were produced by standard transient transfection of HEK cells and purified via protein A column along with XAB5 (MB435), which still carried the NG site.

The NG motif was removed (N56Q) for the XAB2, XAB3, XAB4, but was still present in XAB5. The NS motif in L-CDR3 was removed (N92D) in XAB2, as found during the random affinity maturation approach. Therefore, an optimal set of variants was available to test the susceptibility for deamidation of the potential sites.

The four purified candidates were diluted in a buffer pH 8 and incubated at 40° C. in order to force the deamidation reaction. Aliquots were taken at several time points to determine the degree of deamidation by cation exchange chromatography (CEX), according to principles well known to a person skilled in the art, and the in vitro neutralization activity by a cell based assay was determined (e.g. as described in examples 12 and 13).

CEX results showed an increase of acidic variants percentage over time, as expected for any IgG, likely due to post-translational modification sites in the antibody framework, but the extent of increase was higher for XAB5 than for the other candidates, i.e. 72% vs. 46% after one week and 94% vs. 83% after 4 weeks. Finally, in vitro neutralization activity assay results correlated with the CEX results, showing that XAB5 lost activity after 4 weeks incubation during forced deamidation condition. Size-exclusion chromatography-multi angle light scattering methodology (SEC-MALS), well known to a person skilled in the art, was used to monitor the aggregation levels in the samples.

The data is summarized in Table 13.

TABLE 13

Analysis by SEC-MALS, in vitro neutralization activity and CEX.

| Antibody | M [a] [%] | $EC_{50}$ [b] [ng/ml] | CEX[c] [%] | M [a] [%] | $EC_{50}$ [b] [ng/ml] | CEX[c] [%] |
|---|---|---|---|---|---|---|
| | T = 0 weeks | | | T = 1 weeks | | |
| XAB2 | 99 | 45 | 15 | 98 | n.d. | 45 |
| XAB3 | 99 | 40 | 14 | 98 | n.d. | 44 |
| XAB5 | 99 | 45 | 18 | 98 | n.d. | 72 |
| XAB4 | 99 | 48 | 15 | 98 | n.d. | 48 |

TABLE 13-continued

Analysis by SEC-MALS, in vitro neutralization activity and CEX.

| Antibody | M [a] [%] | $EC_{50}$ [b] [ng/ml] | CEX[c] [%] | NG[d] sites | NS[d] sites |
|---|---|---|---|---|---|
| | T = 4 weeks | | | | |
| XAB2 | 95 | 47 | 85 | 0 | 0 |
| XAB3 | 97 | 40 | 81 | 0 | 1 |
| XAB5 | 94 | 61 | 94 | 1 | 1 |
| XAB4 | 94 | 47 | 84 | 0 | 1 |

[a] monomer by SEC-MALS,
[b] inhibition of IL-6 secretion after cell stimulation with 80 ng/ml IL-17,
[c] acidic variants by exchange chromatography,
[d] number of sites in CDRs (framework region not considered)

These data indicated successful removal of a potential post-translational deamidation site, which could have had an effect on antibody activity. This is advantageous, since XAB2, XAB3 and XAB4 are therefore likely to achieve a more homogeneous product than XAB1 as no post-translational deamidation can occur during production or storage affecting the antibody activity.

Example 5

X-Ray Analysis of Antibody Variants Derived by Affinity Maturation: XAB2

In brief, the XAB2 Fv was cloned and expressed in *E. coli* TGf1- with a C-terminal hexahistidine tag on the heavy-chain and a C-terminal Strep-tag on the light-chain, according to principles well known to a person skilled in the art. The recombinant protein was purified by Ni-chelate chromatography and size-exclusion chromatography (SPX-75).

The XAB2 Fv fragment complex with human IL-17A was then prepared using standard methodology. In brief, human IL-17A (1.5 mg) was mixed with an excess of XAB2 Fv (3.7 mg) and the complex was run on a S100 size-exclusion chromatography, in 10 mM TRIS pH 7.4, 25 mM NaCl. The protein complex was then concentrated by ultra-filtration to 26.3 mg/ml and crystallized.

Standard crystallization protocols were followed. In brief, crystals were grown at 19° C. in SD2 96-well plates, using the method of vapour diffusion in sitting drops. The protein stock was mixed 1:1 with a crystallization buffer containing 0.2M calcium acetate, 20% PEG 3,350. Total drop size was 0.4 μl. Prior to X-ray data collection, one crystal was briefly transferred into a 1:1 mix of the crystallization buffer with 30% PEG 3,350, 30% glycerol, and then flash cooled into liquid nitrogen.

X-ray data collection and processing was carried out using standard protocols. Briefly, X-ray data to 2.0 Å resolution were collected at the Swiss Light Source, beamline X06DA, with a MAR225 CCD detector, using 1.0000 Å X-ray radiation. In total, 360 images of 0.5° oscillation each were recorded at a crystal-to-detector distance of 190 mm and processed with the XDS software package. The crystal belonged to space group $P2_12_12$ with cell parameters a=184.72 Å, b=55.56 Å, c=71.11 Å, $\alpha=\beta=\gamma=90°$. R-sym to 2.0 Å resolution was 5.2% and data completeness 100.0%.

As the crystal of the XAB2 Fv complex was highly isomorphous with the crystal of the XAB1 Fv complex (Example 2), the structure of the latter was used as input model for an initial run of crystallographic refinement with the program CNX. Iterative model correction and refinement was performed with Coot (Crystallographic Object-Oriented Toolkit) and CNX (Crystallography & NMR eXplorer) version 2002, until no further significant improvements could be made to the crystallographic model. Final R- and R-free for all data were 0.214 and 0.259, respectively. The final refined model showed a root-mean-square deviation (RMSD) from ideal bond lengths and bond angles of 0.005 Å and 0.9°, respectively.

Results

The results of the X-ray refinement of the XAB2 Fv complex with human IL-17A are provided in Table 14 and the three-dimensional structure of this complex is shown in FIG. 4. The X-ray crystallography analysis confirmed that the variant antibody XAB2 retained the target specificity and bound with high affinity to essentially the same epitope as the parental XAB1 antibody. However, in the XAB1 complex structure, the light-chain loop comprising Gly66 adopts a conformation that is no longer possible when this residue is mutated to a valine. As a consequence, in the XAB2 complex, the Gly66 to valine mutation (G66V) forces the loop to adopt a new conformation, and the valine side-chain makes hydrophobic contacts to Ile51 of IL-17A (FIG. 5). Two more IL-17A residues, Pro42 and Arg43, become visible (ordered) in this crystal structure. These antigen residues make additional binding interactions with the XAB2 antibody, in particular hydrophobic contacts to Val28 (FIG. 5).

TABLE 14

X-ray refinement of the XAB2 Fv complex with IL-17A obtained by the program CNX.

```
REMARK 3
REMARK 3    REFINEMENT.
REMARK 3    PROGRAM    : CNX 2002
REMARK 3    AUTHORS    : Brunger, Adams, Clore, Delano,
REMARK 3                 Gros, Grosse-Kunstleve, Jiang,
REMARK 3                 Kuszewski, Nilges, Pannu, Read,
REMARK 3                 Rice, Simonson, Warren
REMARK 3                   and
REMARK 3                 Accelrys Inc.,
REMARK 3                 (Badger, Berard, Kumar, Szalma,
REMARK 3                 Yip, Dzakula).
REMARK 3
REMARK 3    DATA USED IN REFINEMENT.
REMARK 3       RESOLUTION RANGE HIGH (ANGSTROMS) : 2.00
REMARK 3       RESOLUTION RANGE LOW  (ANGSTROMS) : 71.11
REMARK 3       DATA CUTOFF    (SIGMA(F)) : 0.0
REMARK 3       DATA CUTOFF HIGH    (ABS(F)) : 2329350.20
REMARK 3       DATA CUTOFF LOW     (ABS(F)) :   0.000000
REMARK 3       COMPLETENESS (WORKING+TEST) (%) : 99.8
REMARK 3       NUMBER OF REFLECTIONS    : 50409
REMARK 3
REMARK 3    FIT TO DATA USED IN REFINEMENT.
REMARK 3       CROSS-VALIDATION METHOD   : THROUGHOUT
REMARK 3       FREE R VALUE TEST SET SELECTION : RANDOM
REMARK 3       R VALUE      (WORKING SET) : 0.214
REMARK 3       FREE R VALUE              : 0.259
REMARK 3       FREE R VALUE TEST SET SIZE (%) : 5.0
REMARK 3       FREE R VALUE TEST SET COUNT   : 2521
REMARK 3       ESTIMATED ERROR OF FREE RVALUE : 0.005
REMARK 3
REMARK 3    FIT IN THE HIGHEST RESOLUTION BIN.
REMARK 3       TOTAL NUMBER OF BINS USED      : 6
REMARK 3       BIN RESOLUTION RANGE HIGH    (A) : 2.00
REMARK 3       BIN RESOLUTION RANGE LOW     (A) : 2.13
REMARK 3       BIN COMPLETENESS (WORKING+TEST) (%) :100.0
REMARK 3       REFLECTIONS IN BIN (WORKING SET) : 7858
REMARK 3       BIN R VALUE        (WORKING SET) : 0.262
REMARK 3       BIN FREE RVALUE                 : 0.304
REMARK 3       BIN FREE RVALUE TEST SET SIZE (%) : 5.0
REMARK 3       BIN FREE RVALUE TEST SET COUNT   : 414
REMARK 3       ESTIMATED ERROR OF BIN FREE R VALUE : 0.015
REMARK 3
REMARK 3    NUMBER OF NON-HYDROGEN ATOMS USED IN REFINEMENT.
REMARK 3       PROTEIN ATOMS    : 5055
REMARK 3       NUCLEIC ACID ATOMS   :  0
REMARK 3       HETEROGEN ATOMS      :  0
REMARK 3       SOLVENT ATOMS    : 376
REMARK 3
REMARK 3    B VALUES.
REMARK 3       FROM WILSON PLOT       (A**2) : 27.8
```

TABLE 14-continued

X-ray refinement of the XAB2 Fv complex
with IL-17A obtained by the program CNX.

| | | |
|---|---|---|
| REMARK 3 | MEAN B VALUE (OVERALL, A**2) : 37.3 | |
| REMARK 3 | OVERALL ANISOTROPIC B VALUE. | |
| REMARK 3 | B11 (A**2) : −0.85 | |
| REMARK 3 | B22 (A**2) : 3.93 | |
| REMARK 3 | B33 (A**2) : −3.08 | |
| REMARK 3 | B12 (A**2) : 0.00 | |
| REMARK 3 | B13 (A**2) : 0.00 | |
| REMARK 3 | B23 (A**2) : 0.00 | |
| REMARK 3 | | |
| REMARK 3 | BULK SOLVENT MODELING. | |
| REMARK 3 | METHOD USED : FLAT MODEL | |
| REMARK 3 | KSOL : 0.338594 | |
| REMARK 3 | BSOL : 46.0594 (A**2) | |
| REMARK 3 | | |
| REMARK 3 | ESTIMATED COORDINATE ERROR. | |
| REMARK 3 | ESD FROM LUZZATI PLOT (A) : 0.25 | |
| REMARK 3 | ESD FROM SIGMAA (A) : 0.19 | |
| REMARK 3 | LOW RESOLUTION CUTOFF (A) : 5.00 | |
| REMARK 3 | | |
| REMARK 3 | CROSS-VALIDATED ESTIMATED COORDINATE ERROR. | |
| REMARK 3 | ESD FROM C-V LUZZATI PLOT (A) : 0.31 | |
| REMARK 3 | ESD FROM C-V SIGMAA (A) : 0.22 | |
| REMARK 3 | | |
| REMARK 3 | RMS DEVIATIONS FROM IDEAL VALUES. | |
| REMARK 3 | BOND LENGTHS (A) : 0.005 | |
| REMARK 3 | BOND ANGLES (DEGREES) : 0.9 | |
| REMARK 3 | DIHEDRAL ANGLES (DEGREES) : 21.0 | |
| REMARK 3 | IMPROPER ANGLES (DEGREES) : 0.70 | |
| REMARK 3 | | |
| REMARK 3 | ISOTROPIC THERMAL MODEL : RESTRAINED | |
| REMARK 3 | | |
| REMARK 3 | ISOTROPIC THERMAL FACTOR RESTRAINTS. RMS SIGMA | |
| REMARK 3 | MAIN-CHAIN BOND (A**2) : 1.49 ; 1.50 | |
| REMARK 3 | MAIN-CHAIN ANGLE (A**2) : 2.44 ; 2.00 | |
| REMARK 3 | SIDE-CHAIN BOND (A**2) : 1.95 ; 2.00 | |
| REMARK 3 | SIDE-CHAIN ANGLE (A**2) : 2.93 ; 2.50 | |
| REMARK 3 | | |
| REMARK 3 | NCS MODEL : NONE | |
| REMARK 3 | | |
| REMARK 3 | NCS RESTRAINTS. RMS SIGMA/WEIGHT | |
| REMARK 3 | GROUP 1 POSITIONAL (A) : NULL ; NULL | |
| REMARK 3 | GROUP 1 B-FACTOR (A**2) : NULL ; NULL | |
| REMARK 3 | | |
| REMARK 3 | PARAMETER FILE 1 : protein_rep.param | |
| REMARK 3 | PARAMETER FILE 2 : water_rep.param | |
| REMARK 3 | PARAMETER FILE 3 : ion.param | |
| REMARK 3 | TOPOLOGY FILE 1 : protein.top | |
| REMARK 3 | TOPOLOGY FILE 2 : water.top | |
| REMARK 3 | TOPOLOGY FILE 4 : ion.top | |
| REMARK 3 | | |
| REMARK 3 | OTHER REFINEMENT REMARKS: NULL | |
| SSBOND 1 | CYS L 23 CYS L 88 | |
| SSBOND 2 | CYS H 22 CYS H 96 | |
| SSBOND 3 | CYS A 23 CYS A 88 | |
| SSBOND 4 | CYS B 22 CYS B 96 | |
| SSBOND 5 | CYS C 94 CYS C 144 | |
| SSBOND 6 | CYS C 99 CYS C 146 | |
| SSBOND 7 | CYS D 94 CYS D 144 | |
| SSBOND 8 | CYS D 99 CYS D 146 | |
| CRYST1 | 184.719 55.558 71.109 90.00 90.00 90.00 P 21 21 2 24 | |
| ORIGX1 | 1.000000 0.000000 0.000000 0.00000 | |
| ORIGX2 | 0.000000 1.000000 0.000000 0.00000 | |
| ORIGX3 | 0.000000 0.000000 1.000000 0.00000 | |
| SCALE1 | 0.005414 0.000000 0.000000 0.00000 | |
| SCALE2 | 0.000000 0.017999 0.000000 0.00000 | |
| SCALE3 | 0.000000 0.000000 0.014063 0.00000 | |

Figure 4A:
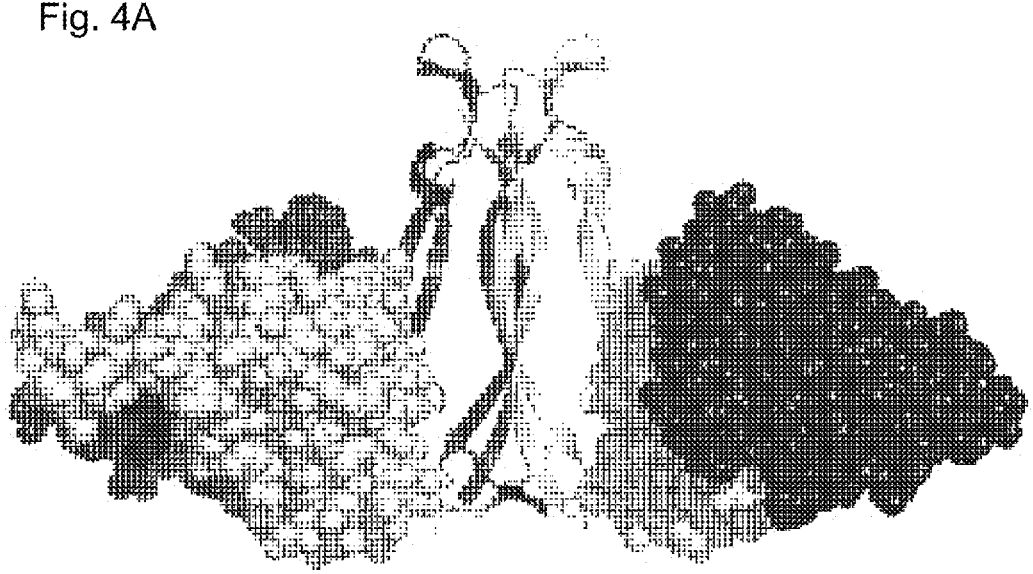
FIG. 4A shows the two XAB2 Fv fragments in complex with human IL-17A in space-filling representation and FIG. 4B shows the two XAB2 Fv fragments in complex with human IL-17A in cartoon representation.
Figure 4B:
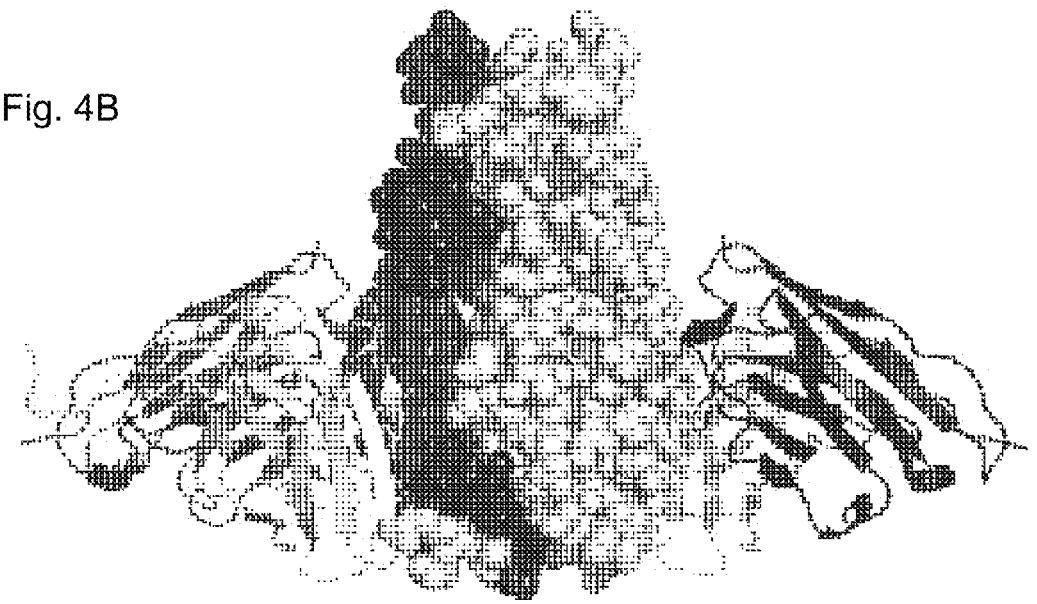
Figure 5:
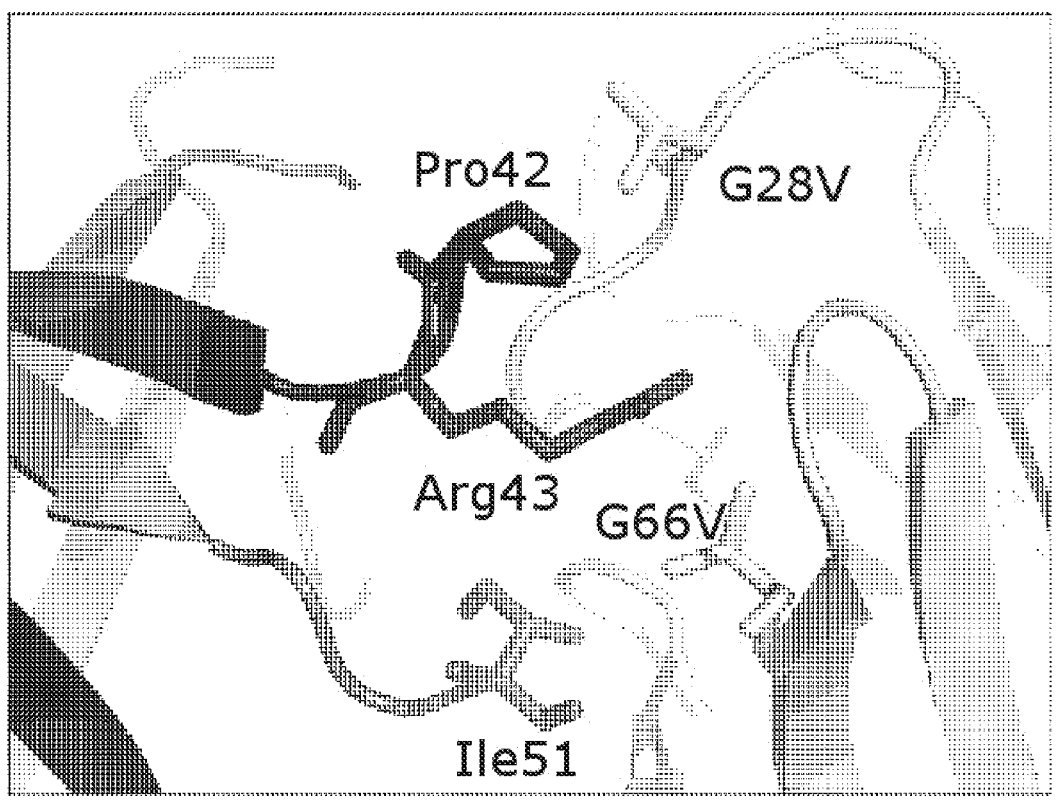
FIG. 5 provides the three-dimensional structure of the XAB2 Fv complex with human IL-17A as a close-up view.

FIG. 4 provides the three-dimensional structure of the XAB2 Fv complex with human IL-17A. FIG. 4A shows the two XAB2 Fv fragments in space-filling representation, and the IL-17A homodimer is shown in cartoon representation. FIG. 4B shows the two XAB2 Fv fragments in cartoon representation, and the IL-17A homodimer is shown in space-filling representation. The heavy- and light-chain of the XAB2 Fv are shown in dark and light grey, respectively. One chain of the IL-17A homodimer is shown in light grey, the other is shown in dark grey.

FIG. 5 provides the three-dimensional structure of the XAB2 Fv complex with human IL-17A as a close-up view of the antibody L-CDR1 and outer loop regions, bearing the glycine to valine mutations (G28V and G66V, respectively).

The G66V mutation leads to a change in the conformation of the outer loop, as well as to additional antibody-antigen contacts to IL-17A residues Pro42, Arg43 and Ile51. The XAB2 Fv is represented in light-grey cartoon, and the human IL-17A homodimer in darker shades of grey. Ile51 does not belong to the same IL-17A subunit as Pro42 and Arg43.

Example 6

X-Ray Analysis of Antibody Variants Derived by Affinity Maturation: XAB5

The XAB5 Fv was cloned and expressed in *E. coli* TGf1- with a C-terminal hexahistidine tag on the heavy-chain and a C-terminal Strep-tag on the light-chain. The recombinant protein was purified by Ni-chelate chromatography followed by size-exclusion chromatography on a SPX-75 column, in PBS buffer. LC-MS analysis showed the expected mass for the heavy-chain (13703.4 Da), and the presence of two forms of the light-chain: full-length (115aa; 12627.3 Da; ca. 27%) and with truncated Strep-tag (A1 to Q112; 12222.8 Da; ca. 73%).

The XAB5 Fv fragment complex with human IL-17A was then prepared using standard methodology. In brief, human IL-17A (1.4 mg) was mixed with an excess of XAB5 Fv (3.4 mg) and the complex was run on a S100 size-exclusion chromatography, in 10 mM TRIS pH 7.4, 25 mM NaCl. The protein complex was then concentrated by ultra-filtration to 16.5 mg/ml and crystallized.

Standard crystallization protocols were followed. In brief, crystals were grown at 19° C. in SD2 96 well-plates, using the method of vapour diffusion in sitting drops. The protein stock was mixed 1:1 with a crystallization buffer containing 15% PEG 5,000 MME, 0.1 M MES pH 6.5, 0.2M ammonium sulfate. Total drop size was 0.4 µl. Prior to X-ray data collection, one crystal was briefly transferred into a 1:1 mix of the crystallization buffer with 20% PEG 5,000 MME, 40% glycerol, and then flash cooled into liquid nitrogen.

X-ray data collection and processing was carried out using standard protocols. Briefly, X-ray data to 3.1 Å resolution were collected at the Swiss Light Source, beamline X10SA, with a Pilatus detector, using 1.00000 Å X-ray radiation. In total, 720 images of 0.25° oscillation each were recorded at a crystal-to-detector distance of 520 mm and processed with the XDS software package. The crystal belonged to space group C222$_1$ with cell parameters a=55.37 Å, b=84.08 Å, c=156.35 Å, α=β=γ=90°. R-sym to 3.1 Å resolution was 8.9% and data completeness 99.7%.

The structure was determined by molecular replacement with the program Phaser, using search models derived from the previously-determined XAB2 Fv complex. Iterative model correction and refinement was performed with Coot (Crystallographic Object-Oriented Toolkit) and CNX (Crystallography & NMR eXplorer) version 2002, until no further significant improvements could be made to the crystallographic model Final R- and R-free for all data were 0.222 and 0.305, respectively. The final refined model showed a root-mean-square deviation (RMSD) from ideal bond lengths and bond angles of 0.008 Å and 1.2°, respectively.

Results

The results of the X-ray refinement of the XAB5 Fv complex with human IL-17A are provided in Table 15 and the three-dimensional structure of this complex is shown in FIG. 6. In this crystal structure, the XAB5 Fv complex has exact crystallographic 2-fold symmetry: the asymmetric unit of the crystal contains only one half of the whole, dimeric complex. The XAB5 Fv makes contacts to both IL-17A subunits, but the vast majority of the intermolecular contacts are to only one subunit (around 90% of the IL-17A surface buried by the XAB5 Fv is contributed by one IL-17A subunit). The X-ray crystallography analysis confirmed that the variant antibody XAB5 retained the target specificity and bound with high affinity to essentially the same epitope as the parental XAB1 antibody. However, in the XAB5 complex structure, the light-chain CDRL1 bears three point mutations which provide enhanced binding to human IL-17A. Trp 31 of the XAB5 light-chain is engaged in strong hydrophobic/aromatic interactions with Tyr 85 of IL-17A and, to a lesser extent, Phe 133 of IL-17A. Asn 30 of the XAB5 light-chain donates a H-bond to the main-chain carbonyl of Pro 130 of IL-17A and is in van der Waals contact to Leu 49 (same IL-17A subunit) and Val 45 (other IL-17A subunit). Glu 32 of the XAB5 light-chain stabilizes the CDRL1 loop through intramolecular H-bonded interactions. Furthermore, Glu 32 makes favorable electrostatic interactions with Arg 124 of IL-17A, but is not engaged into a "head-to-head" salt-bridge interaction (FIG. 7).

TABLE 15

X-ray refinement of the XAB5 Fv complex with IL-17A obtained by the program CNX.

| | |
|---|---|
| REMARK 3 | |
| REMARK 3 | REFINEMENT. |
| REMARK 3 | PROGRAM   : CNX 2002 |
| REMARK 3 | AUTHORS    : Brunger, Adams, Clore, Delano, |
| REMARK 3 | Gros, Grosse-Kunstleve, Jiang, |
| REMARK 3 | Kuszewski, Nilges, Pannu, Read, |
| REMARK 3 | Rice, Simonson, Warren |
| REMARK 3 | and |
| REMARK 3 | Accelrys Inc., |
| REMARK 3 | (Badger, Berard, Kumar, Szalma, |
| REMARK 3 | Yip, Dzakula). |
| REMARK 3 | |
| REMARK 3 | DATA USED IN REFINEMENT. |
| REMARK 3 | RESOLUTION RANGE HIGH (ANGSTROMS) : 3.11 |
| REMARK 3 | RESOLUTION RANGE LOW (ANGSTROMS) : 46.25 |
| REMARK 3 | DATA CUTOFF    (SIGMA(F)) : 0.0 |
| REMARK 3 | DATA CUTOFF HIGH    (ABS(F)) : 3778977.84 |
| REMARK 3 | DATA CUTOFF LOW     (ABS(F)) : 0.000000 |
| REMARK 3 | COMPLETENESS (WORKING+TEST) (%) : 99.0 |
| REMARK 3 | NUMBER OF REFLECTIONS    : 6801 |
| REMARK 3 | |
| REMARK 3 | FIT TO DATA USED IN REFINEMENT. |

TABLE 15-continued

X-ray refinement of the XAB5 Fv complex
with IL-17A obtained by the program CNX.

```
REMARK  3      CROSS-VALIDATION METHOD   : THROUGHOUT
REMARK  3      FREE R VALUE TEST SET SELECTION : RANDOM
REMARK  3      R VALUE        (WORKING SET) : 0.222
REMARK  3      FREE R VALUE              : 0.305
REMARK  3      FREE R VALUE TEST SET SIZE (%) : 5.0
REMARK  3      FREE R VALUE TEST SET COUNT   : 340
REMARK  3      ESTIMATED ERROR OF FREE R VALUE : 0.017
REMARK  3
REMARK  3   FIT IN THE HIGHEST RESOLUTION BIN.
REMARK  3      TOTAL NUMBER OF BINS USED       : 6
REMARK  3      BIN RESOLUTION RANGE HIGH   (A) : 3.10
REMARK  3      BIN RESOLUTION RANGE LOW    (A) : 3.29
REMARK  3      BIN COMPLETENESS (WORKING+TEST) (%) : 89.9
REMARK  3      REFLECTIONS IN BIN   (WORKING SET) : 961
REMARK  3      BIN R VALUE       (WORKING SET) : 0.293
REMARK  3      BIN FREE R VALUE            : 0.403
REMARK  3      BIN FREE R VALUE TEST SET SIZE (%) : 4.9
REMARK  3      BIN FREE R VALUE TEST SET COUNT   : 50
REMARK  3      ESTIMATED ERROR OF BIN FREE R VALUE : 0.057
REMARK  3
REMARK  3   NUMBER OF NON-HYDROGEN ATOMS USED IN REFINEMENT.
REMARK  3      PROTEIN ATOMS   : 2492
REMARK  3      NUCLEIC ACID ATOMS  :   0
REMARK  3      HETEROGEN ATOMS    :   5
REMARK  3      SOLVENT ATOMS   : 4
REMARK  3
REMARK  3   B VALUES.
REMARK  3      FROM WILSON PLOT       (A**2) : 85.2
REMARK  3      MEAN B VALUE    (OVERALL, A**2) : 71.0
REMARK  3      OVERALL ANISOTROPIC B VALUE.
REMARK  3      B11 (A**2) : 23.21
REMARK  3      B22 (A**2) : 7.23
REMARK  3      B33 (A**2) :−30.44
REMARK  3      B12 (A**2) : 0.00
REMARK  3      B13 (A**2) : 0.00
REMARK  3      B23 (A**2) : 0.00
REMARK  3
REMARK  3   BULK SOLVENT MODELING.
REMARK  3      METHOD USED : FLAT MODEL
REMARK  3      KSOL   : 0.389339
REMARK  3      BSOL   : 59.5295 (A**2)
REMARK  3
REMARK  3   ESTIMATED COORDINATE ERROR.
REMARK  3      ESD FROM LUZZATI PLOT   (A) : 0.35
REMARK  3      ESD FROM SIGMAA      (A) : 0.42
REMARK  3      LOW RESOLUTION CUTOFF   (A) : 5.00
REMARK  3
REMARK  3   CROSS-VALIDATED ESTIMATED COORDINATE ERROR.
REMARK  3      ESD FROM C-V LUZZATI PLOT   (A) : 0.51
REMARK  3      ESD FROM C-V SIGMAA     (A) : 0.45
REMARK  3
REMARK  3   RMS DEVIATIONS FROM IDEAL VALUES.
REMARK  3      BOND LENGTHS       (A) : 0.008
REMARK  3      BOND ANGLES    (DEGREES) : 1.2
REMARK  3      DIHEDRAL ANGLES  (DEGREES) : 23.1
REMARK  3      IMPROPER ANGLES  (DEGREES) : 0.73
REMARK  3
REMARK  3   ISOTROPIC THERMAL MODEL : RESTRAINED
REMARK  3
REMARK  3   ISOTROPIC THERMAL FACTOR RESTRAINTS.  RMS  SIGMA
REMARK  3      MAIN-CHAIN BOND   (A**2) : 1.40 ; 1.50
REMARK  3      MAIN-CHAIN ANGLE  (A**2) : 2.49 ; 2.00
REMARK  3      SIDE-CHAIN BOND   (A**2) : 1.82 ; 2.00
REMARK  3      SIDE-CHAIN ANGLE  (A**2) : 2.93 ; 2.50
REMARK  3
REMARK  3   NCS MODEL : NONE
REMARK  3
REMARK  3   NCS RESTRAINTS.           RMS SIGMA/WEIGHT
REMARK  3      GROUP 1 POSITIONAL  (A) : NULL ; NULL
REMARK  3      GROUP 1 B-FACTOR  (A**2) : NULL ; NULL
REMARK  3
REMARK  3   PARAMETER FILE 1 : protein_rep.param
REMARK  3   PARAMETER FILE 2 : water_rep.param
REMARK  3   PARAMETER FILE 3 : ion.param
REMARK  3   TOPOLOGY FILE 1 : protein_no_cter.top
REMARK  3   TOPOLOGY FILE 2 : water.top
REMARK  3   TOPOLOGY FILE 4 : ion.top
```

TABLE 15-continued

X-ray refinement of the XAB5 Fv complex
with IL-17A obtained by the program CNX.

| | | | | |
|---|---|---|---|---|
| REMARK | 3 | | | |
| REMARK | 3 | OTHER REFINEMENT REMARKS: NULL | | |
| SSBOND | 1 | CYS S 23 | CYS S 88 | |
| SSBOND | 2 | CYS S 22 | CYS S 96 | |
| SSBOND | 3 | CYS S 94 | CYS S 144 | |
| SSBOND | 4 | CYS S 99 | CYS S 146 | |
| CRYST1 | 55.372 84.082 | 156.350 90.00 | 90.00 90.00 C 2 2 21 | 24 |
| ORIGX1 | 1.000000 0.000000 0.000000 | 0.00000 | | |
| ORIGX2 | 0.000000 1.000000 0.000000 | 0.00000 | | |
| ORIGX3 | 0.000000 0.000000 1.000000 | 0.00000 | | |
| SCALE1 | 0.018060 0.000000 0.000000 | 0.00000 | | |
| SCALE2 | 0.000000 0.011893 0.000000 | 0.00000 | | |
| SCALE3 | 0.000000 0.000000 0.006396 | 0.00000 | | |

Figure 6A:
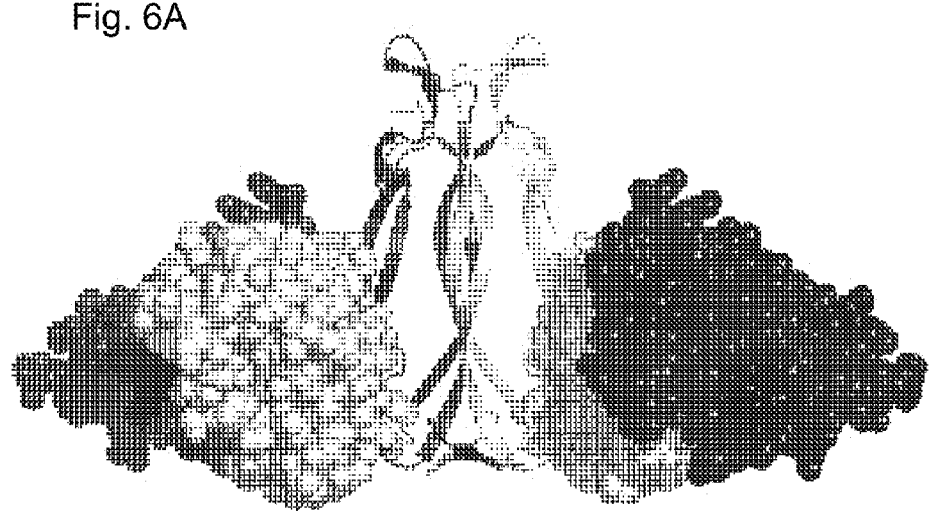
FIG. 6A shows the two XAB5 Fv fragments in complex with human IL-17A in space-filling representation and FIG. 6B shows the two XAB5 Fv fragments in complex with human IL-17A in cartoon representation.
Figure 6B:
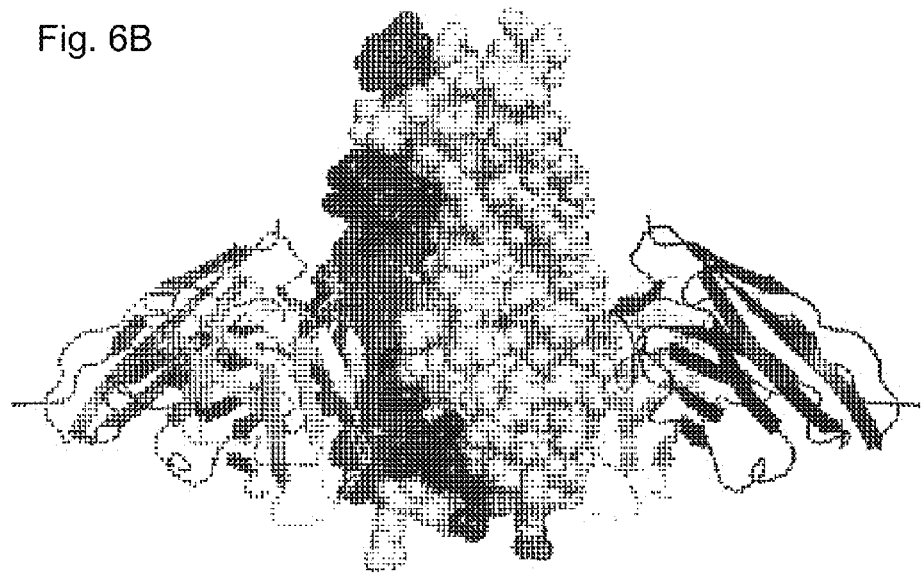
Figure 7:
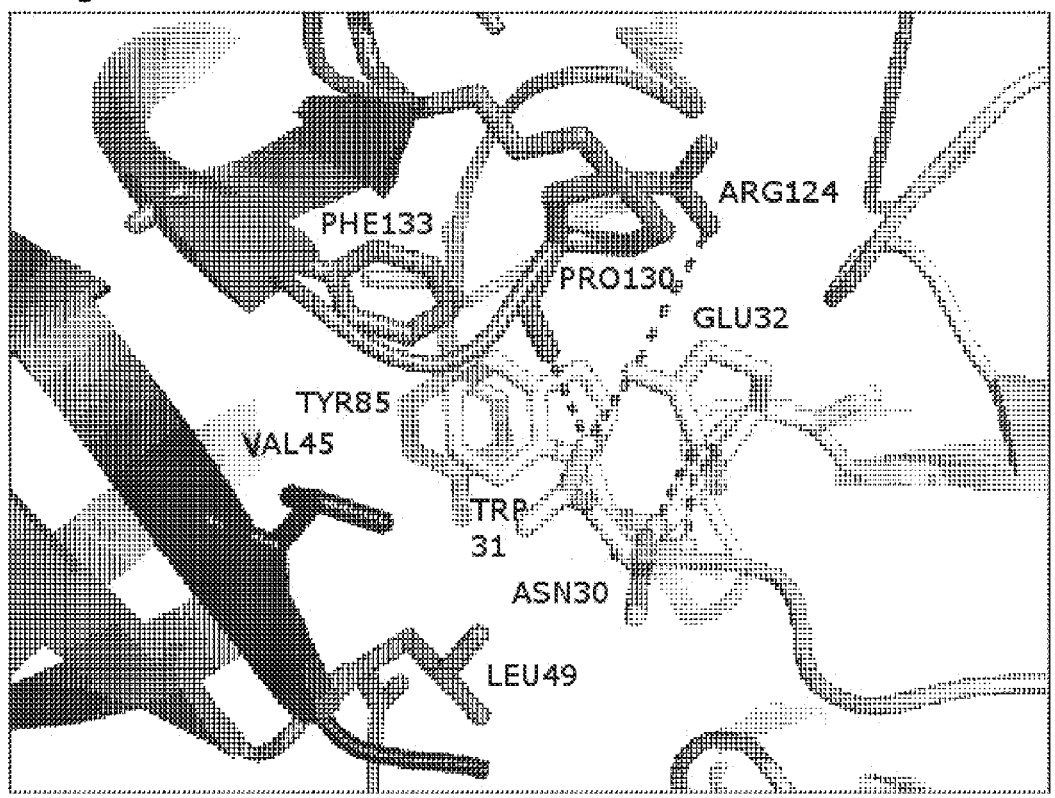
FIG. 7 provides the three-dimensional structure of the XAB5 Fv complex with human IL-17A, as a close-up view of the antibody L-CDR1.

FIG. 6 provides the three-dimensional structure of the XAB5 Fv complex with human IL-17A. The full homodimeric complex with exact crystallographic two-fold symmetry is shown here. FIG. 6A shows the two XAB5 Fv fragments in space-filling representation, and the IL-17A homodimer is shown in cartoon representation. FIG. 6B shows the two XAB5 Fv fragments in cartoon representation, and the IL-17A homodimer is shown in space-filling representation. The heavy- and light-chain of the XAB5 Fv are shown in dark and light grey, respectively. One chain of the IL-17A homodimer is shown in light grey, the other is shown in dark grey.

FIG. 7 provides the three-dimensional structure of the XAB5 Fv complex with human IL-17A. Close-up view of the antibody L-CDR1 bearing the three mutations found by the structure-guided biased library approach: Asn 30, Trp 31 and Glu 32. These XAB5 side-chains contribute new binding interactions to the antigen human IL-17A, in particular to IL-17A residues Tyr85, Phe133, Arg124, Pro 130, Leu 49 (all from the same IL-17A subunit) and Val 45 (from the other IL-17A subunit).

Example 7

X-Ray Analysis of Antibody Variants Derived by Affinity Maturation: XAB4

The XAB4 Fv was cloned and expressed in *E. coli* TG1 cells with a C-terminal hexahistidine tag on the heavy-chain and a C-terminal Strep-tag on the light-chain. The recombinant protein was purified by Ni-chelate chromatography.

The XAB4 Fv fragment complex with human IL-17A was then prepared using standard methodology. In brief, human IL-17A (0.5 mg) was mixed with an excess of XAB4 Fv (1.2 mg) and the complex was run on a SPX-75 size-exclusion chromatography, in 10 mM TRIS pH 7.4, 25 mM NaCl. The protein complex was then concentrated by ultra-filtration to 6.9 mg/ml and crystallized.

Standard crystallization protocols were followed. In brief, crystals were grown at 19° C. in VDX 24 well-plates, using the method of vapour diffusion in hanging drops. The protein stock was mixed 2:1 with a crystallization buffer containing 15% PEG 5,000 MME, 0.1 M MES pH 6.5, 0.2M ammonium sulfate. Total drop size was 3.0 µl. Prior to X-ray data collection, one crystal was briefly transferred into a 1:1 mix of the crystallization buffer with 25% PEG 5,000 MME, 20% glycerol, and then flash cooled into liquid nitrogen.

X-ray data collection and processing was carried out using standard protocols. Briefly, X-ray data to 3.15 Å resolution were collected at the Swiss Light Source, beamline X10SA, with a Pilatus detector, using 0.99984 Å X-ray radiation. In total, 720 images of 0.25° oscillation each were recorded at a crystal-to-detector distance of 500 mm and processed with the XDS software package. The crystal belonged to space group $C222_1$ with cell parameters a=55.76 Å, b=87.11 Å, c=156.31 Å, $\alpha=\beta=\gamma=90°$. R-sym to 3.15 Å resolution was 5.5% and data completeness 99.9%.

As the crystal of the XAB4 Fv complex was nearly isomorphous with the crystal of the XAB5 Fv complex (Example 6), the structure of the latter was used as input model for structure determination by molecular replacement with the program Phaser. Iterative model correction and refinement was performed with Coot (Crystallographic Object-Oriented Toolkit) and Autobuster version 1.11.2 (Buster version 2.11.2), until no further significant improvements could be made to the crystallographic model. Final R- and R-free for all data were 0.197 and 0.253, respectively. The final refined model showed a root-mean-square deviation (RMSD) from ideal bond lengths and bond angles of 0.009 Å and 1.0°, respectively.

(i) Results

Figure 9:
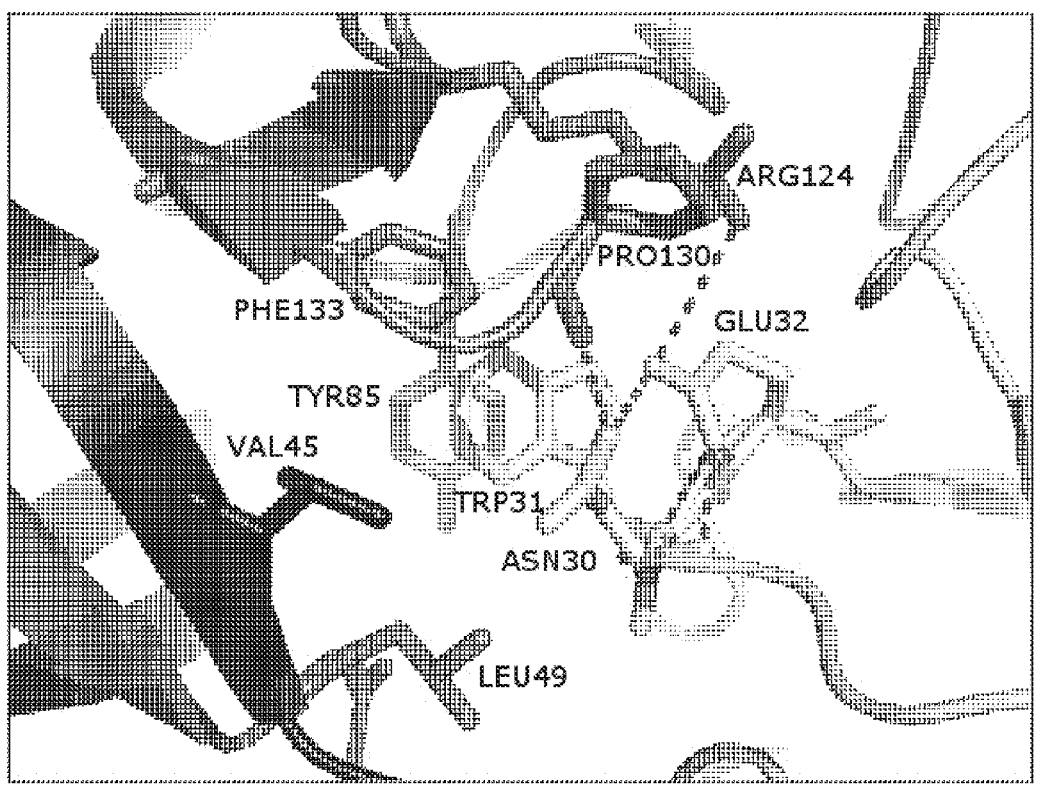
FIG. 9 provides the three-dimensional structure of the XAB4 Fv complex with human IL-17A as a close-up view of the antibody L-CDR1.
Figure 10:
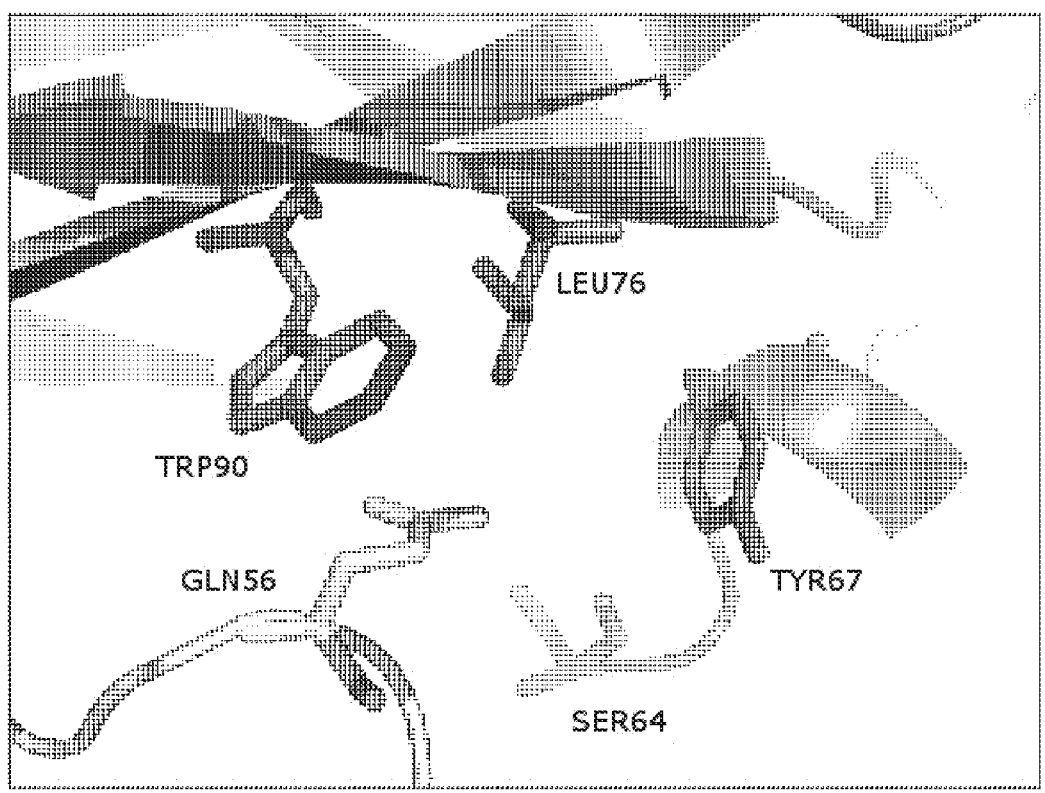
FIG. 10 provides the three-dimensional structure of the XAB4 Fv complex with human IL-17A as a close-up view of the antibody L-CDR2.

The results of the X-ray refinement of the XAB4 Fv complex with human IL-17A are provided in Table 16 and the three-dimensional structure of this complex is shown in FIG. 8. In this crystal structure, as in the XAB5 complex (Example 6), the XAB4 Fv complex has exact crystallographic 2-fold symmetry: the asymmetric unit of the crystal contains only one half of the whole, dimeric complex. The XAB4 Fv makes contacts to both IL-17A subunits, but the vast majority of the intermolecular contacts are to only one subunit (93% of the IL-17A surface buried by one XAB4 Fv is contributed by one subunit). The X-ray crystallography analysis confirmed that the variant antibody XAB4 retained the target specificity and bound with high affinity to essentially the same epitope as the parental XAB1 antibody. However, in the XAB4 complex structure, as in the XAB5 complex structure, the light-chain CDRL1 bears three point mutations which provide enhanced binding to human IL-17A. As already described for the XAB5 complex (Example 6), Trp 31 of the XAB4 light-chain is engaged in strong hydrophobic/aromatic interactions with Tyr 85 of IL-17A and, to a lesser extent, Phe 133 of IL-17A. Asn 30 of the XAB4 light-chain donates a H-bond to the main-chain carbonyl of Pro 130 of IL-17A and is in van der Waals contact to Leu 49 (same IL-17A subunit) and Val 45 (other IL-17A subunit). Glu 32 of the XAB4 light-chain stabilizes the CDRL1 loop through intramolecular H-bonded interactions. Furthermore, Glu 32 makes favorable electrostatic interactions with Arg 124 of IL-17A, but is not engaged into a "head-to-head" salt-bridge interaction (FIG. 9). XAB4 also differs from XAB1 in position 56 of the light-chain, as a result of an Asn to Gln mutation designed to remove a potential deamidation site. The X-ray analysis shows that Gln 56 of XAB4 makes contacts to the protein antigen residues Leu 76 and Trp 90, and reduces the solvent-accessibility of Tyr 67 and Ser 64 (FIG. 10).

TABLE 16

X-ray refinement of the XAB4 Fv complex with IL-17A obtained by the program Autobuster.

```
REMARK  3
REMARK  3  REFINEMENT.
REMARK  3   PROGRAM   : BUSTER 2.11.2
REMARK  3   AUTHORS   : BRICOGNE,BLANC,BRANDL,FLENSBURG,KELLER,
REMARK  3             : PACIOREK,ROVERSI,SHARFF,SMART,VONRHEIN,WOMACK;
REMARK  3             : MATTHEWS,TEN EYCK,TRONRUD
REMARK  3
REMARK  3  DATA USED IN REFINEMENT.
REMARK  3    RESOLUTION RANGE HIGH (ANGSTROMS) : 3.15
REMARK  3    RESOLUTION RANGE LOW  (ANGSTROMS) : 78.15
REMARK  3    DATA CUTOFF    (SIGMA(F)) : 0.0
REMARK  3    COMPLETENESS FOR RANGE    (%) : 99.85
REMARK  3    NUMBER OF REFLECTIONS       : 6881
REMARK  3
REMARK  3  FIT TO DATA USED IN REFINEMENT.
REMARK  3    CROSS-VALIDATION METHOD   : THROUGHOUT
REMARK  3    FREE R VALUE TEST SET SELECTION : RANDOM
REMARK  3    R VALUE   (WORKING + TEST SET) : 0.1998
REMARK  3    R VALUE         (WORKING SET) : 0.1972
REMARK  3    FREE R VALUE             : 0.2531
REMARK  3    FREE R VALUE TEST SET SIZE (%) : 5.01
REMARK  3    FREE R VALUE TEST SET COUNT   : 345
REMARK  3    ESTIMATED ERROR OF FREE R VALUE : NULL
REMARK  3
REMARK  3  FIT IN THE HIGHEST RESOLUTION BIN.
REMARK  3    TOTAL NUMBER OF BINS USED    : 5
REMARK  3    BIN RESOLUTION RANGE HIGH (ANGSTROMS) : 3.15
REMARK  3    BIN RESOLUTION RANGE LOW  (ANGSTROMS) : 3.52
REMARK  3    BIN COMPLETENESS (WORKING+TEST)   (%) : 99.85
REMARK  3    REFLECTIONS IN BIN (WORKING + TEST SET) : 1916
REMARK  3    BIN R VALUE   (WORKING + TEST SET) : 0.2376
REMARK  3    REFLECTIONS IN BIN   (WORKING SET) : 1820
REMARK  3    BIN R VALUE        (WORKING SET) : 0.2326
REMARK  3    BIN FREE R VALUE           : 0.3295
REMARK  3    BIN FREE R VALUE TEST SET SIZE (%) : 5.01
REMARK  3    BIN FREE R VALUE TEST SET COUNT   : 96
REMARK  3    ESTIMATED ERROR OF BIN FREE R VALUE   : NULL
REMARK  3
REMARK  3  NUMBER OF NON-HYDROGEN ATOMS USED IN REFINEMENT.
REMARK  3    PROTEIN ATOMS    : 2499
REMARK  3    NUCLEIC ACID ATOMS : 0
REMARK  3    HETEROGEN ATOMS   : 5
REMARK  3    SOLVENT ATOMS    : 0
REMARK  3
REMARK  3  B VALUES.
REMARK  3    FROM WILSON PLOT       (A**2) : 102.42
REMARK  3    MEAN B VALUE    (OVERALL, A**2) : 124.95
REMARK  3    OVERALL ANISOTROPIC B VALUE.
REMARK  3     B11 (A**2) : -11.5511
REMARK  3     B22 (A**2) : -28.0012
REMARK  3     B33 (A**2) : 39.5523
REMARK  3     B12 (A**2) : 0.0000
REMARK  3     B13 (A**2) : 0.0000
REMARK  3     B23 (A**2) : 0.0000
REMARK  3
REMARK  3  ESTIMATED COORDINATE ERROR.
REMARK  3    ESD FROM LUZZATI PLOT       (A) : 0.787
REMARK  3    DPI (BLOW EQ-9) BASED ON FREE R VALUE  (A) : 0.474
REMARK  3
REMARK  3    REFERENCES: BLOW, D. (2002) ACTA CRYST D58, 792-797
REMARK  3
REMARK  3  CORRELATION COEFFICIENTS.
REMARK  3    CORRELATION COEFFICIENT FO-FC   : 0.9113
REMARK  3    CORRELATION COEFFICIENT FO-FC FREE : 0.8848
REMARK  3
```

TABLE 16-continued

X-ray refinement of the XAB4 Fv complex with IL-17A obtained by the program Autobuster.

```
REMARK  3   X-RAY WEIGHT : 20.89
REMARK  3
REMARK  3   GEOMETRY FUNCTION.
REMARK  3       RESTRAINT LIBRARIES.
REMARK  3       NUMBER OF LIBRARIES USED : 8
REMARK  3       LIBRARY 1 : protgeo_eh99.dat (V1.8) 20110121 STANDARD
REMARK  3           AMINO ACID DICTIONARY. BONDS AND ANGLES FROM
REMARK  3           ENGH AND HUBER EH99. OTHER VALUES BASED ON
REMARK  3           PREVIOUS TNT OR TAKEN FROM CCP4. INCLUDES
REMARK  3           HYDROGEN ATOMS.
REMARK  3       LIBRARY 2 : exoticaa.dat (V1.8) 20100430 COLLECTION OF
REMARK  3           NON-STANDARD AMINO ACIDS, MAINLY EH91 WITHOUT
REMARK  3           IDEAL DISTANCE INFO
REMARK  3       LIBRARY 3 nuclgeo.dat (V1.14) 20091104
REMARK  3       LIBRARY 4 bcorrel.dat (V1.15) 20080423
REMARK  3       LIBRARY 5 contact.dat (V1.20.2.1) 20110510
REMARK  3       LIBRARY 6 : idealdist contact.dat (V1.7) 20110119
REMARK  3           IDEAL-DISTANCE CONTACT TERM DATA AS USED IN
REMARK  3           PROLSQ. VALUES USED HERE ARE BASED ON THE REFMAC
REMARK  3           5.5 IMPLEMENTATION.
REMARK  3       LIBRARY 7 : restraints for SO4 (SULFATE ION) from cif
REMARK  3           dictionary SO4.cif using refmacdict2tnt revision
REMARK  3           1.23.2.7; buster common-compounds v 1.0 (05 May
REMARK  3           2011)
REMARK  3       LIBRARY 8 : assume.dat (V1.10) 20110113
REMARK  3
REMARK  3   NUMBER OF GEOMETRIC FUNCTION TERMS DEFINED : 15
REMARK  3       TERM        COUNT WEIGHT FUNCTION.
REMARK  3       BOND LENGTHS       : 2566 ; 2.00 ; HARMONIC
REMARK  3       BOND ANGLES    : 3486 ; 2.00 ; HARMONIC
REMARK  3       TORSION ANGLES      : 860 ; 2.00 ; SINUSOIDAL
REMARK  3       TRIGONAL CARBON PLANES : 61 ; 2.00 ; HARMONIC
REMARK  3       GENERAL PLANES     : 369 ; 5.00 ; HARMONIC
REMARK  3       ISOTROPIC THERMAL FACTORS : 2566 ; 20.00 ; HARMONIC
REMARK  3       BAD NON-BONDED CONTACTS : NULL ; NULL ; NULL
REMARK  3       IMPROPER TORSIONS   : NULL ; NULL ; NULL
REMARK  3       PSEUDOROTATION ANGLES : NULL ; NULL ; NULL
REMARK  3       CHIRAL IMPROPER TORSION : 323 ; 5.00 ; SEMIHARMONIC
REMARK  3       SUM OF OCCUPANCIES : NULL ; NULL ; NULL
REMARK  3       UTILITY DISTANCES    : NULL ; NULL ; NULL
REMARK  3       UTILITY ANGLES   : NULL ; NULL ; NULL
REMARK  3       UTILITY TORSION     : NULL ; NULL ; NULL
REMARK  3       IDEAL-DIST CONTACT TERM : 2984 ; 4.00 ; SEMIHARMONIC
REMARK  3
REMARK  3   RMS DEVIATIONS FROM IDEAL VALUES.
REMARK  3       BOND LENGTHS       (A) : 0.009
REMARK  3       BOND ANGLES        (DEGREES) : 1.00
REMARK  3       PEPTIDE OMEGA TORSION ANGLES (DEGREES) :   4.39
REMARK  3       OTHER TORSION ANGLES   (DEGREES) :   18.96
REMARK  3
REMARK  3   SIMILARITY.
REMARK  3       NCS.
REMARK  3       NCS REPRESENTATION : NONE
REMARK  3       TARGET RESTRAINTS.
REMARK  3       TARGET REPRESENTATION : LSSR
REMARK  3       TARGET STRUCTURE : xab5_il17a_complex_final_buster.pdb
REMARK  3
REMARK  3   TLS DETAILS.
REMARK  3       NUMBER OF TLS GROUPS :   3
REMARK  3
REMARK  3   TLS GROUP :  1
REMARK  3       SET : { H|* }
REMARK  3       ORIGIN FOR THE GROUP (A): 10.9676 -8.7396 -10.1379
REMARK  3       T TENSOR
REMARK  3        T11:  -0.1266 T22:   0.0257
REMARK  3        T33:  -0.2829 T12:  -0.3040
REMARK  3        T13:  -0.0312 T23:   0.1050
REMARK  3       L TENSOR
REMARK  3        L11:   7.4496 L22:   4.4770
REMARK  3        L33:   4.2880 L12:   1.1123
REMARK  3        L13:  -1.8044 L23:   3.0307
REMARK  3       S TENSOR
REMARK  3        S11:   0.2013 S12:   0.3070 S13:  -0.5774
REMARK  3        S21:   0.4752 S22:  -0.5377 S23:   0.7096
REMARK  3        S31:   1.0885 S32:  -1.0885 S33:   0.3364
REMARK  3
REMARK  3   TLS GROUP :  2
REMARK  3       SET : { I|* }
```

TABLE 16-continued

X-ray refinement of the XAB4 Fv complex with IL-17A obtained by the program Autobuster.

| | | |
|---|---|---|
| REMARK 3 | | ORIGIN FOR THE GROUP (A): 22.7365 0.7101 −35.1243 |
| REMARK 3 | | T TENSOR |
| REMARK 3 | | T11: −0.1883 T22: 0.1529 |
| REMARK 3 | | T33: −0.3560 T12: 0.0318 |
| REMARK 3 | | T13: −0.1985 T23: 0.0144 |
| REMARK 3 | | L TENSOR |
| REMARK 3 | | L11: 2.7494 L22: 9.3427 |
| REMARK 3 | | L33: 3.8648 L12: 0.8073 |
| REMARK 3 | | L13: −0.6650 L23: −2.0544 |
| REMARK 3 | | S TENSOR |
| REMARK 3 | | S11: 0.0485 S12: 0.3188 S13: 0.0579 |
| REMARK 3 | | S21: 0.0595 S22: 0.1433 S23: 0.7000 |
| REMARK 3 | | S31: 0.0050 S32: −0.6066 S33: −0.1917 |
| REMARK 3 | | |
| REMARK 3 | | TLS GROUP : 3 |
| REMARK 3 | | SET : { L\|* } |
| REMARK 3 | | ORIGIN FOR THE GROUP (A): 33.2517 −11.1794 −14.2151 |
| REMARK 3 | | T TENSOR |
| REMARK 3 | | T11: 0.0667 T22: −0.1645 |
| REMARK 3 | | T33: −0.2360 T12: 0.1870 |
| REMARK 3 | | T13: −0.2270 T23: −0.1209 |
| REMARK 3 | | L TENSOR |
| REMARK 3 | | L11: 3.3694 L22: 3.7848 |
| REMARK 3 | | L33: 8.8916 L12: −0.6497 |
| REMARK 3 | | L13: −2.6132 L23: 0.8234 |
| REMARK 3 | | S TENSOR |
| REMARK 3 | | S11: −0.0839 S12: −0.2629 S13: −0.1560 |
| REMARK 3 | | S21: 0.3804 S22: 0.7574 S23: −0.5378 |
| REMARK 3 | | S31: 1.0885 S32: 1.0885 S33: −0.6736 |
| REMARK 3 | | |
| REMARK 3 | | REFINEMENT NOTES. |
| REMARK 3 | | NUMBER OF REFINEMENT NOTES : 1 |
| REMARK 3 | | NOTE 1 : IDEAL-DIST CONTACT TERM CONTACT SETUP. ALL ATOMS |
| REMARK 3 | | HAVE CCP4 ATOM TYPE FROM LIBRARY |
| REMARK 3 | | |
| REMARK 3 | | OTHER REFINEMENT REMARKS: NULL |
| REMARK 3 | | |
| SSBOND | 1 | CYS H 22    CYS H 96         1555 1555 2.03 |
| SSBOND | 2 | CYS I 94    CYS I 144        1555 1555 2.05 |
| SSBOND | 3 | CYS I 99    CYS I 146        1555 1555 2.04 |
| SSBOND | 4 | CYS L 23    CYS L 88         1555 1555 2.07 |
| CISPEP | 1 | TYR I 85    PRO I 86    0    3.67 |
| CISPEP | 2 | GLU I 125   PRO I 126   0   −9.25 |
| CISPEP | 3 | PRO I 126   PRO I 127   0    5.92 |
| CISPEP | 4 | SER L 7     PRO L 8     0   −6.50 |
| CISPEP | 5 | TYR L 94    PRO L 95    0   −6.52 |
| CRYST1 | | 55.760 87.109 156.306 90.00 90.00 90.00 C 2 2 21 |

Figure 8A:
FIG. 8A shows the two XAB4 Fv fragments in complex with human IL-17A in space-filling representation
Figure 8B:
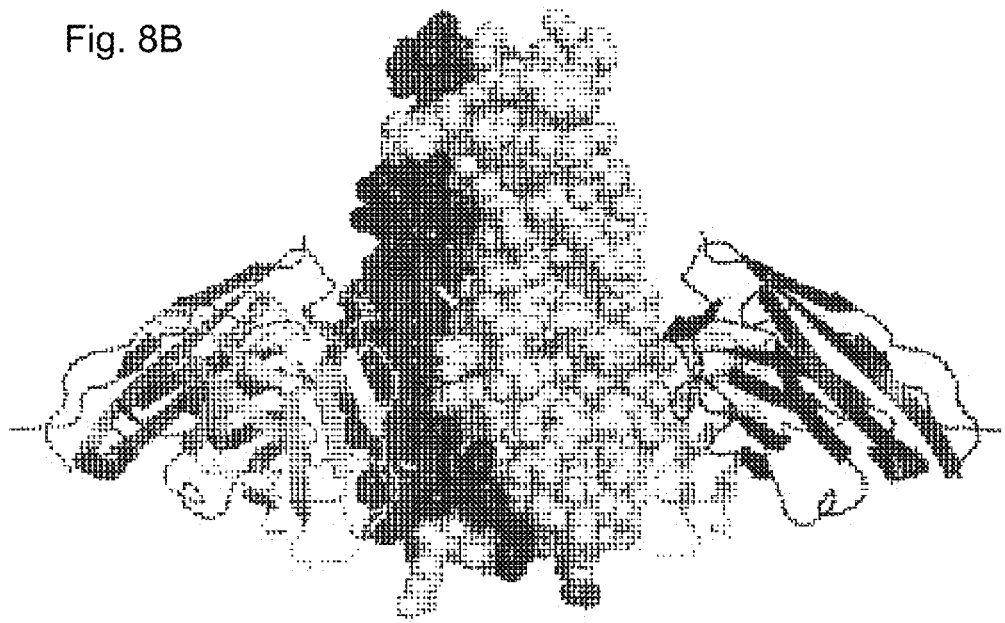
FIG. 8B shows the two XAB4 Fv fragments in complex with human IL-17A in cartoon representation.

FIG. 8 provides the three-dimensional structure of the XAB4 Fv complex with human IL-17A. FIG. 8A shows the two XAB4 Fv fragments in space-filling representation, and the IL-17A homodimer is shown in cartoon representation. FIG. 8B shows the two XAB4 Fv fragments in cartoon representation, and the IL-17A homodimer is shown in space-filling representation. The heavy- and light-chain of the XAB4 Fv are shown in dark and light grey, respectively. One chain of the IL-17A homodimer is shown in light grey, the other is shown in dark grey.

FIG. 9 provides the three-dimensional structure of the XAB4 Fv complex with human IL-17A as a close-up view of the antibody L-CDR1 bearing the three mutations found by the structure-guided biased library approach: Asn 30, Trp 31 and Glu 32. These XAB4 side-chains contribute new binding interactions to the antigen human IL-17A, in particular to IL-17A residues Tyr85, Phe133, Arg124, Pro 130, Leu 49 (all from the same IL-17A subunit) and Val 45 (from the other IL-17A subunit).

FIG. 10 provides the three-dimensional structure of the XAB4 Fv complex with human IL-17A as a close-up view of the antibody L-CDR2 showing the Asn 56 to Gln mutation. This XAB4 side-chain contributes binding contacts to IL-17A residues Trp 90 and Leu 76, and reduces the solvent-accessibility of Tyr 67 and Ser 64 (all from the same IL-17A subunit).

To summarize, X-ray crystallography analysis confirmed that the variant antibodies selected for further analysis retained their target specificity and bound with high affinity to essentially the same epitope as the parental XAB1 antibody. Tighter binding between each of the variant antibodies and IL-17A was observed, as a result of additional or improved binding contacts (see Table 17 below).

Further characterisation of the variant antibodies was conducted as described below.

TABLE 17

X-ray analyses of the IL-17A epitope bound by XAB1, XAB2, XAB4 and XAB5: summary and structure-based, qualitative classification of epitope residues.

| | Epitope residue class | | | |
|---|---|---|---|---|
| | XAB1 | XAB2 | XAB4 | XAB5 |
| Very important epitope residues | Arg 78, Glu 80, Trp 90 | Arg 78, Glu 80, Trp 90 | Arg 78, Glu 80, Tyr 85, Trp 90, Arg 124 | Arg 78, Glu 80, Tyr 85, Trp 90, Arg 124 |
| Other important epitope residues | Pro 82, Ser 87, Val 88, Arg 124 | Arg 43*, Pro 82, Ser 87, Val 88, Arg 124 | Pro 82, Ser 87, Val 88 | Pro 82, Ser 87, Val 88 |
| Additional contributions | Val 45*, Leu 49, Ile 51, Asp 81, Glu 83, Tyr 85, Asn 131, Lys 137* | Pro 42*, Val 45*, Leu 49, Ile 51, Asp 81, Glu 83, Tyr 85, Asn 131, Lys 137* | Val 45*, Leu 49, Asp 81, Glu 83, Pro 86, Pro 130, Phe 133, Lys 137* | Val 45*, Leu 49, Asp 81, Glu 83, Pro 86, Pro 130, Phe 133, Lys 137* |
| Little or no direct contribution | Thr 44*, Leu 76, His 77, Asn 79, Arg 84, Pro 86, Lys 93, Glu 118*, Pro 130, Phe 133 | Leu 76, His 77, Asn 79, Arg 84, Pro 86, Lys 93, Glu 118*, Pro 130, Phe 133 | Arg 43*, Asn 50, Ser 64, Tyr 67, Leu 76, His 77, Asn 79, Arg 84, Glu 118*, Leu 122, Asn 131, Leu 135* | Arg 43*, Asn 50, Leu 76, His 77, Asn 79, Arg 84, Glu 118*, Leu 122, Asn 131, Leu 135* |

*residue contributed by the second IL-17A subunit.

Example 8

Affinity Measurements and Cross-Reactivity Measured by Biacore™

Determination of kinetic binding parameters was achieved by surface plasmon resonance measurements using the optical biosensor Biacore™ T200 or T100 (http://www.biacore.com). This technology allows the label-free determination of the microscopic rate constants for binding ($k_a$) and dissociation ($k_d$) of a ligand to a receptor. It is therefore especially suited for characterizing the antibody-antigen interactions.

Indirect binding of antibodies to the Biacore™ chip surface was done via an anti-human Ig antibody (GE Healthcare Bio-Sciences AB; Cat. No. BR-1008-39) 25 µg/ml in immobilization buffer (10 mM Sodium acetate pH 5.0) or through protein A (RepliGen: rPA-50) 20 µg/ml in immobilization buffer (10 mM Sodium acetate pH 5.0 or pH 4.0).

Antibody was diluted into blank buffer to a final concentration of 1.00 or 1.25 µg/ml.

Affinity measurements for the determination of dissociation constants of XAB4 or XAB1 was performed for recombinant huIL-17A (SEQ ID NO: 78, e.g. 2-fold increasing concentrations from 0.14 to 8.8 nM), recombinant huIL-17A/F heterodimer (e.g. 2-fold increasing concentrations from 0.13 to 8 nM), recombinant huIL-17F (SEQ ID NO: 77; e.g. 2-fold increasing concentrations from 7.8 to 500 nM) cynomolgus IL-17A (SEQ ID NO: 79; e.g. 2-fold increasing concentrations from 0.63 to 40 nM) rhesus IL-17A (SEQ ID NO: 82; e.g. 2-fold increasing concentrations from 1.6 to 100 nM), marmoset IL-17A (SEQ ID NO: 82; e.g. 2-fold increasing concentrations from 0.63 to 40 nM), recombinant mIL-17A (SEQ ID NO: 83; e.g. 2-fold increasing concentrations from 0.78 to 50 nM), recombinant mIL-17A/F (R&D Systems® Cat#5390-IL; e.g. 2-fold increasing concentrations from 1.25 to 40 nM) rat IL-17A (SEQ ID NO: 85; e.g. 2-fold increasing concentrations from 0.78 to 50 nM), using the indirect coupling/binding method (see above) and surface was regenerated with 10 mM glycine pH 1.75 or $MgCl_2$ (3 M). One chip surface was coated and reused without significant loss of binding capacity. Ligand concentrations were chosen to start below the $K_D$ and to end at a concentration higher than ten times the $K_D$.

Similar but not identical conditions were used to measure affinity of XAB2 and XAB3.

The kinetic traces were evaluated with the Biacore™ T200 Control Software version 1.0. The full set of these traces with increasing concentrations is taken together and is called a run. Two zero concentration samples (blank runs) were included in each analyte concentration series to allow double-referencing during data evaluation Results The binding of the anti-IL-17 antibodies XAB4, XAB1, XAB2 and XAB3 to human, cynomolgus monkey, marmoset monkey, rhesus monkey, mouse and rat IL-17A, to human and mouse IL-17A/F heterodimer and to human IL-17F was determined by surface plasmon resonance using the Biacore™ technology.

The kinetic rate constants for association ($k_a$) and dissociation ($k_d$), as well as the dissociation equilibrium constant ($K_D$) were calculated.

The affinity data of XAB4 is shown in Table 18, the affinity data of XAB1 is shown in Table 19, the affinity data of XAB2 is shown in Table 20, and the affinity data of XAB3 is shown in Table 21. Affinity maturation of XAB1, XAB2 and XAB3 increased the affinity towards human, cynomolgus monkey, mouse and rat IL-17A.

TABLE 18

Affinity and kinetic rate constants of XAB4 binding.

| Antigen | $k_a$ (1/Ms) | $k_d$ (1/Ms) | $K_D$ (M) |
|---|---|---|---|
| huIL-17A | 4.1 ± 0.1E+06 | 2.3 ± 0.1E−05 | 5.7 ± 0.0E−12 |
| huIL-17A/F | 8.9 ± 0.2E+5 | <1.0 ± 0.0E−05* | <1.1 ± 0.0E−11* |
| huIL-17F | n.d. | n.d. | n.d. |
| cynoIL-17A | 4.1 ± 0.5E+05 | 1.3 ± 0.0E−05 | 3.1 ± 0.4E−11 |
| marmIL-17A | 1.2 ± 0.0E+06 | 2.2 ± 0.0E−05 | 1.8 ± 0.0E−11 |
| rhesIL-17A | 3.0 ± 0.1E+05 | 1.2 ± 0.1E−05 | 4.0 ± 0.1E−11 |
| mIL-17A | 3.8 ± 0.1E+05 | 6.2 ± 0.3E−05 | 1.6 ± 0.1E−10 |
| mIL-17A/F | 2.421E+05 | 6.305E−05 | 2.604E−10 |
| ratIL-17A | 5.5 ± 0.4E+05 | 4.6 ± 0.9E−05 | 8.4 ± 1.0E−11 | n.d. = not determinable, applied antigen conc. range too low and non-specific binding of antigen to reference flow cell observed at the highest antigen concentrations (500-50 pM).
*dissociation rate outside the limits that can be measured by the instrument ($k_d$ < 1 × 10⁻⁵ 1/s)

TABLE 19

Affinity and kinetic rate constants of XAB1 binding.

| Antigen | $k_a$ (1/Ms) | $k_d$ (1/s) | $K_D$ (M) |
|---|---|---|---|
| huIL-17A | 2.33E+06 | 9.39E−05 | 4.03E−11 |
| huIL-17A/F | 9.097E+05 | 0.001342 | 1.475E−09 |
| huIL-17F | n.d. | n.d. | n.d. |
| cynoIL-17A | 2.14E+05 | 1.13E−04 | 5.26E−10 |
| rhesIL-17A | 8.87E+05 | 9.97E−05 | 1.12E−09 |
| mIL-17A | 4.05E+05 | 1.43E−04 | 3.53E−10 |
| mIL-17A/F | 1.8757E+05 | 9.547E−04 | 5.093E−09 |
| ratIL-17A | 5.44E+05 | 1.64E−04 | 3.01E−10 | n.d. = not determinable, applied antigen conc. range too low and non-specific binding of antigen to reference flow cell observed at three highest antigen concentrations (500-50 pM).

TABLE 20

Affinity and kinetic rate constants of XAB2 binding.

| Antigen | $k_a$ (1/Ms) | $k_d$ (1/s) | $K_D$ (M) |
|---|---|---|---|
| huIL-17A | 4.09E+06 | 7.12E−05 | 1.76E−11 |

TABLE 21

Affinity and kinetic rate constants of XAB3 binding.

| Antigen | $k_a$ (1/Ms) | $K_d$ (1/s) | $K_D$ (M) |
|---|---|---|---|
| huIL-17A | 5.48E+06 | 5.01E−05 | 9.58E−12 |
| huIL-17A/F | 3.37E+06 | 1.03E−04 | 3.29E−11 |
| huIL-17F | n.d. | n.d. | n.d. |
| cynoIL-17A | 1.21E+06 | 4.23E−05 | 3.49E−11 |
| mIL-17A | 5.87E+05 | 1.01E−04 | 1.74E−10 |
| ratIL-17A | 9.05E+05 | 7.59E−05 | 8.26E−11 | n.d. = not determinable

The affinities and kinetic rate constants for XAB2, XAB3 and XAB5 are comparable to those observed for XAB4.

Example 9

Binding in ELISA to IL-17A and Other Family Members

A titration of the antibodies of interest on different antigens was carried out. Briefly, wells of ELISA microtiter plates (Nunc Immuno plates MaxiSorp: Invitrogen, Cat#4-39454A) were coated with 1 µg/ml of recombinant huIL-17A (SEQ ID NO: 76; 1.8 mg/ml), recombinant huIL-17A/F (0.59 mg/ml), recombinant huIL-17F (SEQ ID NO: 77; 1.8 mg/ml)), recombinant huIL-17B (R&D Systems® Cat#12481B/CF), recombinant huIL-17C (R&D Systems® Cat#12341L/CF), recombinant huIL-17D (R&D Systems® Cat#15041L/CF), recombinant huIL-17E (R&D Systems® Cat#1258-IL/CF), recombinant cynoIL-17A (SEQ ID NO: 79; 0.21 mg/ml), recombinant cynoIL-17F (SEQ ID NO: 80; 1.525 mg/ml), recombinant mIL-17A (SEQ ID NO: 83; 2.8 mg/ml), recombinant mIL-17A/F (R&D Systems® Cat#5390-IL), recombinant mIL-17F (SEQ ID NO: 84; 0.2 mg/ml) and recombinant ratIL-17A (SEQ ID NO: 85; 3.8 mg/ml) (100 µl/well) in phosphate buffered saline (PBS) without Ca and Mg (10×; Invitrogen Cat#14200-083) 0.02% $NaN_3$ (Sigma Cat# S-8032) and incubated overnight at 4° C.

The following day, microtiter plates were blocked with 300 µl of PBS/2% BSA (fraction V; Roche Cat#10 735 094 001)/0.02% $NaN_3$ for 1 h at 37° C. Plates were then washed 4 times with PBS/0.05% Tween 20 (Sigma Cat# P7949)/0.02% $NaN_3$. XAB4 or XAB1 were added at 1 µg/ml in triplicate wells (100 µl/well) for 3 h at room temperature.

To verify coating of antigens to the plates, control antibodies were used and in particular, a mouse mAb anti-huIL-17F, (Novartis, 5 µg/ml) a goat anti-hu-IL-17B (R&D Systems® Cat# AF1248; 10 µg/ml), a mouse mAb anti-huIL-17C (R&D Systems® Cat# MAB1234; 10 µg/ml), a goat anti-huIL-17D (R&D Systems® Cat# AF1504; 10 µg/ml), a mouse mAb anti hu-IL-17E (R&D Systems® Cat# MAB1258; 10 µg/ml), a mouse anti-mIL-17A or anti-mIL-17A/F (Novartis; 1 µg/ml), and a rat anti-mIL-17F (R&D Systems® Cat# MAB2057; 1 µg/ml;) (100 µl/well in PBS, 0.02% $NaN_3$ for 3 h at RT).

Plates were then washed 4 times with PBS/0.05% Tween 20/0.02% $NaN_3$. Then, an alkaline phosphatase-conjugated goat anti-human IgG antibody (Sigma Cat# A9544) was added to the wells that received test antibody at a dilution of 1/20000 (100 µl/well) for 2 h 30 min at RT. To the wells, that received mouse mAb, an alkaline phosphatase-conjugated goat anti-mouse IgG antibody (Sigma Cat# A7434) was added at a dilution of 1/10000 (100 µl/well) for 2 h 30 min at RT. An alkaline phosphatase conjugated mouse anti goat IgG antibody (Sigma Cat# A8062) was added to the goat antibodies at a dilution of 1/50000 (100 µl/well) for 2 h 30 min at RT. Plates were then washed 4 times and 100 µl of the substrate (p-nitrophenyl phosphate tablets; Sigma; 5 mg Cat# N9389; 20 mg Cat#. N2765) dissolved in diethanolamine buffer pH 9.8, to give a final concentration of 1 mg/ml, were added to each well.

Plates were read after 30 min in a Spectra Max M5 Microplate Reader (Molecular Devices) using filters of 405 and 490 nm. Values are the means±SEM of triplicate values.

Results

These studies show that XAB4 and XAB1 are able to bind human and mouse IL-17A, and human and mouse IL-17A/F. In addition it is shown that XAB4 is able to bind cynomolgus and rat IL-17A. Binding to human, cynomolgus and mouse IL-17F was not detected under these experimental conditions as well as binding to other human family members (IL-17B, IL-17C, IL-17D and IL-17E).

TABLE 22

Cross-reactivity of XAB4 and XAB1 to human, cynomolgus monkey, mouse and rat IL-17 family members, by ELISA.

| | XAB4 (1 µg/ml) O.D values (mean ± SEM) | Control antibody (1 or 10 µg/ml) O.D values (mean ± SEM) | XAB1 (1 µg/ml) O.D values (mean ± SEM) | Control antibody (1 or 10 µg/ml) O.D values (mean ± SEM) |
|---|---|---|---|---|
| hu IL-17A | 2.471 ± 0.0448 | | 1.302 ± 0.0554 | |
| hu IL-17A/F | 2.137 ± 0.0429 | | 1.222 ± 0.0202 | |
| hu IL-17F | 0.049 ± 0.0056 | | 0.032 ± 0.0005 | 1.913 ± 0.0483 |
| hu IL-17B | 0.034 ± 0.0007 | 0.283 ± 0.0066 | 0.049 ± 0.0013 | 1.441 ± 0.0283 |

TABLE 22-continued

Cross-reactivity of XAB4 and XAB1 to human, cynomolgus monkey, mouse and rat IL-17 family members, by ELISA.

|  | XAB4 (1 µg/ml) O.D values (mean ± SEM) | Control antibody (1 or 10 µg/ml) O.D values (mean ± SEM) | XAB1 (1 µg/ml) O.D values (mean ± SEM) | Control antibody (1 or 10 µg/ml) O.D values (mean ± SEM) |
|---|---|---|---|---|
| hu IL-17C | 0.036 ± 0.0002 | 0.290 ± 0.0027 | 0.032 ± 0.0002 | 0.558 ± 0.0169 |
| hu IL-17D | 0.034 ± 0.0005 | 0.292 ± 0.0048 | 0.031 ± 0.0010 | 0.867 ± 0.0372 |
| hu IL-17E | 0.035 ± 0.0014 | 0.833 ± 0.0239 | 0.033 ± 0.0003 | 2.054 ± 0.0378 |
| cyno IL-17A | 1.926 ± 0.0355 | | | |
| cyno IL-17F | 0.085 ± 0.0336 | | | |
| mouse IL-17A | 1.585 ± 0.0428 | 1.086 ± 0.0119 | 1.439 ± 0.0354 | 3.697 ± 0.0602 |
| mouse IL-17A/F | 2.263 ± 0.0243 | 1.142 ± 0.0315 | 1.762 ± 0.0097 | 2.084 ± 0.0223 |
| mouse IL-17F | 0.098 ± 0.0060 | 1.294 ± 0.0134 | 0.044 ± 0.0008 | 1.770 ± 0.0302 |
| rat IL-17A | 1.772 ± 0.1668 | | | |

Example 10

Cross-Reactivity to Other Human, Mouse and Rat Interleukins by ELISA

In another set of experiments the cross-reactivity of antibodies of the disclosure for selected human, mouse or rat cytokines was evaluated.

Triplicate wells of ELISA microtiter plates (Nunc Immuno plates MaxiSorp: Invitrogen Cat#4-39454A) were coated with 100 µl/well of the following cytokines: recombinant huIL1β (Novartis), recombinant huIL-3 (R&D Systems® Cat#203-IL/CF), recombinant huIL-4 (R&D Systems® Cat#204-IL/CF), recombinant huIL-6 (R&D Systems® Cat#206-IL-1010/CF), recombinant huIL-8 (R&D Systems® Cat#208-IL-010/CF), recombinant huIL-12 (R&D Systems® Cat#219-IL-005/CF), recombinant huIL-13 (Novartis), recombinant huIL-17A (SEQ ID NO: 76), recombinant huIL-17A/F, recombinant huIL-17F (SEQ ID NO: 77), recombinant huIL-18 (MBL Cat# B003-5), recombinant huIL-20 (Novartis), recombinant huIL-23 (R&D Systems® Cat#1290-IL-010/CF), recombinant huIFNγ (Roche), recombinant huTNFα (Novartis), recombinant huEGF (Sigma Cat#E9644.), recombinant huTGFβ2 (Novartis), recombinant mIL-1β (R&D Systems® Cat#401-ML), recombinant mIL-2 (R&D Systems® 402-ML-020/CF), recombinant mIL-6 (R&D Systems® Cat#406-ML-010/CF), recombinant mIL-12 (R&D Systems® Cat#419-ML-010/CF), recombinant mIL-17A (SEQ ID NO: 83), recombinant mIL-17A/F (R&D Systems® Cat#5390-IL), recombinant mIL-17F (R&D Systems® Cat#2057-IL/CF), recombinant mIL-18 (MBL Cat#B004-5), recombinant mIL-23 (R&D Systems® Cat#1887-ML), recombinant mIFN-γ (R&D Systems® Cat#485-MT), recombinant mTNFα (R&D Systems® Cat#410-MT), recombinant rat IL-4 (R&D Systems® Cat#504-RL/CF), recombinant rat IL-6 (R&D Systems® Cat#506-RL-010), recombinant ratIL-12 (R&D Systems® Cat#1760-RL/CF), recombinant ratIL-17A (SEQ ID NO: 85), recombinant ratIL-23 (R&D Systems® Cat#3136-RL-010/CF), recombinant ratTNFα (R&D Systems® Cat#510-RT/CF), at 1 µg/ml with the exception of recombinant mIL-6, recombinant mIL-12 and recombinant mTNFα which were coated at 0.5 µg/ml in phosphate buffered saline (PBS) without Ca and Mg (10×; Invitrogen Cat#14200-083) 0.02% NaN$_3$ (Sigma Cat# S-8032) and incubated overnight at 4° C.

The following day, microtiter plates were blocked with 300 µl of PBS/2% BSA (fraction V; Roche Cat#10 735 094 001)/0.02% NaN$_3$ for 1 h at 37° C. Plates were then washed 4 times with PBS/0.05% Tween 20 (Sigma Cat# P7949)/0.02% NaN$_3$.

The antibodies of the disclosure were added at 10 µg/ml (100 µl/well) for 3 h at room temperature. To verify coating of antigens to the plates, 100 µl/well of the following control antibodies were used: a mouse anti-huIL1β (R&D Systems® Cat# MAB601), a mouse anti-huIL-3 (R&D Systems® Cat# MAB603), a mouse anti-huIL4 (R&D Systems® Cat# MAB604), a mouse anti-huIL-6 (R&D Systems® Cat# MAB206), a mouse anti-hu-IL8 (R&D Systems® Cat# MAB208), a mouse anti-huIL-12 (R&D Systems® Cat# MAB219), a mouse anti-huIL-13 (Novartis), a mouse anti-huIL-17A (Novartis), a mouse anti-huIL-17F (Novartis), a mouse anti-huIL-18 (MBL Cat# D043-3), a mouse anti-huIL-20 (Abcam Cat# ab57227), a goat anti-huIL-23 (R&D Systems® Cat# AF1716), a mouse anti-huIFN-γ (R&D Systems® Cat# MAB285), a mouse anti-huTNF-α (R&D Systems® Cat# MAB610), a mouse anti-hu-EGF (R&D Systems® Cat# MAB236), a human anti-huTGFβ2 (Novartis), a rat anti-mIL-1β (R&D Systems® Cat# MAB401), a rat anti-mIL-2 (R&D Systems® Cat# MAB402), a rat anti-mIL-6 (R&D Systems® Cat# MAB406), a rat anti-mIL-12 (R&D Systems® Cat# MAB419), a mouse anti-m/ratIL-17A (Novartis), a rat anti-mIL-17F (R&D Systems® Cat# MAB2057), a rat anti-mIL-18 (MBL Cat# D047-3), a rat anti-mIFN-γ (R&D Systems® Cat# MAB485), a goat anti-mTNFα (R&D Systems® Cat# AF-410-NA), a mouse anti-rat IL-4 (R&D Systems® Cat# MAB504), a goat anti-rat IL-6 (R&D Systems® Cat# AF506), a goat anti-rat IL-12 (R&D Systems® Cat# AF1760), a mouse anti-rat IL-23 (R&D Systems® Cat# MAB3510), a mouse anti-rat TNFα (R&D Systems® Cat# MAB510). They were added at 1 or 5 µg/ml, in PBS, 0.02% NaN$_3$ for 3 h at RT.

Plates were then washed 4 times with PBS/0.05% Tween 20/0.02% NaN$_3$. Then, an alkaline phosphatase-conjugated goat anti-human IgG antibody (Sigma Cat# A9544) was added to the wells with human antibodies at a dilution of 1/20000 (100 µl/well). An alkaline phosphatase-conjugated goat anti-mouse IgG antibody (Sigma Cat# A1047) was added to the wells with mouse antibodies at a dilution of 1/10000 (100 μl/well). An alkaline phosphatase-conjugated rabbit anti-goat IgG antibody (Sigma Cat# A7650) was added to the wells with goat antibodies at a dilution of 1/1000 (100 μl/well) and an alkaline phosphatase-conjugated rabbit anti rat-IgG antibody (Sigma Cat# A6066) was added to the wells with rat antibodies at a dilution of 1/20000 (100 μl/well). The secondary antibodies were incubated for 2 h 30 min at RT. Plates were then washed 4 times and 100 μl of the substrate (p-nitrophenyl phosphate tablets; Sigma; 5 mg Cat#. N9389 or 20 mg Cat# N2765) dissolved in diethanolamine buffer pH 9.8, to give a final concentration of 1 mg/ml, were added to each well.

Plates were read after 30 min at RT or ON at 4oC in a Spectra Max M5 Microplate Reader (Molecular Devices) using filters of 405 and 490 nm. Values are the means±SEM of triplicate values.

Results

The data obtained show that both XAB4 and XAB1 are highly selective for IL-17A of human, mouse and rat origin and for IL-17A/F of human and mouse origin. In addition, under the conditions tested, the reactivity of XAB1 at 10 μg/ml for human IL-17F (not seen at 1 μg/ml, see above) is not observed with XAB4. Reactivity for the other cytokines tested was not detected.

TABLE 23

Cross-reactivity of XAB4 and XAB1 to human cytokines by ELISA.

|  | XAB4 (10 μg/ml) O.D values (mean ± SEM) | Control antibody (5 μg/ml) O.D values (mean ± SEM) | XAB1 (10 μg/ml) O.D values (mean ± SEM) | Control antibody (1 μg/ml) O.D values (mean ± SEM) |
| --- | --- | --- | --- | --- |
| IL1β | 0.015 ± 0.0075 | 0.867 ± 0.0107 | −0.110 ± 0.0901 | 3.071 ± 0.0486 |
| IL3 | 0.167 ± 0.1288 | 0.732 ± 0.0194 | −0.049 ± 0.0738 | 2.931 ± 0.0779 |
| IL4 | 0.047 ± 0.0089 | 0.806 ± 0.0617 | 0.057 ± 0.0458 | 2.555 ± 0.1499 |
| IL6 | −0.015 ± 0.0103 | 1.452 ± 0.2020 | −0.044 ± 0.0838 | 2.976 ± 0.1025 |
| IL8 | 0.018 ± 0.0078 | 3.130 ± 0.0109 | 0.058 ± 0.0431 | 3.153 ± 0.1228 |
| IL12 | 0.009 ± 0.0058 | 0.853 ± 0.0496 | −0.097 ± 0.1600 | 2.964 ± 0.1370 |
| IL13 | 0.019 ± 0.0085 | 2.639 ± 0.0309 | 0.125 ± 0.0706 | 2.639 ± 0.0309 |
| IL17A | 3.178 ± 0.0697 | 3.136 ± 0.0644 | 2.745 ± 0.0879 | 2.731 ± 0.0850 |
| IL17A/F | 3.100 ± 0.0458 | 3.024 ± 0.0816 | 2.644 ± 0.2517 | 3.024 ± 0.0816 |
| IL17F | 0.035 ± 0.0138 | 3.114 ± 0.0672 | 0.613 ± 0.4162 | 3.185 ± 0.0110 |
| IL18 | −0.001 ± 0.0234 | 3.313 ± 0.2080 | −0.086 ± 0.0170 | 3.313 ± 0.2080 |
| IL20 | 0.039 ± 0.0117 | 3.039 ± 0.0671 | 0.335 ± 0.2442 | 3.118 ± 0.0252 |
| IL23 | −0.022 ± 0.0450 | 3.435 ± 0.0878 | 0.085 ± 0.0678 | 3.350 ± 0.0886 |
| IFN-γ | 0.048 ± 0.0676 | 3.419 ± 0.0404 | 0.059 ± 0.0511 | 3.236 ± 0.0312 |
| TNF-α | 0.009 ± 0.0197 | 3.373 ± 0.0550 | 0.289 ± 0.0318 | 3.275 ± 0.0440 |
| EGF | 0.126 ± 0.0858 | 3.432 ± 0.1050 | 0.062 ± 0.0427 | 3.233 ± 0.1126 |
| TGFβ2 | 0.018 ± 0.0190 | 3.397 ± 0.0358 | 0.146 ± 0.0653 | 3.246 ± 0.0303 |
| BSA | 0.009 ± 0.0194 | 0.010 ± 0.0192 | 0.043 ± 0.0033 | 0.149 ± 0.0558 |

N.B. the negative values are due to the fact that the blank (O.D. value of wells without specific antibodies) is subtracted.

TABLE 24

Cross-reactivity of XAB4 and XAB1 to mouse cytokines by ELISA.

|  | XAB4 (10 μg/ml) O.D values (mean ± SEM) | Control antibody (5 μg/ml) O.D values (mean ± SEM) | XAB1 (10 μg/ml) O.D values (mean ± SEM) | Control antibody (5 μg/ml) O.D values (mean ± SEM) |
| --- | --- | --- | --- | --- |
| IL-1β | 0.022 ± 0.0057 | 0.611 ± 0.0665 | 0.007 ± 0.0123 | 0.624 ± 0.0455 |
| IL2 | 0.024 ± 0.0227 | 3.548 ± 0.1283 | 0.022 ± 0.0125 | 3.295 ± 0.0557 |
| IL6 | 0.031 ± 0.0063 | 3.291 ± 0.0174 | 0.038 ± 0.0091 | 3.340 ± 0.1115 |
| IL12 | 0.035 ± 0.0110 | 3.359 ± 0.0094 | −0.005 ± 0.0121 | 3.295 ± 0.0331 |
| IL17A | 3.285 ± 0.0445 | 3.180 ± 0.0702 | 2.974 ± 0.0281 | 3.186 ± 0.0505 |
| IL17A/F | 3.342 ± 0.1047 | 3.407 ± 0.1102 | 3.169 ± 0.0340 | 3.214 ± 0.0145 |
| IL17F | 0.034 ± 0.0122 | 3.359 ± 0.0247 | −0.058 ± 0.0326 | 3.264 ± 0.0309 |
| IL18 | 0.054 ± 0.0149 | 2.650 ± 0.0227 | 0.022 ± 0.0123 | 2.572 ± 0.0145 |
| IL23 | 0.058 ± 0.0139 | 0.601 ± 0.0314 | 0.009 ± 0.0007 | 0.590 ± 0.0378 |
| IFN-γ | 0.038 ± 0.0114 | 2.751 ± 0.0515 | 0.048 ± 0.0063 | 2.388 ± 0.2351 |
| TNF-α | 0.065 ± 0.0154 | 3.258 ± 0.1097 | 0.025 ± 0.0081 | 3.476 ± 0.0714 |
| BSA | 0.015 ± 0.0078 | 0.035 ± 0.0047 | 0.015 ± 0.0078 | 0.035 ± 0.0047 |

N.B. the negative values are due to the fact that the blank (O.D. value of wells without specific antibodies) is subtracted.

TABLE 25

Cross-reactivity of XAB4 and XAB1 to rat cytokines by ELISA.

|       | XAB4 (10 µg/ml) O.D values (mean ± SEM) | Control antibody (5 µg/ml) O.D values (mean ± SEM) | XAB1 (10 µg/ml) O.D values (mean ± SEM) | Control antibody (5 µg/ml) O.D values (mean ± SEM) |
|-------|------------------------------------------|-----------------------------------------------------|------------------------------------------|-----------------------------------------------------|
| IL4   | 0.026 ± 0.0082 | 3.168 ± 0.0297 | 0.017 ± 0.0092 | 3.324 ± 0.1092 |
| IL6   | 0.021 ± 0.0028 | 3.116 ± 0.0318 | 0.000 ± 0.0141 | 3.253 ± 0.1078 |
| IL12  | 0.009 ± 0.0113 | 3.185 ± 0.0921 | −0.007 ± 0.0082 | 3.310 ± 0.0692 |
| IL17A | 3.483 ± 0.0910 | 3.156 ± 0.0890 | 1.202 ± 0.0136 | 3.359 ± 0.0670 |
| IL23  | 0.023 ± 0.0050 | 3.380 ± 0.2127 | 0.011 ± 0.0010 | 3.199 ± 0.1078 |
| TNF-α | 0.020 ± 0.0104 | 3.346 ± 0.1376 | 0.003 ± 0.0029 | 3.159 ± 0.0854 |
| BSA   | 0.015 ± 0.0078 | 0.035 ± 0.0047 | 0.015 ± 0.0078 | 0.035 ± 0.0047 |

N.B. the negative values are due to the fact that the blank (O.D. value of wells without specific antibodies) is subtracted.

Example 11

IL-17A-IL-17RA and IL-17A/F-IL-17RA In Vitro Competitive Binding Inhibition Assay Human IL-17RA was used from a stock solution (BTP22599: 1.68 mg/ml=46.2 µM). ELISA microtiter plates were coated with human IL-17RA (100 µl/well, 1 µg/ml, ~27.5 nM) in PBS/0.02% NaN₃ and incubated overnight at room temperature. The following day the plates were blocked with 300 µl of PBS/2% BSA/0.02% NaN₃ for 1 h at 37° C. Then the plates were washed 4 times with PBS/0.05% Tween20/0.02% NaN₃.

Following this preparation, titration of antibody variants (50 µl, concentrations from 12 nM to 0.12 nM for IL-17A and 1200 nM to 40 nM for IL-17A/F, steps of 3) were pre-incubated with human IL-17A biotin (50 µl at 0.94 nM) or IL-17A/F (50 µl at 31 nM) for 30 minutes at room temperature.

100 µl of the mixture were added to the well for 3 hours and 30 minutes at room temperature. After washing with PBS/0.05% Tween20/0.02% NaN₃, four times alkaline phosphatase-conjugated streptavidin was added at a final dilution of 1/10000 (100 µl/well). After 45 minutes at room temperature plates were washed again 4 times with PBS/0.05% Tween20/0.02% NaN₃ and the substrate p-nitrophenylphosphate in diethanolamine buffer pH 9.8 (1 mg/ml), was added (100 µl/well).

Plates were read after 30 minutes in spectra Max M5 Microplate reader, filters 405 and 490 nm (triplicates). The calculation of the percentage of inhibition and $IC_{50}$ for different antibody variants was done using a four parameter logistic model (Excel Xlfit; FIT model 205).

Results

Data show that both XAB4 and XAB1 are able to block the binding of huIL-17A and huIL-17A/F to the huIL-17RA. The higher affinity of XAB4 for IL-17A and IL-17A/F is reflected in a higher inhibitory capacity. $IC_{50}$ values are reported in the table. The higher concentrations needed to block the IL-17A/F-IL-17RA interaction are mostly explained by the fact that about 30 fold higher concentrations of IL-17A/F were used in the assay. The antibody binds to the A subunit of A/F and therefore cannot prevent binding of the F subunit to the IL-17RA. However, binding of F to IL-17RA is rather weak, in the 300 nM range.

TABLE 26

XAB4 and XAB1 inhibit the binding of huIL-17A and huIL-17A/F to huIL-17RA.

| Ligand\Receptor interaction | XAB4 IC50 (nM) (mean ± SEM) | XAB1 IC50 (nM) (mean ± SEM) | Control antibody (nM) |
|---|---|---|---|
| huIL-17A\huIL-17RA | 0.321 ± 0.037 | 0.830 ± 0.112 | >60 |
| huIL-17A/F\huIL-17RA | 153.9 ± 18.9 | 301.3 ± 51.9 | |

Example 12

In vitro neutralisation of human IL-17A and IL-17A/F activity by antibody variants of the disclosure (i) Assay on C20A4C16 cells (human chondrocyte cell line)

C20A4C16, or C-20/A4, clone 6, (Goldring M B, et al 1994, J Clin Invest; 94:2307-16) cells were cultured in RPMI (Gibco Cat#61870-010) supplemented with 10% fetal calf serum ultra-low IgG (Gibco Cat#16250-078; lot 1074403), β-mercapto ethanol ($5\times10^{-5}$ M final), and Normocin (0.1 mg/ml; InvivoGen Cat# ant-nr-2).

The cells were detached from plastic using an Accutase solution (PAA Cat# L11-007). Cells were distributed into 96 well microtiter plates at a density of $5\times10^3$ in 100 µl well in RPMI 1640 (Gibco Cat#61870-010) without fetal calf serum, β-mercaptoethanol ($5\times10^{-5}$ M final) and Normocin (0.1 mg/ml).

The C20A4C16 cells were allowed to adhere to the plates overnight. The next morning, different concentrations of recombinant huIL-17A (SEQ ID NO: 76; MW 32000), recombinant huIL-17A/F (MW 32800), recombinant huIL-17F (SEQ ID NO: 77; MW 30000), or control medium in the presence of human TNFα (Novartis; MW 17500) were added in a volume of 50 µl to triplicate wells in the presence of 50 µl of different concentrations of test antibody (XAB4; XAB1), control antibody (Simulect® 1.1% solution, Batch C0011; 831179) or control medium to reach the final volume of 200 µl/well and the final concentration of 0.5% fetal calf serum.

HuIL-17A (30 µM), huIL-17A/F (300 µM) and huIL-17F (10 nM) were added together with huTNFα (6 µM). XAB4 (MW 150000) was added in a concentration range from 1 to 0.003 nM to neutralize huIL-17A, in a concentration range from 10 to 0.03 nM to neutralize huIL-17A/F and in a concentration range from 3 µM to 30 nM for huIL-17F. XAB1 (MW 150000) was added in a concentration range from 3 to 0.01 nM to neutralize huIL-17A, in a concentration range from 10 to 0.03 nM to neutralize huIL-17A/F and in a concentration range from 3 µM to 30 nM for huIL-17F. Simulect® was added in a concentration range between 3 µM to 100 nM. Culture supernatants were collected after an incubation of 24 h and huIL-6 production was measured by ELISA.

(ii) Assay on BJ Cells (Human Fibroblasts)

BJ cells (human skin fibroblasts from ATCC Cat# CRL 2522) were cultured in RPMI (Gibco Cat#61870-010) supplemented with 10% fetal calf serum ultra-low IgG (Gibco Cat#16250-078; lot 1074403), β-mercaptoethanol ($5 \times 10^{-5}$ M final) and Normocin (0.1 mg/ml; InvivoGen Cat# ant-nr-2). The cells were detached from plastic using an Accutase solution (PAA Cat# L11-007).

The cells were distributed into 96 well microtiter plates at a density of $5 \times 10^3$ in 100 µl well in RPMI 1640 without fetal calf serum, R-mercaptoethanol ($5 \times 10^{-5}$ M final) and Normocin (0.1 mg/ml). The BJ cells were allowed to adhere to the plates overnight. The next morning, different concentrations of rhuIL-17A (SEQ ID NO: 76; MW 32000), rhuIL-17A/F (MW 32800) and rhuIL-17F (SEQ ID NO: 77; MW 30000), or control medium in the presence of human TNFα (Novartis; MW 17500) were added in a volume of 50 µl to triplicate wells in the presence of 50 µl of different concentrations of test antibody (XAB4; XAB1), control antibody (Simulect® 1.1% solution, Batch # C0011; 831179), or control medium to reach the final volume of 200 µl/well and the final concentration of 2.5% fetal calf serum.

HuIL-17A (30 µM), huIL-17A/F (300 µM) and huIL-17F (10 nM) were added together with huTNFα (6 µM). XAB4 (MW 150000) was added in a concentration range from 1 to 0.003 nM to neutralize huIL-17A, in a concentration range from 10 to 0.03 nM to neutralize huIL-17A/F and in a concentration range from 3 µM to 30 nM for huIL-17F. XAB1 (MW 150000) was added in a concentration range from 3 to 0.01 nM to neutralize huIL-17A, in a concentration range from 10 to 0.03 nM to neutralize huIL-17A/F and in a concentration range from 3 µM to 30 nM for huIL-17F. Simulect® was added in a concentration range between 3 µM to 100 nM. Culture supernatants were collected after an incubation of 24 h and huIL-6 and huGROα production were measured by ELISA.

(iii) Detection Assays

1) ELISA for Detection of Human IL-6 Production

ELISA microtiter plates were coated with an anti-human IL-6 mouse Mab (R&D Systems® Cat# MAB206; 100 µl/well at 1 µg/ml) in PBS 0.02% NaN$_3$ and incubated overnight at +4° C. The following day, microtiter plates were blocked with 300 µl of PBS/2% BSA/0.02% NaN$_3$ for 3 h at room temperature. Plates were then washed 4 times with PBS/0.05% Tween20/0.02% NaN$_3$. Culture supernatants of C20A4C16 (final dilution 1:5 for cultures stimulated with huIL-17A plus huTNFα, or 1:2 for cultures stimulated with huTNFα plus huIL-17A/F or IL-17F; 100 µl/well) or BJ cells (final dilution 1:10 for cultures stimulated with huIL-17A plus huTNFα, or 1:5 for cultures stimulated with huTNFα plus huIL-17A/F or IL-17F; 100 µl/well) were added.

To establish a titration curve, rhuIL-6 (Novartis; 100 µl/well) was titrated from 500 µg/ml to 7.8 µg/ml in 1:2 dilution steps. After an overnight incubation at room temperature, plates were washed 4 times with PBS/0.05% Tween 20/0.02% NaN$_3$. A biotin-conjugated goat anti-human IL-6 antibody was added (R&D Systems® Cat# BAF206; 30 ng/ml; 100 µl/well). Samples were left to react for 4 h at room temperature. After washing (4 times), alkaline phosphatase-conjugated streptavidin (Jackson Immunoresearch Cat#016-050-084) was added at a final dilution of 1/10000 (100 µl/well).

After 40 minutes at room temperature, plates were washed again 4 times. P-Nitrophenyl Phosphate substrate tablets (Sigma; 5 mg, Cat# N9389; 20 mg, Cat# N2765) were dissolved in diethanolamine buffer pH 9.8 to give a final concentration of 1 mg/ml. 100 µl were added to each well and the O.D. was read after 1 h in a Spectra Max M5 Microplate Reader (Molecular Devices) using filters of 405 and 490 nm.

2) ELISA for Detection of Human GROα Production

ELISA microtiter plates were coated with an anti-human GROα mouse mAb (R&D Systems® Systems® Cat# MAB275; 100 µl/well at 1.5 µg/ml) in PBS/0.02% NaN$_3$ and incubated overnight at 4° C. The following day, microtiter plates were blocked with 300 µl of PBS/2% BSA/0.02% NaN$_3$ for 3 h at room temperature. Plates were then washed 4 times with PBS/0.05% Tween20/0.02% NaN$_3$. Culture supernatants of BJ cells (final dilution 1:2; 100 µl/well) were added.

To establish a titration curve, human GROα (R&D Systems® Cat#275-GR/CF; 100 µl/well) was titrated from 2 ng/ml to 0.03 ng/ml in 1:2 dilution steps.) After an overnight incubation at room temperature, plates were washed 4 times with PBS/0.05% Tween 20/0.02% NaN$_3$.

A biotin-conjugated goat anti-human GROα antibody was added (R&D Systems® Cat# BAF275; 100 ng/ml; 100 µl/well). Samples were left to react for 4 h at room temperature. After washing (4 times), alkaline phosphatase-conjugated streptavidin (Jackson immunoresearch Cat#016-050-084) was added at a final dilution of 1/10000 (100 µl/well). After 40 minutes at room temperature, plates were washed again 4 times. P-Nitrophenyl Phosphate substrate tablets (Sigma; 5 mg Cat# N9389; 20 mg, Cat# N2765) were dissolved in diethanolamine buffer pH 9.8 to give a final concentration of 1 mg/ml. 100 µl were added to each well and the O.D. was read after 1 h in a Spectra Max M5 Microplate Reader (Molecular Devices) using filters of 405 and 490 nm.

3) Calculations

Data are reported as Means+/−SEM. Four parameter curve fitting was used for ELISA calculations. IC$_{50}$ values for inhibition of IL-6 and GRO-α secretion by antibodies were calculated using Xlfit (FIT model 205).

(iv) Results

1) Assay on C20A4C16 Cells (Human Chondrocyte Cell Line)

Both XAB4 and XAB1 are able to neutralize the induction of huIL-6 secretion by C20A4C16 cells stimulated with rhuIL-17A and rhuIL-17A/F in the presence of rhuTNFα. Control antibody (Simulect®) at 100 nM has no effect. IC$_{50}$ values (means±SEM) for XAB4 and XAB1 are reported in Table 27. No inhibition on huIL-17F is observed even at Ab concentrations of 3 µM.

TABLE 27

Inhibitory effects of XAB4 and XAB1 on huIL-6 secretion by C20A4CI6 cells.

| Stimuli | XAB4 IC50 (nM) (means ± SEM) | XAB1 IC50 (nM) (means ± SEM) | Control antibody (nM) |
|---|---|---|---|
| rhuIL-17A (1 nM)[a] | 0.44 ± 0.06 | | >100 |
| rhuIL-17A/F (3 nM)[a] | 1.30 ± 0.18 | | >100 |
| rhuIL-17F (30 nM)[a] | >3000 | | >1000 |
| rhuIL-17A (30 pM) + rhuTNF-α (6 pM)[b] | 0.024 ± 0.004 | 1.21 ± 0.09 | >3000 |
| rhuIL-17A/F (300 pM) + rhuTNF-α (6 pM)[b] | 0.108 ± 0.02 | >10 | >3000 |
| rhuIL-17F (10 nM) + rhuTNF-α (6 pM)[b] | >3000 | >3000 | >3000 |

[a]Background of huIL-6 production without stimulation (0.13 ± 0.003) is subtracted
[b]Background of huIL-6 production in cultures with TNF alone (0.20 ± 0.003) is subtracted From these experiments it is evident that the parental XAB1 antibody shares neutralizing activity with its derivatives. The XAB4 variant is also seen to have a higher neutralizing activity than XAB1.

In an additional experiment, analogous to the experiment described above, all the antibodies XAB1-XAB5 were compared, as seen in Table 28. Here it can be seen that the inhibition profiles for XAB2, XAB3 and XAB5 are comparable to those observed for XAB4 and XAB1, especially to XAB4.

TABLE 28

Table Inhibitory effects of XAB antibodies on huIL-6 secretion by C20A4CI6 cells.

| Stimuli | XAB1 IC50 (nM) Means ± SEM | XAB2 IC50 (nM) Means ± SEM | XAB3 IC50 (nM) Means ± SEM | XAB4 IC50 (nM) Means ± SEM | XAB5 IC50 (nM) Means ± SEM |
|---|---|---|---|---|---|
| rhuIL-17A (0.5 nM)[a] | 0.29 ± 0.03 | 0.72 ± 0.08 | 0.63 ± 0.15 | 0.51 ± 0.04 | 0.55 ± 0.01 |

[a]Background of HuIL-6 production without stimuli (0.04 ± 1.13 ng/ml) is subtracted.

2) Assay on BJ Cells (Human Fibroblasts)

Both XAB4 and XAB1 neutralize the induction of huIL-6 and huGROα secretion by BJ cells stimulated with rhuIL-17A and rhuIL-17A/F in the presence of huTNFα. Control antibody (Simulect®) at 100 nM has no effect. IC$_{50}$ values for inhibition of IL-6 and hu GROα are reported in Table 29 and Table 30. Inhibition on huIL-17F is not observed even at Ab concentrations of 3 μM. From these experiments it is evident that the parental XAB1 antibody shares neutralizing activity with its derivatives.

The XAB4 variant is also seen to have a higher neutralizing activity than XAB1.

TABLE 29

Inhibitory effect of XAB4 and XAB1 on huIL-6 secretion by BJ cells.

| Stimuli | XAB4 IC50 (nM) Means ± SEM | XAB1 IC50 (nM) Means ± SEM | Control antibody (nM) |
|---|---|---|---|
| rhuIL-17A (1 nM)[a] | 0.63 ± 0.02 | | >100 |
| rhuIL-17A/F (3 nM)[a] | 1.68 ± 0.05 | | >100 |
| rhuIL-17F (30 nM)[a] | >3000 | | >1000 |
| rhuIL-17A (30 pM) + rhuTNF-α (6 pM)[b] | 0.012 ± 0.002 | 0.47 ± 0.02 | >3000 |
| rhuIL-17A/F (300 pM) + rhuTNF-α (6 pM)[b] | 0.17 ± 0.01 | 3.83 ± 0.63 | >3000 |
| rhuIL-17F (10 nM) + rhuTNF-α (6 pM)[b] | >3000 | >3000 | >3000 |

[a]Background of huIL-6 production without stimuli (0.32 ± 0.002 ng/ml) is subtracted.
[b]Background of huIL-6 production in cultures stimulated with TNF alone (0.45 ± 0.02 ng/ml) is subtracted.

TABLE 30

Inhibitory effect of XAB4 and XAB1 on hu-GRO-alpha secretion by BJ cells.

| Stimuli | XAB4 IC50 (nM) Means ± SEM | XAB1 IC50 (nM) Means ± SEM | Control antibody (nM) |
|---|---|---|---|
| IL-17A (1 nM)[a] | 0.35 ± 0.01 | | >100 |
| IL-17A/F (3 nM)[a] | 1.11 ± 0.05 | | >100 |
| IL-17F (30 nM)[a] | >3000 | | >1000 |
| IL-17A (30 pM) + TNF-α (6 pM)[b] | 0.007 ± 0.0004 | 0.72 ± 0.12 | >3000 |
| IL-17A/F (300 pM) + TNF-α (6 pM)[b] | 0.1 ± 0.01 | 6.22 ± 0.44 | >3000 |
| IL-17F (10 nM) + TNF-α (6 pM)[b] | >3000 | >3000 | >3000 |

[a]Background of hu GROα production without stimuli (0.03 ± 0.01 ng/ml) is subtracted.
[b]Background of hu GROα production in cultures with TNF alone (0.15 ± 0.008 ng/ml) is subtracted.

In additional experiments, analogous to the experiments described above, all the antibodies XAB1-XAB5 were compared, as seen in Table 31 and Table 32. Here it can be seen that the inhibition profiles for XAB2, XAB3 and XAB5 are comparable to those observed for XAB4 and XAB1, especially to XAB4.

TABLE 31

Inhibitory effects of XAB antibodies on huIL-6 secretion by BJ cells.

| Stimuli | XAB1 IC50 (nM) Means ± SEM | XAB2 IC50 (nM) Means ± SEM | XAB3 IC50 (nM) Means ± SEM | XAB4 IC50 (nM) Means ± SEM | XAB5 IC50 (nM) Means ± SEM |
|---|---|---|---|---|---|
| rhuIL-17A (0.5 nM)[a] | 4.97 ± 0.59 | 0.64 ± 0.22 | 0.50 ± 0.002 | 0.55 ± 0.04 | 0.54 ± 0.02 |

[a]Background of HuIL-6 production without stimuli (0.15 ± 4.06 ng/ml) is subtracted

TABLE 32

Inhibitory effects of XAB antibodies on huGROa secretion by BJ cells.

| Stimuli | XAB1 IC50 (nM) Means ± SEM | XAB2 IC50 (nM) Means ± SEM | XAB3 IC50 (nM) Means ± SEM | XAB4 IC50 (nM) Means ± SEM | XAB5 IC50 (nM) Means ± SEM |
|---|---|---|---|---|---|
| rhuIL-17A (0.5 nM)[a] | 1.39 ± 0.07 | 0.40 ± 0.06 | 0.42 ± 0.01 | 0.44 ± 0.04 | 0.46 ± 0.05 |

[a]Background of HuGROα production without stimuli (0.03 ± 0.02 ng/ml) is subtracted Example 13

In Vitro Neutralization of Mouse IL-17A and IL-17A/F Activity by Antibody Variants of the Disclosure CMT-93 cells (ATCC CCL-223) were cultured in RPMI (Gibco Cat#61870-010) supplemented with 10% fetal calf serum ultra-low IgG (Gibco Cat#16250-078; lot 1074403), β-mercaptoethanol ($5 \times 10^{-5}$ M final) and Normocin (0.1 mg/ml; InvivoGen Cat# ant-nr-2).

The cells were detached from plastic using an Accutase solution (PAA Cat# L11-007) and distributed into 96 wells microtiter plates at a density of $5 \times 10^3$ in 100 μl well in RPMI 1640 without fetal calf serum, β-mercaptoethanol and normocin.

The cells were allowed to adhere to the plates overnight. The next morning, rmIL-17A (SEQ ID NO: 83, MW 31000) at 1 nM, rmIL-17A/F (R&D Systems® Cat#5390-IL; MW 30400) at 3 nM, rmIL-17F (SEQ ID NO: 84; MW 30000) at 30 nM, rratIL-17A (SEQ ID NO: 85; MW 31000) at 1 nM or control medium were added in a volume of 50 μl to triplicate wells in the presence of 50 μl of different concentrations of test antibodies (XAB4 or XAB1), control antibodies (Simulect® 1.1% solution; C0011, 831179) or control medium to reach the final volume of 200 μl/well and the final concentration of 1% fetal calf serum.

Culture supernatants were collected after an incubation of 24 h and KC production was measured by ELISA.

(i) ELISA for Detection of Mouse KC Production

ELISA microtiter plates were coated with a rat anti-mouse KC MAb (R&D Systems® Cat# MAB453; 100 μl/well at 1 μg/ml) in PBS/0.02% NaN$_3$ and incubated overnight at 4° C. The following day, microtiter plates were blocked with 300 μl of PBS/2% BSA/0.02% NaN$_3$ for 3 h at room temperature. Plates were then washed 4 times with PBS/0.05% Tween20/ 0.02% NaN$_3$. Culture supernatants of CMT-93 cells (final dilution 1:5; 100 μl/well) were added.

To establish a titration curve, mouse KC (R&D Systems® #453-KC, 100 μl/well) was titrated from 1 ng/ml to 0.016 ng/ml in 1:2 dilution steps. After an overnight incubation at room temperature, plates were washed 4 times with PBS/ 0.05% Tween 20/0.02% NaN$_3$. A biotin-conjugated goat anti-mouse KC antibody (R&D Systems® Cat# BAF453; 100 μl/well) at 0.1 μg/ml was added. Samples were left to react for 4 h at room temperature. After washing (4 times), alkaline phosphatase-conjugated streptavidin (Jackson immunoresearch Cat#016-050-084) was added at a final dilution of 1/10000 (100 μl/well). After 40 minutes at room temperature, plates were washed again 4 times. P-Nitrophenyl Phosphate substrate tablets (Sigma; 5 mg Cat# N9389; 20 mg Cat# N2765) were dissolved in diethanolamine buffer pH 9.8 to give a final concentration of 1 mg/ml. 100 μl culture supernatants were added to each well and the O.D. was read after 1 h in a Spectra Max M5 Microplate Reader (Molecular Devices) using filters of 405 and 490 nm.

(ii) Calculations

Data are reported as Means+/−SEM. Four parameter curve fitting was used for ELISA calculations. IC$_{50}$ values for inhibition of KC secretion by antibodies were calculated using Xlfit™ (FIT model 205).

(iii) Results

Both XAB4 and XAB1 are able to neutralize the induction of mouse KC secretion by CMT-93 cells stimulated with mouse or rat IL-17A and mouse IL-17A/F. Control antibody (Simulect®) has no effect. IC$_{50}$ values (means±SEM) for XAB4 and XAB1 are reported in Table 33. Inhibition on huIL-17F is not observed even at Ab concentrations of 10 μM.

TABLE 33

Inhibitory effect of XAB4 and XAB1 on mouse KC secretion by CMT-93 cells.

| Stimuli | XAB4 IC50 (nM) Means ± SEM | XAB1 IC50 (nM) Means ± SEM | Control antibody (nM) |
|---|---|---|---|
| mIL-17A (1 nM)[a] | 13.8 ± 0.48 | 539 ± 29.4 | >3000 |
| mIL-17A/F (3 nM)[a] | 10.3 ± 1.06 | >1000 | >3000 |
| mIL-17F (30 nM)[a] | >10000 | >10000 | >3000 |
| rIL-17A (1 nM)[a] | 6.7 ± 0.84 | 467 ± 25.1 | >3000 |

[a]Background of KC production without stimuli (0.07 ± 0.001 ng/ml) is subtracted.

From these experiments it is evident that both the parental XAB1 antibody, as well as its derivates, has neutralizing activity. The XAB4 variant is also seen to have a higher neutralizing activity than XAB1.

In an additional experiment, analogous to the experiment described above, all the antibodies XAB1-XAB5 were compared, as seen in Table 34. Here it can be seen that the inhibition profiles for XAB2, XAB3 and XAB5 are comparable to those observed for XAB4 and XAB1, especially to XAB4.

TABLE 34

Inhibitory effects of XAB antibodies on KC secretion by CMT-93 cells.

| Stimuli | XAB1 IC50 (nM) Means ± SEM | XAB2 IC50 (nM) Means ± SEM | XAB3 IC50 (nM) Means ± SEM | XAB4 IC50 (nM) Means ± SEM | XAB5 IC50 (nM) Means ± SEM |
|---|---|---|---|---|---|
| mIL-17A (0.15 nM)[a] | 128 ± 14.2 | 20.9 ± 0.96 | <1 | 7.0 ± 0.29 | 7.8 ± 0.78 |

[a]Background of KC production without stimuli (0.19 ± 5.81 ng/ml) is subtracted.

Example 14

Rat Antigen-Induced Arthritis Assay (Rat AIA)

Female Lewis rats (120-150 g) were sensitized intradermally on the back at two sites to methylated bovine serum albumin (mBSA) homogenized 1:1 with complete Freund's adjuvant on days −21 and −14 (0.1 ml containing 5 mg/ml mBSA). On day 0, the rats were anaesthetized using a 5% isoflurane/air mixture and maintained using isoflurane at 3.5% via a face mask for the intra-articular injections. The right knee received 50 µl of 10 mg/ml mBSA in 5% glucose solution (antigen injected knee), while the left knee received 50 µl of 5% glucose solution alone (vehicle injected knee). The diameters of the left and right knees were then measured using calipers immediately after the intra-articular injections and again on days 2, 4, and 7.

Treatments were administered by single subcutaneous injection on day −3. The antibody of the disclosure was injected at 0.15, 1.5, 15 and 116 mg/kg. Right knee swelling was calculated as a ratio of left knee swelling, and the R/L knee swelling ratio plotted against time to give Area Under the Curve (AUC) graphs for control and treatment groups. The percentage inhibitions of the individual animals in each treatment group AUCs were calculated vs. the control group AUC (0% inhibition) using an Excel spreadsheet.

Results

Results are shown in Table 35. Dose related inhibition of right knee swelling was demonstrated for XAB4 with a calculated $ED_{50}$ of 1.68 mg/kg s.c.

TABLE 35

Effects of single dose treatment with XAB4 on knee swelling from day 0 to day 7 in Lewis rat antigen-induced arthritis.

| Antibody dose (mg/kg) | Percentage inhibition of knee swelling AUC |
|---|---|
| 0.15 | 18.46 ± 1.61* |
| 1.5 | 65.76 ± 3.41** |
| 15 | 71.59 ± 1.27** |
| 116 | 77.01 ± 1.72** |

Data points represent the means ± SEM of n = 5 animals.
*p < 0.05 and **p < 0.01
ANOVA followed by Dunnett's test vs Control curve.

Similarly, dose related inhibition of knee swelling was demonstrated for XAB4 in a model using Wistar rats (data not shown), and in a model using mouse antigen-induced arthritis model (data not shown).

Example 15

Angiogenesis Mechanistic Model

Chambers containing human IL-17A (between 150 and 200 ng), when placed subcutaneously in a mouse, cause new blood vessel growth around the implant. The amount of angiogenesis correlates with the weight of newly formed tissue in this area. Prophylactic treatment with XAB4 at 0.01, 0.03, 0.1, 0.3, 1 and 3 mg/kg inhibited human IL-17 induced angiogenesis. The 5 higher doses all led to a potent and significant inhibition of tissue chamber weight. The 4 higher doses showed no dose dependency, however, the dose of 0.03 mg/kg was less efficacious than doses of 0.1 mg/kg and above.

This study demonstrates that the potent angiogenic effect of IL-17A can be neutralized with an anti-IL-17A antibody and provides experimental evidence of the effectiveness of XAB4 for human IL-17A in vivo.

Example 16

Experimental Autoimmune Encephalomyelitis (EAE) Model

The experimental autoimmune encephalomyelitis (EAE) model is a known animal model for multiple sclerosis (reviewed e.g in Constantinescu et al., Br J Pharmacol 2011). It has been shown that inhibition of IL-17 reduces EAE severity in C57Bl/6 mice (Haak S et al 2009, JCI; 119:61-69).

Female C57Bl/6 mice (aged 9 weeks, Harlan, Germany) were immunized with a 50/50 mixture of recombinant rat myelin oligodendrocyte glycoprotein peptide ($MOG_{1-125}$) (generated in-house) and complete Freund's adjuvant (CFA, generated by adding 8 mg/ml Mycobacterium tuberculosis strain H37RA (Difco) to Incomplete Freund's adjuvant (IFA, Sigma). Immunization was performed by subcutaneous injection with 200 µg/animal of $MOG_{1-125}$ at the base of tail on day 0. In addition, 200 ng/animal pertussis toxin (PT) was injected intraperitoneally on days 0 and 2.

Both therapeutic treatment effect and prophylactic treatment effect of XAB4 was tested.

Therapeutic Treatment

For the therapeutic treatment 16 mice were used (8 for XAB4 and 8 for control). Treatment was initiated once the animals had a clinical score of at least 2.5 (severe hind limb weakness) for 3 days. After this, 15 mg/kg XAB4 or isotype control antibody was injected subcutaneously each week with a single dose.

Figure 11:
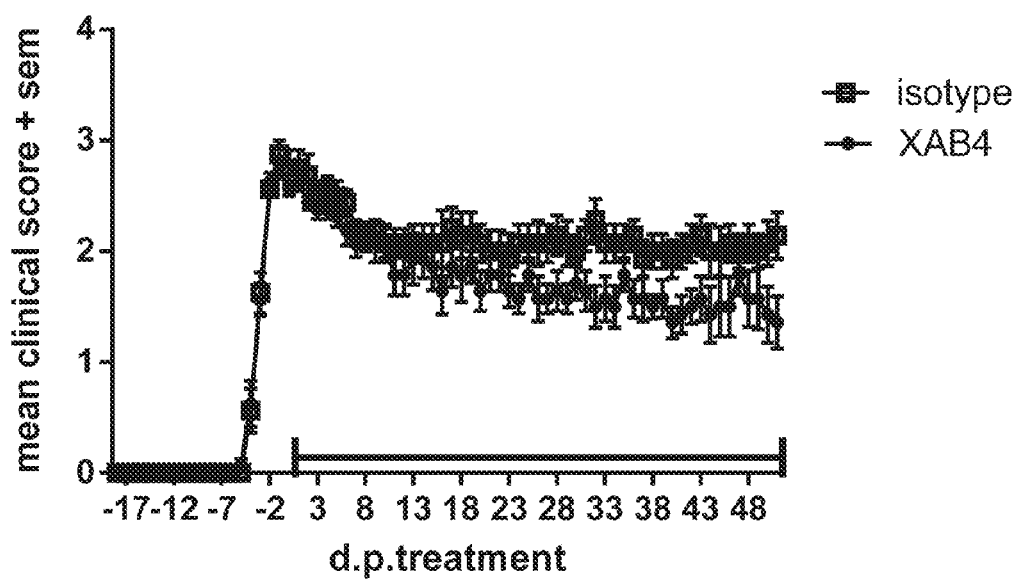
FIG. 11 is a graph showing the therapeutic score for XAB4 in an experimental autoimmune encephalomyelitis (EAE) model.
Figure 12:
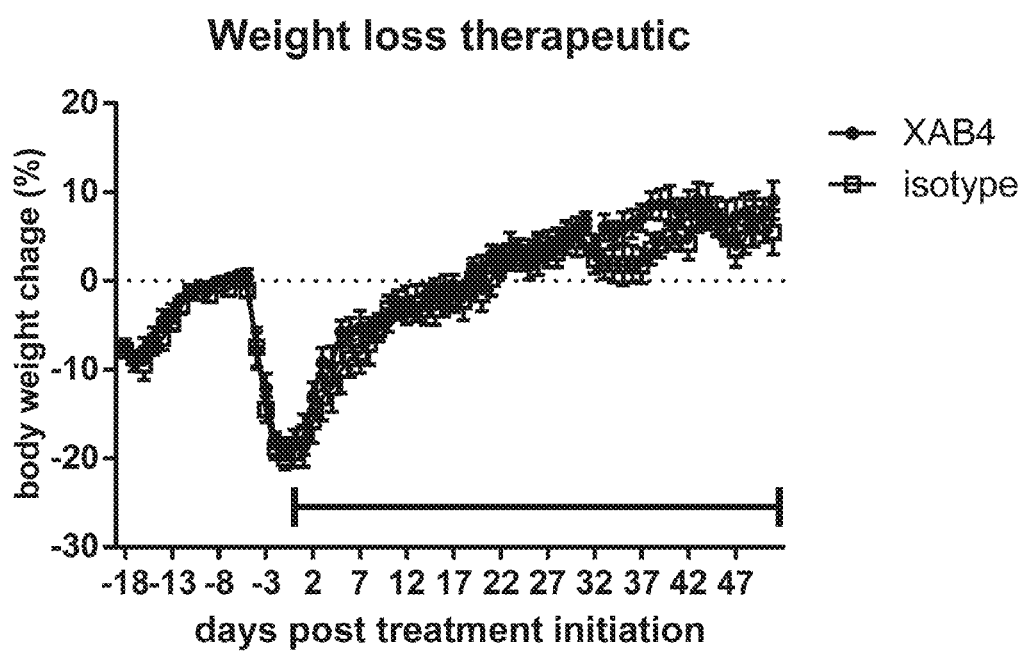
FIG. 12 is a graph showing the therapeutic weight change (%) of animals in the EAE model.
Figure 13:
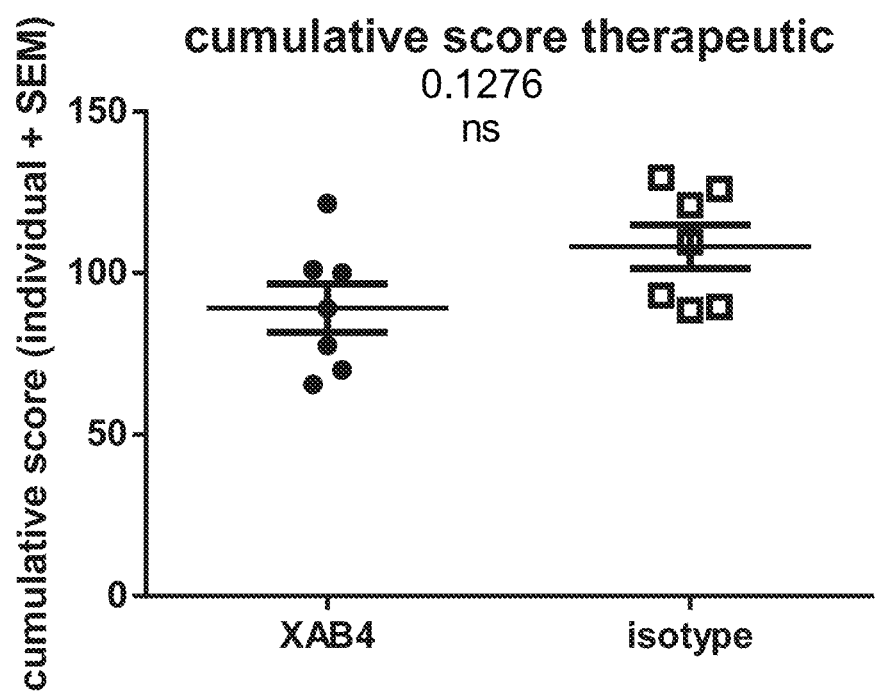
FIG. 13 is a graph showing the cumulative therapeutic scores in the EAE model.
Figure 14:
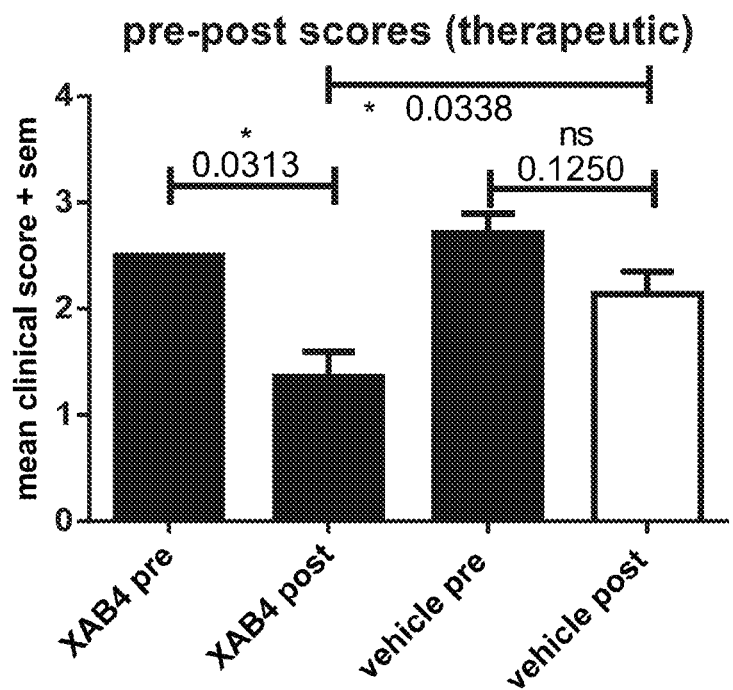
FIG. 14 shows a comparison of the therapeutic score pre- and post-treatment in the EAE model.
Figure 15A:
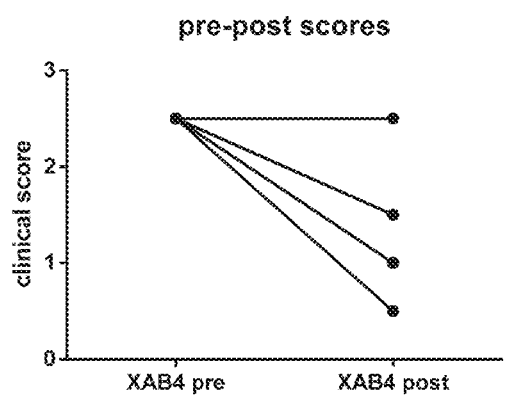
FIG. 15A show the therapeutic score pre- and post-treatment in the EAE model, with XAB4.
Figure 15B:
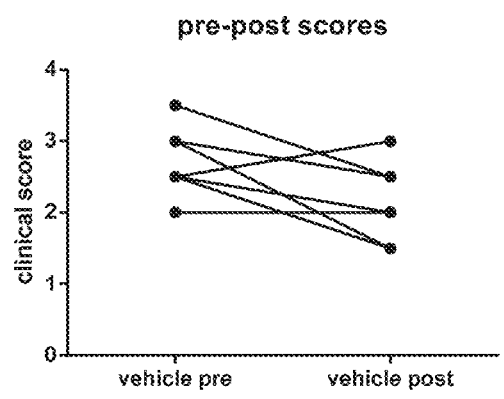
FIG. 15B show the therapeutic score pre- and post-treatment in the EAE model, with vehicle

The results are shown in FIGS. 11 to 15 (d.p.i is days post immunization). In all figures, XAB4 is represented by circles and the isotype control is represented by squares. The therapeutic score (mean+SEM) is shown in FIG. 11. It is clearly seen that animals treated with XAB4 has a lower mean clinical score than isotype control. FIG. 12 shows the weight change (%) for the two groups of mice, and FIG. 13 shows the cumulative therapeutic scores. FIGS. 14 and 15 are comparisons of the therapeutic score pre- and post-treatment. It is clearly seen in all graphs that XAB4 has a therapeutic effect compared to the isotype control. Thus, therapeutic treatment with XAB4 significantly reduced the severity of EAE.

Prophylactic Treatment

For the prophylactic treatment 19 mice were used (10 for XAB4 and 9 for control). Each animal was treated one day prior to immunization with 15 mg/kg XAB4 or isotype control, through a single subcutaneous injection. After this, 15 mg/kg XAB4 or isotype control antibody was injected subcutaneously each week with a single dose.

Figure 16:
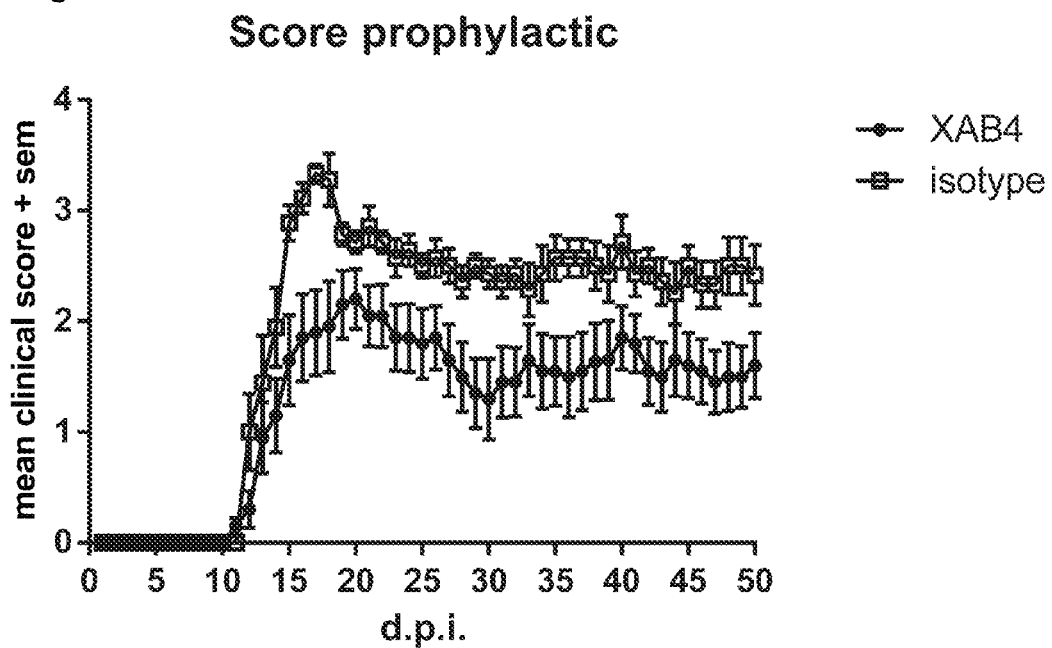
FIG. 16 is a graph showing the prophylactic score for XAB4 in the EAE model.
Figure 17:
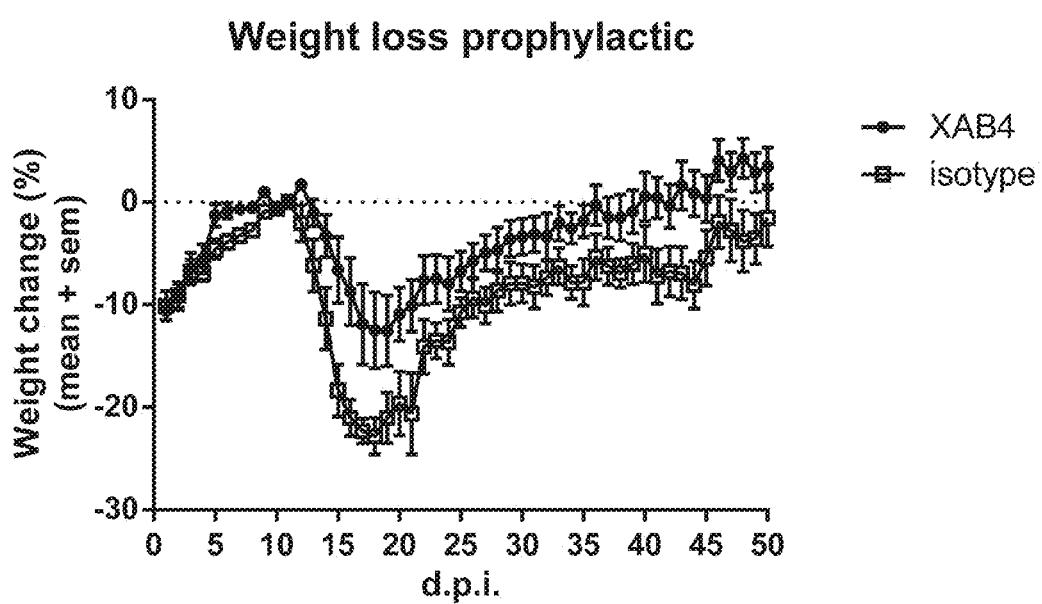
FIG. 17 is a graph showing the prophylactic weight change (%) of animals in the EAE model.
Figure 18:
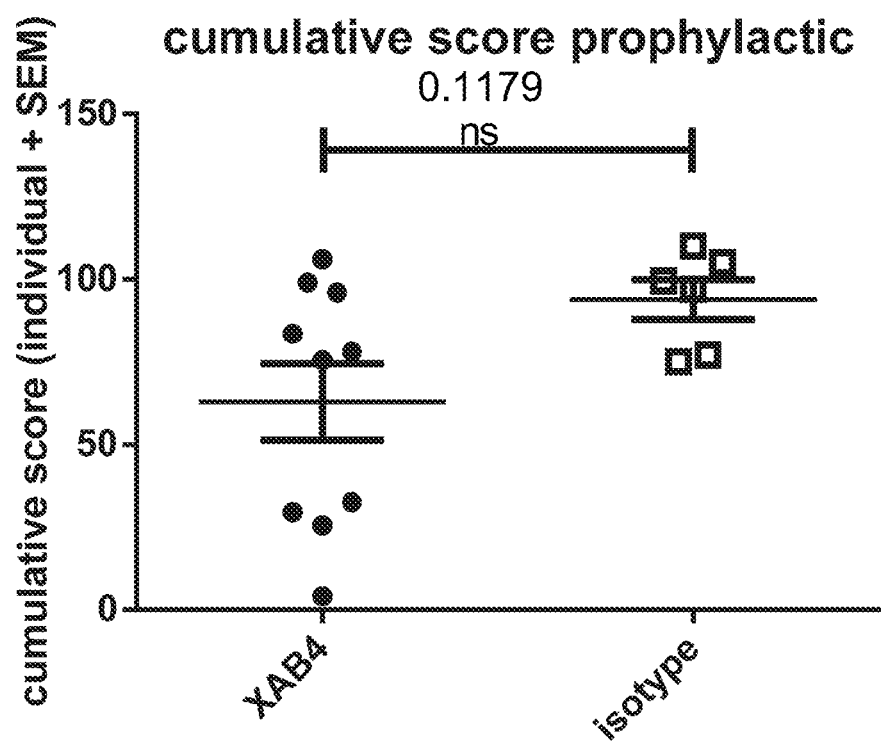
FIG. 18 is a graph showing the cumulative prophylactic scores in the EAE model.
Figure 19:
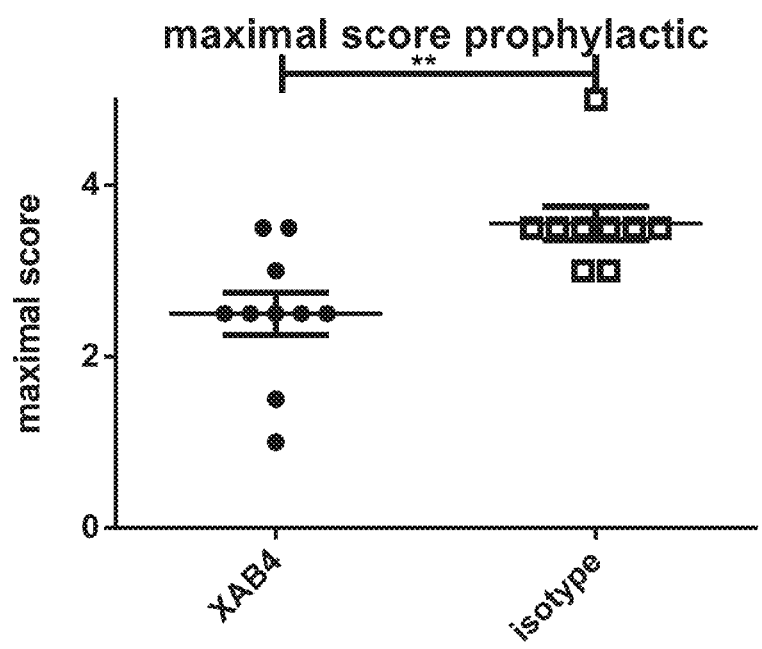
FIG. 19 is a graph showing the maximum prophylactic scores in the EAE model.
Figure 20:
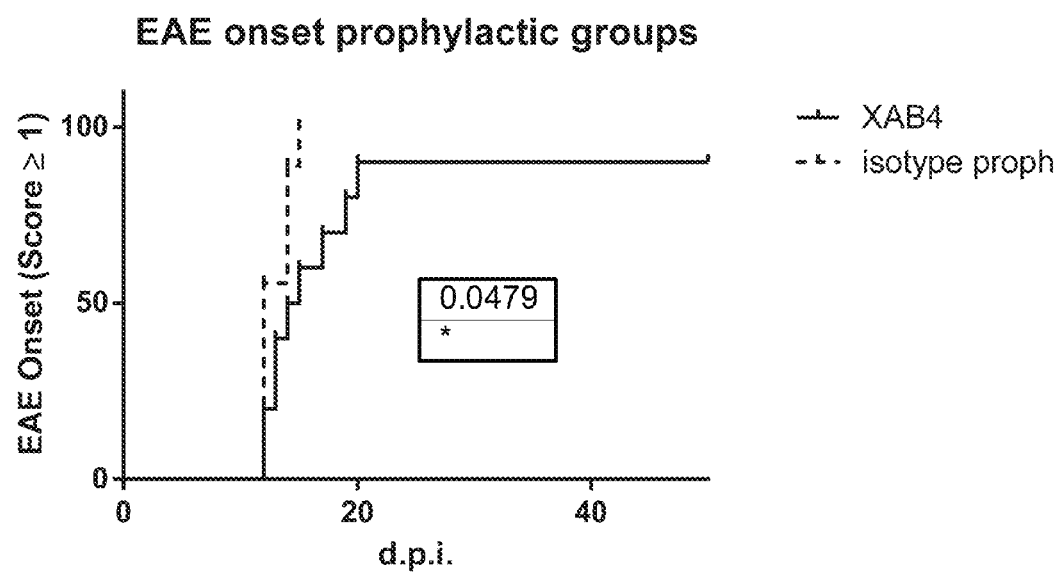
FIG. 20 is a graph showing the EAE onset in the EAE model.

The results are shown in FIGS. 16 to 20 (d.p.i is days post immunization). In FIGS. 16 to 19, XAB4 is represented by closed circles and the isotype control is represented by open squares. The prophylactic score (mean+SEM) is shown in FIG. 16. It is clearly seen that animals treated with XAB4 has a lower mean clinical score. FIG. 17 shows the weight change (%) for the two groups of mice, and FIG. 18 shows the cumulative prophylactic scores. The maximum prophylactic score is seen in FIG. 19. It is clearly seen in all graphs that XAB4 has an effect compared to the isotype control. Furthermore, in FIG. 20, where XAB4 is represented by a solid line and isotype control is represented by a dotted line, it is seen that EAE onset is later for the group of mice treated with XAB4, compared to the group of mice treated with isotype control.

Thus, it is shown that prophylactic treatment with XAB4 significantly delayed EAE onset and reduced maximal EAE severity.

Example 17

Attenuation of 107A-Induced Levels of IL6, CXCL1, IL-8, GM-CSF, and CCL2 in Human Astrocytes The effects of XAB4 on the levels of IL-6, CXCL1, IL-8, GM-CSF, and CCL2 in astrocytes isolated from the cerebral cortex of the human brain were investigated. Astrocytes release a number of growth factors, cytokines and chemokines that allow them to regulate cellular communication, migration and survival of neuronal, glial and immune cells. The direct communication of astrocytic end-feet with endothelial cells also allows astrocytes to control function of the blood-brain-barrier. Moreover, astrocytes release and uptake neurotransmitters, such as glutamate, at the synaptic cleft that allow them to regulate synaptic transmission and excitoxicity. It is significant that astrocytes form scar pathology after CNS injury, thus having apparent opposing roles in normal physiology and pathophysiology. In disease, astrocytes are suggested to play roles in a range of psychiatric, neurological and neurodegenerative disorders, where their role in neuroinflammation is likely to be important.

The data showed that co-stimulation with IL-17A and TNFα enhanced the release of IL-6, CXCL1, IL-8, GM-CSF, and CCL2, and that XAB4 inhibited levels of IL-6, CXCL1, IL-8, GM-CSF, and CCL2 in human astrocytes. These data indicate a dominate role for IL-17A in cytokine release from astrocytes and support their use as drug targets for neuroinflammatory diseases. It is noteworthy that the pretreatment of human astrocytes with XAB4 inhibited IL-17A-induced and IL-17A/TNFα-induced, without affecting TNFα-induced, levels of IL-6, CXCL1, IL-8, GM-CSF, and CCL2. Taken together, the data suggested that selective inhibition of IL-17A signaling with XAB4 attenuates the level of pro-inflammatory cytokines in human astrocytes. In disease, astrocytes are suggested to play roles in a range of psychiatric, neurological and neurodegenerative disorders, where their role in neuroinflammation is likely to be important. Novel drugs that alter astrocyte function are thus of potential value, where regulation of astrocyte function may prove therapeutically useful. Consequently, since XAB4 was shown to have an effect on IL-6, CXCL1, IL-8, GM-CSF, and CCL2 production of astrocytes, it can be concluded that XAB4 may be a useful therapeutic agent, such as for treatment of Multiple Sclerosis (MS).

Materials and Methods

All cytokines were purchased from R&D Systems. Basiliximab (Novartis, Basel, Switzerland) was used as isotype control. Primary antibodies used were: anti-IL17RA Alexa Fluor 647 (BG/hIL17AR, Biolegend), anti-IL17RC Alexa Fluor 488 (309822, R&D Systems, UK), anti-p65 (Santa Cruz, USA), mouse IgG Alexa Fluor 647 (MOPC-21, Biolegend, UK), mouse IgG Alexa Fluor 488 (133303, R&D System, UK), mouse IgG Biotin (G155-178, BD Biosciences, Switzerland) and rat IgG PE (A95-1, BD Biosciences, Switzerland). Secondary antibodies and dyes used were: biotinylated goat anti-rabbit IgG (BA1000, Vector, UK), streptavidin conjugated Alexa Fluor 488 and Alexa Fluor 633 (S11223 and S2137, Life Technology, USA), goat anti-mouse Alexa Fluor 488 and Alexa Fluor 633 (A1101 and A21050, Life Technology, USA), streptavidin BV421 (405226, Biolegend, UK), Hoechst 34580 (H21486, Life Technology, USA).

Human astrocytes derived from cerebral cortex were purchased from ScienCell Research Laboratory (USA) (catalogue number 1800). Cells were grown as per provider's instructions. Briefly cells were grown in human astrocyte media (ScienCell catalogue number 1801) supplemented with 1% astrocyte growth supplement (ScienCell catalogue number 1852), 5% fetal calf serum (ScienCell catalogue number 0010) and 1% Penicillin/Streptomycin (ScienCell catalogue number 0503). Cells were maintained in T75 culture flasks at 5% $CO_2$ and 37° C. with the media changed every three days until 80% confluent. For all treatments, 70,000 cells well plated in 24-well plates, grown for 3 days, serum starved for 2-4 hr, after which astrocytes were treated for 2 hr with XAB4, and thereafter treated for 18-20 hr with recombinant human cytokines as indicated in the figure legends. The cell pellets were used to quantify mRNA levels of cytokines by qPCR and the supernatants were used to quantify the protein levels of cytokines by HTRF (Cisbio, France, used for IL-6, IL-8 & CXCL1) or AlphaLISA (PerkinElmer, USA, used for CCL2 & GM-CSF).

Measurement of cytokine mRNA was performed by real time-polymerase chain reaction (RT-PCR). Briefly, astrocytes were lysed for 5 min at room temperature by gently shaking in 350 μl lysis buffer (RLT buffer with 1% β-mercaptoethanol) and total RNA was extracted using RNeasy Microkit (74004, Qiagen, Switzerland). The cDNA was synthesized using SuperScript III reverse transcriptase (18080-400, Life Technology, Switzerland). The expression level of each gene was assessed by q-PCR in a Viia7 Real-time PCR machine (Life Technology, Switzerland). Taqman probes were purchased from Life Technology, Switzerland. Each sample was analyzed in triplicate and normalized to hypoxanthine-guanine phosphoribosyltransferase (HPRT). Levels of human IL6, IL8, CXCL1 protein (ng/ml) in human astrocyte supernatant (10 μl) were assessed by HTRF (IL6:

62IL6PEC; IL8: 62IL8PEC; CXCL1: 6FGROPEG, Cisbio, France) and the level of human CCL2 protein (ng/ml) in human astrocyte supernatant (5 µl) was assessed by AlphaL-ISA human CCL2/MCP1 (AL244C, PerkinElmer, USA). All measurements were performed according to manufacturer's instructions.

Cells suspensions of human astrocytes were obtained from adherent cultures using PBS-5 mM EDTA. For extracellular staining cells were incubated with whole mouse IgG for 10 min at 4° C. in PBS 2% BSA, and then stained with antibodies for 30 min at 4° C. in PBS 2% BSA. For intracellular staining, cells were permeabilized with Cytofix/Cytoperm solution (554714, BD Biosciences, Switzerland) for 20 min at 4° C. before incubating with antibodies for 30 min at 4° C. After filtration through 70 µm strainer, cells were acquired on a BDFortessa (BD Biosciences, Switzerland) and data analyzed using FlowJo software (Tree Star Inc., USA).

After compound treatment, cells were washed in PBS (Sigma Aldrich, Germany) followed by fixation in ice-cold 100% methanol for 10 min. Cells were washed 3×5 min in sterile PBS then permeabilized by incubation with 0.2% Triton-X-100 (Sigma Aldrich, Germany) in PBS for 5 min at room temperature. Non-reactive sites were blocked overnight at +4° C. with blocking buffer which consisted of 10% normal goat serum (Life Technology, USA) and 2% bovine serum albumin (Sigma Aldrich, Germany) in PBS. The cells were then incubated in primary antibody overnight at 4° C. The primary antibody was removed and the cells washed 3×5 min PBS after which the secondary fluorescent antibody was applied for 2 hr at room temperature. The coverslips were then washed 5×5 min in PBS and counter stained with Hoescht 34580 nuclear stain. The coverslips were finally mounted on microscope slides in VectashieldR mounting medium (Vector, UK) and the edges of the coverslip sealed with nail varnish. The cells were imaged using a Zeiss LSM 510 META confocal laser scanning microscope utilizing an Axiovert 200M inverted microscope (Zeiss Ltd, Germany).

Results

Figure 21A:
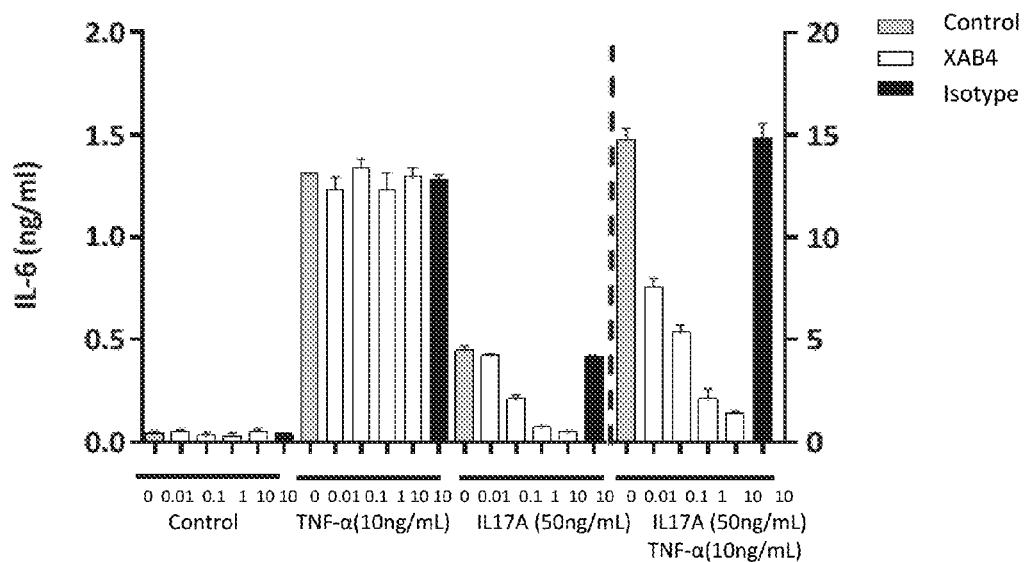
FIG. 21A shows antagonism of TNF-α or IL-17A stimulation, or IL-17A/TNF-α co-stimulation by XAB4, by IL-6.
Figure 21B:
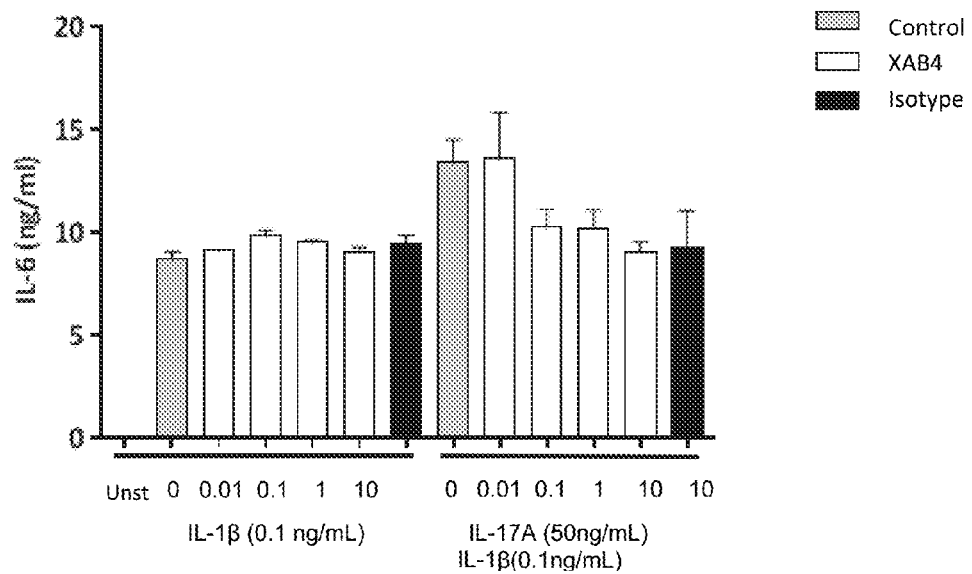
FIG. 21B shows antagonism of IL-1β or IL-17N IL-1β co-stimulation by XAB4, by IL-6. The model used is a human astrocyte model.

Antagonism of TNF-α or IL-17A stimulation, or IL-17A/TNF-α co-stimulation by XAB4 is shown in FIGS. 21A to 25A. Antagonism of IL-1β or IL-17N IL-1β co-stimulation by XAB4 is shown in FIGS. 21 B to 25 B.

FIG. 21 shows antagonistic effect on IL-6 release, FIG. 22 shows antagonistic effect on CXCL1 release, FIG. 23 shows antagonistic effect on IL-8, FIG. 24 shows antagonistic effect on GM-CSF and FIG. 25 shows antagonistic effect on CCL2.

Primary human astrocytes were treated with increasing concentrations of XAB4 (0.01 nM, 0.1 nM 1 nM and 10 nM), with or without IL-17A (50 ng/ml), TNF-α (10 ng/ml), IL-1β, IL-17A/TNF-α and IL-1β/TNF-α. All concentrations used are indicated in the figures. The data shown is a representative of two experiments for XAB4 0.01 nM, and of three experiments for XAB4 0.1 nM, 1 nM and 10 nM. Values shown are means±S.E.M.

As seen in FIG. 21A, XAB4 (all concentrations) has an antagonistic effect, compared to both control and isotype, on release of IL-6 from astrocytes stimulated with IL-17A, or IL-17A/TNF-α. Concentration of IL-6 (ng/ml) is represented by the y-axis and concentration of XAB4 is represented on the x-axis (0, i.e. control, 0.01 nM, 0.1 nM 1 nM and 10 nM) for each dataset, and 10 nM for isotype. The dataset to the left relates to unstimulated cells, the next dataset relates to cells stimulated with TNF-α (10 ng/ml), the next dataset relates to cells stimulated with IL-17A (50 ng/ml) and the last dataset relates to cells co-stimulated with TNF-α (10 ng/ml) and IL-17A (50 ng/ml). The last dataset has about 10 fold higher scale of the y-axis. As seen in FIG. 21 B, XAB4 (all concentrations) has no antagonistic effect on cells stimulated with IL-1β (0.1 ng/ml) or co-stimulated with IL-1β (0.1 ng/ml) and IL-17A (50 ng/ml), compared to isotype.

Figure 22A:
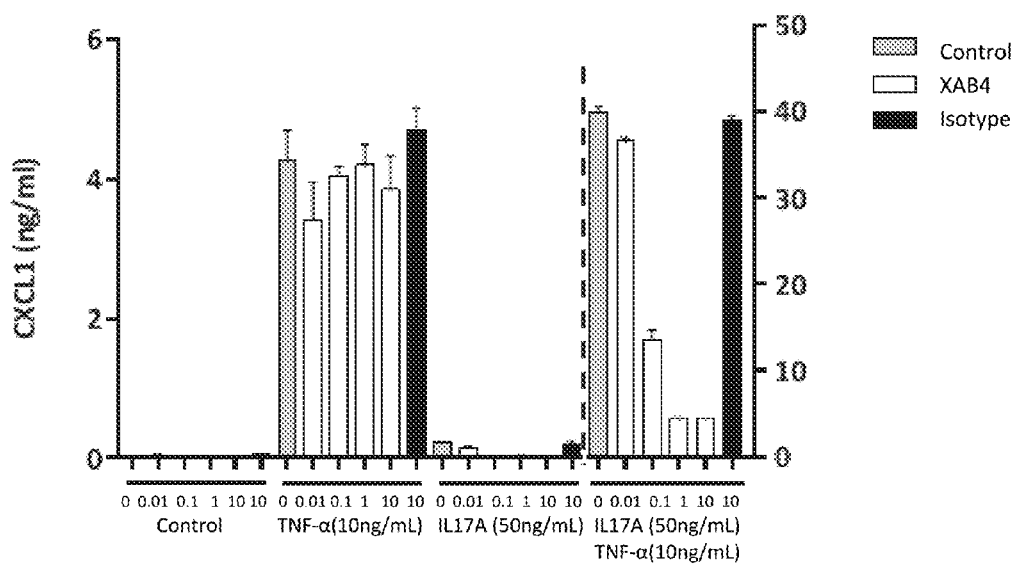
FIG. 22A shows antagonism of TNF-α or IL-17A stimulation, or IL-17A/TNF-α co-stimulation by XAB4, by CXCL1.
Figure 22B:
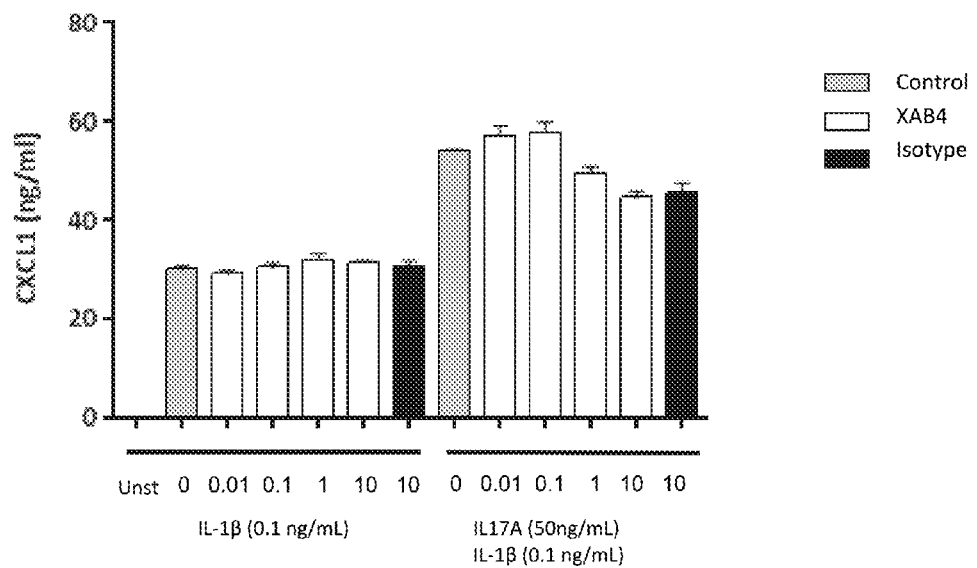
FIG. 22B shows antagonism of IL-1β or IL-17A/IL-1β co-stimulation by XAB4, by CXCL1. The model used is a human astrocyte model.

As seen in FIG. 22A, XAB4 (all concentrations) has an antagonistic effect, compared to both control and isotype, on release of CXCL1 from astrocytes stimulated with IL-17A, or IL-17A/TNF-α. Concentration of CXCL1 (ng/ml) is represented by the y-axis and concentration of XAB4 is represented on the x-axis (0, i.e. control, 0.01 nM, 0.1 nM 1 nM and 10 nM) for each dataset, and 10 nM for isotype. The dataset to the left relates to unstimulated cells, the next dataset relates to cells stimulated with TNF-α (10 ng/ml), the next dataset relates to cells stimulated with IL-17A (50 ng/ml) and the last dataset relates to cells co-stimulated with TNF-α (10 ng/ml) and IL-17A (50 ng/ml). The last dataset has about 10 fold higher scale of the y-axis. As seen in FIG. 22B, XAB4 (all concentrations) has no antagonistic effect on cells stimulated with IL-1β (0.1 ng/ml) or co-stimulated with IL-1β (0.1 ng/ml) and IL-17A (50 ng/ml), compared to isotype.

Figure 23A:
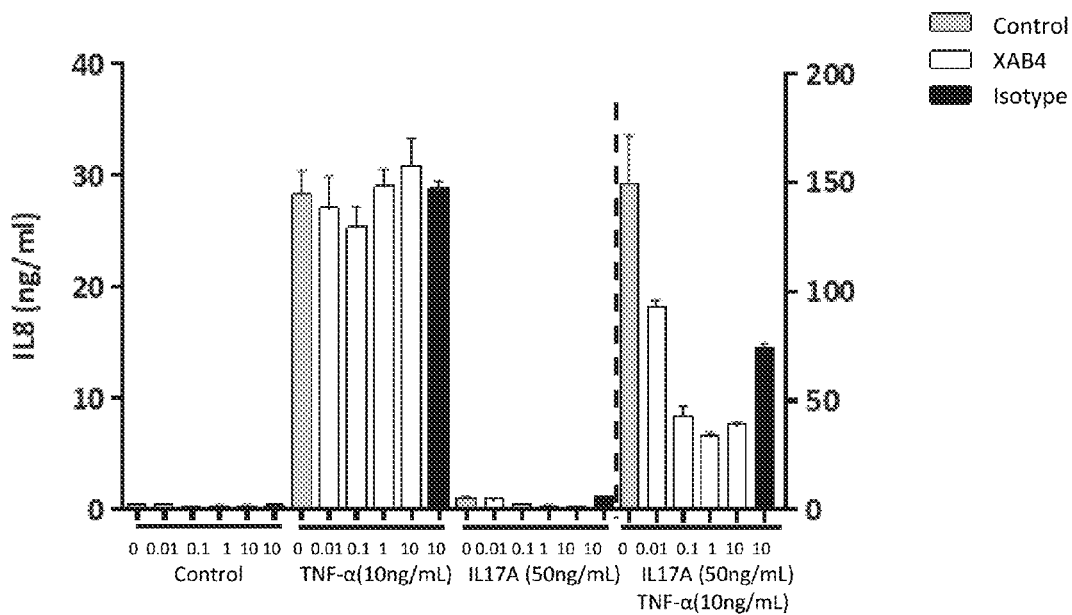
FIG. 23A shows antagonism of TNF-α or IL-17A stimulation, or IL-17A/TNF-α co-stimulation by XAB4, by IL8.
Figure 23B:
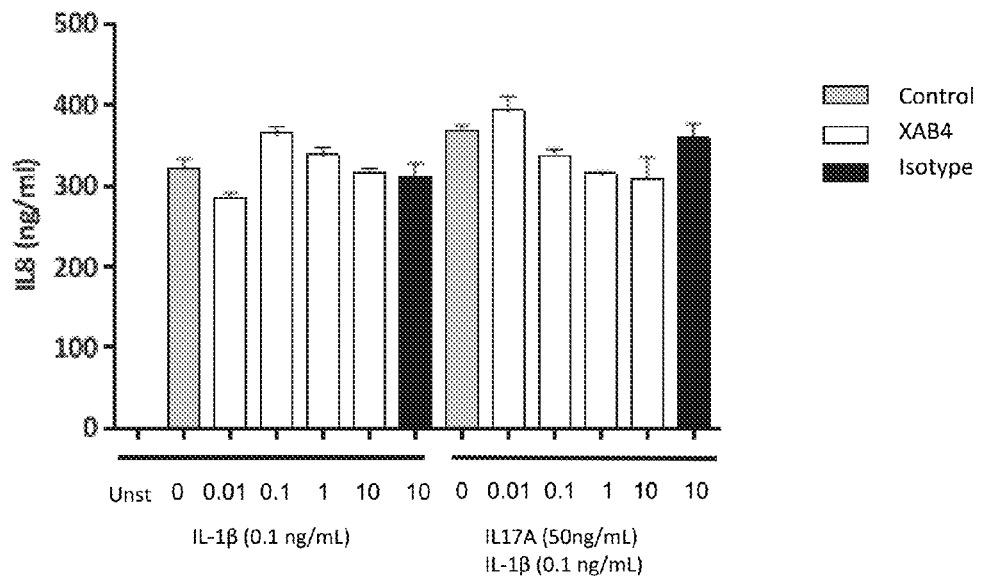
FIG. 23B shows antagonism of IL-1β or IL-17A/IL-1β co-stimulation by XAB4, by IL8. The model used is in a human astrocyte model.

As seen in FIG. 23A, XAB4 (all concentrations) has an antagonistic effect, compared to control, on release of IL-8 from astrocytes stimulated with IL-17A, or IL-17A/TNF-α. Compared to isotype, XAB4 (0.1 nM, 1 nM and 10 nM) has an antagonistic effect on release of IL-8. Concentration of IL-8 (ng/ml) is represented by the y-axis and concentration of XAB4 is represented on the x-axis (0, i.e. control, 0.01 nM, 0.1 nM 1 nM and 10 nM) for each dataset, and 10 nM for isotype. The dataset to the left relates to unstimulated cells, the next dataset relates to cells stimulated with TNF-α (10 ng/ml), the next dataset relates to cells stimulated with IL-17A (50 ng/ml) and the last dataset relates to cells co-stimulated with TNF-α (10 ng/ml) and IL-17A (50 ng/ml). The last dataset has about 5 fold higher scale of the y-axis. As seen in FIG. 23B, XAB4 (all concentrations) has no antagonistic effect on cells stimulated with IL-1β (0.1 ng/ml) or co-stimulated with IL-1β (0.1 ng/ml) and IL-17A (50 ng/ml), compared to isotype.

Figure 24A:
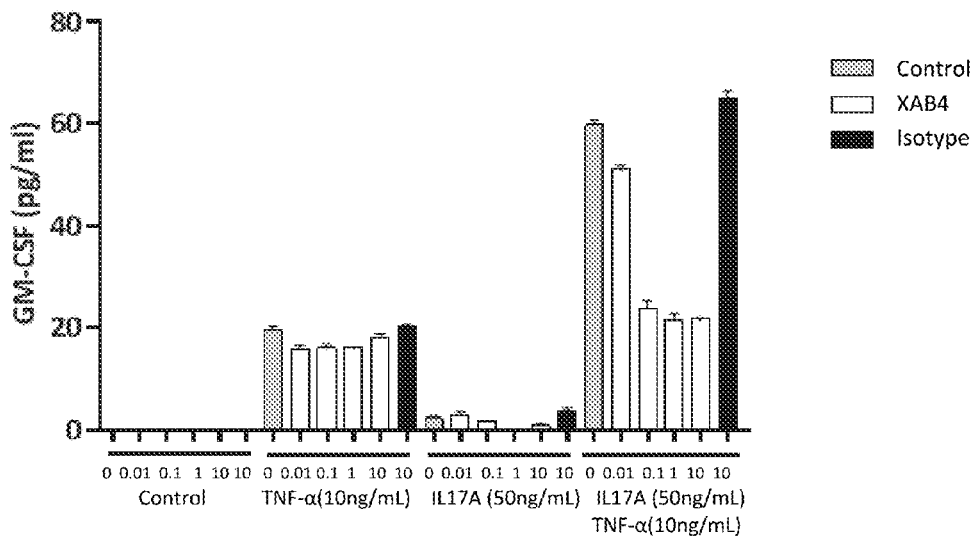
FIG. 24A shows antagonism of TNF-α or IL-17A stimulation, or IL-17A/TNF-α co-stimulation by XAB4, by GM-CSF.
Figure 24B:
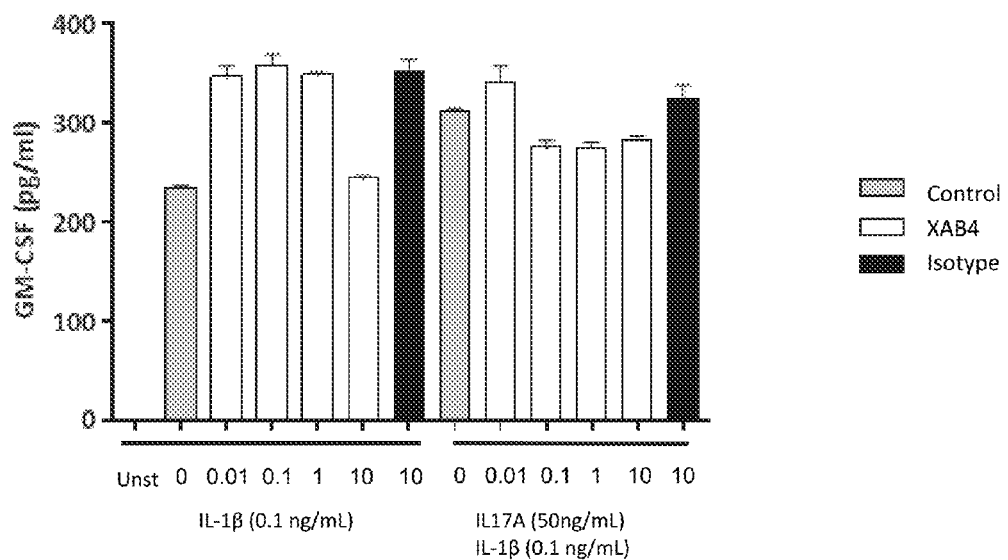
FIG. 24B shows antagonism of IL-1β or IL-17N IL-1β co-stimulation by XAB4, by GM-CSF. The model used is a human astrocyte model.

As seen in FIG. 24A, XAB4 (all concentrations) has an antagonistic effect, compared to both control and isotype, on release of GM-CSF from astrocytes stimulated with IL-17A/TNF-α. XAB4 (0.1 nM, 1 nM and 10 nM) has an antagonistic effect on release of GM-CSF from astrocytes stimulated with IL-17A, compared to isotype and control. Concentration of GM-CSF (ng/ml) is represented by the y-axis and concentration of XAB4 is represented on the x-axis (0, i.e. control, 0.01 nM, 0.1 nM 1 nM and 10 nM) for each dataset, and 10 nM for isotype. The dataset to the left relates to unstimulated cells, the next dataset relates to cells stimulated with TNF-α (10 ng/ml), the next dataset relates to cells stimulated with IL-17A (50 ng/ml) and the last dataset relates to cells co-stimulated with TNF-α (10 ng/ml) and IL-17A (50 ng/ml). As seen in FIG. 24B, XAB4 (all concentrations) has no or low antagonistic effect on cells stimulated with IL-1β (0.1 ng/ml) or co-stimulated with IL-1β (0.1 ng/ml) and IL-17A (50 ng/ml), compared to isotype.

Figure 25A:
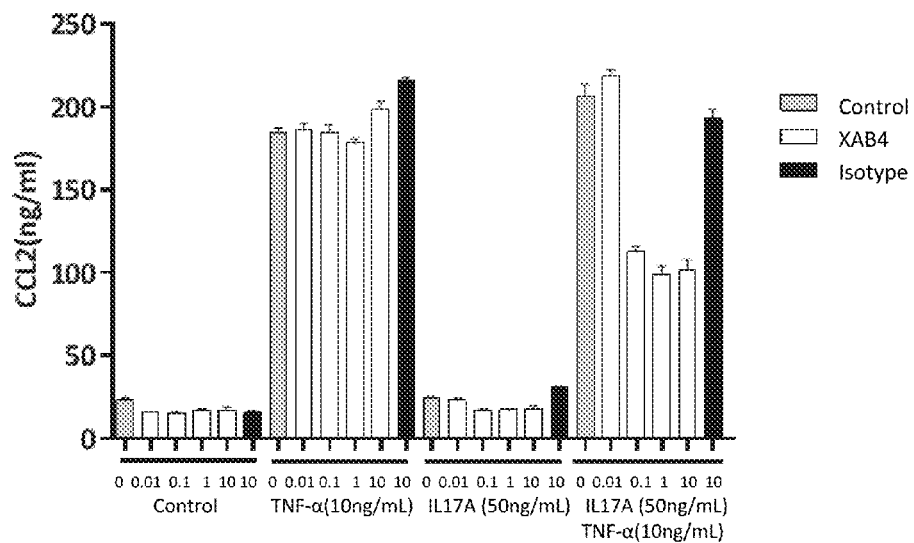
FIG. 25A shows antagonism of TNF-α or IL-17A stimulation, or IL-17A/TNF-α co-stimulation by XAB4, by CCL2.
Figure 25B:
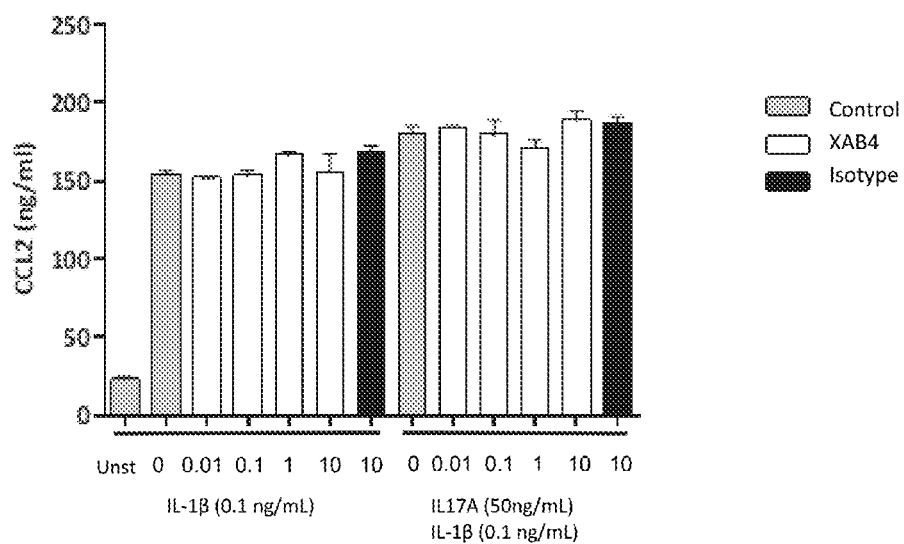
FIG. 25B shows antagonism of IL-1β or IL-17N IL-1β co-stimulation by XAB4, by CCL2. The model used is a human astrocyte model.

As seen in FIG. 25A, XAB4 (all concentrations) has an antagonistic effect, compared to both control and isotype, on release of CCL2 from astrocytes stimulated with IL-17A. XAB4 (0.1 nM, 1 nM and 10 nM) has an antagonistic effect on release of CCL2 from astrocytes stimulated with IL-17A/TNF-α, compared to isotype and control. Concentration of CCL2 (ng/ml) is represented by the y-axis and concentration of XAB4 is represented on the x-axis (0, i.e. control, 0.01 nM, 0.1 nM 1 nM and 10 nM) for each dataset, and 10 nM for isotype. The dataset to the left relates to unstimulated cells, the next dataset relates to cells stimulated with TNF-α (10 ng/ml), the next dataset relates to cells stimulated with IL-17A (50 ng/ml) and the last dataset relates to cells co-stimulated with TNF-α (10 ng/ml) and IL-17A (50 ng/ml). As seen in FIG. 25B, XAB4 (all concentrations) has no antagonistic effect on cells stimulated with IL-1β (0.1 ng/ml) or co-stimulated with IL-1β (0.1 ng/ml) and IL-17A (50 ng/ml), compared to isotype.

Taken together, the data suggested that selective inhibition of IL-17A signaling with XAB4 attenuates the level of pro-inflammatory cytokines in human astrocytes. In disease, astrocytes are suggested to play roles in a range of psychiatric, neurological and neurodegenerative disorders, where their role in neuroinflammation is likely to be important. Since XAB4 was shown to have an effect on IL-6, CXCL1, IL-8, GM-CSF, and CCL2 production of astrocytes, XAB4 may be a useful therapeutic agent, such as for treatment of Multiple Sclerosis (MS).

Sequence Information

Sequence data relating to XAB1, XAB2, XAB3, XAB4 and XAB5 is summarized below for ease of reference.

Table 1 describes the amino acid sequences (SEQ ID NOs) of the full length heavy and light chains of examples XAB1, XAB2, XAB3, XAB4 and XAB5.

The antibodies XAB1, XAB2, XAB3, XAB4 or XAB5 can be produced using conventional antibody recombinant production and purification processes. For example, the coding sequences as described in Table 3 or Table 4 are cloned into a production vector for recombinant expression in mammalian production cell line.

Table 2 summarizes the variable heavy (VH) and light chain (VL) amino acid sequence of XAB1, XAB2, XAB3, XAB4 or XAB5, which can be used to generate chimeric antibodies from XAB1, XAB2, XAB3, XAB4 or XAB5.

Table 5 summarizes the useful CDR sequences of XAB1, XAB2, XAB3, XAB4 and XAB5 (plus consensus sequences) to generate alternative CDR grafted antibodies, wherein the CDR regions from XAB1, XAB2, XAB3, XAB4 and XAB5 are defined according to Kabat definition.

Table 6 summarizes the useful CDR sequences of XAB1, XAB2, XAB3, XAB4 and XAB5 (plus consensus sequences) to generate alternative CDR grafted antibodies, wherein the CDR regions from XAB1, XAB2, XAB3, XAB4 and XAB5 are defined according to Chothia definition.

All the sequences referred to in this specification (SEQ ID NOs) are found in Table 36.

Sequence List

Useful amino acids and nucleotide sequences for practicing the invention are found in Table 36.

TABLE 36

| Antibody/Fragment | Sequence Identifier (SEQ ID NO:) | Amino acid sequence or polynucleotide sequence (PN) |
|---|---|---|
| XAB1, CDRH1 (CHOTHIA) | 1 | GFTFSSY |
| XAB1, CDRH2 (CHOTHIA) | 2 | KQDGSE |
| XAB1, CDRH3 (CHOTHIA) | 3 | DRGSLYY |
| XAB1, CDRL1 (CHOTHIA) | 4 | SQGIISA |
| XAB1, CDRL2 (CHOTHIA) | 5 | DAS |
| XAB1, CDRL3 (CHOTHIA) | 6 | FNSYPL |
| XAB1, CDRH1 (KABAT) | 7 | SYWMS |
| XAB1, CDRH2 (KABAT) | 8 | NIKQDGSEKYYVDSVKG |
| XAB1, CDRH3 (KABAT) | 3 | DRGSLYY |
| XAB1, CDRL1 (KABAT) | 9 | RPSQGIISALA |
| XAB1, CDRL2 (KABAT) | 10 | DASSLEN |
| XAB1, CDRL3 (KABAT) | 11 | QQFNSYPLT |
| XAB1, VH | 12 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSS |

TABLE 36-continued

Sequence list

| Antibody/Fragment | Sequence Identifier (SEQ ID NO:) | Amino acid sequence or polynucleotide sequence (PN) |
|---|---|---|
| XAB1, VL | 13 | AIQLTQSPSSLSASVGDRVTITCRPSQGIISALAWYQ QKPGKAPKLLIYDASSLENGVPSRFSGSGSGTDFTL TISSLQPEDFATYYCQQFNSYPLTFGGGTKVEIK |
| XAB1, HEAVY CHAIN | 14 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSR EEMTKNQVSLTCLVKGFYPSDIAVEWESNGQPENN YKTTPPVLDSDGSFFLYSKLTVDKSRWQQGNVFSC SVMHEALHNHYTQKSLSLSPGK |
| XAB1, LIGHT CHAIN | 15 | AIQLTQSPSSLSASVGDRVTITCRPSQGIISALAWYQ QKPGKAPKLLIYDASSLENGVPSRFSGSGSGTDFTL TISSLQPEDFATYYCQQFNSYPLTFGGGTKVEIKRTV AAPSVFIFPPSDEQLKSGTASVVCLLNNFYPREAKV QWKVDNALQSGNSQESVTEQDSKDSTYSLSSTLTL SKADYEKHKVYACEVTHQGLSSPVTKSFNRGEC |
| PN ENCODING SEQ ID NO: 12 | 16 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGC |
| PN ENCODING SEQ ID NO: 13 | 17 | GCCATCCAGTTGACCCAGTCTCCATCCTCCCTGT CTGCATCTGTGGGAGACAGAGTCACCATCACTTG CCGGCCAAGTCAGGGCATTATCAGTGCTTTAGCC TGGTATCAGCAGAAACCAGGGAAAGCTCCTAAGC TCCTGATCTATGATGCCTCCAGTTTGGAAAATGGG GTCCCATCAAGGTTCAGCGGCAGTGGATCTGGGA CAGATTTCACTCTCACCATCAGCAGCCTGCAGCC TGAAGATTTTGCAACTTATTACTGTCAACAGTTTAA TAGTTACCCTCTCACTTTCGGCGGAGGGACCAAG GTGGAGATCAAA |
| PN ENCODING SEQ ID NO: 14 | 18 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGCGCTAGCACCAAGGGCCC CAGCGTGTTCCCCCTGGCCCCCAGCAGCAAGAG CACCAGCGGCGGCACAGCCGCCCTGGGCTGCCT GGTGAAGGACTACTTCCCCGAGCCCGTGACCGT GTCCTGGAACAGCGGAGCCCTGACCTCCGGCGT GCACACCTTCCCCGCCGTGCTGCAGAGCAGCGG CCTGTACAGCCTGTCCAGCGTGGTGACAGTGCCC AGCAGCAGCCTGGGCACCCAGACCTACATCTGCA ACGTGAACCACAAGCCCAGCAACACCAAGGTGGA CAAGAGAGTGGAGCCCAAGAGCTGCGACAAGAC CCACACCTGCCCCCCCTGCCCAGCCCCAGAGCT GCTGGGCGGACCCTCCGTGTTCCTGTTCCCCCCC AAGCCCAAGGACACCCTGATGATCAGCAGGACCC CCGAGGTGACCTGCGTGGTGGTGGACGTGAGCC ACGAGGACCCAGAGGTGAAGTTCAACTGGTACGT |

TABLE 36-continued

Sequence list

| Antibody/ Fragment | Sequence Identifier (SEQ ID NO:) | Amino acid sequence or polynucleotide sequence (PN) |
|---|---|---|
| | | GGACGGCGTGGAGGTGCACAACGCCAAGACCAA GCCCAGAGAGGAGCAGTACAACAGCACCTACAG GGTGGTGTCCGTGCTGACCGTGCTGCACCAGGA CTGGCTGAACGGCAAGGAATACAAGTGCAAGGTC TCCAACAAGGCCCTGCCAGCCCCCATCGAAAAGA CCATCAGCAAGGCCAAGGGCCAGCCACGGGAGC CCCAGGTGTACACCCTGCCCCCCTCCCGGGAGG AGATGACCAAGAACCAGGTGTCCCTGACCTGTCT GGTGAAGGGCTTCTACCCCAGCGACATCGCCGT GGAGTGGGAGAGCAATGGCCAGCCCGAGAACAA CTACAAGACCACCCCCCCAGTGCTGGACAGCGAC GGCAGCTTCTTCCTGTACAGCAAGCTGACCGTGG ACAAGTCCAGGTGGCAGCAGGGCAACGTGTTCA GCTGCAGCGTGATGCACGAGGCCCTGCACAACC ACTACACCCAGAAGAGCCTGAGCCTGTCCCCCGG CAAG |
| PN ENCODING SEQ ID NO: 15 | 19 | GCCATCCAGTTGACCCAGTCTCCATCCTCCCTGT CTGCATCTGTGGGAGACAGAGTCACCATCACTTG CCGGCCAAGTCAGGGCATTATCAGTGCTTTAGCC TGGTATCAGCAGAAACCAGGGAAAGCTCCTAAGC TCCTGATCTATGATGCCTCCAGTTTGGAAAATGGG GTCCCATCAAGGTTCAGCGGCAGTGGATCTGGGA CAGATTTCACTCTCACCATCAGCAGCCTGCAGCC TGAAGATTTTGCAACTTATTACTGTCAACAGTTTAA TAGTTACCCTCTCACTTTCGGCGGAGGGACCAAG GTGGAGATCAAACGTACGGTGGCCGCTCCCAGC GTGTTCATCTTCCCCCCAGCGACGAGCAGCTGA AGAGCGGCACCGCCAGCGTGGTGTGCCTGCTGA ACAACTTCTACCCCCGGGAGGCCAAGGTGCAGTG GAAGGTGGACAACGCCCTGCAGAGCGGCAACAG CCAGGAGAGCGTCACCGAGCAGGACAGCAAGGA CTCCACCTACAGCCTGAGCAGCACCCTGACCCTG AGCAAGGCCGACTACGAGAAGCATAAGGTGTACG CCTGCGAGGTGACCCACCAGGGCCTGTCCAGCC CCGTGACCAAGAGCTTCAACAGGGGCGAGTGC |
| XAB2, CDRH1 (CHOTHIA) | 1 | GFTFSSY |
| XAB2, CDRH2 (CHOTHIA) | 2 | KQDGSE |
| XAB2, CDRH3 (CHOTHIA) | 3 | DRGSLYY |
| XAB2, CDRL1 (CHOTHIA) | 20 | SQVIISA |
| XAB2, CDRL2 (CHOTHIA) | 5 | DAS |
| XAB2, CDRL3 (CHOTHIA) | 21 | FDSYPL |
| XAB2, CDRH1 (KABAT) | 7 | SYWMS |
| XAB2, CDRH2 (KABAT) | 8 | NIKQDGSEKYYVDSVKG |
| XAB2, CDRH3 (KABAT) | 3 | DRGSLYY |
| XAB2, CDRL1 (KABAT) | 22 | RPSQVIISALA |
| XAB2, CDRL2 (KABAT) | 23 | DASSLEQ |
| XAB2, CDRL3 (KABAT) | 24 | QQFDSYPLT |

TABLE 36-continued

Sequence list

| Antibody/ Fragment | Sequence Identifier (SEQ ID NO:) | Amino acid sequence or polynucleotide sequence (PN) |
| --- | --- | --- |
| XAB2, VH | 12 | EVQLVESGGDLVQPGGSLRLSCAASGFTFSSYWMS<br>WVRQAPGKGLEWVANIKQDGSEKYYVDSVKGRFTI<br>SRDNAKNSLYLQMNSLRAEDTAVYYCARDRGSLYY<br>WGQGTLVTVSS |
| XAB2, VL | 25 | AIQLTQSPSSLSASVGDRVTITCRPSQVIISALAWYQ<br>QKPGKAPKLLIYDASSLEQGVPSRFSGSVSGTDFTL<br>TISSLQPEDFATYYCQQFDSYPLTFGGGTKVEIK |
| XAB2, HEAVY CHAIN | 14 | EVQLVESGGDLVQPGGSLRLSCAASGFTFSSYWMS<br>WVRQAPGKGLEWVANIKQDGSEKYYVDSVKGRFTI<br>SRDNAKNSLYLQMNSLRAEDTAVYYCARDRGSLYY<br>WGQGTLVTVSSASTKGPSVFPLAPSSKSTSGGTAA<br>LGCLVKDYFPEPVTVSWNSGALTSGVHTFPAVLQS<br>SGLYSLSSVVTVPSSSLGTQTYICNVNHKPSNTKVD<br>KRVEPKSCDKTHTCPPCPAPELLGGPSVFLFPPKPK<br>DTLMISRTPEVTCVVVDVSHEDPEVKFNWYVDGVE<br>VHNAKTKPREEQYNSTYRVVSVLTVLHQDWLNGKE<br>YKCKVSNKALPAPIEKTISKAKGQPREPQVYTLPPSR<br>EEMTKNQVSLTCLVKGFYPSDIAVEWESNGQPENN<br>YKTTPPVLDSDGSFFLYSKLTVDKSRWQQGNVFSC<br>SVMHEALHNHYTQKSLSLSPGK |
| XAB2, LIGHT CHAIN | 26 | AIQLTQSPSSLSASVGDRVTITCRPSQVIISALAWYQ<br>QKPGKAPKLLIYDASSLEQGVPSRFSGSVSGTDFTL<br>TISSLQPEDFATYYCQQFDSYPLTFGGGTKVEIKRTV<br>AAPSVFIFPPSDEQLKSGTASVVCLLNNFYPREAKV<br>QWKVDNALQSGNSQESVTEQDSKDSTYSLSSTLTL<br>SKADYEKHKVYACEVTHQGLSSPVTKSFNRGEC |
| PN ENCODING SEQ ID NO: 12 | 16 | GAGGTGCAGCTGGTCGAGTCTGGCGGCGACCTG<br>GTGCAGCCTGGCGGCAGCCTGAGACTGAGCTGC<br>GCCGCCAGCGGCTTCACCTTCAGCAGCTACTGGA<br>TGTCCTGGGTCCGCCAGGCCCCTGGCAAAGGCC<br>TCGAATGGGTGGCCAACATCAAGCAGGACGGCA<br>GCGAGAAGTACTACGTGGACAGCGTGAAGGGCC<br>GGTTCACCATCAGCCGGGACAACGCCAAGAACAG<br>CCTGTACCTGCAGATGAACAGCCTGCGGGCCGA<br>GGACACCGCCGTGTACTACTGCGCCAGGGACCG<br>GGGCAGCCTGTACTATTGGGGCCAGGGCACCCT<br>GGTCACCGTGTCCAGC |
| PN ENCODING SEQ ID NO: 25 | 27 | GCCATCCAGCTGACCCAGAGCCCCAGCAGCCTG<br>AGCGCCAGCGTGGGCGACAGAGTGACCATCACC<br>TGTCGGCCCAGCCAGGTCATCATCAGCGCCCTG<br>GCCTGGTATCAGCAGAAGCCTGGCAAGGCCCCC<br>AAGCTGCTGATCTACGACGCCAGCTCCCTGGAAC<br>AGGGCGTGCCCAGCCGGTTCAGCGGCAGCGTGT<br>CCGGCACCGACTTCACCCTGACCATCAGCTCCCT<br>GCAGCCCGAGGACTTCGCCACCTACTACTGCCAG<br>CAGTTCGACAGCTACCCCCTGACCTTCGGCGGAG<br>GCACCAAGGTGGAAATCAAG |
| PN ENCODING SEQ ID NO: 14 | 18 | GAGGTGCAGCTGGTCGAGTCTGGCGGCGACCTG<br>GTGCAGCCTGGCGGCAGCCTGAGACTGAGCTGC<br>GCCGCCAGCGGCTTCACCTTCAGCAGCTACTGGA<br>TGTCCTGGGTCCGCCAGGCCCCTGGCAAAGGCC<br>TCGAATGGGTGGCCAACATCAAGCAGGACGGCA<br>GCGAGAAGTACTACGTGGACAGCGTGAAGGGCC<br>GGTTCACCATCAGCCGGGACAACGCCAAGAACAG<br>CCTGTACCTGCAGATGAACAGCCTGCGGGCCGA<br>GGACACCGCCGTGTACTACTGCGCCAGGGACCG<br>GGGCAGCCTGTACTATTGGGGCCAGGGCACCCT<br>GGTCACCGTGTCCAGCGCTAGCACCAAGGGCCC<br>CAGCGTGTTCCCCCTGGCCCCCAGCAGCAAGAG<br>CACCAGCGGCGGCACAGCCGCCCTGGGCTGCCT<br>GGTGAAGGACTACTTCCCCGAGCCCGTGACCGT<br>GTCCTGGAACAGCGGAGCCCTGACCTCCGGCGT<br>GCACACCTTCCCCGCCGTGCTGCAGAGCAGCGG<br>CCTGTACAGCCTGTCCAGCGTGGTGACAGTGCCC<br>AGCAGCAGCCTGGGCACCCAGACCTACATCTGCA<br>ACGTGAACCACAAGCCCAGCAACACCAAGGTGGA<br>CAAGAGAGTGGAGCCCAAGAGCTGCGACAAGAC |

TABLE 36-continued

Sequence list

| Antibody/Fragment | Sequence Identifier (SEQ ID NO:) | Amino acid sequence or polynucleotide sequence (PN) |
|---|---|---|
| | | CCACACCTGCCCCCCCTGCCCAGCCCCAGAGCT GCTGGGCGGACCCTCCGTGTTCCTGTTCCCCCCC AAGCCCAAGGACACCCTGATGATCAGCAGGACCC CCGAGGTGACCTGCGTGGTGGTGGACGTGAGCC ACGAGGACCCAGAGGTGAAGTTCAACTGGTACGT GGACGGCGTGGAGGTGCACAACGCCAAGACCAA GCCCAGAGAGGAGCAGTACAACAGCACCTACAG GGTGGTGTCCGTGCTGACCGTGCTGCACCAGGA CTGGCTGAACGGCAAGGAATACAAGTGCAAGGTC TCCAACAAGGCCCTGCCAGCCCCCATCGAAAAGA CCATCAGCAAGGCCAAGGGCCAGCCACGGGAGC CCCAGGTGTACACCCTGCCCCCCTCCCGGGAGG AGATGACCAAGAACCAGGTGTCCCTGACCTGTCT GGTGAAGGGCTTCTACCCCAGCGACATCGCCGT GGAGTGGGAGAGCAACGGCCAGCCCGAGAACAA CTACAAGACCACCCCCCCAGTGCTGGACAGCGAC GGCAGCTTCTTCCTGTACAGCAAGCTGACCGTGG ACAAGTCCAGGTGGCAGCAGGGCAACGTGTTCA GCTGCAGCGTGATGCACGAGGCCCTGCACAACC ACTACACCCAGAAGAGCCTGAGCCTGTCCCCCGG CAAG |
| PN ENCODING SEQ ID NO: 26 | 28 | GCCATCCAGCTGACCCAGAGCCCCAGCAGCCTG AGCGCCAGCGTGGGCGACAGAGTGACCATCACC TGTCGGCCCAGCCAGGTCATCATCAGCGCCCTG GCCTGGTATCAGCAGAAGCCTGGCAAGGCCCCC AAGCTGCTGATCTACGACGCCAGCTCCCTGGAAC AGGGCGTGCCCAGCCGGTTCAGCGGCAGCGTGT CCGGCACCGACTTCACCCTGACCATCAGCTCCCT GCAGCCCGAGGACTTCGCCACCTACTACTGCCAG CAGTTCGACAGCTACCCCCTGACCTTCGGCGGAG GCACCAAGGTGGAAATCAAGCGTACGGTGGCCG CTCCCAGCGTGTTCATCTTCCCCCCCAGCGACGA GCAGCTGAAGAGCGGCACCGCCAGCGTGGTGTG CCTGCTGAACAACTTCTACCCCGGGAGGCCAAG GTGCAGTGGAAGGTGGACAACGCCCTGCAGAGC GGCAACAGCCAGGAGAGCGTCACCGAGCAGGAC AGCAAGGACTCCACCTACAGCCTGAGCAGCACCC TGACCCTGAGCAAGGCCGACTACGAGAAGCATAA GGTGTACGCCTGCGAGGTGACCCACCAGGGCCT GTCCAGCCCCGTGACCAAGAGCTTCAACAGGGG CGAGTGC |
| ALTERNATIVE PN ENCODING SEQ ID NO: 12 | 29 | GAGGTGCAGCTGGTGGAATCAGGAGGCGACCTG GTGCAGCCTGGCGGCTCACTGAGACTGAGCTGC GCCGCTAGTGGCTTCACCTTTAGTAGCTACTGGA TGAGCTGGGTGCGACAGGCCCCTGGCAAGGGAC TGGAGTGGGTGGCCAATATTAAGCAGGACGGCTC AGAGAAGTACTACGTGGACTCAGTGAAGGGCCG GTTCACTATTAGCCGGGATAACGCTAAGAATAGC CTGTACCTGCAGATGAATAGCCTGAGAGCCGAGG ACACCGCCGTGTACTACTGCGCTAGAGATAGAGG CTCACTGTACTACTGGGGCCAGGGCACCCTGGTG ACAGTGTCTTCT |
| ALTERNATIVE PN ENCODING SEQ ID NO: 25 | 30 | GCTATTCAGCTGACTCAGTCACCTAGTAGCCTGA GCGCTAGTGTGGGCGATAGAGTGACTATCACCTG TAGACCTAGTCAGGTGATCATTAGCGCCCTGGCC TGGTATCAGCAGAAGCCCGGCAAGGCCCCTAAG CTGCTGATCTACGACGCTAGTAGTCTGGAACAGG GCGTGCCCTCTAGGTTTAGCGGCTCAGTGTCAGG CACCGACTTCACCCTGACTATTAGTAGCCTGCAG CCCGAGGACTTCGCTACCTACTACTGTCAGCAGT TCGATAGCTACCCCCTGACCTTCGGCGGAGGCAC TAAGGTGGAAATCAAG |
| ALTERNATIVE PN ENCODING SEQ ID NO: 14 | 31 | GAGGTGCAGCTGGTGGAATCAGGAGGCGACCTG GTGCAGCCTGGCGGCTCACTGAGACTGAGCTGC GCCGCTAGTGGCTTCACCTTTAGTAGCTACTGGA TGAGCTGGGTGCGACAGGCCCCTGGCAAGGGAC TGGAGTGGGTGGCCAATATTAAGCAGGACGGCTC AGAGAAGTACTACGTGGACTCAGTGAAGGGCCG GTTCACTATTAGCCGGGATAACGCTAAGAATAGC |

TABLE 36-continued

Sequence list

| Antibody/Fragment | Sequence Identifier (SEQ ID NO:) | Amino acid sequence or polynucleotide sequence (PN) |
|---|---|---|
| | | CTGTACCTGCAGATGAATAGCCTGAGAGCCGAGG ACACCGCCGTGTACTACTGCGCTAGAGATAGAGG CTCACTGTACTACTGGGGCCAGGGCACCCTGGTG ACAGTGTCTTCTGCTAGCACCAAGGGCCCAAGTG TCTTTCCCCTGGCCCCCAGCAGCAAGTCCACAAG CGGAGGCACTGCAGCTCTGGGTTGTCTGGTGAA GGACTACTTCCCCGAGCCCGTGACAGTGTCCTGG AACAGCGGAGCCCTGACCTCCGGCGTGCACACC TTCCCCGCCGTGCTGCAGAGCAGCGGCCTGTAC AGCCTGAGCAGCGTCGTGACTGTGCCTAGTTCCA GCCTGGGCACCCAGACCTATATCTGCAACGTGAA CCACAAGCCCAGCAACACCAAGGTGGACAAGAGA GTGGAGCCCAAGAGCTGCGACAAGACCCACACC TGCCCCCCCTGCCCAGCTCCAGAACTGCTGGGA GGACCCAGCGTGTTCCTGTTCCCCCCCAAGCCCA AGGACACCCTGATGATCAGCAGGACCCCCGAGG TGACCTGCGTGGTGGTGGACGTGTCCCACGAGG ACCCAGAGGTGAAGTTCAACTGGTACGTGGACGG GGTGGAGGTGCACAACGCCAAGACCAAGCCCAG AGAGGAGCAGTACAACAGCACCTACAGGGTGGT GTCCGTCCTGACAGTGCTGCACCAGGATTGGCTG AACGGCAAAGAATACAAGTGCAAAGTCTCCAACA AGGCCCTGCCAGCCCCAATCGAAAAGACAATCAG CAAGGCCAAGGGCCAGCCACGGGAGCCCCAGGT GTACACCCTGCCCCCCAGCCGGGAGGAGATGAC CAAGAACCAGGTGTCCCTGACCTGTCTGGTGAAG GGCTTCTACCCCAGCGATATCGCCGTGGAGTGG GAGAGCAACGGCCAGCCCGAGAACAACTACAAG ACCACCCCCCAGTGCTGGACAGCGACGGCAGC TTCTTCCTGTACAGCAAGCTGACCGTGGACAAGT CCAGGTGGCAGCAGGGCAACGTGTTCAGCTGCA GCGTGATGCACGAGGCCCTGCACAACCACTACAC CCAGAAGTCCCTGAGCCTGAGCCCCGGCAAG |
| ALTERNATIVE PN ENCODING SEQ ID NO: 26 | 32 | GCTATTCAGCTGACTCAGTCACCTAGTAGCCTGA GCGCTAGTGTGGGCGATAGAGTGACTATCACCTG TAGACCTAGTCAGGTGATCATTAGCGCCCTGGCC TGGTATCAGCAGAAGCCCGGCAAGGCCCCTAAG CTGCTGATCTACGACGCTAGTAGTCTGGAACAGG GCGTGCCCTCTAGGTTTAGCGGCTCAGTGTCAGG CACCGACTTCACCCTGACTATTAGTAGCCTGCAG CCCGAGGACTTCGCTACCTACTACTGTCAGCAGT TCGATAGCTACCCCCTGACCTTCGGCGGAGGCAC TAAGGTGGAAATCAAGCGTACGGTGGCCGCTCCC AGCGTGTTCATCTTCCCCCCCAGCGACGAGCAGC TGAAGAGCGGCACCGCCAGCGTGGTGTGCCTGC TGAACAACTTCTACCCCGGGAGGCCAAGGTGCA GTGGAAGGTGGACAACGCCCTGCAGAGCGGCAA CAGCCAGGAGAGCGTCACCGAGCAGGACAGCAA GGACTCCACCTACAGCCTGAGCAGCACCCTGACC CTGAGCAAGGCCGACTACGAGAAGCATAAGGTGT ACGCCTGCGAGGTGACCCACCAGGGCCTGTCCA GCCCCGTGACCAAGAGCTTCAACAGGGGCGAGT GC |
| XAB3, CDRH1 (CHOTHIA) | 1 | GFTFSSY |
| XAB3, CDRH2 (CHOTHIA) | 2 | KQDGSE |
| XAB3, CDRH3 (CHOTHIA) | 3 | DRGSLYY |
| XAB3, CDRL1 (CHOTHIA) | 33 | SQGIYWE |
| XAB3, CDRL2 (CHOTHIA) | 5 | DAS |
| XAB3, CDRL3 (CHOTHIA) | 6 | FNSYPL |

TABLE 36-continued

Sequence list

| Antibody/Fragment | Sequence Identifier (SEQ ID NO:) | Amino acid sequence or polynucleotide sequence (PN) |
|---|---|---|
| XAB3, CDRH1 (KABAT) | 7 | SYWMS |
| XAB3, CDRH2 (KABAT) | 8 | NIKQDGSEKYYVDSVKG |
| XAB3, CDRH3 (KABAT) | 3 | DRGSLYY |
| XAB3, CDRL1 (KABAT) | 34 | RPSQGIYWELA |
| XAB3, CDRL2 (KABAT) | 23 | DASSLEQ |
| XAB3, CDRL3 (KABAT) | 11 | QQFNSYPLT |
| XAB3, VH | 12 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSS |
| XAB3, VL | 35 | AIQLTQSPSSLSASVGDRVTITCRPSQGIYWELAWY QQKPGKAPKLLIYDASSLEQGVPSRFSGSGSGTDFT LTISSLQPEDFATYYCQQFNSYPLTFGGGTKVEIK |
| XAB3, HEAVY CHAIN | 14 | EVQLVESGGDLVQPGGSLRLSCAASGFTFSSYWMS WVRQAPGKGLEEVANIKQDGSEKYYVDSVKGRFTI SRDNAKNSLYLQMNSLRAEDTAVYYCARDRGSLYY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSR EEMTKNQVSLTCLVKGFYPSDIAVEWESNGQPENN YKTTPPVLDSDGSFFLYSKLTVDKSRWQQGNVFSC SVMHEALHNHYTQKSLSLSPGK |
| XAB3, LIGHT CHAIN | 36 | AIQLTQSPSSLSASVGDRVTITCRPSQGIYWELAWY QQKPGKAPKLLIYDASSLEQGVPSRFSGSGSGTDFT LTISSLQPEDFATYYCQQFNSYPLTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| PN ENCODING SEQ ID NO: 12 | 16 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGC |
| PN ENCODING SEQ ID NO: 35 | 37 | GCCATCCAGCTGACCCAGAGCCCCAGCAGCCTG AGCGCCAGCGTGGGCGACAGAGTGACCATCACC TGTCGGCCCAGCCAGGGCATCTACTGGGAGCTG GCCTGGTATCAGCAGAAGCCTGGCAAGGCCCCC AAGCTGCTGATCTACGACGCCAGCTCCCTGGAAC AGGGCGTGCCCAGCCGGTTCAGCGGCAGCGGAT CCGGCACCGACTTCACCCTGACCATCAGCTCCCT GCAGCCCGAGGACTTCGCCACCTACTACTGCCAG CAGTTCAACAGCTACCCCCTGACCTTCGGCGGAG GCACCAAGGTGGAAATCAAG |
| PN ENCODING SEQ ID NO: 14 | 18 | GAGGTGCAGCTGGTCGAGTCTGGCGGCGACCTG GTGCAGCCTGGCGGCAGCCTGAGACTGAGCTGC |

TABLE 36-continued

Sequence list

| Antibody/Fragment | Sequence Identifier (SEQ ID NO:) | Amino acid sequence or polynucleotide sequence (PN) |
|---|---|---|
| | | GCCGCCAGCGGCTTCACCTTCAGCAGCTACTGGA
TGTCCTGGGTCCGCCAGGCCCCTGGCAAAGGCC
TCGAATGGGTGGCCAACATCAAGCAGGACGGCA
GCGAGAAGTACTACGTGGACAGCGTGAAGGGCC
GGTTCACCATCAGCCGGGACAACGCCAAGAACAG
CCTGTACCTGCAGATGAACAGCCTGCGGGCCGA
GGACACCGCCGTGTACTACTGCGCCAGGGACCG
GGGCAGCCTGTACTATTGGGGCCAGGGCACCCT
GGTCACCGTGTCCAGCGCTAGCACCAAGGGCCC
CAGCGTGTTCCCCCTGGCCCCCAGCAGCAAGAG
CACCAGCGGCGGCACAGCCGCCCTGGGCTGCCT
GGTGAAGGACTACTTCCCCGAGCCCGTGACCGT
GTCCTGGAACAGCGGAGCCCTGACCTCCGGCGT
GCACACCTTCCCCGCCGTGCTGCAGAGCAGCGG
CCTGTACAGCCTGTCCAGCGTGGTGACAGTGCCC
AGCAGCAGCCTGGGCACCCAGACCTACATCTGCA
ACGTGAACCACAAGCCCAGCAACACCAAGGTGGA
CAAGAGAGTGGAGCCCAAGAGCTGCGACAAGAC
CCACACCTGCCCCCCCTGCCCAGCCCCAGAGCT
GCTGGGCGGACCCTCCGTGTTCCTGTTCCCCCCC
AAGCCCAAGGACACCCTGATGATCAGCAGGACCC
CCGAGGTGACCTGCGTGGTGGTGGACGTGAGCC
ACGAGGACCCAGAGGTGAAGTTCAACTGGTACGT
GGACGGCGTGGAGGTGCACAACGCCAAGACCAA
GCCCAGAGAGGAGCAGTACAACAGCACCTACAG
GGTGGTGTCCGTGCTGACCGTGCTGCACCAGGA
CTGGCTGAACGGCAAGGAATACAAGTGCAAGGTC
TCCAACAAGGCCCTGCCAGCCCCCATCGAAAAGA
CCATCAGCAAGGCCAAGGGCCAGCCACGGGAGC
CCCAGGTGTACACCCTGCCCCCCTCCCGGGAGG
AGATGACCAAGAACCAGGTGTCCCTGACCTGTCT
GGTGAAGGGCTTCTACCCCAGCGACATCGCCGT
GGAGTGGGAGAGCAACGGCCAGCCCGAGAACAA
CTACAAGACCACCCCCCCAGTGCTGGACAGCGAC
GGCAGCTTCTTCCTGTACAGCAAGCTGACCGTGG
ACAAGTCCAGGTGGCAGCAGGGCAACGTGTTCA
GCTGCAGCGTGATGCACGAGGCCCTGCACAACC
ACTACACCCAGAAGAGCCTGAGCCTGTCCCCCGG
CAAG |
| PN ENCODING SEQ ID NO: 36 | 38 | GCCATCCAGCTGACCCAGAGCCCCAGCAGCCTG
AGCGCCAGCGTGGGCGACAGAGTGACCATCACC
TGTCGGCCCAGCCAGGGCATCTACTGGGAGCTG
GCCTGGTATCAGCAGAAGCCTGGCAAGGCCCCC
AAGCTGCTGATCTACGACGCCAGCTCCCTGGAAC
AGGGCGTGCCCAGCCGGTTCAGCGGCAGCGGAT
CCGGCACCGACTTCACCCTGACCATCAGCTCCCT
GCAGCCCGAGGACTTCGCCACCTACTACTGCCAG
CAGTTCAACAGCTACCCCCTGACCTTCGGCGGAG
GCACCAAGGTGGAAATCAAGCGTACGGTGGCCG
CTCCCAGCGTGTTCATCTTCCCCCCCAGCGACGA
GCAGCTGAAGAGCGGCACCGCCAGCGTGGTGTG
CCTGCTGAACAACTTCTACCCCGGGAGGCCAAG
GTGCAGTGGAAGGTGGACAACGCCCTGCAGAGC
GGCAACAGCCAGGAGAGCGTCACCGAGCAGGAC
AGCAAGGACTCCACCTACAGCCTGAGCAGCACCC
TGACCCTGAGCAAGGCCGACTACGAGAAGCATAA
GGTGTACGCCTGCGAGGTGACCCACCAGGGCCT
GTCCAGCCCCGTGACCAAGAGCTTCAACAGGGG
CGAGTGC |
| ALTERNATIVE PN ENCODING SEQ ID NO: 12 | 29 | GAGGTGCAGCTGGTGGAATCAGGAGGCGACCTG
GTGCAGCCTGGCGGCTCACTGAGACTGAGCTGC
GCCGCTAGTGGCTTCACCTTTAGTAGCTACTGGA
TGAGCTGGGTGCGACAGGCCCCTGGCAAGGGAC
TGGAGTGGGTGGCCAATATTAAGCAGGACGGCTC
AGAGAAGTACTACGTGGACTCAGTGAAGGGCCG
GTTCACTATTAGCCGGGATAACTCAAGAATAGC
CTGTACCTGCAGATGAATAGCCTGAGAGCCGAGG
ACACCGCCGTGTACTACTGCGCTAGAGATAGGG
CTCACTGTACTACTGGGGCCAGGGCACCCTGGTG
ACAGTGTCTTCT |

TABLE 36-continued

Sequence list

| Antibody/Fragment | Sequence Identifier (SEQ ID NO:) | Amino acid sequence or polynucleotide sequence (PN) |
|---|---|---|
| ALTERNATIVE PN ENCODING SEQ ID NO: 35 | 39 | GCTATTCAGCTGACTCAGTCACCTAGTAGCCTGA GCGCTAGTGTGGGCGATAGAGTGACTATCACCTG TAGACCTAGCCAGGGAATCTACTGGGAGCTGGCC TGGTATCAGCAGAAGCCCGGCAAGGCCCCTAAG CTGCTGATCTACGACGCTAGTAGTCTGGAACAGG GCGTGCCCTCTAGGTTTAGCGGCTCAGGCTCAGG CACCGACTTCACCCTGACTATTAGTAGCCTGCAG CCCGAGGACTTCGCTACCTACTACTGTCAGCAGT TTAACTCCTACCCCCTGACCTTCGGCGGAGGCAC TAAGGTGGAAATCAAG |
| ALTERNATIVE PN ENCODING SEQ ID NO: 14 | 31 | GAGGTGCAGCTGGTGGAATCAGGAGGCGACCTG GTGCAGCCTGGCGGCTCACTGAGACTGAGCTGC GCCGCTAGTGGCTTCACCTTTAGTAGCTACTGGA TGAGCTGGGTGCGACAGGCCCCTGGCAAGGGAC TGGAGTGGGTGGCCAATATTAAGCAGGACGGCTC AGAGAAGTACTACGTGGACTCAGTGAAGGGCCG GTTCACTATTAGCCGGGATAACGCTAAGAATAGC CTGTACCTGCAGATGAATAGCCTGAGAGCCGAGG ACACCGCCGTGTACTACTGCGCTAGAGATAGAGG CTCACTGTACTACTGGGGCCAGGGCACCCTGGTG ACAGTGTCTTCTGCTAGCACCAAGGGCCCAAGTG TCTTTCCCCTGGCCCCCAGCAGCAAGTCCACAAG CGGAGGCACTGCAGCTCTGGGTTGTCTGGTGAA GGACTACTTCCCCGAGCCCGTGACAGTGTCCTGG AACAGCGGAGCCCTGACCTCCGGCGTGCACACC TTCCCCGCCGTGCTGCAGAGCAGCGGCCTGTAC AGCCTGAGCAGCGTCGTGACTGTGCCTAGTTCCA GCCTGGGCACCCAGACCTATATCTGCAACGTGAA CCACAAGCCCAGCAACACCAAGGTGGACAAGAGA GTGGAGCCCAAGAGCTGCGACAAGACCCACACC TGCCCCCCCTGCCCAGCTCCAGAACTGCTGGGA GGACCCAGCGTGTTCCTGTTCCCCCCCAAGCCCA AGGACACCCTGATGATCAGCAGGACCCCCGAGG TGACCTGCGTGGTGGTGGACGTGTCCCACGAGG ACCCAGAGGTGAAGTTCAACTGGTACGTGGACGG GGTGGAGGTGCACAACGCCAAGACCAAGCCCAG AGAGGAGCAGTACAACAGCACCTACAGGGTGGT GTCCGTCCTGACAGTGCTGCACCAGGATTGGCTG AACGGCAAAGAATACAAGTGCAAAGTCTCCAACA AGGCCCTGCCAGCCCCAATCGAAAAGACAATCAG CAAGGCCAAGGGCCAGCCACGGGAGCCCCAGGT GTACACCCTGCCCCCCAGCCGGGAGGAGATGAC CAAGAACCAGGTGTCCCTGACCTGTCTGGTGAAG GGCTTCTACCCCAGCGATATCGCCGTGGAGTGG GAGAGCAACGGCCAGCCCGAGAACAACTACAAG ACCACCCCCCCAGTGCTGGACAGCGACGGCAGC TTCTTCCTGTACAGCAAGCTGACCGTGGACAAGT CCAGGTGGCAGCAGGGCAACGTGTTCAGCTGCA GCGTGATGCACGAGGCCCTGCACAACCACTACAC CCAGAAGTCCCTGAGCCTGAGCCCCGGCAAG |
| ALTERNATIVE PN ENCODING SEQ ID NO: 36 | 40 | GCTATTCAGCTGACTCAGTCACCTAGTAGCCTGA GCGCTAGTGTGGGCGATAGAGTGACTATCACCTG TAGACCTAGCCAGGGAATCTACTGGGAGCTGGCC TGGTATCAGCAGAAGCCCGGCAAGGCCCCTAAG CTGCTGATCTACGACGCTAGTAGTCTGGAACAGG GCGTGCCCTCTAGGTTTAGCGGCTCAGGCTCAGG CACCGACTTCACCCTGACTATTAGTAGCCTGCAG CCCGAGGACTTCGCTACCTACTACTGTCAGCAGT TTAACTCCTACCCCCTGACCTTCGGCGGAGGCAC TAAGGTGGAAATCAAGCGTACGGTGGCCGCTCCC AGCGTGTTCATCTTCCCCCCCAGCGACGAGCAGC TGAAGAGCGGCACCGCCAGCGTGGTGTGCCTGC TGAACAACTTCTACCCCCGGGAGGCCAAGGTGCA GTGGAAGGTGGACAACGCCCTGCAGAGCGGCAA CAGCCAGGAGAGCGTCACCGAGCAGGACAGCAA GGACTCCACCTACAGCCTGAGCAGCACCCTGACC CTGAGCAAGGCCGACTACGAGAAGCATAAGGTGT ACGCCTGCGAGGTGACCCACCAGGGCCTGTCCA GCCCCGTGACCAAGAGCTTCAACAGGGGCGAGT GC |

TABLE 36-continued

Sequence list

| Antibody/Fragment | Sequence Identifier (SEQ ID NO:) | Amino acid sequence or polynucleotide sequence (PN) |
|---|---|---|
| XAB4, CDRH1 (CHOTHIA) | 1 | GFTFSSY |
| XAB4, CDRH2 (CHOTHIA) | 2 | KQDGSE |
| XAB4, CDRH3 (CHOTHIA) | 3 | DRGSLYY |
| XAB4, CDRL1 (CHOTHIA) | 41 | SQGINWE |
| XAB4, CDRL2 (CHOTHIA) | 5 | DAS |
| XAB4, CDRL3 (CHOTHIA) | 6 | FNSYPL |
| XAB4, CDRH1 (KABAT) | 7 | SYWMS |
| XAB4, CDRH2 (KABAT) | 8 | NIKQDGSEKYYVDSVKG |
| XAB4, CDRH3 (KABAT) | 3 | DRGSLYY |
| XAB4, CDRL1 (KABAT) | 42 | RPSQGINWELA |
| XAB4, CDRL2 (KABAT) | 23 | DASSLEQ |
| XAB4, CDRL3 (KABAT) | 11 | QQFNSYPLT |
| XAB4, VH | 12 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSS |
| XAB4, VL | 43 | AIQLTQSPSSLSASVGDRVTITCRPSQGINWELAWY QQKPGKAPKLLIYDASSLEQGVPSRFSGSGSGTDFT LTISSLQPEDFATYYCQQFNSYPLTFGGGTKVEIK |
| XAB4, HEAVY CHAIN | 14 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSR EEMTKNQVSLTCLVKGFYPSDIAVEWESNGQPENN YKTTPPVLDSDGSFFLYSKLTVDKSRWQQGNVFSC SVMHEALHNHYTQKSLSLSPGK |
| XAB4, LIGHT CHAIN | 44 | AIQLTQSPSSLSASVGDRVTITCRPSQGINWELAWY QQKPGKAPKLLIYDASSLEQGVPSRFSGSGSGTDFT LTISSLQPEDFATYYCQQFNSYPLTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| PN ENCODING SEQ ID NO: 12 | 16 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG |

TABLE 36-continued

Sequence list

| Antibody/ Fragment | Sequence Identifier (SEQ ID NO:) | Amino acid sequence or polynucleotide sequence (PN) |
|---|---|---|
| | | CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGC |
| PN ENCODING SEQ ID NO: 43 | 45 | GCCATCCAGCTGACCCAGAGCCCCAGCAGCCTG AGCGCCAGCGTGGGCGACAGAGTGACCATCACC TGTCGGCCCAGCCAGGGCATCAACTGGGAGCTG GCCTGGTATCAGCAGAAGCCTGGCAAGGCCCCC AAGCTGCTGATCTACGACGCCAGCTCCCTGGAAC AGGGCGTGCCCAGCCGGTTCAGCGGCAGCGGAT CCGGCACCGACTTCACCCTGACCATCAGCTCCCT GCAGCCCGAGGACTTCGCCACCTACTACTGCCAG CAGTTCAACAGCTACCCCCTGACCTTCGGCGGAG GCACCAAGGTGGAAATCAAG |
| PN ENCODING SEQ ID NO: 14 | 18 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGCGCTAGCACCAAGGGCCC CAGCGTGTTCCCCCTGGCCCCCAGCAGCAAGAG CACCAGCGGCGGCACAGCCGCCCTGGGCTGCCT GGTGAAGGACTACTTCCCCGAGCCCGTGACCGT GTCCTGGAACAGCGGAGCCCTGACCTCCGGCGT GCACACCTTCCCCGCCGTGCTGCAGAGCAGCGG CCTGTACAGCCTGTCCAGCGTGGTGACAGTGCCC AGCAGCAGCCTGGGCACCCAGACCTACATCTGCA ACGTGAACCACAAGCCCAGCAACACCAAGGTGGA CAAGAGAGTGGAGCCCAAGAGCTGCGACAAGAC CCACACCTGCCCCCCCTGCCCAGCCCCAGAGCT GCTGGGCGGACCCTCCGTGTTCCTGTTCCCCCCC AAGCCCAAGGACACCCTGATGATCAGCAGGACCC CCGAGGTGACCTGCGTGGTGGTGGACGTGAGCC ACGAGGACCCAGAGGTGAAGTTCAACTGGTACGT GGACGGCGTGGAGGTGCACAACGCCAAGACCAA GCCCAGAGAGGAGCAGTACAACAGCACCTACAG GGTGGTGTCCGTGCTGACCGTGCTGCACCAGGA CTGGCTGAACGGCAAGGAATACAAGTGCAAGGTC TCCAACAAGGCCCTGCCAGCCCCCATCGAAAAGA CCATCAGCAAGGCCAAGGGCCAGCCACGGGAGC CCCAGGTGTACACCCTGCCCCCCTCCCGGGAGG AGATGACCAAGAACCAGGTGTCCCTGACCTGTCT GGTGAAGGGCTTCTACCCCAGCGACATCGCCGT GGAGTGGGAGAGCAACGGCCAGCCCGAGAACAA CTACAAGACCACCCCCCCAGTGCTGGACAGCGAC GGCAGCTTCTTCCTGTACAGCAAGCTGACCGTGG ACAAGTCCAGGTGGCAGCAGGGCAACGTGTTCA GCTGCAGCGTGATGCACGAGGCCCTGCACAACC ACTACACCCAGAAGAGCCTGAGCCTGTCCCCCGG CAAG |
| PN ENCODING SEQ ID NO: 44 | 46 | GCCATCCAGCTGACCCAGAGCCCCAGCAGCCTG AGCGCCAGCGTGGGCGACAGAGTGACCATCACC TGTCGGCCCAGCCAGGGCATCAACTGGGAGCTG GCCTGGTATCAGCAGAAGCCTGGCAAGGCCCCC AAGCTGCTGATCTACGACGCCAGCTCCCTGGAAC AGGGCGTGCCCAGCCGGTTCAGCGGCAGCGGAT CCGGCACCGACTTCACCCTGACCATCAGCTCCCT GCAGCCCGAGGACTTCGCCACCTACTACTGCCAG CAGTTCAACAGCTACCCCCTGACCTTCGGCGGAG GCACCAAGGTGGAAATCAAGCGTACGGTGGCCG CTCCCAGCGTGTTCATCTTCCCCCCCAGCGACGA GCAGCTGAAGAGCGGCACCGCCAGCGTGGTGTG CCTGCTGAACAACTTCTACCCCGGGGAGGCCAAG GTGCAGTGGAAGGTGGACAACGCCCTGCAGAGC GGCAACAGCCAGGAGAGCGTCACCGAGCAGGAC |

TABLE 36-continued

Sequence list

| Antibody/<br>Fragment | Sequence<br>Identifier<br>(SEQ ID<br>NO:) | Amino acid sequence or<br>polynucleotide sequence (PN) |
|---|---|---|
| | | AGCAAGGACTCCACCTACAGCCTGAGCAGCACCC<br>TGACCCTGAGCAAGGCCGACTACGAGAAGCATAA<br>GGTGTACGCCTGCGAGGTGACCCACCAGGGCCT<br>GTCCAGCCCCGTGACCAAGAGCTTCAACAGGGG<br>CGAGTGC |
| ALTERNATIVE PN<br>ENCODING SEQ ID<br>NO: 12 | 29 | GAGGTGCAGCTGGTGGAATCAGGAGGCGACCTG<br>GTGCAGCCTGGCGGCTCACTGAGACTGAGCTGC<br>GCCGCTAGTGGCTTCACCTTTAGTAGCTACTGGA<br>TGAGCTGGGTGCGACAGGCCCCTGGCAAGGGAC<br>TGGAGTGGGTGGCCAATATTAAGCAGGACGGCTC<br>AGAGAAGTACTACGTGGACTCAGTGAAGGGCCG<br>GTTCACTATTAGCCGGGATAACGCTAAGAATAGC<br>CTGTACCTGCAGATGAATAGCCTGAGAGCCGAGG<br>ACACCGCCGTGTACTACTGCGCTAGAGATAGAGG<br>CTCACTGTACTACTGGGGCCAGGGCACCCTGGTG<br>ACAGTGTCTTCT |
| ALTERNATIVE PN<br>ENCODING SEQ ID<br>NO: 43 | 47 | GCTATTCAGCTGACTCAGTCACCTAGTAGCCTGA<br>GCGCTAGTGTGGGCGATAGAGTGACTATCACCTG<br>TAGACCTAGTCAGGGGATTAACTGGGAGCTGGCC<br>TGGTATCAGCAGAAGCCCGGCAAGGCCCCTAAG<br>CTGCTGATCTACGACGCTAGTAGTCTGGAACAGG<br>GCGTGCCCTCTAGGTTTAGCGGCTCAGGCTCAGG<br>CACCGACTTCACCCTGACTATTAGTAGCCTGCAG<br>CCCGAGGACTTCGCTACCTACTACTGTCAGCAGT<br>TTAACTCCTACCCCCTGACCTTCGGCGGAGGCAC<br>TAAGGTGGAAATCAAG |
| ALTERNATIVE PN<br>ENCODING SEQ ID<br>NO: 14 | 31 | GAGGTGCAGCTGGTGGAATCAGGAGGCGACCTG<br>GTGCAGCCTGGCGGCTCACTGAGACTGAGCTGC<br>GCCGCTAGTGGCTTCACCTTTAGTAGCTACTGGA<br>TGAGCTGGGTGCGACAGGCCCCTGGCAAGGGAC<br>TGGAGTGGGTGGCCAATATTAAGCAGGACGGCTC<br>AGAGAAGTACTACGTGGACTCAGTGAAGGGCCG<br>GTTCACTATTAGCCGGGATAACGCTAAGAATAGC<br>CTGTACCTGCAGATGAATAGCCTGAGAGCCGAGG<br>ACACCGCCGTGTACTACTGCGCTAGAGATAGAGG<br>CTCACTGTACTACTGGGGCCAGGGCACCCTGGTG<br>ACAGTGTCTTCTGCTAGCACCAAGGGCCCAAGTG<br>TCTTTCCCCTGGCCCCCAGCAGCAAGTCCACAAG<br>CGGAGGCACTGCAGCTCTGGGTTGTCTGGTGAA<br>GGACTACTTCCCCGAGCCCGTGACAGTGTCCTGG<br>AACAGCGGAGCCCTGACCTCCGGCGTGCACACC<br>TTCCCCGCCGTGCTGCAGAGCAGCGGCCTGTAC<br>AGCCTGAGCAGCGTCGTGACTGTGCCTAGTTCCA<br>GCCTGGGCACCCAGACCTATATCTGCAACGTGAA<br>CCACAAGCCCAGCAACACCAAGGTGGACAAGAGA<br>GTGGAGCCCAAGAGCTGCGACAAGACCCACACC<br>TGCCCCCCCTGCCCAGCTCCAGAACTGCTGGGA<br>GGACCCAGCGTGTTCCTGTTCCCCCCCAAGCCCA<br>AGGACACCCTGATGATCAGCAGGACCCCCGAGG<br>TGACCTGCGTGGTGGTGGACGTGTCCCACGAGG<br>ACCCAGAGGTGAAGTTCAACTGGTACGTGGACGG<br>GGTGGAGGTGCACAACGCCAAGACCAAGCCCAG<br>AGAGGAGCAGTACAACAGCACCTACAGGGTGGT<br>GTCCGTCCTGACAGTGCTGCACCAGGATTGGCTG<br>AACGGCAAAGAATACAAGTGCAAAGTCTCCAACA<br>AGGCCCTGCCAGCCCCAATCGAAAAGACAATCAG<br>CAAGGCCAAGGGCCAGCCACGGGAGCCCCAGGT<br>GTACACCCTGCCCCCCAGCCGGGAGGAGATGAC<br>CAAGAACCAGGTGTCCCTGACCTGTCTGGTGAAG<br>GGCTTCTACCCCAGCGATATCGCCGTGGAGTGG<br>GAGAGCAACGGCCAGCCCGAGAACAACTACAAG<br>ACCACCCCCCCAGTGCTGGACAGCGACGGCAGC<br>TTCTTCCTGTACAGCAAGCTGACCGTGGACAAGT<br>CCAGGTGGCAGCAGGGCAACGTGTTCAGCTGCA<br>GCGTGATGCACGAGGCCCTGCACAACCACTACAC<br>CCAGAAGTCCCTGAGCCTGAGCCCCGGCAAG |
| ALTERNATIVE PN<br>ENCODING SEQ ID<br>NO: 44 | 48 | GCTATTCAGCTGACTCAGTCACCTAGTAGCCTGA<br>GCGCTAGTGTGGGCGATAGAGTGACTATCACCTG<br>TAGACCTAGTCAGGGGATTAACTGGGAGCTGGCC |

TABLE 36-continued

Sequence list

| Antibody/ Fragment | Sequence Identifier (SEQ ID NO:) | Amino acid sequence or polynucleotide sequence (PN) |
|---|---|---|
| | | TGGTATCAGCAGAAGCCCGGCAAGGCCCCTAAG CTGCTGATCTACGACGCTAGTAGTCTGGAACAGG GCGTGCCCTCTAGGTTTAGCGGCTCAGGCTCAGG CACCGACTTCACCCTGACTATTAGTAGCCTGCAG CCCGAGGACTTCGCTACCTACTACTGTCAGCAGT TTAACTCCTACCCCCTGACCTTCGGCGGAGGCAC TAAGGTGGAAATCAAGCGTACGGTGGCCGCTCCC AGCGTGTTCATCTTCCCCCCCAGCGACGAGCAGC TGAAGAGCGGCACCGCCAGCGTGGTGTGCCTGC TGAACAACTTCTACCCCCGGGAGGCCAAGGTGCA GTGGAAGGTGGACAACGCCCTGCAGAGCGGCAA CAGCCAGGAGAGCGTCACCGAGCAGGACAGCAA GGACTCCACCTACAGCCTGAGCAGCACCCTGACC CTGAGCAAGGCCGACTACGAGAAGCATAAGGTGT ACGCCTGCGAGGTGACCCACCAGGGCCTGTCCA GCCCCGTGACCAAGAGCTTCAACAGGGGCGAGT GC |
| SECOND ALTERNATIVE PN ENCODING SEQ ID NO: 12 | 49 | GAGGTGCAGCTGGTGGAATCTGGCGGCGACCTG GTGCAGCCTGGCGGCTCTCTGAGACTGTCTTGCG CCGCCTCCGGCTTCACCTTCTCCAGCTACTGGAT GTCCTGGGTGCGACAGGCCCCTGGCAAGGGACT GGAATGGGTGGCCAACATCAAGCAGGACGGCTC CGAGAAGTACTACGTGGACTCCGTGAAGGGCCG GTTCACCATCTCCCGGGACAACGCCAAGAACTCC CTGTACCTGCAGATGAACTCCCTGCGGGCCGAG GACACCGCCGTGTACTACTGCGCCAGGGACCGG GGCTCCCTGTACTATTGGGGCCAGGGCACCCTG GTGACAGTGTCCTCC |
| SECOND ALTERNATIVE PN ENCODING SEQ ID NO: 43 | 50 | GCCATCCAGCTGACCCAGTCCCCCTCCAGCCTGT CTGCCTCCGTGGGCGACAGAGTGACCATCACCTG TCGGCCCTCCCAGGGCATCAACTGGGAACTGGC CTGGTATCAGCAGAAGCCCGGCAAGGCCCCCAA GCTGCTGATCTACGACGCCAGCTCCCTGGAACAG GGCGTGCCCTCCAGATTCTCCGGCTCTGGCTCCG GCACCGACTTCACCCTGACCATCTCCAGCCTGCA GCCCGAGGACTTCGCCACCTACTACTGCCAGCAG TTCAACTCCTACCCCCTGACCTTCGGCGGAGGCA CCAAGGTGGAAATCAAG |
| SECOND ALTERNATIVE PN ENCODING SEQ ID NO: 14 | 51 | GAGGTGCAGCTGGTGGAATCTGGCGGCGACCTG GTGCAGCCTGGCGGCTCTCTGAGACTGTCTTGCG CCGCCTCCGGCTTCACCTTCTCCAGCTACTGGAT GTCCTGGGTGCGACAGGCCCCTGGCAAGGGACT GGAATGGGTGGCCAACATCAAGCAGGACGGCTC CGAGAAGTACTACGTGGACTCCGTGAAGGGCCG GTTCACCATCTCCCGGGACAACGCCAAGAACTCC CTGTACCTGCAGATGAACTCCCTGCGGGCCGAG GACACCGCCGTGTACTACTGCGCCAGGGACCGG GGCTCCCTGTACTATTGGGGCCAGGGCACCCTG GTGACAGTGTCCTCCGCCTCCACCAAGGGCCCAA GCGTGTTCCCCCTGGCCCCCAGCAGCAAGAGCA CCAGCGGCGGCACAGCCGCCCTGGGCTGCCTGG TGAAGGACTACTTCCCCGAGCCCGTGACCGTGTC CTGGAACAGCGGAGCCCTGACCTCCGGCGTGCA CACCTTCCCCGCCGTGCTGCAGAGCAGCGGCCT GTACAGCCTGAGCAGCGTGGTGACCGTGCCCAG CAGCAGCCTGGGCACCCAGACCTACATCTGTAAC GTGAACCACAAGCCCAGCAACACCAAGGTGGACA AGAGAGTGGAGCCCAAGAGCTGTGACAAGACCC ACACCTGCCCCCCCTGCCCAGCCCCCGAGCTGC TGGGCGGACCCAGCGTGTTCCTGTTCCCCCCCAA GCCCAAGGACACCCTGATGATCAGCAGAACCCCC GAGGTGACCTGTGTGGTGGTGGACGTGTCCCAC GAGGACCCAGAGGTGAAGTTCAACTGGTACGTGG ACGGCGTGGAGGTGCACAACGCCAAGACCAAGC CCAGAGAGGAGCAGTACAACAGCACCTACAGGGT GGTGTCCGTGCTGACCGTGCTGCACCAGGACTG GCTGAACGGCAAGGAGTACAAGTGTAAGGTGTCC AACAAGGCCCTGCCAGCCCCAATCGAAAAGACCA TCAGCAAGGCCAAGGGCCAGCCAAGAGAGCCCC AGGTGTACACCCTGCCACCCAGCAGGGAGGAGA |

TABLE 36-continued

Sequence list

| Antibody/Fragment | Sequence Identifier (SEQ ID NO:) | Amino acid sequence or polynucleotide sequence (PN) |
|---|---|---|
| | | TGACCAAGAACCAGGTGTCCCTGACCTGTCTGGT GAAGGGCTTCTACCCAAGCGACATCGCCGTGGA GTGGGAGAGCAACGGCCAGCCCGAGAACAACTA CAAGACCACCCCCCCAGTGCTGGACAGCGACGG CAGCTTCTTCCTGTACAGCAAGCTGACCGTGGAC AAGAGCAGATGGCAGCAGGGCAACGTGTTCAGCT GCTCCGTGATGCACGAGGCCCTGCACAACCACTA CACCCAGAAGAGCCTGAGCCTGTCCCCAGGCAA G |
| SECOND ALTERNATIVE PN ENCODING SEQ ID NO: 44 | 52 | GCCATCCAGCTGACCCAGTCCCCCTCCAGCCTGT CTGCCTCCGTGGGCGACAGAGTGACCATCACCTG TCGGCCCTCCCAGGGCATCAACTGGGAACTGGC CTGGTATCAGCAGAAGCCCGGCAAGGCCCCCAA GCTGCTGATCTACGACGCCAGCTCCCTGGAACAG GGCGTGCCCTCCAGATTCTCCGGCTCTGGCTCCG GCACCGACTTCACCCTGACCATCTCCAGCCTGCA GCCCGAGGACTTCGCCACCTACTACTGCCAGCAG TTCAACTCCTACCCCCTGACCTTCGGCGGAGGCA CCAAGGTGGAAATCAAGCGTACGGTGGCCGCTC CCAGCGTGTTCATCTTCCCCCCAAGCGACGAGCA GCTGAAGAGCGGCACCGCCAGCGTGGTGTGTCT GCTGAACAACTTCTACCCCAGGGAGGCCAAGGTG CAGTGGAAGGTGGACAACGCCCTGCAGAGCGGC AACAGCCAGGAGAGCGTCACCGAGCAGGACAGC AAGGACTCCACCTACAGCCTGAGCAGCACCCTGA CCCTGAGCAAGGCCGACTACGAGAAGCACAAGG TGTACGCCTGTGAGGTGACCCACCAGGGCCTGTC CAGCCCCGTGACCAAGAGCTTCAACAGGGGCGA GTGC |
| XAB5, CDRH1 (CHOTHIA) | 1 | GFTFSSY |
| XAB5, CDRH2 (CHOTHIA) | 2 | KQDGSE |
| XAB5, CDRH3 (CHOTHIA) | 3 | DRGSLYY |
| XAB5, CDRL1 (CHOTHIA) | 41 | SQGINWE |
| XAB5, CDRL2 (CHOTHIA) | 5 | DAS |
| XAB5, CDRL3 (CHOTHIA) | 6 | FNSYPL |
| XAB5, CDRH1 (KABAT) | 7 | SYWMS |
| XAB5, CDRH2 (KABAT) | 8 | NIKQDGSEKYYVDSVKG |
| XAB5, CDRH3 (KABAT) | 3 | DRGSLYY |
| XAB5, CDRL1 (KABAT) | 42 | RPSQGINWELA |
| XAB5, CDRL2 (KABAT) | 10 | DASSLEN |
| XAB5, CDRL3 (KABAT) | 11 | QQFNSYPLT |
| XAB5, VH | 12 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSS |

TABLE 36-continued

Sequence list

| Antibody/ Fragment | Sequence Identifier (SEQ ID NO:) | Amino acid sequence or polynucleotide sequence (PN) |
|---|---|---|
| XAB5, VL | 53 | AIQLTQSPSSLSASVGDRVTITCRPSQGINWELAWY QQKPGKAPKLLIYDASSLENGVPSRFSGSGSGTDFT LTISSLQPEDFATYYCQQFNSYPLTFGGGTKVEIK |
| XAB5, HEAVY CHAIN | 14 | EVQLVESGGDLVQPGGSLRLSCAASGFTFSSYWMS WVRQAPGKGLEWVANIKQDGSEKYYVDSVKGRFTI SRDNAKNSLYLQMNSLRAEDTAVYYCARDRGSLYY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSR EEMTKNQVSLTCLVKGFYPSDIAVEWESNGQPENN YKTTPPVLDSDGSFFLYSKLTVDKSRWQQGNVFSC SVMHEALHNHYTQKSLSLSPGK |
| XAB5, LIGHT CHAIN | 54 | AIQLTQSPSSLSASVGDRVTITCRPSQGINWELAWY QQKPGKAPKLLIYDASSLENGVPSRFSGSGSGTDFT LTISSLQPEDFATYYCQQFNSYPLTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| PN ENCODING SEQ ID NO: 12 | 16 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGC |
| PN ENCODING SEQ ID NO: 53 | 55 | GCCATCCAGCTGACCCAGAGCCCCAGCAGCCTG AGCGCCAGCGTGGGCGACAGAGTGACCATCACC TGTCGGCCCAGCCAGGGCATCAACTGGGAGCTG GCCTGGTATCAGCAGAAGCCTGGCAAGGCCCCC AAGCTGCTGATCTACGACGCCAGCTCCCTGGAAA ACGGCGTGCCCAGCCGGTTCAGCGGCAGCGGAT CCGGCACCGACTTCACCCTGACCATCAGCTCCCT GCAGCCCGAGGACTTCGCCACCTACTACTGCCAG CAGTTCAACAGCTACCCCCTGACCTTCGGCGGAG GCACCAAGGTGGAAATCAAG |
| PN ENCODING SEQ ID NO: 14 | 18 | GAGGTGCAGCTGGTCGAGTCTGGCGGCGACCTG GTGCAGCCTGGCGGCAGCCTGAGACTGAGCTGC GCCGCCAGCGGCTTCACCTTCAGCAGCTACTGGA TGTCCTGGGTCCGCCAGGCCCCTGGCAAAGGCC TCGAATGGGTGGCCAACATCAAGCAGGACGGCA GCGAGAAGTACTACGTGGACAGCGTGAAGGGCC GGTTCACCATCAGCCGGGACAACGCCAAGAACAG CCTGTACCTGCAGATGAACAGCCTGCGGGCCGA GGACACCGCCGTGTACTACTGCGCCAGGGACCG GGGCAGCCTGTACTATTGGGGCCAGGGCACCCT GGTCACCGTGTCCAGCGCTAGCACCAAGGGCCC CAGCGTGTTCCCCCTGGCCCCCAGCAGCAAGAG CACCAGCGGCGGCACAGCCGCCCTGGGCTGCCT GGTGAAGGACTACTTCCCCGAGCCCGTGACCGT GTCCTGGAACAGCGGAGCCCTGACCTCCGGCGT GCACACCTTCCCCGCCGTGCTGCAGAGCAGCGG CCTGTACAGCCTGTCCAGCGTGGTGACAGTGCCC AGCAGCAGCCTGGGCACCCAGACCTACATCTGCA ACGTGAACCACAAGCCCAGCAACACCAAGGTGGA CAAGAGAGTGGAGCCCAAGAGCTGCGACAAGAC CCACACCTGCCCCCCCTGCCCAGCCCCAGAGCT GCTGGGCGGACCCTCCGTGTTCCTGTTCCCCCCC AAGCCCAAGGACACCCTGATGATCAGCAGGACCC CCGAGGTGACCTGCGTGGTGGTGGACGTGAGCC ACGAGGACCCAGAGGTGAAGTTCAACTGGTACGT |

TABLE 36-continued

Sequence list

| Antibody/ Fragment | Sequence Identifier (SEQ ID NO:) | Amino acid sequence or polynucleotide sequence (PN) |
|---|---|---|
| | | GGACGGCGTGGAGGTGCACAACGCCAAGACCAA GCCCAGAGAGGAGCAGTACAACAGCACCTACAG GGTGGTGTCCGTGCTGACCGTGCTGCACCAGGA CTGGCTGAACGGCAAGGAATACAAGTGCAAGGTC TCCAACAAGGCCCTGCCAGCCCCCATCGAAAAGA CCATCAGCAAGGCCAAGGGCCAGCCACGGGAGC CCCAGGTGTACACCCTGCCCCCCTCCCGGGAGG AGATGACCAAGAACCAGGTGTCCCTGACCTGTCT GGTGAAGGGCTTCTACCCCAGCGACATCGCCGT GGAGTGGGAGAGCAACGGCCAGCCCGAGAACAA CTACAAGACCACCCCCCCAGTGCTGGACAGCGAC GGCAGCTTCTTCCTGTACAGCAAGCTGACCGTGG ACAAGTCCAGGTGGCAGCAGGGCAACGTGTTCA GCTGCAGCGTGATGCACGAGGCCCTGCACAACC ACTACACCCAGAAGAGCCTGAGCCTGTCCCCCGG CAAG |
| PN ENCODING SEQ ID NO: 54 | 56 | GCCATCCAGCTGACCCAGAGCCCCAGCAGCCTG AGCGCCAGCGTGGGCGACAGAGTGACCATCACC TGTCGGCCCAGCCAGGGCATCAACTGGGAGCTG GCCTGGTATCAGCAGAAGCCTGGCAAGGCCCCC AAGCTGCTGATCTACGACGCCAGCTCCCTGGAAA ACGGCGTGCCCAGCCGGTTCAGCGGCAGCGGAT CCGGCACCGACTTCACCCTGACCATCAGCTCCCT GCAGCCCGAGGACTTCGCCACCTACTACTGCCAG CAGTTCAACAGCTACCCCCTGACCTTCGGCGGAG GCACCAAGGTGGAAATCAAGCGTACGGTGGCCG CTCCCAGCGTGTTCATCTTCCCCCCCAGCGACGA GCAGCTGAAGAGCGGCACCGCCAGCGTGGTGTG CCTGCTGAACAACTTCTACCCCGGGAGGCCAAG GTGCAGTGGAAGGTGGACAACGCCCTGCAGAGC GGCAACAGCCAGGAGAGCGTCACCGAGCAGGAC AGCAAGGACTCCACCTACAGCCTGAGCAGCACCC TGACCCTGAGCAAGGCCGACTACGAGAAGCATAA GGTGTACGCCTGCGAGGTGACCCACCAGGGCCT GTCCAGCCCCGTGACCAAGAGCTTCAACAGGGG CGAGTGC |
| ALTERNATIVE PN ENCODING SEQ ID NO: 12 | 29 | GAGGTGCAGCTGGTGGAATCAGGAGGCGACCTG GTGCAGCCTGGCGGCTCACTGAGACTGAGCTGC GCCGCTAGTGGCTTCACCTTTAGTAGCTACTGGA TGAGCTGGGTGCGACAGGCCCCTGGCAAGGGAC TGGAGTGGGTGGCCAATATTAAGCAGGACGGCTC AGAGAAGTACTACGTGGACTCAGTGAAGGGCCG GTTCACTATTAGCCGGGATAACGCTAAGAATAGC CTGTACCTGCAGATGAATAGCCTGAGAGCCGAGG ACACCGCCGTGTACTACTGCGCTAGAGATAGAGG CTCACTGTACTACTGGGGCCAGGGCACCCTGGTG ACAGTGTCTTCT |
| ALTERNATIVE PN ENCODING SEQ ID NO: 53 | 57 | GCTATTCAGCTGACTCAGTCACCTAGTAGCCTGA GCGCTAGTGTGGGCGATAGAGTGACTATCACCTG TAGACCTAGTCAGGGGATTAACTGGGAGCTGGCC TGGTATCAGCAGAAGCCCGGCAAGGCCCCTAAG CTGCTGATCTACGACGCTAGTAGTCTGGAAAACG GCGTGCCCTCTAGGTTTAGCGGCTCAGGCTCAGG CACCGACTTCACCCTGACTATTAGTAGCCTGCAG CCCGAGGACTTCGCTACCTACTACTGTCAGCAGT TTAACTCCTACCCCCTGACCTTCGGCGGAGGCAC TAAGGTGGAAATCAAG |
| ALTERNATIVE PN ENCODING SEQ ID NO: 14 | 31 | GAGGTGCAGCTGGTGGAATCAGGAGGCGACCTG GTGCAGCCTGGCGGCTCACTGAGACTGAGCTGC GCCGCTAGTGGCTTCACCTTTAGTAGCTACTGGA TGAGCTGGGTGCGACAGGCCCCTGGCAAGGGAC TGGAGTGGGTGGCCAATATTAAGCAGGACGGCTC AGAGAAGTACTACGTGGACTCAGTGAAGGGCCG GTTCACTATTAGCCGGGATAACGCTAAGAATAGC CTGTACCTGCAGATGAATAGCCTGAGAGCCGAGG ACACCGCCGTGTACTACTGCGCTAGAGATAGAGG CTCACTGTACTACTGGGGCCAGGGCACCCTGGTG ACAGTGTCTTCTGCTAGCACCAAGGGCCCAAGTG TCTTTCCCCTGGCCCCCAGCAGCAAGTCCACAAG |

TABLE 36-continued

Sequence list

| Antibody/ Fragment | Sequence Identifier (SEQ ID NO:) | Amino acid sequence or polynucleotide sequence (PN) |
| --- | --- | --- |
| | | CGGAGGCACTGCAGCTCTGGGTTGTCTGGTGAA GGACTACTTCCCCGAGCCCGTGACAGTGTCCTGG AACAGCGGAGCCCTGACCTCCGGCGTGCACACC TTCCCCGCCGTGCTGCAGAGCAGCGGCCTGTAC AGCCTGAGCAGCGTCGTGACTGTGCCTAGTTCCA GCCTGGGCACCCAGACCTATATCTGCAACGTGAA CCACAAGCCCAGCAACACCAAGGTGGACAAGAGA GTGGAGCCCAAGAGCTGCGACAAGACCCACACC TGCCCCCCCTGCCCAGCTCCAGAACTGCTGGGA GGACCCAGCGTGTTCCTGTTCCCCCCCAAGCCCA AGGACACCCTGATGATCAGCAGGACCCCCGAGG TGACCTGCGTGGTGGTGGACGTGTCCCACGAGG ACCCAGAGGTGAAGTTCAACTGGTACGTGGACGG GGTGGAGGTGCACAACGCCAAGACCAAGCCCAG AGAGGAGCAGTACAACAGCACCTACAGGGTGGT GTCCGTCCTGACAGTGCTGCACCAGGATTGGCTG AACGGCAAAGAATACAAGTGCAAAGTCTCCAACA AGGCCCTGCCAGCCCCAATCGAAAAGACAATCAG CAAGGCCAAGGGCCAGCCACGGGAGCCCCAGGT GTACACCCTGCCCCCCAGCCGGGAGGAGATGAC CAAGAACCAGGTGTCCCTGACCTGTCTGGTGAAG GGCTTCTACCCCAGCGATATCGCCGTGGAGTGG GAGAGCAACGGCCAGCCCGAGAACAACTACAAG ACCACCCCCCAGTGCTGGACAGCGACGGCAGC TTCTTCCTGTACAGCAAGCTGACCGTGGACAAGT CCAGGTGGCAGCAGGGCAACGTGTTCAGCTGCA GCGTGATGCACGAGGCCCTGCACAACCACTACAC CCAGAAGTCCCTGAGCCTGAGCCCCGGCAAG |
| ALTERNATIVE PN ENCODING SEQ ID NO: 54 | 58 | GCTATTCAGCTGACTCAGTCACCTAGTAGCCTGA GCGCTAGTGTGGGCGATAGAGTGACTATCACCTG TAGACCTAGTCAGGGGATTAACTGGGAGCTGGCC TGGTATCAGCAGAAGCCCGGCAAGGCCCCTAAG CTGCTGATCTACGACGCTAGTAGTCTGGAAAACG GCGTGCCCTCTAGGTTTAGCGGCTCAGGCTCAGG CACCGACTTCACCCTGACTATTAGTAGCCTGCAG CCCGAGGACTTCGCTACCTACTACTGTCAGCAGT TAACTCCTACCCCCTGACCTTCGGCGGAGGCAC TAAGGTGGAAATCAAGCGTACGGTGGCCGCTCCC AGCGTGTTCATCTTCCCCCCCAGCGACGAGCAGC TGAAGAGCGGCACCGCCAGCGTGGTGTGCCTGC TGAACAACTTCTACCCCGGGAGGCCAAGGTGCA GTGGAAGGTGGACAACGCCCTGCAGAGCGGCAA CAGCCAGGAGAGCGTCACCGAGCAGGACAGCAA GGACTCCACCTACAGCCTGAGCAGCACCCTGACC CTGAGCAAGGCCGACTACGAGAAGCATAAGGTGT ACGCCTGCGAGGTGACCCACCAGGGCCTGTCCA GCCCCGTGACCAAGAGCTTCAACAGGGGCGAGT GC |
| LEADER SEQUENCE OF THE HEAVY CHAIN | 59 | MEFGLSWVFLVAILEGVHC |
| LEADER SEQUENCE OF THE LIGHT CHAIN | 60 | MDMRVPAQLLGLLLLWLPGARC |
| PN ENCODING SEQ ID NO: 59 | 61 | ATGGAATTCGGCCTGAGCTGGGTGTTCCTGGTCG CGATTCTGGAAGGCGTGCACTGC |
| PN ENCODING SEQ ID NO: 60 | 62 | ATGGACATGAGGGTCCCCGCTCAGCTCCTGGGG CTTCTGCTGCTCTGGCTCCCAGGCGCCAGATGT |
| ALTERNATIVE LEADER SEQUENCE OF THE HEAVY CHAIN | 63 | MAWVWTLPFLMAAAQSVQA |
| ALTERNATIVE LEADER SEQUENCE OF THE LIGHT CHAIN | 64 | MSVLTQVLALLLLWLTGTRC |

TABLE 36-continued

Sequence list

| Antibody/Fragment | Sequence Identifier (SEQ ID NO:) | Amino acid sequence or polynucleotide sequence (PN) |
|---|---|---|
| ALTERNATIVE PN ENCODING SEQ ID NO: 63 | 65 | ATGGCCTGGGTGTGGACCCTGCCCTTCCTGATGG CCGCTGCTCAGTCAGTGCAGGCC |
| ALTERNATIVE PN ENCODING SEQ ID NO: 64 | 66 | ATGAGCGTGCTGACTCAGGTGCTGGCCCTGCTGC TGCTGTGGCTGACCGGCACCCGCTGC |
| SECOND ALTERNATIVE LEADER SEQUENCE OF THE HEAVY CHAIN | 67 | MEWSWVFLFFLSVTTGVHS |
| SECOND ALTERNATIVE LEADER SEQUENCE OF THE LIGHT CHAIN | 68 | MSVPTQVLGLLLLWLTDARC |
| SECOND ALTERNATIVE PN ENCODING SEQ ID NO: 67 | 69 | ATGGAATGGTCCTGGGTGTTCCTGTTCTTCCTGTC CGTGACCACAGGCGTGCACTCC |
| SECOND ALTERNATIVE PN ENCODING SEQ ID NO: 68 | 70 | ATGTCCGTGCCCACACAGGTGCTGGGCCTGCTG CTGCTGTGGCTGACCGACGCCAGATGC |
| CONSENSUS, CDRL1 (CHOTHIA) | 71 | SQX$_1$IX$_2$X$_3$X$_4$ |
| CONSENSUS, CDRL3 (CHOTHIA) | 72 | FX$_1$SYPL |
| CONSENSUS, CDRL1 (KABAT) | 73 | RPSQX$_1$IX$_2$X$_3$X$_4$LA |
| CONSENSUS, CDRL2 (KABAT) | 74 | DASSLEX$_1$ |
| CONSENSUS, CDRL3 (KABAT) | 75 | QQFX$_1$SYPLT |
| huIL-17A | 76 | GITIPRNPGCPNSEDKNFPRTVMVNLNIHNRNTNTN PKRSSDYYNRSTSPWNLHRNEDPERYPSVIWEAKC RHLGCINADGNVDYHMNSVPIQQEILVLRREPPHCP NSFRLEKILVSVGCTCVTPIVHHVAEFRH |
| huIL-17F | 77 | MRKIPKVGHTFFQKPESCPPVPGGSMKLDIGIINEN QRVSMSRNIESRSTSPWNYTVTWDPNRYPSEVVQ AQCRNLGCINAQGKEDISMNSVPIQQETLVVRRKHQ GCSVSFQLEKVLVTVGCTCVTPVIHHVQ |
| alternative huIL-17A | 78 | GPIVKAGITIPRNPGCPNSEDKNFPRTVMVNLNIHNR NTNTNPKRSSDYYNRSTSPWNLHRNEDPERYPSVI WEAKCRHLGCINADGNVDYHMNSVPIQQEILVLRRE PPHCPNSFRLEKILVSVGCTCVTPIVHHVA |
| cynoIL-17A | 79 | GIAIPRNSGCPNSEDKNFPRTVMVNLNIHNRNTSTN PKRSSDYYNRSTSPWNLHRNEDPERYPSVIWEAKC RHLGCVKADGNVDYHMNSVPIQQEILVLRREPRHC PNSFRLEKILVSVGCTCVTPIVHHVA |
| cynoIL-17F | 80 | MRKIPKVGHTFFQKPESCPPVPEGSMKLDTGIINEN QRVSMSRNIESRSTSPWNYTVTWDPNRYPSEVVQ AQCKHLGCINAQGKEDISMNSVPIQQETLVLRRKHQ GCSVSFQLEKVLVTVGCTCVTPVVHHVQ |
| rhesusIL-17A | 81 | GIAIPRNSGCPNSEDKNFPRTVMVNLNIHNRNTSTS PKRSSDYYNRSTSPWNLHRNEDPERYPSVIWEAKC |

TABLE 36-continued

Sequence list

| Antibody/Fragment | Sequence Identifier (SEQ ID NO:) | Amino acid sequence or polynucleotide sequence (PN) |
|---|---|---|
| | | RHLGCVKADGNVDYHMNSVPIQQEILVLRREPRHCPNSFRLEKILVSVGCTCVTPIVHHVA |
| marmosetIL-17A | 82 | SPQNPGCPNAEDKNFPRTVMVNLNIRNRNTNSKRASDYYNRSSSPWNLHRNEDPERYPSVIWEAKCRHLGCVDADGNVDYHMNSVPIQQEILVRREPRHCTNSFRLEKMLVSVGCTCVTPIVHHVA |
| mIL-17A | 83 | MAAIIPQSSACPNTEAKDFLQNVKVNLKVFNSLGAKVSSRRPSDYLNRSTSPWTLHRNEDPDRYPSVIWEAQCRHQRCVNAEGKLDHHMNSVLIQQEILVLKREPESCPFTFRVEKMLVGVGCTCVASIVRQAA |
| mIL-17F | 84 | APEPEFRHRKNPKAGVPALQKAGNCPPLEDNTVRVDIRIFNQNQGISVPREFQNRSSSPWDYNITRDPHRFPSEIAEAQCRHSGCINAQGQEDSTMNSVAIQQEILVLRREPQGCSNSFRLEKMLLKVGCTCVKPIVHQAA |
| ratIL-17A | 85 | MAVLIPQSSVCPNAEANNFLQNVKVNLKVINSLSSKASSRRPSDYLNRSTSPWTLSRNEDPDRYPSVIWEAQCRHQRCVNAEGKLDHHMNSVLIQQEILVLKREPEKCPFTFRVEKMLVGVGCTCVSSIVRHAS |
| huIL-17RA | 86 | NCTVKNSTCLDDSWIHPRNLTPSSPKDLQIQLHFAHTQQGDLFPVAHIEWTLQTDASILYLEGAELSVLQLNTNERLCVRFEFLSKLRHHHRRWRFTFSHFVVDPDQEYEVTVHHLPKPIPDGDPNHQSKNFLVPDCEHARMKVTTPCMSSGSLWDPNITVETLEAHQLRVSFTLWNESTHYQILLTSFPHMENHSCFEHMHHIPAPRPEEFHQRSNVTLTLRNLKGCCRHQVQIQPFFSSCLNDCLRHSATVSCPEMPDTPEPIPDYMPLWEFRHDSGGGLNDIFEAQKIEWHE |

What is claimed is:

1. An isolated antibody that binds human homodimeric IL-17A and human heterodimeric IL-17AF or antigen-binding portion thereof, comprising a heavy chain variable region ($V_H$) and a light chain variable region ($V_L$):
   a. wherein said $V_H$ comprises, in sequence, the three Complementarity Determining Regions (CDRs) set forth as amino acid sequences SEQ ID NO:7, SEQ ID NO:8, SEQ ID NO:3 and wherein said $V_L$ comprises, in sequence, the three CDRs set forth as amino acid sequences SEQ ID NO:42, SEQ ID NO:23, SEQ ID NO:11; or
   b. wherein said $V_H$ comprises, in sequence, the three CDRs set forth as amino acid sequences SEQ ID NO:1, SEQ ID NO:2, SEQ ID NO:3 and wherein said $V_L$ comprises, in sequence, the three CDRs set forth as amino acid sequences SEQ ID NO:41, SEQ ID NO:5, SEQ ID NO:6.

2. An isolated antibody that binds human homodimeric IL-17A and human heterodimeric IL-17AF or antigen-binding portion thereof, comprising a $V_H$ and a $V_L$, wherein said $V_H$ comprises the three CDRs of the amino acid sequence set forth as SEQ ID NO:12 and wherein said $V_L$ comprise the three CDRs of the amino acid sequence set forth as SEQ ID NO:43.

3. The isolated antibody or antigen-binding portion thereof according to claim 2, wherein the three CDRs of the amino acid sequence set forth as SEQ ID NO:12 are set forth as amino acid sequences SEQ ID NO:7, SEQ ID NO:8, SEQ ID NO:3 and wherein the three CDRs of the amino acid sequence set forth as SEQ ID NO:43 are set forth as amino acid sequences SEQ ID NO:42, SEQ ID NO:23, SEQ ID NO:11, and further wherein the CDRs are delineated according to the Kabat definition.

4. The isolated antibody or antigen-binding portion thereof according to claim 2, wherein the three CDRs of the amino acid sequence set forth as SEQ ID NO:12 are set forth as amino acid sequences SEC) ID NO:1, SEQ ID NO:2, SEQ ID NO:3 and wherein the three CDRs of the amino acid sequence set forth as SEQ ID NO:43 are set forth as amino acid sequences SEQ ID NO:41, SEQ ID NO:5, SEQ ID NO:6, and further wherein the CDRs are delineated according to the Chothia definition.

5. The isolated antibody or antigen-binding portion thereof according to claim 2, wherein said $V_H$ comprises the amino acid sequence set forth as SEQ ID NO:12 and wherein said $V_L$ comprises the amino acid sequence set forth as SEQ ID NO:43.

6. The isolated antibody or antigen-binding portion thereof according to any one of claims 1-5, which is a human antibody or antigen-binding portion thereof, a monoclonal antibody or antigen-binding portion thereof, a chimeric antibody or antigen-binding portion thereof, a humanized antibody or antigen-binding portion thereof, a F(ab')2 fragment, a Fab fragment, or a Fv fragment.

7. The isolated antibody or antigen-binding portion thereof according to claim 6, which is a human antibody.

8. The isolated antibody or antigen-binding portion thereof according to claim 6, which has a binding affinity for human IL-17A below 200 pM as measured by Biacore assay.

9. The isolated antibody or antigen-binding portion thereof according to claim 8, which has a binding affinity for human IL-17A below 100 pM as measured by Biacore assay.

10. A pharmaceutical composition comprising the isolated antibody or antigen-binding portion thereof according to claim 6 in combination with one or more pharmaceutically acceptable excipient, diluent or carrier.

11. An isolated antibody that binds human homodimeric IL-17A and human heterodimeric IL-17AF, comprising a heavy chain and a light chain, wherein said heavy chain comprises the three CDRs of the amino acid sequence set forth as SEQ ID NO:12 and wherein said light chain comprises the three CDRs of the amino acid sequence set forth as SEQ ID NO:43.

12. The isolated antibody according to claim 11, wherein the three CDRs of the amino acid sequence set forth as SEQ ID NO:12 are set forth as amino acid sequences SEQ ID NO:7, SEQ ID NO:8, SEQ ID NO:3 and wherein the three CDRs of the amino acid sequence set forth as SEQ ID NO:43 are set forth as amino acid sequences SEQ ID NO:42, SEQ ID NO:23, SEQ ID NO:11, and further wherein the CDRs are delineated according to the Kabat definition.

13. The isolated antibody according to claim 11, wherein the three CDRs of the amino acid sequence set forth as SEQ ID NO:12 are set forth as amino acid sequences SEQ ID NO:1, SEQ ID NO:2, SEQ ID NO:3 and wherein the three CDRs of the amino acid sequence set forth as SEQ ID NO:43 are set forth as amino acid sequences SEQ ID NO:41, SEQ ID NO:5, SEQ ID NO:6, and further wherein the CDRs are delineated according to the Chothia definition.

14. The isolated antibody according to claim 11, wherein said heavy chain comprises a $V_H$ comprising the amino acid sequence set forth as SEQ ID NO:12 and a $V_L$ comprising the amino acid sequence set forth as SEO ID NO:43.

15. The isolated antibody according to claim 11, wherein said heavy chain comprises the amino acid sequence set forth as SEQ ID NO:14 and wherein said light chain comprises the amino acid sequence set forth as SEQ ID NO:44.

16. The isolated antibody according to claim 11, which is a human antibody, a monoclonal antibody, a chimeric antibody, or a humanized antibody.

17. The isolated antibody according to claim 16, which is a human antibody.

18. The isolated antibody according to claim 11, which has a binding affinity ($K_D$) for human IL-17A below 200 pM as measured by Biacore assay.

19. The isolated antibody according to claim 11, which has a K for human IL-17A below 100 pM as measured by Biacore assay.

20. A pharmaceutical composition comprising the isolated antibody or antigen-binding portion thereof according to claims 1-5 or claims 11-19 in combination with one or more pharmaceutically acceptable excipient, diluent or carrier.

* * * * *